US008828685B2

(12) United States Patent
Schimmel et al.

(10) Patent No.: US 8,828,685 B2
(45) Date of Patent: Sep. 9, 2014

(54) MONOMERIC FORMS OF HUMAN AMINOACYL-T-RNA SYNTHETASES HAVING NON-CANONICAL BIOLOGICAL ACTIVITIES

(75) Inventors: Paul Schimmel, La Jolla, CA (US); Xiang-Lei Yang, San Diego, CA (US); Bonnie Slike, Ellicott City, MD (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 13/577,090

(22) PCT Filed: Feb. 4, 2011

(86) PCT No.: PCT/US2011/000210
§ 371 (c)(1), (2), (4) Date: Oct. 16, 2012

(87) PCT Pub. No.: WO2011/097031
PCT Pub. Date: Aug. 11, 2011

(65) Prior Publication Data
US 2013/0052177 A1 Feb. 28, 2013

Related U.S. Application Data

(60) Provisional application No. 61/337,489, filed on Feb. 4, 2010, provisional application No. 61/337,488, filed on Feb. 4, 2010, provisional application No. 61/337,528, filed on Feb. 4, 2010.

(51) Int. Cl.
| C07K 14/47 | (2006.01) |
| C07K 1/107 | (2006.01) |
| A61K 38/00 | (2006.01) |
| A61K 38/45 | (2006.01) |
| C12P 21/00 | (2006.01) |
| C12P 21/02 | (2006.01) |

(52) U.S. Cl.
USPC ....... 435/69.1; 435/6.16; 435/7.4; 435/320.1; 424/93.7; 424/94.5; 536/23.1; 530/350; 514/13.3; 514/18.9; 514/19.2

(58) Field of Classification Search
CPC combination set(s) only.
See application file for complete search history.

(56) References Cited

U.S. PATENT DOCUMENTS

| 7,144,984 B2 * | 12/2006 | Schimmel et al. ............ 530/350 |
| 8,026,088 B2 | 9/2011 | Yang |
| 8,481,296 B2 | 7/2013 | Yang |
| 2003/0215827 A1 * | 11/2003 | Yue et al. ............ 435/6 |
| 2009/0227662 A1 | 9/2009 | Schimmel et al. |
| 2010/0092434 A1 * | 4/2010 | Belani et al. ............ 424/93.7 |
| 2010/0297149 A1 * | 11/2010 | Zhou et al. ............ 424/172.1 |
| 2011/0104139 A1 | 5/2011 | Faber |
| 2011/0150885 A1 | 6/2011 | Watkins et al. |
| 2012/0064082 A1 | 3/2012 | Watkins et al. |
| 2013/0108630 A1 | 5/2013 | Watkins et al. |
| 2013/0273045 A1 | 10/2013 | Watkins et al. |

FOREIGN PATENT DOCUMENTS

| WO | WO 2007/064941 | 6/2007 |
| WO | WO 2009/114623 | 9/2009 |
| WO | WO 2009/152247 | 12/2009 |
| WO | WO 2011/072265 | 6/2011 |
| WO | WO 2011/072266 | 6/2011 |

OTHER PUBLICATIONS

Ewalt et al Activation of Angiogenic Signaling Pathways by Two Human tRNA Synthetases, Biochemistry 2002, 41, 13344-49.*
Wakasugi et al A human aminoacyl-tRNA synthetase as a regulator of angiogenesis. PNAS Jan. 8, 2002 vol. 99 No. 1 173-177.*
Kapoor, et al., "Mutational Separation of Aminoacylation and Cytokine Activities of Human Tyrosyl-tRNA Synthetase", *Chemistry and Biology 16*: 531-539 (2009).
Kise, et al., "A short peptide insertion crucial for angiostatic activity of human tryptophanyl-tRNA synthetase", *Nature Struc Mol Bio 11* (2): 149-156 (2004).
Link, et al., "Discovery of aminoacyl-tRNA synthetase activity through cell-surface display of noncanonical amino acids", *PNAS 103* (27): 10180-10185 (2006).
Hou, et al., "Sequence determination and modeling of structural motifs for the smallest monomeric aminoacyl-tRNA synthetase", *PNAS 88*: 976-980 (1991).
Vo, et al., "Dissociating Quaternary Structure Regulates Cell-signaling Functions of a Secreted Human tRNA Synthetase", *J Bio Chem 286* (13)11563-11568: (2011).
Kovaleski, et al., In Vitro Characterization of the Interaction between HIV-1 Gag and Human Lysyl-tRNA Synthetase, *J Bio Chem 281* (28): 19449-19456 (2006).
PCT/US11/00210 international Search Report and Written Opinion dated Aug. 12, 2011.

* cited by examiner

*Primary Examiner* — Kagnew H Gebreyesus
(74) *Attorney, Agent, or Firm* — Hugh Wang; Thomas Fitting

(57) ABSTRACT

Isolated monomelic aminoacyl-tRNA synthetase polypeptides and polynucleotides having non-canonical biological activities are provided, as well as compositions and methods related thereto.

5 Claims, 41 Drawing Sheets

FIG. 2B  Δ159-161 YRS$_{monomer}^{mini}$

FIG. 2C  C130$^{ox}$ YRS$_{dimer}^{mini}$

SEQUENCE LISTING

<160> NUMBER OF SEQ ID NOS: 14

<210> SEQ ID NO 1
<211> LENGTH: 528
<212> TYPE: PRT
<213> ORGANISM: Homo sapiens

<400> SEQUENCE: 1

Met Gly Asp Ala Pro Ser Pro Glu Glu Lys Leu His Leu Ile Thr Arg
1               5                   10                  15

Asn Leu Gln Glu Val Leu Gly Glu Glu Lys Leu Lys Glu Ile Leu Lys
            20                  25                  30

-continued

```
Glu Arg Glu Leu Lys Ile Tyr Trp Gly Thr Ala Thr Thr Gly Lys Pro
             35                  40                  45

His Val Ala Tyr Phe Val Pro Met Ser Lys Ile Ala Asp Phe Leu Lys
 50                  55                  60

Ala Gly Cys Glu Val Thr Ile Leu Phe Ala Asp Leu His Ala Tyr Leu
 65                  70                  75                  80

Asp Asn Met Lys Ala Pro Trp Glu Leu Leu Glu Leu Arg Val Ser Tyr
                 85                  90                  95

Tyr Glu Asn Val Ile Lys Ala Met Leu Glu Ser Ile Gly Val Pro Leu
                100                 105                 110

Glu Lys Leu Lys Phe Ile Lys Gly Thr Asp Tyr Gln Leu Ser Lys Glu
            115                 120                 125

Tyr Thr Leu Asp Val Tyr Arg Leu Ser Ser Val Val Thr Gln His Asp
    130                 135                 140

Ser Lys Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                165                 170                 175

Leu Lys Val Asp Ala Gln Phe Gly Gly Ile Asp Gln Arg Lys Ile Phe
            180                 185                 190

Thr Phe Ala Glu Lys Tyr Leu Pro Ala Leu Gly Tyr Ser Lys Arg Val
    195                 200                 205

His Leu Met Asn Pro Met Val Pro Gly Leu Thr Gly Ser Lys Met Ser
    210                 215                 220

Ser Ser Glu Glu Ser Lys Ile Asp Leu Leu Asp Arg Lys Glu Asp
225                 230                 235                 240

Val Lys Lys Lys Leu Lys Lys Ala Phe Cys Glu Pro Gly Asn Val Glu
                245                 250                 255

Asn Asn Gly Val Leu Ser Phe Ile Lys His Val Leu Phe Pro Leu Lys
                260                 265                 270

Ser Glu Phe Val Ile Leu Arg Asp Glu Lys Trp Gly Gly Asn Lys Thr
            275                 280                 285

Tyr Thr Ala Tyr Val Asp Leu Glu Lys Asp Phe Ala Ala Glu Val Val
    290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
                325                 330                 335

Ala Ser Ala Ala Tyr Pro Asp Pro Ser Lys Gln Lys Pro Met Ala Lys
                340                 345                 350

Gly Pro Ala Lys Asn Ser Glu Pro Glu Glu Val Ile Pro Ser Arg Leu
            355                 360                 365

Asp Ile Arg Val Gly Lys Ile Ile Thr Val Glu Lys His Pro Asp Ala
    370                 375                 380

Asp Ser Leu Tyr Val Glu Lys Ile Asp Val Gly Glu Ala Glu Pro Arg
385                 390                 395                 400

Thr Val Val Ser Gly Leu Val Gln Phe Val Pro Lys Glu Glu Leu Gln
                405                 410                 415

Asp Arg Leu Val Val Leu Cys Asn Leu Lys Pro Gln Lys Met Arg
            420                 425                 430

Gly Val Glu Ser Gln Gly Met Leu Leu Cys Ala Ser Ile Glu Gly Ile
            435                 440                 445

Asn Arg Gln Val Glu Pro Leu Asp Pro Pro Ala Gly Ser Ala Pro Gly
```

```
            450            455            460
Glu His Val Phe Val Lys Gly Tyr Glu Lys Gly Gln Pro Asp Glu Glu
465                 470                 475                 480

Leu Lys Pro Lys Lys Lys Val Phe Glu Lys Leu Gln Ala Asp Phe Lys
                485                 490                 495

Ile Ser Glu Glu Cys Ile Ala Gln Trp Lys Gln Thr Asn Phe Met Thr
                500                 505                 510

Lys Leu Gly Ser Ile Ser Cys Lys Ser Leu Lys Gly Gly Asn Ile Ser
            515                 520                 525

<210> SEQ ID NO 2
<211> LENGTH: 1683
<212> TYPE: DNA
<213> ORGANISM: Homo sapiens

<400> SEQUENCE: 2 atggggacg ctcccagccc tgaagagaaa ctgcacctta tcacccggaa cctgcaggag      60
gttctggggg aagagaagct gaaggagata ctgaaggagc gggaacttaa aatttactgg    120
ggaacggcaa ccacgggcaa accacatgtg gcttactttg tgcccatgtc aaagattgca    180
gacttcttaa aggcagggtg tgaggtaaca attctgtttg cggacctcca cgcatacctg    240
gataacatga agccccatg ggaacttcta gaactccgag tcagttacta tgagaatgtg    300
atcaaagcaa tgctggagag cattggtgtg cccttggaga agctcaagtt catcaaaggc    360
actgattacc agctcagcaa agagtacaca ctagatgtgt acagactctc ctccgtggtc    420
acacagcacg attccaagaa ggctggagct gaggtggtaa agcaggtgga gcaccctttg    480
ctgagtggcc tcttataccc cggactgcag gctttggatg aagagtattt aaaagtagat    540
gcccaatttg gaggcattga tcagagaaag attttcaccct tgcagagaa gtacctccct    600 gcacttggct attcaaaacg ggtccatctg atgaatccta tggttccagg attaacaggc    660
agcaaaatga gctcttcaga agaggagtcc aagattgatc tccttgatcg aaggaggat    720 gtgaagaaaa aactgaagaa ggccttctgt gagccaggaa atgtggagaa caatggggtt    780
ctgtccttca tcaagcatgt ccttttttcc cttaagtccg agtttgtgat cctacgagat    840
gagaaatggg gtggaaacaa aacctacaca gcttacgtgg acctggaaaa ggactttgct    900
gctgaggttg tacatcctgg agacctgaag aattctgttg aagtcgcact gaacaagttg    960
ctggatccaa tccgggaaaa gtttaatacc ctgccctga aaaaactggc cagcgctgcc   1020
tacccagatc cctcaaagca gaagccaatg gccaaaggcc ctgccaagaa ttcagaacca   1080
gaggaggtca tcccatcccg gctggatatc cgtgtgggga aaatcatcac tgtggagaag   1140
cacccagatg cagacagcct gtatgtagag aagattgacg tgggggaagc tgaaccacgg   1200
actgtggtga gcggcctggt acagttcgtg cccaaggagg aactgcagga caggctggta   1260
gtggtgctgt gcaacctgaa accccagaag atgagaggag tcgagtccca aggcatgctt   1320
ctgtgtgctt ctatagaagg gataaaccgc caggttgaac tctgtggaccc tccggcaggc   1380 tctgctcctg gtgagcacgt gtttgtgaag ggctatgaaa agggccaacc agatgaggag   1440
ctcaagccca agaagaaagt cttcgagaag ttgcaggctg acttcaaaat ttctgaggag   1500
tgcatcgcac agtggaagca aaccaacttc atgaccaagc tgggctccat ttcctgtaaa   1560
tcgctgaaag gggggaacat tagctagcca gcccagcatc ttcccccctt cttccaccac   1620
tgagtcatct gctgtctctt cagtctgctc catccatcac ccatttaccc atctctcagg   1680
aca                                                                1683
```

```
<210> SEQ ID NO 3
<211> LENGTH: 364
<212> TYPE: PRT
<213> ORGANISM: Homo sapiens

<400> SEQUENCE: 3

Met Gly Asp Ala Pro Ser Pro Glu Glu Lys Leu His Leu Ile Thr Arg
  1               5                  10                  15

Asn Leu Gln Glu Val Leu Gly Glu Glu Lys Leu Lys Glu Ile Leu Lys
             20                  25                  30

Glu Arg Glu Leu Lys Ile Tyr Trp Gly Thr Ala Thr Thr Gly Lys Pro
         35                  40                  45

His Val Ala Tyr Phe Val Pro Met Ser Lys Ile Ala Asp Phe Leu Lys
 50                  55                  60

Ala Gly Cys Glu Val Thr Ile Leu Phe Ala Asp Leu His Ala Tyr Leu
 65                  70                  75                  80

Asp Asn Met Lys Ala Pro Trp Glu Leu Leu Glu Leu Arg Val Ser Tyr
                 85                  90                  95

Tyr Glu Asn Val Ile Lys Ala Met Leu Glu Ser Ile Gly Val Pro Leu
            100                 105                 110

Glu Lys Leu Lys Phe Ile Lys Gly Thr Asp Tyr Gln Leu Ser Lys Glu
        115                 120                 125

Tyr Thr Leu Asp Val Tyr Arg Leu Ser Ser Val Val Thr Gln His Asp
    130                 135                 140

Ser Lys Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                165                 170                 175

Leu Lys Val Asp Ala Gln Phe Gly Gly Ile Asp Gln Arg Lys Ile Phe
            180                 185                 190

Thr Phe Ala Glu Lys Tyr Leu Pro Ala Leu Gly Tyr Ser Lys Arg Val
        195                 200                 205

His Leu Met Asn Pro Met Val Pro Gly Leu Thr Gly Ser Lys Met Ser
    210                 215                 220

Ser Ser Glu Glu Glu Ser Lys Ile Asp Leu Leu Asp Arg Lys Glu Asp
225                 230                 235                 240

Val Lys Lys Lys Leu Lys Lys Ala Phe Cys Glu Pro Gly Asn Val Glu
                245                 250                 255

Asn Asn Gly Val Leu Ser Phe Ile Lys His Val Leu Phe Pro Leu Lys
            260                 265                 270

Ser Glu Phe Val Ile Leu Arg Asp Glu Lys Trp Gly Gly Asn Lys Thr
        275                 280                 285

Tyr Thr Ala Tyr Val Asp Leu Glu Lys Asp Phe Ala Ala Glu Val Val
    290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
                325                 330                 335

Ala Ser Ala Ala Tyr Pro Asp Pro Ser Lys Gln Lys Pro Met Ala Lys
            340                 345                 350

Gly Pro Ala Lys Asn Ser Glu Pro Glu Glu Val Ile
        355                 360
```

```
<210> SEQ ID NO 4
<211> LENGTH: 361
<212> TYPE: PRT
<213> ORGANISM: Artificial Sequence
<220> FEATURE:
<223> OTHER INFORMATION: Variant of mini-YRS (human tyrosyle tRNA
      synthatase)

<400> SEQUENCE: 4

Met Gly Asp Ala Pro Ser Pro Glu Glu Lys Leu His Leu Ile Thr Arg
 1               5                  10                  15

Asn Leu Gln Glu Val Leu Gly Glu Gly Lys Leu Lys Glu Ile Leu Lys
             20                  25                  30

Glu Arg Glu Leu Lys Ile Tyr Trp Gly Thr Ala Thr Thr Gly Lys Pro
         35                  40                  45

His Val Ala Tyr Phe Val Pro Met Ser Lys Ile Ala Asp Phe Leu Lys
     50                  55                  60

Ala Gly Cys Glu Val Thr Ile Leu Phe Ala Asp Leu His Ala Tyr Leu
65                  70                  75                  80

Asp Asn Met Lys Ala Pro Trp Glu Leu Leu Glu Leu Arg Val Ser Tyr
                 85                  90                  95

Tyr Glu Asn Val Ile Lys Ala Met Leu Glu Ser Ile Gly Val Pro Leu
            100                 105                 110

Glu Lys Leu Lys Phe Ile Lys Gly Thr Asp Tyr Gln Leu Ser Lys Glu
        115                 120                 125

Tyr Thr Leu Asp Val Tyr Arg Leu Ser Ser Val Val Thr Gln His Asp
    130                 135                 140

Ser Lys Lys Ala Gly Ala Glu Val Val Lys Gln Val Glu His Ser Gly
145                 150                 155                 160

Leu Leu Tyr Pro Gly Leu Gln Ala Leu Asp Glu Glu Tyr Leu Lys Val
                165                 170                 175

Asp Ala Gln Phe Gly Gly Ile Asp Gln Arg Lys Ile Phe Thr Phe Ala
            180                 185                 190

Glu Lys Tyr Leu Pro Ala Leu Gly Tyr Ser Lys Arg Val His Leu Met
        195                 200                 205

Asn Pro Met Val Pro Gly Leu Thr Gly Ser Lys Met Ser Ser Ser Glu
    210                 215                 220

Glu Glu Ser Lys Ile Asp Leu Leu Asp Arg Lys Glu Asp Val Lys Lys
225                 230                 235                 240

Lys Leu Lys Lys Ala Phe Cys Glu Pro Gly Asn Val Glu Asn Asn Gly
                245                 250                 255

Val Leu Ser Phe Ile Lys His Val Leu Phe Pro Leu Lys Ser Glu Phe
            260                 265                 270

Val Ile Leu Arg Asp Glu Lys Trp Gly Gly Asn Lys Thr Tyr Thr Ala
        275                 280                 285

Tyr Val Asp Leu Glu Lys Asp Phe Ala Ala Glu Val Val His Pro Gly
    290                 295                 300

Asp Leu Lys Asn Ser Val Glu Val Ala Leu Asn Lys Leu Leu Asp Pro
305                 310                 315                 320

Ile Arg Glu Lys Phe Asn Thr Pro Ala Leu Lys Lys Leu Ala Ser Ala
                325                 330                 335

Ala Tyr Pro Asp Pro Ser Lys Gln Lys Pro Met Ala Lys Gly Pro Ala
            340                 345                 350

Lys Asn Ser Glu Pro Glu Glu Val Ile
        355                 360
```

```
<210> SEQ ID NO 5
<211> LENGTH: 471
<212> TYPE: PRT
<213> ORGANISM: Homo sapiens

<400> SEQUENCE: 5

Met Pro Asn Ser Glu Pro Ala Ser Leu Leu Glu Leu Phe Asn Ser Ile
 1               5                  10                  15

Ala Thr Gln Gly Glu Leu Val Arg Ser Leu Lys Ala Gly Asn Ala Ser
            20                  25                  30

Lys Asp Glu Ile Asp Ser Ala Val Lys Met Leu Val Ser Leu Lys Met
        35                  40                  45

Ser Tyr Lys Ala Ala Gly Glu Asp Tyr Lys Ala Asp Cys Pro Pro
    50                  55                  60

Gly Asn Pro Ala Pro Thr Ser Asn His Gly Pro Asp Ala Thr Glu Ala
 65                 70                  75                  80

Glu Glu Asp Phe Val Asp Pro Trp Thr Val Gln Thr Ser Ser Ala Lys
                85                  90                  95

Gly Ile Asp Tyr Asp Lys Leu Ile Val Arg Phe Gly Ser Ser Lys Ile
            100                 105                 110

Asp Lys Glu Leu Ile Asn Arg Ile Glu Arg Ala Thr Gly Gln Arg Pro
        115                 120                 125

His His Phe Leu Arg Arg Gly Ile Phe Ser His Arg Asp Met Asn
    130                 135                 140

Gln Val Leu Asp Ala Tyr Glu Asn Lys Lys Pro Phe Tyr Leu Tyr Thr
145                 150                 155                 160

Gly Arg Gly Pro Ser Ser Glu Ala Met His Val Gly His Leu Ile Pro
                165                 170                 175

Phe Ile Phe Thr Lys Trp Leu Gln Asp Val Phe Asn Val Pro Leu Val
            180                 185                 190

Ile Gln Met Thr Asp Asp Glu Lys Tyr Leu Trp Lys Asp Leu Thr Leu
        195                 200                 205

Asp Gln Ala Tyr Ser Tyr Ala Val Glu Asn Ala Lys Asp Ile Ile Ala
210                 215                 220

Cys Gly Phe Asp Ile Asn Lys Thr Phe Ile Phe Ser Asp Leu Asp Tyr
225                 230                 235                 240

Met Gly Met Ser Ser Gly Phe Tyr Lys Asn Val Val Lys Ile Gln Lys
                245                 250                 255

His Val Thr Phe Asn Gln Val Lys Gly Ile Phe Gly Phe Thr Asp Ser
            260                 265                 270

Asp Cys Ile Gly Lys Ile Ser Phe Pro Ala Ile Gln Ala Ala Pro Ser
        275                 280                 285

Phe Ser Asn Ser Phe Pro Gln Ile Phe Arg Asp Arg Thr Asp Ile Gln
    290                 295                 300

Cys Leu Ile Pro Cys Ala Ile Asp Gln Asp Pro Tyr Phe Arg Met Thr
305                 310                 315                 320

Arg Asp Val Ala Pro Arg Ile Gly Tyr Pro Lys Pro Ala Leu Leu His
                325                 330                 335

Ser Thr Phe Phe Pro Ala Leu Gln Gly Ala Gln Thr Lys Met Ser Ala
            340                 345                 350

Ser Asp Pro Asn Ser Ser Ile Phe Leu Thr Asp Thr Ala Lys Gln Ile
        355                 360                 365

Lys Thr Lys Val Asn Lys His Ala Phe Ser Gly Gly Arg Asp Thr Ile
    370                 375                 380
```

```
Glu His Arg Gln Phe Gly Gly Asn Cys Asp Val Asp Val Ser Phe
385                 390                 395                 400

Met Tyr Leu Thr Phe Phe Leu Glu Asp Asp Lys Leu Glu Gln Ile
            405                 410                 415

Arg Lys Asp Tyr Thr Ser Gly Ala Met Leu Thr Gly Glu Leu Lys Lys
        420                 425                 430

Ala Leu Ile Glu Val Leu Gln Pro Leu Ile Ala Glu His Gln Ala Arg
    435                 440                 445

Arg Lys Glu Val Thr Asp Glu Ile Val Lys Glu Phe Met Thr Pro Arg
    450                 455                 460

Lys Leu Ser Phe Asp Phe Gln
465             470
```

<210> SEQ ID NO 6
<211> LENGTH: 1959
<212> TYPE: DNA
<213> ORGANISM: Homo sapiens

<400> SEQUENCE: 6

| | | | | | |
|---|---|---|---|---|---|
| cgaaaaaaga | ggggaagagt | attaaagacc | atttctggct | gggcagggca | ctctcagcag | 60 |
| ctcaactgcc | cagcgtgacc | agtggccacc | tctgcagtgt | cttccacaac | ctggtcttga | 120 |
| ctcgtctgct | gaacaaatcc | tctgacctca | ggccggctgt | gaacgtagtt | cctgagagat | 180 |
| agcaaacatg | cccaacagtg | agcccgcatc | tctgctggag | ctgttcaaca | gcatcgccac | 240 |
| acaaggggag | ctcgtaaggt | ccctcaaagc | gggaaatgcg | tcaaaggatg | aaattgattc | 300 |
| tgcagtaaag | atgttggtgt | cattaaaaat | gagctacaaa | gctgccgcgg | gggaggatta | 360 |
| caaggctgac | tgtcctccag | ggaacccagc | acctaccagt | aatcatggcc | cagatgccac | 420 |
| agaagctgaa | gaggattttg | tggacccatg | gacagtacag | acaagcagtg | caaaaggcat | 480 |
| agactacgat | aagctcattg | ttcggtttgg | aagtagtaaa | attgacaaag | agctaataaa | 540 |
| ccgaatagag | agagccaccg | gccaaagacc | acaccacttc | ctgcgcagag | gcatcttctt | 600 |
| ctcacacaga | gatatgaatc | aggttcttga | tgcctatgaa | aataagaagc | cattttatct | 660 |
| gtacacgggc | cggggcccct | cttctgaagc | aatgcatgta | ggtcacctca | ttccatttat | 720 |
| tttcacaaag | tggctccagg | atgtatttaa | cgtgcccttg | gtcatccaga | tgacggatga | 780 |
| cgagaagtat | ctgtggaagg | acctgacccc | tggaccaggc | catggcgatg | ctgttgagaa | 840 |
| tgccaaggac | atcatcgcct | gtggctttga | catcaacaag | actttcatat | tctctgacct | 900 |
| ggactacatg | gggatgagct | caggtttcta | caaaaatgtg | gtgaagattc | aaaagcatgt | 960 |
| taccttcaac | caagtgaaag | catttttcgg | cttcactgac | agcgactgca | ttgggaagat | 1020 |
| cagtttttcct | gccatccagg | ctgctccctc | cttcagcaac | tcattcccac | agatcttccg | 1080 |
| agacaggacg | gatatccagt | gccttatccc | atgtgccatt | gaccaggatc | cttactttag | 1140 |
| aatgacaagg | gacgtcgccc | ccaggatcgg | ctatcctaaa | ccagccctgt | tgcactccac | 1200 |
| cttcttccca | gccctgcagg | gcgcccagac | caaaatgagt | gccagcgacc | caaactcctc | 1260 |
| catcttcctc | accgacacgg | ccaagcagat | caaaaccaag | gtcaataagc | atgcgttttc | 1320 |
| tggagggaga | gacaccatcg | aggagcacag | gcagtttggg | ggcaactgtg | atgtggacgt | 1380 |
| gtctttcatg | tacctgacct | tcttcctcga | ggacgacgac | aagctcgagc | agatcaggaa | 1440 |
| ggattacacc | agcggagcca | tgctcaccgg | tgagctcaag | aaggcactca | tagaggttct | 1500 |
| gcagcccttg | atcgcagagc | accaggcccg | gcgcaaggag | gtcacggatg | agatagtgaa | 1560 |

```
agagttcatg actccccgga agctgtcctt cgactttcag tagcactcgt tttacatatg    1620
cttataaaag aagtgatgta tcagtaatgt atcaataatc ccagcccagt caaagcaccg    1680
ccacctgtag gcttctgtct catggtaatt actgggcctg gcctctgtaa gcctgtgtat    1740
gttatcaata ctgtttcttc ctgtgagttc cattatttct atctcttatg ggcaaagcat    1800
tgtgggtaat tggtgctggc taacattgca tggtcggata gagaagtcca gctgtgagtc    1860 tctcccaaa gcagcccac agtggagcct tcggctggaa gtccatgggc caccctgttc    1920
ttgtccatgg aggacttccg agggttccaa gtatactct                          1959
```

<210> SEQ ID NO 7
<211> LENGTH: 381
<212> TYPE: PRT
<213> ORGANISM: Homo sapiens

<400> SEQUENCE: 7

```
Gln Thr Ser Ser Ala Lys Gly Ile Asp Tyr Asp Lys Leu Ile Val Arg
 1               5                  10                  15

Phe Gly Ser Ser Lys Ile Asp Lys Glu Leu Ile Asn Arg Ile Glu Arg
                20                  25                  30

Ala Thr Gly Gln Arg Pro His His Phe Leu Arg Arg Gly Ile Phe Phe
            35                  40                  45

Ser His Arg Asp Met Asn Gln Val Leu Asp Ala Tyr Glu Asn Lys Lys
        50                  55                  60

Pro Phe Tyr Leu Tyr Thr Gly Arg Gly Pro Ser Ser Glu Ala Met His
 65                  70                  75                  80

Val Gly His Leu Ile Pro Phe Ile Phe Thr Lys Trp Leu Gln Asp Val
                 85                  90                  95

Phe Asn Val Pro Leu Val Ile Gln Met Thr Asp Asp Glu Lys Tyr Leu
                100                 105                 110

Trp Lys Asp Leu Thr Leu Asp Gln Ala Tyr Ser Tyr Ala Val Glu Asn
            115                 120                 125

Ala Lys Asp Ile Ile Ala Cys Gly Phe Asp Ile Asn Lys Thr Phe Ile
        130                 135                 140

Phe Ser Asp Leu Asp Tyr Met Gly Met Ser Ser Gly Tyr Lys Asn
145                 150                 155                 160

Val Val Lys Ile Gln Lys His Val Thr Phe Asn Gln Val Lys Gly Ile
                165                 170                 175

Phe Gly Phe Thr Asp Ser Asp Cys Ile Gly Lys Ile Ser Phe Pro Ala
            180                 185                 190

Ile Gln Ala Ala Pro Ser Phe Ser Asn Ser Phe Pro Gln Ile Phe Arg
        195                 200                 205

Asp Arg Thr Asp Ile Gln Cys Leu Ile Pro Cys Ala Ile Asp Gln Asp
    210                 215                 220

Pro Tyr Phe Arg Met Thr Arg Asp Val Ala Pro Arg Ile Gly Tyr Pro
225                 230                 235                 240

Lys Pro Ala Leu Leu His Ser Thr Phe Phe Pro Ala Leu Gln Gly Ala
                245                 250                 255

Gln Thr Lys Met Ser Ala Ser Asp Pro Asn Ser Ser Ile Phe Leu Thr
            260                 265                 270

Asp Thr Ala Lys Gln Ile Lys Thr Lys Val Asn Lys His Ala Phe Ser
        275                 280                 285

Gly Gly Arg Asp Thr Ile Glu Glu His Arg Gln Phe Gly Gly Asn Cys
    290                 295                 300
```

```
Asp Val Asp Val Ser Phe Met Tyr Leu Thr Phe Leu Glu Asp Asp
305                 310                 315                 320

Asp Lys Leu Glu Gln Ile Arg Lys Asp Tyr Thr Ser Gly Ala Met Leu
            325                 330                 335

Thr Gly Glu Leu Lys Lys Ala Leu Ile Glu Val Leu Gln Pro Leu Ile
            340                 345                 350

Ala Glu His Gln Ala Arg Arg Lys Glu Val Thr Asp Glu Ile Val Lys
        355                 360                 365

Glu Phe Met Thr Pro Arg Lys Leu Ser Phe Asp Phe Gln
    370                 375                 380

<210> SEQ ID NO 8
<211> LENGTH: 378
<212> TYPE: PRT
<213> ORGANISM: Artificial Sequence
<220> FEATURE:
<223> OTHER INFORMATION: Modified T2-WRS (human tryptophanyl tRNA
      synthatase)

<400> SEQUENCE: 8

Ser Ala Lys Gly Ile Asp Tyr Asp Lys Leu Ile Val Arg Phe Gly Ser
1               5                   10                  15

Ser Lys Ile Asp Lys Glu Leu Ile Asn Arg Ile Glu Arg Ala Thr Gly
            20                  25                  30

Gln Arg Pro His His Phe Leu Arg Arg Gly Ile Phe Phe Ser His Arg
        35                  40                  45

Asp Met Asn Gln Val Leu Asp Ala Tyr Glu Asn Lys Lys Pro Phe Tyr
    50                  55                  60

Leu Tyr Thr Gly Arg Gly Pro Ser Ser Glu Ala Met His Val Gly His
65                  70                  75                  80

Leu Ile Pro Phe Ile Phe Thr Lys Trp Leu Gln Asp Val Phe Asn Val
                85                  90                  95

Pro Leu Val Ile Gln Met Thr Asp Asp Glu Lys Glu Leu Trp Lys Asp
            100                 105                 110

Leu Thr Leu Asp Gln Ala Tyr Ser Tyr Ala Val Glu Asn Ala Lys Asp
        115                 120                 125

Ile Ile Ala Cys Gly Phe Asp Ile Asn Lys Thr Phe Ile Phe Ser Asp
    130                 135                 140

Leu Asp Tyr Met Gly Met Ser Ser Gly Phe Tyr Lys Asn Val Val Lys
145                 150                 155                 160

Ile Gln Lys His Val Thr Glu Asn Gln Val Lys Gly Ile Phe Gly Phe
                165                 170                 175

Thr Asp Ser Asp Cys Ile Gly Lys Glu Ser Phe Pro Ala Ile Gln Ala
            180                 185                 190

Ala Pro Ser Phe Ser Asn Ser Phe Pro Gln Ile Phe Arg Asp Arg Thr
        195                 200                 205

Asp Ile Gln Cys Leu Ile Pro Cys Ala Ile Asp Gln Asp Pro Tyr Phe
    210                 215                 220

Arg Met Thr Arg Asp Val Ala Pro Arg Ile Gly Tyr Pro Lys Pro Ala
225                 230                 235                 240

Leu Leu His Ser Thr Phe Phe Pro Ala Leu Gln Gly Ala Gln Thr Lys
                245                 250                 255

Met Ser Ala Ser Asp Pro Asn Ser Ser Ile Phe Leu Thr Asp Thr Ala
            260                 265                 270

Lys Gln Ile Lys Thr Lys Val Asn Lys His Ala Phe Ser Gly Gly Arg
        275                 280                 285
```

```
Asp Thr Ile Glu Glu His Arg Gln Phe Gly Gly Asn Cys Asp Val Asp
    290                 295                 300

Val Ser Phe Met Tyr Leu Thr Phe Phe Leu Glu Asp Asp Lys Leu
305                 310                 315                 320

Glu Gln Ile Arg Lys Asp Tyr Thr Ser Gly Ala Met Leu Thr Gly Glu
                325                 330                 335

Leu Lys Lys Ala Leu Ile Glu Val Leu Gln Pro Leu Ile Ala Glu His
            340                 345                 350

Gln Ala Arg Arg Lys Glu Val Thr Asp Glu Ile Val Lys Glu Phe Met
            355                 360                 365

Thr Pro Arg Lys Leu Ser Phe Asp Phe Gln
    370                 375

<210> SEQ ID NO 9
<211> LENGTH: 378
<212> TYPE: PRT
<213> ORGANISM: Artificial Sequence
<220> FEATURE:
<223> OTHER INFORMATION: Modified T2-WRS (human tryptophanyl tRNA
      synthatase)

<400> SEQUENCE: 9

Ser Ala Lys Gly Ile Asp Tyr Asp Lys Leu Ile Val Arg Phe Gly Ser
1               5                   10                  15

Ser Lys Ile Asp Lys Glu Leu Ile Asn Arg Ile Glu Arg Ala Thr Gly
            20                  25                  30

Gln Arg Pro His His Phe Leu Arg Arg Gly Ile Phe Phe Ser His Arg
        35                  40                  45

Asp Met Asn Gln Val Leu Asp Ala Tyr Glu Asn Lys Lys Pro Phe Tyr
    50                  55                  60

Leu Tyr Thr Gly Arg Gly Pro Ser Ser Glu Ala Met His Val Gly His
65                  70                  75                  80

Leu Ile Pro Phe Ile Phe Thr Lys Trp Leu Gln Asp Val Phe Asn Val
                85                  90                  95

Pro Leu Val Ile Gln Met Thr Asp Asp Glu Lys Glu Leu Trp Lys Asp
            100                 105                 110

Leu Thr Leu Asp Gln Ala Tyr Ser Tyr Ala Val Glu Asn Ala Lys Asp
        115                 120                 125

Ile Ile Ala Cys Gly Phe Asp Ile Asn Lys Thr Phe Ile Phe Ser Asp
    130                 135                 140

Leu Asp Tyr Met Gly Met Ser Ser Gly Phe Tyr Lys Asn Val Val Lys
145                 150                 155                 160

Ile Gln Lys His Val Thr Glu Asn Gln Val Lys Gly Ile Phe Gly Phe
                165                 170                 175

Thr Asp Ser Asp Cys Ile Gly Lys Ile Ser Phe Pro Ala Ile Gln Ala
            180                 185                 190

Ala Pro Ser Phe Ser Asn Ser Phe Pro Gln Ile Phe Arg Asp Arg Thr
        195                 200                 205

Asp Ile Gln Cys Leu Ile Pro Cys Ala Ile Asp Gln Asp Pro Tyr Phe
    210                 215                 220

Arg Met Thr Arg Asp Val Ala Pro Arg Ile Gly Tyr Pro Lys Pro Ala
225                 230                 235                 240

Leu Leu His Ser Thr Phe Phe Pro Ala Leu Gln Gly Ala Gln Thr Lys
                245                 250                 255

Met Ser Ala Ser Asp Pro Asn Ser Ser Ile Phe Leu Thr Asp Thr Ala
```

```
                   260                 265                 270
Lys Gln Ile Lys Thr Lys Val Asn Lys His Ala Phe Ser Gly Gly Arg
            275                 280                 285

Asp Thr Ile Glu Glu His Arg Gln Phe Gly Gly Asn Cys Asp Val Asp
            290                 295                 300

Val Ser Phe Met Tyr Leu Thr Phe Phe Leu Glu Asp Asp Lys Leu
305                 310                 315                 320

Glu Gln Ile Arg Lys Asp Tyr Thr Ser Gly Ala Met Leu Thr Gly Glu
            325                 330                 335

Leu Lys Lys Ala Leu Ile Glu Val Leu Gln Pro Leu Ile Ala Glu His
            340                 345                 350

Gln Ala Arg Arg Lys Glu Val Thr Asp Glu Ile Val Lys Glu Phe Met
            355                 360                 365

Thr Pro Arg Lys Leu Ser Phe Asp Phe Gln
            370                 375

<210> SEQ ID NO 10
<211> LENGTH: 108
<212> TYPE: PRT
<213> ORGANISM: Homo sapiens

<400> SEQUENCE: 10

Asp Trp Ile Trp Asn Gln Met His Ile Asp Glu Glu Lys Asn Thr Ser
1               5                   10                  15

Leu Pro His His Val Gly Lys Ile Lys Ser Ser Val Ser Arg Lys Asn
            20                  25                  30

Ala Lys Tyr Leu Leu Lys Gly Glu Tyr Val Gly Lys Val Phe Arg Val
            35                  40                  45

Asp Ala Glu Thr Gly Asp Val Phe Ala Ile Glu Arg Leu Asp Arg Glu
        50                  55                  60

Asn Ile Ser Glu Tyr His Leu Thr Ala Val Ile Val Asp Lys Asp Thr
65                  70                  75                  80

Gly Glu Asn Leu Glu Thr Pro Ser Ser Phe Thr Ile Lys Val His Asp
                85                  90                  95

Val Asn Asp Asn Trp Pro Val Phe Thr His Arg Leu
            100                 105

<210> SEQ ID NO 11
<211> LENGTH: 597
<212> TYPE: PRT
<213> ORGANISM: Homo sapiens

<400> SEQUENCE: 11

Met Ala Ala Val Gln Ala Ala Glu Val Lys Val Asp Gly Ser Glu Pro
1               5                   10                  15

Lys Leu Ser Lys Asn Glu Leu Lys Arg Arg Leu Lys Ala Glu Lys Lys
            20                  25                  30

Val Ala Glu Lys Glu Ala Lys Gln Lys Glu Leu Ser Lys Gln Leu
            35                  40                  45

Ser Gln Ala Thr Ala Ala Thr Asn His Thr Thr Asp Asn Gly Val
        50                  55                  60

Gly Pro Glu Glu Glu Ser Val Asp Pro Asn Gln Tyr Tyr Lys Ile Arg
65                  70                  75                  80

Ser Gln Ala Ile His Gln Leu Lys Val Asn Gly Glu Asp Pro Tyr Pro
                85                  90                  95

His Lys Phe His Val Asp Ile Ser Leu Thr Asp Phe Ile Gln Lys Tyr
```

-continued

```
                100                 105                 110
Ser His Leu Gln Pro Gly Asp His Leu Thr Asp Ile Thr Leu Lys Val
        115                 120                 125
Ala Gly Arg Ile His Ala Lys Arg Ala Ser Gly Gly Lys Leu Ile Phe
    130                 135                 140
Tyr Asp Leu Arg Gly Glu Gly Val Lys Leu Gln Val Met Ala Asn Ser
145                 150                 155                 160
Arg Asn Tyr Lys Ser Glu Glu Phe Ile His Ile Asn Asn Lys Leu
                165                 170                 175
Arg Arg Gly Asp Ile Ile Gly Val Gln Gly Asn Pro Gly Lys Thr Lys
            180                 185                 190
Lys Gly Glu Leu Ser Ile Ile Pro Tyr Glu Ile Thr Leu Leu Ser Pro
        195                 200                 205
Cys Leu His Met Leu Pro His Leu His Phe Gly Leu Lys Asp Lys Glu
    210                 215                 220
Thr Arg Tyr Arg Gln Arg Tyr Leu Asp Leu Ile Leu Asn Asp Phe Val
225                 230                 235                 240
Arg Gln Lys Phe Ile Ile Arg Ser Lys Ile Ile Thr Tyr Ile Arg Ser
                245                 250                 255
Phe Leu Asp Glu Leu Gly Phe Leu Glu Ile Glu Thr Pro Met Met Asn
            260                 265                 270
Ile Ile Pro Gly Gly Ala Val Ala Lys Pro Phe Ile Thr Tyr His Asn
        275                 280                 285
Glu Leu Asp Met Asn Leu Tyr Met Arg Ile Ala Pro Glu Leu Tyr His
    290                 295                 300
Lys Met Leu Val Val Gly Gly Ile Asp Arg Val Tyr Glu Ile Gly Arg
305                 310                 315                 320
Gln Phe Arg Asn Glu Gly Ile Asp Leu Thr His Asn Pro Glu Phe Thr
                325                 330                 335
Thr Cys Glu Phe Tyr Met Ala Tyr Ala Asp Tyr His Asp Leu Met Glu
            340                 345                 350
Ile Thr Glu Lys Met Val Ser Gly Met Val Lys His Ile Thr Gly Ser
        355                 360                 365
Tyr Lys Val Thr Tyr His Pro Asp Gly Pro Glu Gly Gln Ala Tyr Asp
    370                 375                 380
Val Asp Phe Thr Pro Pro Phe Arg Arg Ile Asn Met Val Glu Glu Leu
385                 390                 395                 400
Glu Lys Ala Leu Gly Met Lys Leu Pro Glu Thr Asn Leu Phe Glu Thr
                405                 410                 415
Glu Glu Thr Arg Lys Ile Leu Asp Asp Ile Cys Val Ala Lys Ala Val
            420                 425                 430
Glu Cys Pro Pro Pro Arg Thr Thr Ala Arg Leu Leu Asp Lys Leu Val
        435                 440                 445
Gly Glu Phe Leu Glu Val Thr Cys Ile Asn Pro Thr Phe Ile Cys Asp
    450                 455                 460
His Pro Gln Ile Met Ser Pro Leu Ala Lys Trp His Arg Ser Lys Glu
465                 470                 475                 480
Gly Leu Thr Glu Arg Phe Glu Leu Phe Val Met Lys Lys Glu Ile Cys
                485                 490                 495
Asn Ala Tyr Thr Glu Leu Asn Asp Pro Met Arg Gln Arg Gln Leu Phe
            500                 505                 510
Glu Glu Gln Ala Lys Ala Lys Ala Ala Gly Asp Asp Glu Ala Met Phe
        515                 520                 525
```

```
Ile Asp Glu Asn Phe Cys Thr Ala Leu Glu Tyr Gly Leu Pro Pro Thr
        530                 535                 540

Ala Gly Trp Gly Met Gly Ile Asp Arg Val Ala Met Phe Leu Thr Asp
545                 550                 555                 560

Ser Asn Asn Ile Lys Glu Val Leu Leu Phe Pro Ala Met Lys Pro Glu
                565                 570                 575

Asp Lys Lys Glu Asn Val Ala Thr Thr Asp Thr Leu Glu Ser Thr Thr
            580                 585                 590

Val Gly Thr Ser Val
            595

<210> SEQ ID NO 12
<211> LENGTH: 515
<212> TYPE: PRT
<213> ORGANISM: Homo sapiens

<400> SEQUENCE: 12

Ser Val Asp Pro Asn Gln Tyr Tyr Lys Ile Arg Ser Gln Ala Ile His
  1               5                  10                  15

Gln Leu Lys Val Asn Gly Glu Asp Pro Tyr Pro His Lys Phe His Val
             20                  25                  30

Asp Ile Ser Leu Thr Asp Phe Ile Gln Lys Tyr Ser His Leu Gln Pro
         35                  40                  45

Gly Asp His Leu Thr Asp Ile Thr Leu Lys Val Ala Gly Arg Ile His
     50                  55                  60

Ala Lys Arg Ala Ser Gly Gly Lys Leu Ile Phe Tyr Asp Leu Arg Gly
 65                  70                  75                  80

Glu Gly Val Lys Leu Gln Val Met Ala Asn Ser Arg Asn Tyr Lys Ser
                 85                  90                  95

Glu Glu Glu Phe Ile His Ile Asn Asn Lys Leu Arg Arg Gly Asp Ile
            100                 105                 110

Ile Gly Val Gln Gly Asn Pro Gly Lys Thr Lys Lys Gly Glu Leu Ser
        115                 120                 125

Ile Ile Pro Tyr Glu Ile Thr Leu Leu Ser Pro Cys Leu His Met Leu
130                 135                 140

Pro His Leu His Phe Gly Leu Lys Asp Lys Glu Thr Arg Tyr Arg Gln
145                 150                 155                 160

Arg Tyr Leu Asp Leu Ile Leu Asn Asp Phe Val Arg Gln Lys Phe Ile
                165                 170                 175

Ile Arg Ser Lys Ile Ile Thr Tyr Ile Arg Ser Phe Leu Asp Glu Leu
            180                 185                 190

Gly Phe Leu Glu Ile Glu Thr Pro Met Met Asn Ile Ile Pro Gly Gly
        195                 200                 205

Ala Val Ala Lys Pro Phe Ile Thr Tyr His Asn Glu Leu Asp Met Asn
210                 215                 220

Leu Tyr Met Arg Ile Ala Pro Glu Leu Tyr His Lys Met Leu Val Val
225                 230                 235                 240

Gly Gly Ile Asp Arg Val Tyr Glu Ile Gly Arg Gln Phe Arg Asn Glu
                245                 250                 255

Gly Ile Asp Leu Thr His Asn Pro Glu Phe Thr Thr Cys Glu Phe Tyr
            260                 265                 270

Met Ala Tyr Ala Asp Tyr His Asp Leu Met Glu Ile Thr Glu Lys Met
        275                 280                 285

Val Ser Gly Met Val Lys His Ile Thr Gly Ser Tyr Lys Val Thr Tyr
```

```
            290                 295                 300
His Pro Asp Gly Pro Glu Gly Gln Ala Tyr Asp Val Asp Phe Thr Pro
305                 310                 315                 320

Pro Phe Arg Arg Ile Asn Met Val Glu Glu Leu Glu Lys Ala Leu Gly
                325                 330                 335

Met Lys Leu Pro Glu Thr Asn Leu Phe Glu Thr Glu Glu Thr Arg Lys
                340                 345                 350

Ile Leu Asp Asp Ile Cys Val Ala Lys Ala Val Glu Cys Pro Pro Pro
                355                 360                 365

Arg Thr Thr Ala Arg Leu Leu Asp Lys Leu Val Gly Glu Phe Leu Glu
                370                 375                 380

Val Thr Cys Ile Asn Pro Thr Phe Ile Cys Asp His Pro Gln Ile Met
385                 390                 395                 400

Ser Pro Leu Ala Lys Trp His Arg Ser Lys Glu Gly Leu Thr Glu Arg
                405                 410                 415

Phe Glu Leu Phe Val Met Lys Lys Glu Ile Cys Asn Ala Tyr Thr Glu
                420                 425                 430

Leu Asn Asp Pro Met Arg Gln Arg Gln Leu Phe Glu Glu Gln Ala Lys
                435                 440                 445

Ala Lys Ala Ala Gly Asp Asp Glu Ala Met Phe Ile Asp Glu Asn Phe
                450                 455                 460

Cys Thr Ala Leu Glu Tyr Gly Leu Pro Pro Thr Ala Gly Trp Gly Met
465                 470                 475                 480

Gly Ile Asp Arg Val Ala Met Phe Leu Thr Asp Ser Asn Asn Ile Lys
                485                 490                 495

Glu Val Leu Leu Phe Pro Ala Met Lys Pro Glu Asp Lys Lys Glu Asn
                500                 505                 510

Val Ala Thr
        515

<210> SEQ ID NO 13
<211> LENGTH: 770
<212> TYPE: PRT
<213> ORGANISM: Artificial Sequence
<220> FEATURE:
<223> OTHER INFORMATION: Truncated human KRS with E. coli flavodoxin
      protein insert

<400> SEQUENCE: 13

Met Ala Ala Val Gln Ala Ala Glu Val Lys Val Asp Gly Ser Glu Pro
1               5                   10                  15

Lys Leu Ser Lys Asn Glu Leu Lys Arg Arg Leu Lys Ala Glu Lys Lys
                20                  25                  30

Val Ala Glu Lys Glu Ala Lys Gln Lys Glu Leu Ser Glu Lys Gln Leu
                35                  40                  45

Ser Gln Ala Thr Ala Ala Ala Thr Asn His Thr Thr Asp Asn Gly Val
                50                  55                  60

Gly Pro Glu Glu Glu Ser Val Asp Pro Asn Gln Tyr Tyr Lys Ile Arg
65                  70                  75                  80

Ser Gln Ala Ile His Gln Leu Lys Val Asn Gly Glu Asp Pro Tyr Pro
                85                  90                  95

His Lys Phe His Val Asp Ile Ser Leu Thr Asp Phe Ile Gln Lys Tyr
                100                 105                 110

Ser His Leu Gln Pro Gly Asp His Leu Thr Asp Ile Thr Leu Lys Val
                115                 120                 125
```

```
Ala Gly Arg Ile His Ala Lys Arg Ala Ser Gly Lys Leu Ile Phe
130                 135                 140

Tyr Asp Leu Arg Gly Glu Gly Val Lys Leu Gln Val Met Ala Asn Ser
145                 150                 155                 160

Arg Asn Tyr Lys Ser Glu Glu Phe Ile His Ile Asn Asn Lys Leu
                165                 170                 175

Arg Arg Gly Asp Ile Ile Gly Val Gln Gly Asn Pro Gly Lys Thr Lys
                180                 185                 190

Lys Gly Glu Leu Ser Ile Ile Pro Tyr Glu Ile Thr Leu Leu Ser Pro
                195                 200                 205

Cys Leu His Met Leu Pro His Leu His Phe Gly Leu Lys Asp Lys Glu
210                 215                 220

Thr Arg Tyr Arg Gln Arg Tyr Leu Asp Leu Ile Leu Asn Asp Phe Val
225                 230                 235                 240

Arg Gln Lys Phe Ile Ile Arg Ser Lys Ile Ile Thr Tyr Ile Arg Ser
                245                 250                 255

Phe Leu Asp Glu Leu Gly Phe Leu Glu Ile Glu Thr Pro Met Met Asn
                260                 265                 270

Ile Ile Pro Gly Gly Ala Val Ala Lys Pro Phe Ile Thr Tyr His Asn
                275                 280                 285

Glu Leu Asp Met Asn Leu Tyr Met Arg Ile Ala Pro Glu Leu Tyr His
                290                 295                 300

Lys Met Leu Val Val Gly Asn Met Gly Leu Phe Tyr Gly Ser Ser Thr
305                 310                 315                 320

Cys Tyr Thr Glu Met Ala Ala Glu Lys Ile Arg Asp Ile Ile Gly Pro
                325                 330                 335

Glu Leu Val Thr Leu His Asn Leu Lys Asp Asp Ser Pro Lys Leu Met
                340                 345                 350

Glu Gln Tyr Asp Val Leu Ile Leu Gly Ile Pro Thr Trp Asp Phe Gly
                355                 360                 365

Glu Ile Gln Glu Asp Trp Glu Ala Val Trp Asp Gln Leu Asp Asp Leu
                370                 375                 380

Asn Leu Glu Gly Lys Ile Val Ala Leu Tyr Gly Leu Gly Asp Gln Leu
385                 390                 395                 400

Gly Tyr Gly Glu Trp Phe Leu Asp Ala Leu Gly Met Leu His Asp Lys
                405                 410                 415

Leu Ser Thr Lys Gly Val Lys Phe Val Gly Tyr Trp Pro Thr Glu Gly
                420                 425                 430

Tyr Glu Phe Thr Ser Pro Lys Pro Val Ile Ala Asp Gly Gln Leu Phe
                435                 440                 445

Val Gly Leu Ala Leu Asp Glu Thr Asn Gln Tyr Asp Leu Ser Asp Glu
450                 455                 460

Arg Ile Gln Ser Trp Cys Glu Gln Ile Leu Asn Glu Met Ala Arg Val
465                 470                 475                 480

Tyr Glu Ile Gly Arg Gln Phe Arg Asn Glu Gly Ile Asp Leu Thr His
                485                 490                 495

Asn Pro Glu Phe Thr Thr Cys Glu Phe Tyr Met Ala Tyr Ala Asp Tyr
                500                 505                 510

His Asp Leu Met Glu Ile Thr Glu Lys Met Val Ser Gly Met Val Lys
                515                 520                 525

His Ile Thr Gly Ser Tyr Lys Val Thr Tyr His Pro Asp Gly Pro Glu
530                 535                 540

Gly Gln Ala Tyr Asp Val Asp Phe Thr Pro Pro Phe Arg Arg Ile Asn
```

```
                      545                 550                 555                 560
Met Val Glu Glu Leu Glu Lys Ala Leu Gly Met Lys Leu Pro Glu Thr
                565                 570                 575

Asn Leu Phe Glu Thr Glu Glu Thr Arg Lys Ile Leu Asp Asp Ile Cys
            580                 585                 590

Val Ala Lys Ala Val Glu Cys Pro Pro Arg Thr Ala Arg Leu
        595                 600                 605

Leu Asp Lys Leu Val Gly Glu Phe Leu Glu Val Thr Cys Ile Asn Pro
    610                 615                 620

Thr Phe Ile Cys Asp His Pro Gln Ile Met Ser Pro Leu Ala Lys Trp
625                 630                 635                 640

His Arg Ser Lys Glu Gly Leu Thr Glu Arg Phe Glu Leu Phe Val Met
                645                 650                 655

Lys Lys Glu Ile Cys Asn Ala Tyr Thr Glu Leu Asn Asp Pro Met Arg
            660                 665                 670

Gln Arg Gln Leu Phe Glu Glu Gln Ala Lys Ala Lys Ala Ala Gly Asp
        675                 680                 685

Asp Glu Ala Met Phe Ile Asp Glu Asn Phe Cys Thr Ala Leu Glu Tyr
    690                 695                 700

Gly Leu Pro Pro Thr Ala Gly Trp Gly Met Gly Ile Asp Arg Val Ala
705                 710                 715                 720

Met Phe Leu Thr Asp Ser Asn Asn Ile Lys Glu Val Leu Leu Phe Pro
                725                 730                 735

Ala Met Lys Pro Glu Asp Lys Lys Glu Asn Val Ala Thr Thr Asp Thr
            740                 745                 750

Leu Glu Ser Thr Thr Val Gly Thr Ser Val Ala Gly His His His
        755                 760                 765

His His
    770

<210> SEQ ID NO 14
<211> LENGTH: 2310
<212> TYPE: DNA
<213> ORGANISM: Artificial Sequence
<220> FEATURE:
<223> OTHER INFORMATION: Truncated human KRS with E. coli flavodoxin
      insert

<400> SEQUENCE: 14
atggcagctg ttcaagcggc ggaagttaaa gttgacggta gcgaacctaa actgagcaaa        60
aacgaactta acgtcgtct gaaggcggaa aaaaaagtag cggaaaagga agctaaacag       120
aaagaactga gcgaaaaaca gctgtcccag gctactgcgg ctgcgactaa ccataccact       180
gacaacggtg taggtcctga agaagaatct gttgacccga accagtacta taaaatccgt       240
agccaagcga tccaccagct taaagttaac ggtgaagacc catcccgca caattccac        300 gttgacatta gcctgacgga cttcatccag aaatactctc atctgcagcc gggtgatcat       360
ctgactgaca tcaccttgaa agtcgcgggt cgtatccatg ctaaacgtgc tagcggtggt       420
aaactgatct tctacgatct gcgtggcgaa ggtgttaaac tgcaggttat ggcaaactct       480
cgtaactaca aatctgaaga agaattcatc cacattaaca caaaactgcg tcgtggtgac       540
atcatcggtg ttcagggtaa cccgggcaaa actaaaaaag gtgaacttag catcatcccg       600
tatgaaatca ccctgttgtc cccgtgcctg cacatgctgc ctcacctgca cttcggtctt       660
aaagataaag aaacccgtta ccgtcagcgt taccttgacc tgatcctgaa tgacttcgtt       720
```

```
cgtcagaaat tcatcatccg ttctaaaatc atcacctata tccgtagctt cctggacgaa    780
ctgggtttcc tggagattga gaccccgatg atgaacatca ttccgggtgg tgcggttgct    840
aagccgttca tcacctacca taacgaactt gacatgaacc tgtacatgcg tatcgctccg    900
gaactgtacc acaaaatgct ggttgtaggt aaatatgggtc ttttttacgg ttccagcacc    960
tgttacaccg aaatggcggc agaaaaaatc cgcgatatta tcggcccaga actggtgacc   1020
ttacataacc tcaaggacga ctccccgaaa ttaatggagc agtacgatgt gctcattctg   1080
ggtatcccga cctgggattt tggtgaaatc caggaagact gggaagccgt ctgggatcag   1140
ctcgacgacc tgaaccttga aggtaaaatt gttgcgctgt atgggcttgg cgatcaactg   1200
ggatacggcg agtggttcct cgatgcgctc ggtatgctgc atgacaaact ctcgaccaaa   1260
ggcgtgaagt tcgtcggcta ctggccaacg gaaggatatg aatttaccag cccgaaaccg   1320
gtgattgctg acgggcaact gttcgtgggt ctggcgctgg atgaaactaa ccagtatgac   1380
cttagcgacg agcgtattca gagctggtgc gagcaaatcc tcaacgaaat ggcacgtgtg   1440
tatgaaatcg gtcgtcagtt tcgtaacgag ggtattgacc tgacccataa cccggaattc   1500
accacctgcg aattctacat ggcatacgct gattaccacg acctgatgga aatcactgaa   1560
aaaatggtta gcggtatggt taaacacatc accggtagct ataaagtgac ctaccacccg   1620
gacggccctg aaggtcaagc gtatgacgtt gacttcaccc cgccgtttcg tcgtattaac   1680
atggttgaag aacttgaaaa agctctgggt atgaaactgc ctgaaactaa cctgttcgaa   1740
accgaagaaa cccgtaaaat cctggacgac atctgcgtag ctaaagctgt tgaatgccct   1800
ccgccgcgta ccaccgctcg tctgcttgac aaactggttg gtgaattcct tgaagtaacc   1860
tgcattaacc cgaccttcat ttgcgaccac ccacagatca tgtctccgct ggctaaatgg   1920
caccgttcta aagaaggtct gaccgaacgt tttgaactgt tcgtaatgaa aaaagaaatc   1980
tgcaatgcgt acactgaact taacgacccg atgcgtcaac gtcagctgtt tgaagaacag   2040
gctaaagcta aggcggcggg tgatgacgaa gccatgttca tcgatgaaaa cttctgcacc   2100
gctctggagt atggtctgcc tccgaccgct ggttggggta tgggtattga ccgtgtggct   2160
atgttcctga ctgactctaa caacatcaaa gaagttctgc tgttccctgc tatgaaacct   2220
gaagacaaaa aagaaaacgt agcgaccact gacacccttg aatctaccac tgtaggtact   2280
agcgtagcgg gtcaccatca ccaccatcac                                    2310
```

US 8,828,685 B2

MONOMERIC FORMS OF HUMAN AMINOACYL-T-RNA SYNTHETASES HAVING NON-CANONICAL BIOLOGICAL ACTIVITIES

CROSS REFERENCE TO RELATED APPLICATIONS

This application is a 35 USC §371 National Stage application of International Application No. PCT/US2011/00210 filed Feb. 4, 2011, now pending; which claims the benefit under 35 USC §119(e) of U.S. Provisional Patent Application No. 61/337,528, filed Feb. 4, 2010; U.S. Provisional Patent Application No. 61/337,488, filed Feb. 4, 2010; and U.S. Provisional Patent Application No. 61/337,489, filed Feb. 4, 2010, each of which is incorporated by reference in its entirety.

STATEMENT OF GOVERNMENT SUPPORT

This invention was made with government support under Grant Nos. CA092577, GM015539 and RR025204 awarded by the National Institutes of Health. The U.S. Government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 120161_423PC_SEQUENCE_LISTING.txt. The text file is about 48 KB, was created on Feb. 3, 2011, and is being submitted electronically via EFS-Web.

BACKGROUND OF THE INVENTION

1. Field of the Invention

The present invention relates generally to monomeric forms of aminoacyl-tRNA synthetase (AARS) polypeptides, compositions comprising such polypeptides, and methods of using same.

2. Description of the Related Art

Aminoacyl-tRNA synthetases, which catalyze the aminoacylation of tRNA molecules, are essential for decoding genetic information during the process of translation. In higher eukaryotes, aminoacyl-tRNA synthetases associate with other polypeptides to form supramolecular multienzyme complexes. Each of the eukaryotic tRNA synthetases consists of a core enzyme, which is closely related to the prokaryotic counterpart of the tRNA synthetase, and an additional domain that is appended to the amino-terminal or carboxyl-terminal end of the core enzyme. Human tyrosyl-tRNA synthetase (YRS), for example, has a carboxyl-terminal domain that is not part of prokaryotic and lower eukaryotic YRS molecules.

Several aminoacyl-tRNA synthetases have been demonstrated to have non-canonical functions distinct from their involvement in translation. For example, mini-tyrosyl tRNA synthetase (mini-YRS), the N-terminal domain of YRS which corresponds to amino acid residues 1-364 and is cleaved by polymorphonuclear cell elastase and plasmin, is a member of the aminoacyl tRNA synthetase "AARS" multifunction cytokine-like proteins and peptides. In vitro, mini-YRS has been shown to stimulate neutrophil activation and chemotaxis, endothelial cell proliferation and migration, and is proangiogenic in chick chorioallantoic membrane (CAM) and mouse matrigel assays. Mini-YRS has an ELR motif that, like CXC-chemokines such as IL-8, confers its chemokine and angiogenic activities. Like other ELR-containing cytokines, mutation of this motif inhibits mini-YRS binding and stimulation of leukocytes and angiogenesis.

In addition, truncated forms or WRS have been demonstrated to have angiogenic properties. In normal human cells, there are two forms of WRS that can be detected: a major form consisting of the full-length molecule (amino acid residues 1-471) and a minor truncated form. The minor form is generated by the deletion of an amino-terminal domain through alternative splicing of the pre-mRNA. The amino-terminus of mini-WRS has been determined to be the methionine residue at position 48 of the full-length WRS molecule. Alternatively, truncated WRS can be generated by proteolysis. For example, bovine WRS is highly expressed in the pancreas and is secreted into the pancreatic juice, thus resulting in the production of a truncated WRS molecule. Additional studies indicate that mini-WRS inhibits VEGF-induced cell proliferation and migration (Wakasugi et al., Proc. Natl. Acad. Sci. 99: 173-177 (2002)). In particular, a chick CAM assay shows that mini WRS blocks angiogenic activity of VEGF. In contrast, the full-length WRS does not inhibit angiogenesis. Thus, removal of the first 48 amino acid residues exposes the anti-angiogenic activity of WRS. Therefore, as with YRS, certain forms of WRS possess activities other than the aminoacylation of tRNA.

Given these observations of non-canonical and therapeutically relevant activities associated alternative forms of YRS and WRS, there is a need to identify biologically relevant forms and/or activities of other aminoacyl-tRNA synthetase proteins in order to exploit the full therapeutic potential of this family of proteins. Accordingly, the present invention addresses these needs and offers other related advantages.

SUMMARY OF THE INVENTION

The present invention stems from the unexpected discovery that dissociated monomeric forms of aminoacyl-tRNA synthetase (AARS) polypeptides possess non-canonical biological activities of therapeutic relevance. In certain aspects, these monomeric forms of AARS polypeptides possess an activity that differs from that of the dimeric form, either by degree or type. Without being bound by any one theory, the dissociated monomer form of certain AARS polypeptides appears to be responsible for many of their non-canonical biological activities, and thus provides a new mechanism for understanding how new surfaces can be exploited to expand the functions of AARS polypeptides. It is also believed that this new paradigm is more generally applicable to understanding the alternative and therapeutically-adaptable functions of tRNA synthetases.

Therefore, according to one aspect, the present invention provides isolated and substantially monomeric AARS polypeptides having at least one non-canonical biological activity, as well active fragments and variants thereof which substantially retain said non-canonical activity. "Non-canonical" activity," as used herein, refers generally to an activity possessed by an AARS polypeptide of the invention that is other than aminoacylation and, more specifically, other than the addition of its cognate amino acid onto a tRNA molecule.

As detailed herein, in certain embodiments, a non-canonical biological activity exhibited by a monomeric AARS polypeptide of the invention may include, but is not limited to, modulation of cell proliferation, modulation of cell differentiation, modulation of apoptosis, modulation of cell signaling, modulation of angiogenesis (e.g., via VE-cadherin), modulation of cell migration, modulation of cell binding, modulation of cellular metabolism, modulation of cytokine production or activity, modulation of cytokine receptor activity (e.g., CXCR-1, CXCR-2), and the like. In certain embodiments, a non-canonical biological activity includes inhibiting or reducing angiogenesis, i.e., an angiostatic activity. In certain embodiments, monomeric AARS (e.g., YRS) polypeptides are cytokine receptor agonists, such as CXCR-1 and CXCR-2 agonists. In certain embodiments, as noted above, isolated monomeric AARS polypeptides possess non-canonical biological activities, such as angiostatic activities, cytokine receptor-agonist activities, and/or cadherin-modulatory activities, which are not possessed by dimeric AARS polypeptide complexes, or which contrast the activity of a dimeric AARS.

Certain embodiments therefore include isolated aminoacyl-tRNA (AARS) synthetase polypeptides having a non-canonical biological activity, or active fragment or variant thereof, wherein the polypeptide is substantially in a monomeric form under physiological conditions or in solution. In certain embodiments, the polypeptide comprises one or more stabilizing modifications in relation to a wild-type sequence that reduce its ability to dimerize with itself or with another AARS polypeptide.

In certain embodiments, the one or more modifications are selected from any one or more of amino acid substitutions, amino acid deletions, amino acid additions, truncations, and chemical modifications. Certain embodiments include one or more stabilizing modifications located within or proximal to the primary, secondary, or tertiary structure of the dimer interface. In certain embodiments, the one or more stabilizing modifications are proximal to the primary structure of the dimer interface by about 1-20 residues.

In certain embodiments, the AARS polypeptide is a tyrosyl-tRNA synthetase (YRS), a tryptophanyl-tRNA synthetase (WRS), a glutaminyl-tRNA synthetase (QRS), a glycyl-tRNA synthetase (GlyRS), a histidyl-tRNA synthetase (HisRS), a seryl-tRNA synthetase (SRS), a phenylalanyl-tRNA synthetase (PheRS), an alanyl-tRNA synthetase (AlaRS), an asparaginyl-tRNA synthetase (AsnRS), an aspartyl-tRNA synthetase (AspRS), a cysteinyl-tRNA synthetase (CysRS), a glutamyl-tRNA synthetase (ERS), a prolyl-tRNA synthetase (ProRS), an arginyl-tRNA synthetase (RRS), an isoleucyl-tRNA synthetase (IRS), a leucyl-tRNA synthetase (LRS), a lysyl-tRNA synthetase (KRS), a threonyl-tRNA synthetase (TRS), a methionyl-tRNA synthetases (MRS), or a valyl-tRNA synthetase (VRS).

In certain embodiments, the monomeric form has an increased non-canonical biological activity as compared to a dimeric form of the polypeptide. In certain embodiments, the monomeric form has a different non-canonical biological activity as compared to a dimeric form of the polypeptide. In certain embodiments, the non-canonical biological activity comprises a cytokine receptor agonist activity or a cadherin-modulatory activity. In certain embodiments, the cytokine receptor is CXCR-1, CXCR-2, or both. In certain embodiments, the cytokine receptor agonist activity modulates an inflammatory response or modulates an angiogenic response. In certain embodiments, the cytokine receptor agonist activity increases an inflammatory response or increases an angiogenic response. In certain embodiments, the inflammatory or angiogenic response comprises increased endothelial cell or polymorphonuclear cell (PMNC) migration or proliferation. In certain embodiments, the cadherin modulatory activity comprises a VE-cadherin inhibitory activity. In certain embodiments, the VE-cadherin inhibitory activity reduces angiogenesis.

Certain embodiments include a substantially monomeric aminoacyl-tRNA (AARS) synthetase polypeptide as described herein, and a pharmaceutically acceptable carrier. Certain embodiments relate to methods of modulating an inflammatory response in a subject, comprising administering to the subject a substantially monomeric aminoacyl-tRNA (AARS) synthetase polypeptide described herein. Certain embodiments include increasing the inflammatory response in the subject. Certain embodiments include reducing or maintaining the inflammatory response in the subject.

Certain embodiments relate to methods of modulating angiogenesis in a subject, comprising administering to the subject a substantially monomeric aminoacyl-tRNA (AARS) synthetase polypeptide described herein. Certain embodiments include increasing angiogenesis in the subject. Certain embodiments include reducing angiogenesis in the subject.

Certain embodiments include methods of modulating the levels or activity of CXCR-1 or CXCR-2 in a cell, comprising contacting the cell with substantially monomeric aminoacyl-tRNA synthetase (AARS) polypeptide. Certain embodiments include increasing the levels or activity of CXCR-1 or CXCR-2 in the cell. In certain embodiments, the cell is in a subject. Certain embodiments include increasing endothelial cell or polymorphonuclear cell (PMNC) migration or proliferation.

Certain embodiments include methods of modulating the levels, phosphorylation state, or a biological activity of VE-cadherin in a cell, comprising contacting the cell with substantially monomeric aminoacyl-tRNA synthetase (AARS) polypeptide. Certain embodiments include reducing the levels of VE-cadherin in the cell. In certain embodiments, the cell is in a subject. Certain embodiments include reducing the levels of circulating VE-cadherin in the subject. Certain embodiments include reducing the phosphorylation of VE-cadherin at one or more tyrosine residues. Certain embodiments include reducing the biological activity of VE-cadherin. In certain embodiments, the biological activity comprises the ability to associate with, or promote the signaling of, vascular endothelial cell growth factor receptor (VEGFR2). In certain embodiments, the biological activity comprises the ability of one or more VE-cadherin polypeptides to self-assemble, or to associate with other VE-cadherin polypeptides.

Certain embodiments include directly binding to VE-cadherin and thereby reducing the biological activity of VE-cadherin. In certain embodiments, the biological activity comprises the ability to associate with, or promote the signaling of, vascular endothelial cell growth factor receptor (VEGFR2). In certain embodiments, the biological activity comprises the ability of one or more VE-cadherin polypeptides to self-assemble, or to associate with other VE-cadherin polypeptides.

Certain embodiments relate to methods of treating a condition comprising administering to a subject in need thereof substantially monomeric aminoacyl-tRNA (AARS) synthetase polypeptide according as described herein, wherein the condition is selected from an inflammatory condition, an autoimmune condition, a neoplastic disease, a metabolic disease, a neurological disease, an infection, an immunodeficiency, a cardiovascular disease, and a condition associated angiogenesis.

In certain embodiments, the inflammatory condition is associated with reduced inflammation. In certain embodiments, the condition is associated with increased inflammation. In certain embodiments, the condition is associated with reduced angiogenesis. In certain embodiments, the condition is associated with increased or aberrant angiogenesis.

Specific embodiments include isolated tyrosyl-tRNA (YRS) synthetase polypeptides having a non-canonical biological activity, or active fragment or variant thereof, wherein the polypeptide is substantially in a monomeric form under physiological conditions or in solution. In certain embodiments, the YRS polypeptide comprises one or more stabilizing modifications in relation to the wild-type sequence such as SEQ ID NO:1 that reduce its ability to dimerize with another YRS polypeptide. In particular embodiments, the one or more stabilizing modifications comprises a modification of Pro 159, Leu 160, or Leu 161, or any combination thereof. In certain embodiments, the one or more stabilizing modifications is proximal to residues 159-161 in the primary, secondary, or tertiary structure of the polypeptide.

In certain embodiments, the YRS monomer polypeptide comprises an amino acid sequence at least 80%, 85%, 90%, 95%, 98%, or 100% identical to SEQ ID NO:1 or 3-4, or a biologically active fragment thereof, wherein the one or more stabilizing modifications comprises a modification of Pro 159, Leu 160, or Leu 161, or any combination thereof. In certain embodiments, the polypeptide an amino acid sequence at least 80%, 85%, 90%, 95%, 98%, or 100% identical to SEQ ID NO:1 or 3-4, or a biologically active fragment thereof, wherein the one or more stabilizing modifications is proximal to residues 159-161 in the primary, secondary, or tertiary structure of the polypeptide. In certain embodiments, the polypeptide comprises an amino acid sequence at least 80%, 85%, 90%, 95%, 98%, or 100% identical to SEQ ID NO:4, and which retains a deletion of Pro 159, Leu 160, and Leu 161 (Δ159-161).

In certain embodiments, the monomeric form has an increased or a different non-canonical biological activity as compared to a dimeric form of a YRS polypeptide. In certain embodiments, the non-canonical biological activity comprises a cytokine receptor agonist activity. In certain embodiments, the cytokine receptor is CXCR-1, CXCR-2, or both. In certain embodiments, the cytokine receptor agonist activity modulates an inflammatory response or modulates an angiogenic response. In certain embodiments, the cytokine receptor agonist activity increases an inflammatory response or increases an angiogenic response. In certain embodiments, the inflammatory or angiogenic response comprises increased endothelial cell or polymorphonuclear cell (PMNC) migration or proliferation.

Certain embodiments include a substantially monomeric tyrosyl-tRNA (YRS) synthetase polypeptide as described herein, and a pharmaceutically acceptable carrier. Certain embodiments relate to methods of modulating an inflammatory response in a subject, comprising administering to the subject a substantially monomeric tyrosyl-tRNA (YRS) synthetase polypeptide described herein. Certain embodiments include increasing the inflammatory response in the subject.

Certain embodiments relate to methods of modulating angiogenesis in a subject, comprising administering to the subject a substantially monomeric tyrosyl-tRNA (YRS) synthetase polypeptide described herein. Certain embodiments include increasing angiogenesis in the subject.

Certain embodiments include methods of modulating the levels or activity of a cytokine receptor in a cell, comprising contacting the cell with substantially monomeric tyrosyl-tRNA synthetase (YRS) polypeptide as described herein, or a pharmaceutical composition comprising the same. Certain embodiments relate to increasing the levels or activity of the cytokine receptor in the cell. In certain embodiments, the cell is in a subject. In certain embodiments, the cytokine receptor is CXCR-1, CXCR-2, or both. In certain embodiments, the increased activity of the cytokine receptor leads to increased endothelial cell or PMNC migration or proliferation.

Specific embodiments include isolated tryptophanyl-tRNA (WRS) synthetase polypeptides having a non-canonical biological activity, or active fragment or variant thereof, wherein the polypeptide is substantially in a monomeric form. In certain embodiments, the polypeptide comprises one or more stabilizing modifications in relation to the wild-type WRS sequence such as SEQ ID NO:5, or the T2-WRS sequence of SEQ ID NO:7, which reduce its ability to dimerize with itself or with another WRS polypeptide. In certain embodiments, the one or more stabilizing modifications comprise a modification F260, Y201, I278, H130, or E408, or any combination thereof. In certain embodiments, the monomeric WRS polypeptide comprises SEQ ID NO:5 or 7, or a biologically active fragment or variant thereof having 80%, 90%, 95%, or 98% sequence identity thereto, wherein the polypeptide comprises one or more stabilizing modifications of F260, Y201, I278, H130, or E408; or any combination thereof. In certain embodiments, the monomeric WRS polypeptide comprises an amino sequence at least 80%, 85%, 90%, 95%, or 98% identical to SEQ ID NO:8 or 9, which comprises one or more stabilizing modifications of F260, Y201, I278, H130, or E408, or any combination thereof. Certain embodiments include a polypeptide of SEQ ID NO:8 or 9.

In certain embodiments, the WRS monomeric form has an increased or a different non-canonical biological activity as compared to a dimeric form of the polypeptide. In certain embodiments, the non-canonical biological activity of the WRS monomer comprises an angiogenesis-modulating activity. In certain embodiments, the angiogenesis-modulating activity is an angiostatic activity.

In certain embodiments, the WRS monomer binds directly to VE-cadherin in a cell or on the surface of the cell. In certain embodiments, the direct binding to VE-cadherin competitively inhibits the interaction of VE-cadherin with one or more angiogenic polypeptides. In certain embodiments, the one or more angiogenic polypeptides include another VE-cadherin polypeptide. In certain embodiments, the polypeptide disrupts VE-cadherin self-assembly in a cell or on the surface of the cell.

Certain embodiments include a substantially monomeric tryptophanyl-tRNA (WRS) synthetase polypeptide as described herein, and a pharmaceutically acceptable carrier. Certain embodiments relate to methods of modulating angiogenesis in a subject, comprising administering to the subject a substantially monomeric tryptophanyl-tRNA (WRS) synthetase polypeptide described herein. Certain embodiments include reducing angiogenesis in the subject.

Certain embodiments include methods of modulating the levels, phosphorylation state, or a biological activity of VE-cadherin in a cell, comprising contacting the cell with substantially monomeric tryptophanyl-tRNA synthetase (WRS) polypeptide as described herein, or a pharmaceutical composition comprising the same. Certain embodiments relate to reducing the levels of VE-cadherin in the cell. In certain embodiments, the cell is in a host.

Certain embodiments relate to the use of WRS polypeptides to reduce the levels of circulating VE-cadherin in the host. Certain embodiments relate to reducing the phosphorylation of VE-cadherin at one or more tyrosine residues.

Certain embodiments relate to WRS polypeptides that reduce the biological activity of VE-cadherin, and related uses thereof. In certain embodiments, the biological activity comprises the ability to associate with, or promote the signaling of, vascular endothelial cell growth factor receptor (VEGFR2). In certain embodiments, the biological activity comprises the ability of one or more VE-cadherin polypeptides to self-assemble, or to associate with other VE-cadherin polypeptides. Certain embodiments relate to directly binding to VE-cadherin and thereby reducing the biological activity of VE-cadherin. In certain embodiments, the biological activity comprises the ability to associate with, or promote the signaling of, vascular endothelial cell growth factor receptor (VEGFR2). In certain embodiments, the biological activity comprises the ability of one or more VE-cadherin polypeptides to self-assemble, or to associate with other VE-cadherin polypeptides.

Certain embodiments relate to methods of treating a condition comprising administering to a subject in need thereof substantially monomeric tryptophanyl-tRNA (WRS) synthetase polypeptide according as described herein, wherein the condition is selected from the group consisting of inflammatory diseases, autoimmune diseases, neoplastic diseases, metabolic diseases, neurological diseases, infections, cardiovascular diseases, and diseases associated with modulation of angiogenesis.

In particular embodiments, the substantially monomeric polypeptide is a lysyl-tRNA synthetase (KRS) polypeptide, or a truncation or variant thereof. One example of a KRS truncant is SEQ ID NO:12. In certain embodiments, the KRS polypeptide comprises one or more stabilizing modifications located within or proximal to the primary, secondary, or tertiary structure of the dimer interface. In particular embodiments, these include one or more modifications of residues E265, 283FIT285, G310, 539YGLLP543 as defined by full-length KRS, and/or proximal residues. In some embodiments, the KRS polypeptide comprises one or more stabilizing modifications, wherein said modification is a polypeptide insertion. In certain embodiments, said insertion comprises a heterologous polypeptide sequence. In particular embodiments, said insertion comprises one or more of the following characteristics: (i) the polypeptide is not derived from a membrane protein, (ii) the polypeptide has a globular 3D structure, (iii) the polypeptide has a dimension of about 30-40 Å, (iv) the N-terminus and C-terminus of the polypeptide are located in close three-dimensional proximity, or any combination of (i)-(iv). In specific embodiments, the insertion comprises flavodoxin from *E. coli*. In preferred embodiments, the KRS polypeptide comprises the amino acid sequence of SEQ ID NO:13.

In certain embodiments, said insertion is inserted proximal to or within the dimer interface of KRS. In some embodiments, said insertion is inserted at the periphery of the dimer interface. In specific embodiments, said insertion is inserted proximal to or at residue G310, as defined by the full-length KRS sequence of SEQ ID NO:11.

Also included are methods of drug discovery and related compositions. For example, certain embodiments include compositions (e.g., in vitro compositions), comprising a human immunodeficiency virus (HIV) Gag protein and a substantially monomeric lysyl tRNA synthetase (KRS) described herein, which typically or optionally comprises one or more stabilizing modifications that do not significantly reduce KRS binding to HIV Gag. Also included are modified cells, comprising a human immunodeficiency virus (HIV) Gag protein and an exogenous (e.g., recombinantly introduced), substantially monomeric lysyl tRNA synthetase (KRS) polypeptide described herein, which comprises one or more stabilizing modifications that do not significantly reduce KRS binding to HIV Gag. In some embodiments, the HIV Gag protein comprises the Gag-CA-CTD domain. In specific embodiments, the Gag-CA-CTD domain comprises regions H3 and H4.

Certain embodiments include methods of identifying a compound that specifically reduces binding between a human immunodeficiency virus (HIV) Gag protein and a substantially monomeric lysyl tRNA synthetase (KRS) polypeptide, comprising (a) combining the composition or cell described above with at least one test compound under suitable conditions, and (b) detecting reduced binding between the HIV Gag protein and the substantially monomer KRS polypeptide, thereby identifying a compound that specifically reduces binding between the HIV Gag protein and the KRS polypeptide. In certain embodiments, the test compound is a polypeptide or peptide, an antibody or antigen-binding fragment thereof, a peptide mimetic, or a small molecule. In some embodiments, the test compound binds to the Gag-CA-CTD domain. In particular embodiments, the test compound binds to H3 or H4 or both of the Gag-CA-CTD domain. In specific embodiments, the test compound binds to the bottom side of H3 or H4 or both (see FIG. 18E).

Also included are compounds or binding agents (e.g., antibodies and fragments thereof) that specifically bind to (a) an H3 and/or H4 region of a human immunodeficiency virus (HIV) Gag-CA-CTD domain, (b) an inter-domain cavity of substantially monomeric KRS which interacts with the H3 and/or H3 region of Gag-CA-CTD domain, or both (a) and (b), and reduce the interaction between HIV Gag and monomeric KRS. In certain embodiments, the compound or binding agent binds to the bottom side of H3 or H4 or both. In certain embodiments, the compound or binding agent mimics the three-dimensional structure of the Gag-CA-CTD domain comprising the H3 and/or H4 region. Certain methods include reducing assembly of a human immunodeficiency virus (HIV), comprising contacting an HIV-infected cell with a compound or binding described above. Such methods, compounds, and agents can be used in the treatment of HIV infection.

According to another aspect of the invention, there are provided fusion proteins comprising at least one substantially monomeric AARS polypeptide as described herein and a heterologous fusion partner.

According to another aspect of the invention, there are provided isolated polynucleotides encoding the polypeptides and fusion proteins as described herein, as well as expression vectors comprising such polynucleotides, and host cell comprising such expression vectors.

According to yet another aspect of the invention, there are provided compositions, e.g., pharmaceutical compositions, comprising physiologically acceptable carriers and at least one of the isolated polypeptides, fusion proteins, antibodies, isolated polynucleotides, expression vectors, host cells, etc., of the invention, as described herein.

Also provided by the present invention, in other aspects, are methods for modulating a cellular activity by contacting a cell or tissue with a composition of the invention, as described herein, wherein the cellular activity to be modulated is selected from the group consisting of cell proliferation, apoptosis, cell signaling, cellular metabolism, angiogenesis, cell migration, cell binding, cytokine production, cytokine receptor activity, and the like.

In other aspects, the present invention provides methods for treating a disease, disorder or other condition in a subject in need thereof by administering a composition according to the present invention. By way of illustration, such diseases, disorders or conditions may include, but are not limited to, cancer, inflammatory disease or condition, immune disease (including autoimmune disease) and/or conditions associated with abnormal angiogenesis.

Also included are methods of drug discovery. For example, certain embodiments include methods of identifying a compound that specifically binds to a substantially monomeric aminoacyl-tRNA synthetase (AARS) polypeptide, and/or one or more of its binding partners (e.g., host cell, viral, bacterial binding partners), comprising a) combining the substantially monomeric AARS polypeptide or its binding partner or both with at least one test compound under suitable conditions, and b) detecting binding of the substantially monomeric AARS polypeptide or its binding partner or both to the test compound, thereby identifying a compound that specifically binds to the substantially monomeric AARS polypeptide or its binding partner or both.

BRIEF DESCRIPTION OF SEQUENCE IDENTIFIERS

SEQ ID NO: 1 is the full length amino acid sequence of human tyrosyl-tRNA synthetase (YRS).
SEQ ID NO:2 is the polynucleotide sequence that encodes full-length human YRS.
SEQ ID NO:3 is the amino acid sequence of mini-YRS.
SEQ ID NO:4 is the amino acid sequence of the non-associating monomeric Δ159-161 variant of mini-YRS.
SEQ ID NO:5 is the full length amino acid sequence of human tryptophanyl-tRNA synthetase (WRS).
SEQ ID NO:6 is the polynucleotide sequence that encodes full-length human WRS.
SEQ ID NO:7 is the amino acid sequence of T2-WRS (residues 94-471 of full-length WRS).
SEQ ID NO:8 is the amino acid sequence of the F260EY201EI278E T2-WRS variant, which forms a stable monomer.
SEQ ID NO:9 is the amino acid sequence of the F260EY201EH130R T2-WRS variant, which forms a stable monomer.
SEQ ID NO:10 is the amino acid sequence of the VE-cadherin extracellular domain EC1.
SEQ ID NO:11 is the full-length amino acid sequence of human lysyl-tRNA synthetase (KRS or LysRS).
SEQ ID NO:12 is the amino acid sequence of a truncated human KRS (residues 70-584 of full-length KRS).
SEQ ID NO:13 is the amino acid sequence of truncated human KRS having an insertion of the 180 amino acid *E. coli* flavodoxin (pdb:1ahn) protein at the G130 position of KRS (Flavo-KRS).
SEQ ID NO:14 is the polynucleotide sequence that encodes the Flavo-KRS monomer of SEQ ID NO:13.

BRIEF DESCRIPTION OF THE DRAWINGS

FIG. 2 shows the rational design of an exemplary non-associating monomeric form of mini-YRS, and a disulfide link non-dissociating dimeric form of mini-YRS. FIG. 2B shows the structure of the dimer interface with the three residue deletion (P159, L160, L161; indicated by arrows)—these deletions generated an exemplary non-associating monomer of YRS (Δ159-161). FIG. 2C shows the dimer interface, in which the Thr 130 was replaced with Cys, and upon I2 oxidation formed a disulfide bond linkage across the dimer interface to generate a non-dissociating dimer ($C130^{OX}$).

FIG. 3 shows the characterization of the Δ159-161 and $C130^{OX}$ variants.

FIG. 5 illustrates the effects of WT, Δ159-161 and $C130^{OX}$ on PMN cell migration activity.

FIG. 10A shows the results for T2-WRS. FIG. 10B shows the results for VE-Cadherin EC1 domain. FIG. 10C shows the results for T2-WRS and VE-EC1 at 1:1 ratio with 0.1 mM $Zn^{2+}$. FIG. 10D shows the results for T2-WRS and VE-EC1 at 1:1 ratio with 0.1 mM $Zn^{2+}$ and 30 uM Trp-SA.

FIG. 16 shows that WT T2-WRS and monomer T2-WRS induce degradation of β-catenin.

FIG. 18 show the results of an ab initio model of the docking of the Gag-CA-CTD domain onto human KRS. The Gag binding site is at the dimerization interface of KRS, suggesting that the monomeric KRS is the functional unit for HIV Gag protein binding.

FIG. 20 illustrates the engineering of human KRS into a monomer.

FIG. 21 shows the characterization of monomeric Flavo-KRS.

FIG. 22 shows that monomeric Flavo-KRS retains Gag and tRNA$^{Lys3}$ binding.

DETAILED DESCRIPTION OF THE INVENTION

Figure 1:
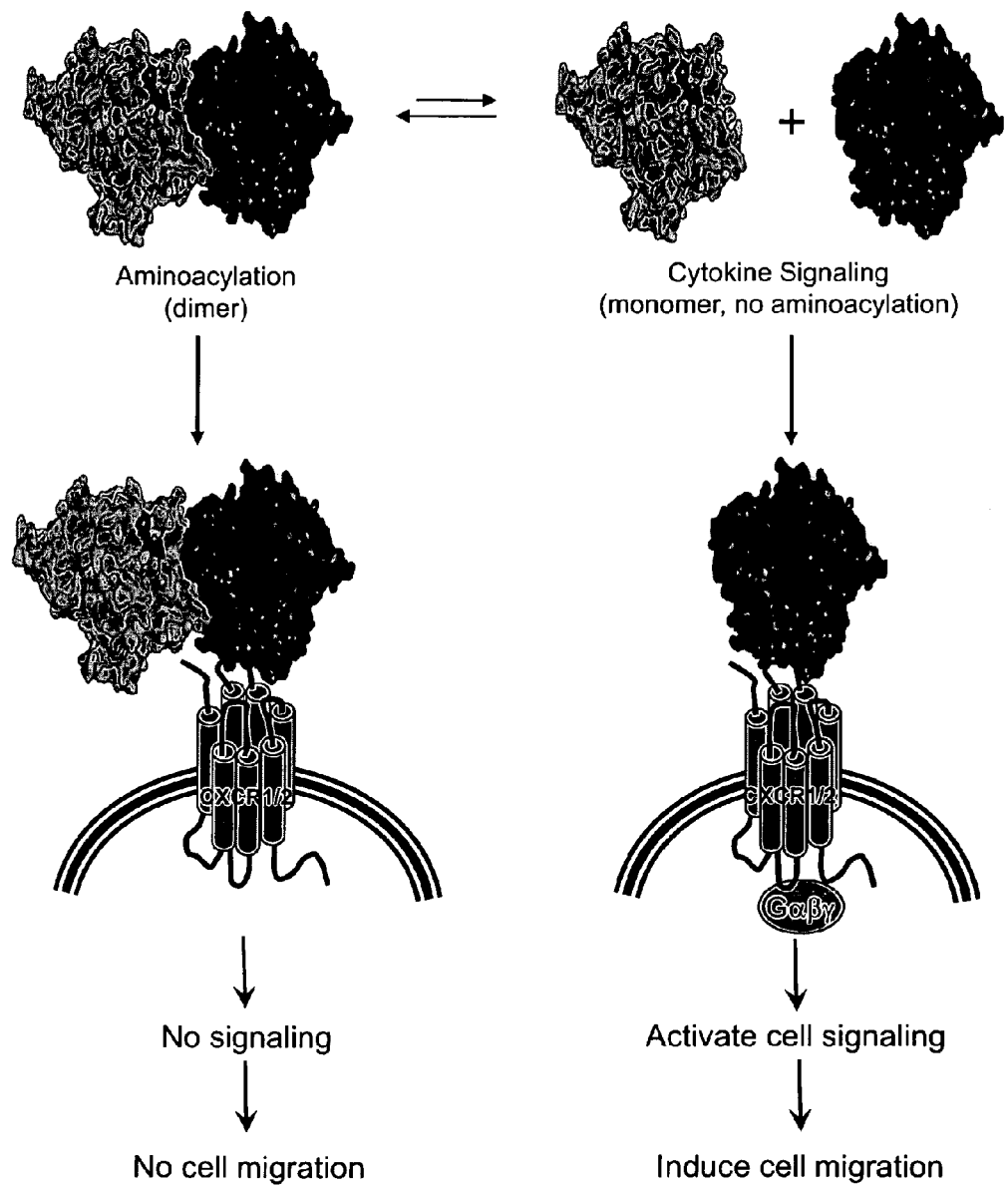
FIG. 1 is a schematic diagram which illustrates a mechanism of mini-YRS-mediated cytokine signaling. In this model, the dissociated monomer form of the homodimeric mini-YRS is the active cytokine and the dimer is a nonfunctional receptor binding form. Dimeric YRS with individual monomers are shown in light grey and dark grey and the ELR motif for the light grey monomer is shown in slightly darker grey.

The practice of the present invention will employ, unless indicated specifically to the contrary, conventional methods of molecular biology and recombinant DNA techniques within the skill of the art, many of which are described below for the purpose of illustration. Such techniques are explained fully in the literature. See, e.g., Sambrook, et al., *Molecular Cloning: A Laboratory Manual* (2nd Edition, 1989); Maniatis et al., *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); *A Practical Guide to Molecular Cloning* (B. Perbal, ed., 1984).

All publications, patents and patent applications cited herein are hereby incorporated by reference in their entirety.

DEFINITIONS

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length.

An AARS polypeptide may be characterized as "substantially monomeric" or "non-associating" if, for example, its ability to dimerize with itself (i.e., homodimerize) or dimerize with a second AARS polypeptide (e.g., heterodimerize with a full-length wild-type YRS polypeptide of SEQ ID NO:1 or mini-YRS of SEQ ID NO:3) is reduced by a statistically significant amount as compared to the ability of a control AARS polypeptide to dimerize. In certain embodiments, the control peptide may include a full-length wild-type AARS polypeptide, or a naturally-occurring splice variant or fragment that has the ability to dimerize. Hence, in certain embodiments, a substantially monomeric AARS polypeptide may be characterized by its reduced ability to dimerize with itself, as compared to the ability of a full-length or truncated AARS polypeptide to dimerize with itself, or a naturally-occurring fragment to dimerize with itself, typically measured and compared at a selected concentration of polypeptide (e.g., mini-YRS exists predominantly as a dimer in solution at µM concentrations). A statistically significant reduction may include, for instance, a 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% reduction or decrease in its ability to dimerize, including all integers in between.

In certain embodiments, the AARS polypeptide is substantially in a monomeric form, or substantially monomeric, under physiological conditions or in solution. Examples of physiological conditions include, without limitation, the in vivo conditions encountered in blood or other tissues, the in vitro conditions encountered in mammalian cell cultures, and other in vitro conditions such as in a salt solution (e.g., 25 mM Tris-Cl pH8.0, 150 mM NaCl) or a pharmaceutical formulation described herein.

The term "biologically active fragment," as applied to fragments of a reference polynucleotide or polypeptide sequence, refers to a substantially monomeric AARS fragment that has at least about 0.1, 0.5, 1, 2, 5, 10, 12, 14, 16, 18, 20, 22, 24, 26, 28, 30, 35, 40, 45, 50, 55, 60, 65, 70, 75, 80, 85, 90, 95, 96, 97, 98, 99, 100, 110, 120, 150, 200, 300, 400, 500, 600, 700, 800, 900, 1000% or more of the non-canonical activity of a reference sequence. Included within the scope of the present invention are monomeric and biologically active fragments of at least about 10, 11, 12, 13, 14, 15, 16, 16, 18, 19, 20, 21, 22, 23, 24, 25, 26, 27, 28, 29, 30, 40, 50, 60, 70, 80, 90, 100, 120, 140, 160, 180, 200, 220, 240, 260, 280, 300, 320, 340, 360, 380, 400, 420, 440, 450, 460, 465 or more contiguous nucleotides or amino acid residues in length of SEQ ID NOS:1, 3-5, 7-9, or 11-13 (or Table A), including all integers in between, all or any portion of which encodes or comprises a monomeric AARS polypeptide having a non-canonical biological activity of a reference polynucleotide or polypeptide, such as the monomeric reference polypeptides of SEQ ID NOS:4, 8-9, or 13.

Hence, in certain embodiments, a biologically active and substantially monomeric AARS polypeptide fragment of about 10, 11, 12, 13, 14, 15, 16, 16, 18, 19, 20, 21, 22, 23, 24, 25, 26, 27, 28, 29, 30, 40, 50, 60, 70, 80, 90, 100, 120, 140, 160, 180, 200, 220, 240, 260, 280, 300, 320, 340, 360, 380, 400, 420, 440, 450, 460, 465 or more amino acid residues in length could contain only about 10%, 20%, 30%, 40%, 50%, 60%, 70%, 80%, or 90% AARS-specific residues, such as about 10, 11, 12, 13, 14, 15, 16, 16, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 120, 140, 160, 180, 200, 220, 240, 260, 280, 300, 320, 340, 360, 380, 400, 420, 440, 460, or 470 AARS-specific residues, contiguous or non-contiguous, with the rest of the fragment being made of any selected polypeptide sequences.

Representative biologically active fragments generally participate in an interaction, e.g., an intramolecular or an inter-molecular interaction. An inter-molecular interaction can be a specific binding interaction or an enzymatic interaction. An inter-molecular interaction can be between an AARS polypeptide and target molecule, such as a target molecule involved in modulation of cell proliferation, modulation of apoptosis, modulation of cell signaling, modulation of angiogenesis, modulation of cell migration, modulation of cell binding, modulation of cellular metabolism, modulation of cytokine production or activity, cytokine receptor activity, and the like. Examples of target molecules include CXCR-1 and CXCR-2 and VE-cadherin, among others. In certain embodiments, a specific binding interaction as with the extracellular domain EC1 of VE-cadherin.

In certain embodiments, a monomeric WRS or its biologically active fragment may be characterized by its ability to bind to VE-cadherin in the absence of $Zn^{2+}$, in the presence of low levels of zinc, or in the presence of a zinc chelator, i.e., the interaction between the monomeric WRS polypeptide is characterized by its relative $Zn^{2+}$ independence, as compared to a dimer WRS control, such as T2-WRS. Monomeric and biologically active fragments of a WRS polypeptide include polypeptide fragments comprising amino acid sequences with sufficient similarity or identity to, or which are derived from, the amino acid sequences of SEQ ID NOS:5 or 7-9, or are encoded by all or part of the nucleotide sequence of SEQ ID NO:6, and which in certain embodiments do not substantially dimerize with another WRS polypeptide.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands.

By "corresponds to" or "corresponding to" is meant (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

By "derivative" is meant a polypeptide that has been derived from the basic sequence by modification, for example by conjugation or complexing with other chemical moieties (e.g., pegylation) or by post-translational modification techniques as would be understood in the art. The term "derivative" also includes within its scope alterations that have been made to a parent sequence including additions or deletions that provide for functionally equivalent molecules.

As used herein, the terms "function" and "functional" and the like refer to a biological, enzymatic, or therapeutic function.

By "gene" is meant a unit of inheritance that occupies a specific locus on a chromosome and consists of transcriptional and/or translational regulatory sequences and/or a coding region and/or non-translated sequences (i.e., introns, 5' and 3' untranslated sequences).

"Homology" refers to the percentage number of amino acids that are identical or constitute conservative substitutions. Homology may be determined using sequence comparison programs such as GAP (Deveraux et al., 1984, *Nucleic Acids Research* 12, 387-395), which is incorporated herein by reference. In this way sequences of a similar or substantially different length to those cited herein could be compared by insertion of gaps into the alignment, such gaps being determined, for example, by the comparison algorithm used by GAP.

The term "host cell" includes an individual cell or cell culture that can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell which comprises a recombinant vector of the invention is a recombinant host cell.

By "isolated" is meant material that is substantially or essentially free from components that normally accompany it in its native state. For example, an "isolated polynucleotide," as used herein, includes a polynucleotide that has been purified from the sequences that flank it in its naturally-occurring state, e.g., a DNA fragment which has been removed from the sequences that are normally adjacent to the fragment. Alternatively, an "isolated peptide" or an "isolated polypeptide" and the like, as used herein, includes the in vitro isolation and/or purification of a peptide or polypeptide molecule from its natural cellular environment, and from association with other components of the cell; i.e., it is not significantly associated with in vivo substances.

By "obtained from" is meant that a sample such as, for example, a polynucleotide extract or polypeptide extract is isolated from, or derived from, a particular source of the subject. For example, the extract can be obtained from a tissue or a biological fluid isolated directly from the subject. "Derived" or "obtained from" can also refer to the source of a polypeptide or polynucleotide sequence. For instance, an isolated AARS polypeptide of the present invention may be "derived" from the sequence information of an AARS proteolytic fragment or AARS splice variant, whether naturally-occurring or artificially generated, and may thus comprise, consist essentially of, or consist of that sequence.

The term "oligonucleotide" as used herein refers to a polymer composed of a multiplicity of nucleotide residues (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotide residues and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule can vary depending on the particular application. An oligonucleotide is typically rather short in length, generally from about 10 to 30 nucleotide residues, but the term can refer to molecules of any length, although the term "polynucleotide" or "nucleic acid" is typically used for large oligonucleotides.

The term "operably linked" as used herein means placing a structural gene under the regulatory control of a promoter, which then controls the transcription and optionally translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting; i.e., the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting; i.e., the genes from which it is derived.

The recitation "polynucleotide" or "nucleic acid" as used herein designates mRNA, RNA, cRNA, cDNA or DNA. The term typically refers to polymeric form of nucleotides of at least 10 bases in length, either ribonucleotides or deoxynucleotides or a modified form of either type of nucleotide. The term includes single and double stranded forms of DNA.

The terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide. Polynucleotide variants include, for example, polynucleotides having at least 50% (and at least 51% to at least 99% and all integer percentages in between) sequence identity with the sequence set forth in SEQ ID NO:2, 6, or 13, or portions thereof that encode a substantially monomeric and biologically active fragment of an AARS polypeptide. The terms "polynucleotide variant" and "variant" also include naturally occurring allelic variants.

"Polypeptide," "polypeptide fragment," "peptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers.

The term "aminoacyl-tRNA synthetase" (AARS) refers generally to enzymes that in their natural or wild-type form are capable of catalyzing the esterification of a specific amino acid or its precursor to one of all its compatible cognate tRNAs to form an aminoacyl-tRNA. In this "canonical" activity, aminoacyl-tRNA synthetases catalyse a two-step reaction: first, they activate their respective amino acid by forming an aminoacyl-adenylate, in which the carboxyl of the amino acid is linked in to the alpha-phosphate of ATP by displacing pyrophosphate, and then, when the correct tRNA is bound, the aminoacyl group of the aminoacyl-adenylate is transferred to the 2' or 3' terminal OH of the tRNA.

Class I aminoacyl-tRNA synthetases typically have two highly conserved sequence motifs. These enzymes aminoacylate at the 2'-OH of an adenosine nucleotide, and are usually monomeric or dimeric. Class II aminoacyl-tRNA synthetases typically have three highly conserved sequence motifs. These enzymes aminoacylate at the 3'-OH of the same adenosine, and are usually dimeric or tetrameric. The active sites of class II enzymes are mainly made up of a seven-stranded anti-parallel β-sheet flanked by α-helices. Although phenylalanine-tRNA synthetase is class II, it aminoacylates at the 2'-OH.

Monomeric AARS polypeptides of the present invention include tyrosyl-tRNA synthetase (YRS), a tryptophanyl-tRNA synthetase (WRS), a glutaminyl-tRNA synthetase (QRS), a glycyl-tRNA synthetase (GlyRS), a histidyl-tRNA synthetase (HisRS), a seryl-tRNA synthetase (SRS), a phenylalanyl-tRNA synthetase (PheRS), an alanyl-tRNA synthetase (AlaRS), an asparaginyl-tRNA synthetase (AsnRS), an aspartyl-tRNA synthetase (AspRS), a cysteinyl-tRNA synthetase (CysRS), a glutamyl-tRNA synthetase (ERS), a prolyl-tRNA synthetase (ProRS), an arginyl-tRNA synthetase (RRS), an isoleucyl-tRNA synthetase (IRS), a leucyl-tRNA synthetase (LRS), a lysyl-tRNA synthetase (KRS), a threonyl-tRNA synthetase (TRS), a methionyl-tRNA synthetases (MRS), or a valyl-tRNA synthetase (VRS). The wild-type sequences of these AARS polypeptides are known in the art.

The recitations "polypeptides" "polypeptide fragments," "truncated polypeptides" or "variants thereof" encompass, without limitation, substantially monomeric or non-associating AARS polypeptides having an amino acid sequence that shares at least 50% (and at least 51% to at least 99% and all integer percentages in between) sequence identity with a reference sequences set forth in SEQ ID NOS:1, 3-5, 7-9, or 11-13 (or Table A), such as fragments having at least about 10, 20, 30, 40, 50, 60, 70, 80, 90, 100, 120, 140, 160, 180, 200, 220, 240, 260, 280, 300, 350, 400 or more contiguous amino acids of the reference sequences, including all integers in between. These recitations further encompass natural allelic variation of AARS polypeptides that may exist and occur from one genus or species to another.

Monomeric AARS polypeptides, including truncations and/or variants thereof, encompass polypeptides that exhibit at least about 10%, 20%, 30%, 40%, 50%, 60%, 70%, 80%, 90%, 100%, 110%, 120%, 130%, 140%, 150%, 200%, 300%, 400%, 500%, 600%, 700%, 800%, 900%, 1000% or more of the specific biological activity (e.g., a CXC receptor agonist activity) of a reference monomeric AARS polypeptide, such as the exemplary monomeric polypeptide of SEQ ID NOS:4, 8-9, and 13. In certain exemplary embodiments, AARS-related biological activity may be quantified, for example, by measuring the ability of a substantially monomeric AARS polypeptide (e.g., WRS) to bind to VE-cadherin, or to reduce angiogenesis (see, e.g., Example 4), among other activities apparent from the description herein.

In still further exemplary embodiments, AARS-related biological activity may be quantified, for example, by measuring the ability of a substantially monomeric AARS polypeptide (e.g., YRS) to bind to CXCR-1 or CXCR-2, to agonize the activity of CXCR-1 or CXCR-2, or to increase polymorphonuclear cell migration (see, e.g., Example 2), among other activities apparent from the description herein. CXCR-1 or CXCR-2 mediated biological activities include, for example, intracellular $Ca^{2+}$ mobilization, phosphoinositide hydrolysis, chemotaxis, exocytosis, phosphorylation, desensitization, β-arrestin translocation and internalization, any one or more of which can be modulated by a monomeric AARS polypeptide. Certain KRS monomers can be tested for their ability to bind HIV-Gag and/or $tRNA^{Lys3}$ and/or to facilitate incorporation of $tRNA^{Lys3}$ into the HIV virion.

Monomeric AARS polypeptides, including truncations and/or variants thereof, having substantially reduced biological activity relative to a reference AARS polypeptide are those that exhibit less than about 25%, 10%, 5% or 1% of the specific activity of a reference AARS polypeptide (i.e., having a non-canonical activity).

The recitation polypeptide "variant" refers to polypeptides that are distinguished from a reference polypeptide by the addition, deletion or substitution of at least one amino acid residue. In certain embodiments, a polypeptide variant is distinguished from a reference polypeptide by one or more substitutions, which may be conservative or non-conservative. In certain embodiments, the polypeptide variant comprises conservative substitutions and, in this regard, it is well understood in the art that some amino acids may be changed to others with broadly similar properties without changing the nature of the activity of the polypeptide. Polypeptide variants also encompass polypeptides in which one or more amino acids have been added or deleted, or replaced with different amino acid residues.

The present invention contemplates the use of variants of full-length AARS polypeptides, truncated fragments of full-length AARS polypeptides, splice variants, fragments, and variants of such fragments, as well as their related biologically active fragments, which are substantially monomeric in form, i.e., they do not substantially dimerize with another AARS polypeptide, typically under physiological conditions or in solution. Monomeric and biologically active fragments of an AARS polypeptide include peptides comprising amino acid sequences sufficiently similar to, or derived from, the amino acid sequences of a (putative) full-length or wild-type AARS polypeptide sequence (see, e.g., Table A), or from exemplary monomeric AARS polypeptides (e.g., SEQ ID NOS:4, 8-9, and 13).

Typically, biologically active fragments comprise a domain or motif with at least one activity of an AARS polypeptide and may include one or more (and in some cases all) of the various active domains, and include fragments having the ability to interact with or agonize CXC receptors such as CXCR-1 and/or CXCR-1, stimulate PMNC migration, stimulate angiogenesis, interact with VE-cadherin, reduce angiogenesis, or other activity described herein. In some cases, monomeric and biologically active fragments of an AARS polypeptide have a non-canonical biological activity that is unique to the particular monomeric fragment or variant, such that the full-length or dimeric forms of the AARS polypeptide may or may not have that activity, or may have it to a lesser degree. In certain cases, the biological activity may be revealed by separating the biologically active AARS polypeptide fragment from the other full-length AARS polypeptide sequences, or by altering certain residues of the AARS wild-type polypeptide sequence to unmask the biologically active domains, such as to prevent or reduce dimerization between AARS polypeptides. In certain embodiments, a monomeric and biologically active fragment comprises an angiogenic response-modulating sequence, domain, or motif, such as a domain that interacts with VE-cadherin, which may or may not be possessed by a dimeric polypeptide. In certain embodiments, a monomeric and biologically active fragment comprises a cytokine-modulatory sequence, domain, or motif, such as a domain that interacts with and agonizes CXC receptors such as CXCR-1 and/or CXCR-1, which may or may not be possessed by a dimeric polypeptide. Additional examples of motifs include the Glu-Leu-Arg (ELR) motif. Suitably, the monomeric and biologically-active fragment has no less than about 1%, 10%, 25%, 50% of an activity of a reference AARS polypeptide from which it is derived.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology," John Wiley & Sons Inc, 1994-1998, Chapter 15.

A "subject," as used herein, includes any animal that exhibits a symptom, or is at risk for exhibiting a symptom, which can be treated with a substantially monomeric AARS polypeptide of the invention. Suitable subjects (patients) include laboratory animals (such as mouse, rat, rabbit, or guinea pig), farm animals, and domestic animals or pets (such as a cat or dog). Non-human primates and, preferably, human patients, are included.

An "effective concentration" of a substantially monomeric AARS polypeptide refers to an amount that is capable of altering a desired biological activity or response in any desired way, as compared to a control polypeptide or no polypeptide, whether in a cell in vitro or ex vivo, or in a cell in a subject. One illustrative example of a biological activity includes agonizing the activity of CXC receptors such as CXCR-1 and/or CXCR-2, similar to the pro-inflammatory chemokine interleukin-8 (IL-8). Another illustrative example of a biological activity includes inhibiting or reducing angiogenesis. Other examples include, without limitation, modulation of cell proliferation, modulation of apoptosis, modulation of cell signaling, modulation of cell migration, modulation of cell binding, modulation of cellular metabolism, modulation of inflammation, and the like An "immune cell" includes any cell of the vertebrate immune system, including lymphocytes such as B-cells, killer T-cells (i.e., CD8+ T-cells), helper T-cells (i.e., CD4+ T-cells, including $T_h1$ and $T_h2$ cells), natural killer cells, and γδ T-cells, monocytes, macrophages, neutrophils, dendritic cells, mast cells, eosinophils, and basophils.

A "megakaryocyte" refers generally to a bone marrow cell that is responsible for the production of blood thrombocytes (i.e., platelets), which are necessary for normal blood clotting. Megakaryocytes typically account for 1 out of 10,000 bone marrow cells. Megakaryocytes are derived from pluripotent hematopoietic stem cell precursor cells in the bone marrow. Thrombopoietin (TPO) is the primary signal for megakaryocyte production, i.e., TPO is sufficient but not absolutely necessary for inducing differentiation of progenitor cells in the bone marrow towards a final megakaryocyte phenotype. Other molecular signals for megakaryocyte differentiation include GM-CSF, IL-3, IL-6, IL-11, chemokines (SDF-1; FGF-4), and erythropoietin.

Megakaryocytes are believed to develop through the following lineage: CFU-Me (pluripotential hematopoietic stem cell or hemocytoblast)→megakaryoblast→promegakaryocyte→megakaryocyte. At the megakaryoblast stage, the cell loses its ability to divide, but is still able to replicate its DNA and continue development, becoming polyploid. Upon maturation, megakaryocytes begin the process of producing platelets, or thrombocytes. Thrombopoietin plays a role in inducing the megakaryocyte to form small proto-platelet processes, or cytoplasmic internal membranes for storing platelets prior to release. Upon release, each of these proto-platelet processes can give rise to 2000-5000 new platelets. Overall, about ⅔ of the newly-released platelets will remain in circulation and about ⅓ will be sequestered by the spleen. After releasing the platelets, the remaining cell nucleus typically crosses the bone marrow barrier to the blood and is consumed in the lung by alveolar macrophages. Megakaryocytopenia, also referred to as megakaryophthisis, is a scarcity of megakaryocytes in the bone marrow.

An "erythrocyte" refers to a red blood cell that consists mainly of hemoglobin, a complex metalloprotein containing heme groups whose iron atoms temporarily link to oxygen molecules ($O_2$) in the lungs. Erythrocytes are produced by a process called erythropoiesis, in which they develop from committed stem cells through reticulocytes to mature erythrocytes in about 7 days and live a total of about 100-120 days. "Polycythemias" (or erythrocytoses) are diseases characterized by a surplus of erythrocytes, in which the increased viscosity of the blood can cause a number of symptoms. "Anemias" are diseases characterized by low oxygen transport capacity of the blood, because of low red cell count or some abnormality of the red blood cells or the hemoglobin.

A "granulocyte" refers to a white blood cell that is characterized by the presence of granules in its cytoplasm. Granulocytes are also referred to as polymorphonuclear leukocytes (PMN or PML), because of the varying shapes of the nuclei. Examples of granulocytes include neutrophils, eosinophils, and basophils.

A "neutrophil," or neutrophil granulocyte, refers generally to an abundant type of white blood cells in humans, which, together with basophils and eosinophils, form part of the polymorphonuclear cell family (PMNs). Neutrophils can be readily identified according to their unique staining characteristics on hematoxylin and eosin (H&E) histological or cytological preparations. Neutrophils are normally found in the blood stream, but are one of the first group of inflammatory cells to migrate toward inflammation sites during the beginning (i.e., acute) phase of inflammation, mainly as a result of infection or cancer. Typically, neutrophils first migrate through the blood vessels, and then through interstitial tissues, following chemical signals (e.g., interleukin-8 (IL-8), interferon-gamma (IFN-gamma), and C5a) that originate at the site of inflammation. "Neutropenia" refers to the presence of low neutrophil counts, which may result from a congenital (genetic) disorder, or may develop due to other conditions, as in the case of aplastic anemia or some kinds of leukemia. "Neutrophilia" refers to an abnormally high neutrophil count.

"Eosinophils," also called eosinophilic leukocytes, refer to leukocytes that have coarse round granules of uniform size within their cytoplasm, and which typically have a bilobate (two-lobed) nucleus. The cytoplasmic granules of eosinophils stain red with the dye eosin. Eosinophils normally constitute about 1% to about 3% of the peripheral blood leukocytes, at a count of about 350 to 650 per cubic millimeter. Eosinophil counts in blood often rise above the normal range during allergic reactions and parasitic infections, such as worms. "Eosinopenia" refers to a form of agranulocytosis in which the number of eosinophil granulocyte is lower than expected. "Eosinophilia" refers to an abnormally high number of eosinophils in the blood. For example, eosinophilia can be categorized as mild (less than about 1500 eosinophils per cubic millimeter), moderate (about 1500 to about 5000 per cubic millimeter), or severe (more than about 5000 per cubic millimeter). In primary eosinophilia, the increased production of eosinophils is typically due to an abnormality in hematopoietic stem cells, such as in eosinophilic leukemia. In secondary eosinophilia, the increased production of eosinophils is typically due to a reactive process driven by cytokines.

Basophils, also called basophilic leukocytes, refer to leukocytes that have coarse bluish-black granules of uniform size within the cytoplasm, and which typically have a bilobate (two-lobed) nucleus. The cytoplasmic granules of basophils stain with basic dyes. Basophils normally constitute about 0.5% to 3% of the peripheral blood leukocytes. Basophils store and release histamine and serotonin, among other chemicals. Basophils are capable of ingesting foreign particles, and also produce, store and release heparin, serotonin, and histamine. The release of inflammatory chemicals such as heparin and histamine is often associated with asthma and allergies. Basophils are produced continually by stem cells in the bone marrow. "Basopenia" refers to a low basophil count (e.g., less than about $0.01 \times 10^9$ per liter of blood), and "basophilia" refers to a high basophil count (e.g., more than about $10^{10}$ per liter of blood).

"Lymphocytes" refer generally to white blood cells of the vertebrate immune system, and include B-cells, T-cells (e.g., helper T-cells, cytotoxic T-cells, γε T-cells), and natural killer (NK) cells. Generally, and merely for illustrative purposes, B-cells produce and secrete antibodies, T-helper cells release cytokines and growth factors that regulate other immune cells, cytotoxic T-cells (CTLs) lyse virally infected cells, tumor cells and allografts, and NK cells lyse virally infected cells and tumor cells. "Lymphocytopenia" is characterized by abnormally low level of lymphocytes in the blood. The normal total lymphocyte count is typically about 1000 to 4800/μL in adults, and about 3000 to 9500/μL in children younger than 2 years. At age 6, the lower limit of normal total lymphocyte count is about 1500/μL. Lymphocytopenia is often characterized by a total lymphocyte count of <1000/μL in adults or <3000/μL in children younger than 2 years. Specific examples of lymphocytopenia include T-lymphocytopenia, in which there are too few T-cells (e.g., CD4+ T-cell counts below about 300 cells/μL) but often normal numbers of other lymphocytes, B lymphocytopenia, in which there are too few B lymphocytes but often normal numbers of other lymphocytes, and NK lymphocytopenia, in which there are there are too few natural killer cells but often normal numbers of other lymphocytes.

"Lymphocytosis" refers to an abnormally high lymphocyte count, often characterized by a total lymphocyte count that is more than 40% above normal. In adults, absolute lymphocytosis is typically present when the absolute lymphocyte count is greater than 4000 per microliter, in older children greater than 7000 per microliter, and in infants greater than 9000 per microliter. Relative lymphocytosis may occur when there is a higher proportion (greater than 40%) of lymphocytes among the white blood cells, and when lymphocyte count (ALC) is normal (less than about 4000 per microliter).

The term "modulating" includes "increasing" or "stimulating," as well as "decreasing" or "reducing," typically in a statistically significant or a physiologically significant amount.

By "enhance" or "enhancing," or "increase" or "increasing," or "stimulate" or "stimulating," refers generally to the ability of one or agents or compositions to produce or cause a greater physiological response (i.e., downstream effects) in a cell, as compared to the response caused by either no monomeric AARS polypeptide or a control molecule/composition. Examples of measurable physiological responses include increased levels or activity of CXC receptors such as CXCR-1 and CXCR-2, increased migration of PMNCs such as leukocytes, or increases in an inflammatory or angiogenic response. Other examples will be apparent from the understanding in the art and the description herein. An "increased" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and decimal points in between and above 1), e.g., 1.5, 1.6, 1.7. 1.8, etc.) the amount produced by no monomeric AARS polypeptide (the absence of an agent) or a control composition.

The term "reduce" or "inhibit" may relate generally to the ability of one or more monomeric AARS polypeptides of the invention to "decrease" a relevant physiological or cellular response, including a symptom of a disease or condition described herein, as measured according to routine techniques in the diagnostic art. Relevant physiological or cellular responses (in vivo or in vitro) will be apparent to persons skilled in the art, and may include, for example, reductions in inflammation or other physiological response. Also included, for example, are reductions in angiogenesis. Merely by way of illustration, exemplary symptoms may include reductions in tumor growth, often associated with decreased angiogenesis. A "decrease" in a response may be statistically significant as compared to the response produced by no monomeric AARS polypeptide or a control composition, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

As noted above, also included are increases in migration, such as the migration induced by chemokine receptor signaling. Also included are reductions in migration, such as the migration induced by angiogenic signaling. "Migration" refers to cellular migration, a process that can be measured according to routine in vitro assays, as described herein and known in the art. Migration also refers to in vivo migration, such as the migration of cells from one tissue to another tissue (e.g., from bone marrow to peripheral blood, or from peripheral blood to a particular tissue), or from a site within one tissue to another site within the same tissue. Migration in vivo (e.g., chemotaxis) often occurs in a response to infection or damaged/irritated tissue, or in response to angiogenic signals.

"Treatment" or "treating," as used herein, includes any desirable effect on the symptoms or pathology of a disease or condition associated with the modulatory activities of a monomeric AARS polypeptide as described herein, and may include even minimal changes or improvements in one or more measurable markers of the disease or condition being treated. "Treatment" or "treating" does not necessarily indicate complete eradication or cure of the disease or condition, or associated symptoms thereof. The subject receiving this treatment is any animal in need, including primates, in particular humans, and other mammals such as equines, cattle, swine and sheep; and poultry and pets in general. Exemplary markers of clinical improvement include an altered (e.g., increased or decreased) inflammatory or immune response.

In certain embodiments, monomeric AARS polypeptides possess angiostatic activity, and can be used to treat essentially any condition that would benefit from decreased angiogenesis. For example, angiostatic compositions of the invention may be used in treating or ameliorating the symptoms of disease conditions which rely upon angiogenesis and/or neovascularization, such as treating a solid tumor or tumor metastasis. The angiostatic compositions may also be used to treat conditions characterized by abnormal angiogenesis, such as rheumatoid arthritis, other arthritides, psoriasis, hyperangiogenic diseases, diabetic retinopathy, retinopathy of prematurity, ischemic retinopathy, macular degeneration, diabetic nephropathy. Further still, angiostatic compositions of the invention may be used to oppose the angiogenic activity of endogenous and/or exogenous angiogenic factors.

By "vector" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extra-chromosomal entity, the replication of which is independent of chromosomal replication, e.g., a linear or closed circular plasmid, an extra-chromosomal element, a minichromosome, or an artificial chromosome. The vector can contain any means for assuring self-replication. Alternatively, the vector can be one which, when introduced into the host cell, is integrated into the genome and replicated together with the chromosome(s) into which it has been integrated. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector is preferably one which is operably functional in a bacterial cell. The vector can also include a selection marker such as an antibiotic resistance gene that can be used for selection of suitable transformants.

The terms "wild-type" and "naturally occurring" are used interchangeably to refer to a gene or gene product that has the characteristics of that gene or gene product when isolated from a naturally occurring source. A wild-type gene or gene product (e.g., a polypeptide) is that which is most frequently observed in a population and is thus arbitrarily designed the "normal" or "wild-type" form of the gene.

Aminoacyl-tRNA Synthetase Polypeptides

The present invention relates generally to isolated and substantially monomeric aminoacyl-tRNA synthetases (AARS) polypeptides having non-canonical biological activities, polynucleotides encoding such polypeptides, binding agents that bind such polypeptides, analogs, variants and fragments of such polypeptides, etc., as well as compositions and methods of using any of the foregoing. An AARS polypeptide is typically characterized as monomeric when it does not substantially dimerize with itself or with a second AARS polypeptide, as described herein.

As noted above, monomeric AARS polypeptides of the present invention include tyrosyl-tRNA synthetase (YRS), a tryptophanyl-tRNA synthetase (WRS), a glutaminyl-tRNA synthetase (QRS), a glycyl-tRNA synthetase (GlyRS), a histidyl-tRNA synthetase (HisRS), a seryl-tRNA synthetase (SRS), a phenylalanyl-tRNA synthetase (PheRS), an alanyltRNA synthetase (AlaRS), an asparaginyl-tRNA synthetase (AsnRS), an aspartyl-tRNA synthetase (AspRS), a cysteinyl-tRNA synthetase (CysRS), a glutamyl-tRNA synthetase (ERS), a prolyl-tRNA synthetase (ProRS), an arginyl-tRNA synthetase (RRS), an isoleucyl-tRNA synthetase (IRS), a leucyl-tRNA synthetase (LRS), a lysyl-tRNA synthetase (KRS), a threonyl-tRNA synthetase (TRS), a methionyl-tRNA synthetases (MRS), or a valyl-tRNA synthetase (VRS). Exemplary wild-type sequences of these AARS polypeptides are known in the art, and are referred to in Table A below.

TABLE A

Human AARS Polypeptide Sequences

| AARS | UniProtKB/Swiss-Prot |
| --- | --- |
| YRS | P54577 (SYYC_HUMAN) |
|  | Q9Y2Z4 (SYYM_HUMAN) |
| WRS | P23381 (SYWC_HUMAN) |
| QRS | P47897 (SYQ_HUMAN) |
| GlyRS | P41250 (SYG_HUMAN) |
| HisRS | P12081 (SYHC_HUMAN) |
| SRS | P49591 (SYSC_HUMAN) |
|  | Q9NP81 (SYSM_HUMAN) |
| PheRS | O95363 (SYFM_HUMAN) |
|  | Q9Y285 (SYFA_HUMAN) |
|  | Q9NSD9 (SYFB_HUMAN) |
| AlaRS | P49588 (SYAC_HUMAN) |
|  | Q5JTZ9 (SYAM_HUMAN) |
| AsnRS | O43776 (SYNC_HUMAN) |
|  | Q96I59 (SYNM_HUMAN) |
| AspRS | P14868 (SYDC_HUMAN) |
|  | Q6PI48 (SYDM_HUMAN) |
| CysRS | P49589 (SYCC_HUMAN) |
|  | Q9HA77 (SYCM_HUMAN) |
| ERS | P07814 (SYEP_HUMAN) |
|  | Q5JPH6 (SYEM_HUMAN) |
| ProRS | P07814 (SYEP_HUMAN) |
|  | Q7L3T8 (SYPM_HUMAN) |
| RRS | P54136 (SYRC_HUMAN) |
|  | Q5T160 (SYRM_HUMAN) |
| IRS | P41252 (SYIC_HUMAN) |
|  | Q9NSE4 (SYIM_HUMAN) |
| LRS | Q9P2J5 (SYLC_HUMAN) |
|  | Q15031 (SYLM_HUMAN) |
| KRS | Q15046 (SYK_HUMAN) |
| TRS | P26639 (SYTC_HUMAN) |
|  | Q9BW92 (SYTM_HUMAN) |
|  | A2RTX5 (SYTC2_HUMAN) |
| MRS | P56192 (SYMC_HUMAN) |
| VRS | P26640 (SYVC_HUMAN) |
|  | Q5ST30 (SYVM_HUMAN) |

As one exemplary AARS polypeptide, tyrosyl-tRNA synthetases (YRS or TyrRS) belong to the class I tRNA synthetase family, which has two highly conserved sequence motifs at the active site, HIGH and KMSKS. Class I tRNA synthetases aminoacylate at the 2'-OH of an adenosine nucleotide, and are usually monomeric or dimeric (one or two subunits, respectively).

The human tyrosyl-tRNA synthetase is composed of three domains: 1) an amino-terminal Rossmann fold domain that is responsible for formation of the activated E.Tyr-AMP intermediate and is conserved among bacteria, archeae, and eukaryotes; 2) a tRNA anticodon recognition domain that has not been conserved between bacteria and eukaryotes; and 3) a carboxyl-terminal domain that is unique to the human tyrosyl-tRNA synthetase, and whose primary structure is 49% identical to the putative human cytokine endothelial monocyte-activating protein II, 50% identical to the carboxyl-terminal domain of methionyl-tRNA synthetase from *Caenorhabditis elegans*, and 43% identical to the carboxyl-terminal domain of Arc1p from *Saccharomyces cerevisiae*.

The first two domains of the human tyrosyl-tRNA synthetase are 52, 36, and 16% identical to tyrosyl-tRNA synthetases from *S. cerevisiae, Methanococcus jannaschii*, and *Bacillus stearothermophilus*, respectively. Nine of fifteen amino acids known to be involved in the formation of the tyrosyl-adenylate complex in *B. stearothermophilus* are conserved across all of the organisms, whereas amino acids involved in the recognition of tRNA$^{Tyr}$ are not conserved. Kinetic analyses of recombinant human and *B. stearothermophilus* tyrosyl-tRNA synthetases expressed in *Escherichia coli* indicate that human tyrosyl-tRNA synthetase aminoacylates human but not *B. stearothermophilus* tRNA$^{Tyr}$, and vice versa. It is believed that the carboxyl-terminal domain of human tyrosyl-tRNA synthetase evolved from gene duplication of the carboxyl-terminal domain of methionyl-tRNA synthetase and may direct tRNA to the active site of the enzyme.

Biological fragments of eukaryotic tyrosyl-tRNA synthetases connect protein synthesis to cell-signaling pathways. These fragments may be produced naturally by either alternative splicing or proteolysis, or by artificial proteolytic treatment. For example, the N-terminal fragment mini-YRS is capable of modulating inflammatory responses in vivo. In addition, certain mutations in the full-length YRS polypeptide sequence confer increased inflammatory response-modulating activity on the reference sequence (e.g., Y341A). Examples of truncated splice variants of the full-length YRS polypeptide sequence include the SP1-SP5 polypeptides.

The full-length amino acid sequence of human tyrosyl-tRNA synthetase is set forth in SEQ ID NO:1. The structure of human mini-YRS (SEQ ID NO:3), which contains both the catalytic and the anticodon recognition domain, has been reported to a resolution of 1.18 Å. Whereas the catalytic domains of the human and bacterial enzymes superimpose, the spatial disposition of the anticodon recognition domain relative to the catalytic domain is unique in mini-YRS relative to the bacterial orthologs. Certain embodiments may exclude the YRS polypeptides of SEQ ID NO:1 or 3, and/or certain YRS C-domain fragments.

Particular examples of biologically active YRS fragments include, but are not limited to, C-terminally truncated tyrosyl-tRNA synthetase polypeptides comprising or consisting of amino acids 1-343, amino acids 1-344, amino acids 1-350, amino acids 1-353, or amino acids 1-364 of the amino acid sequence set forth in SEQ ID NO:1, in addition to the polypeptides of SEQ ID NOS:3 and 4, which have been modified to be substantially monomeric in form. Specific examples of YRS polypeptide variants include full-length YRS polypeptides, or truncations or splice variants thereof, having one or more amino acid substitutions selected from an R93Q substitution, an I14L substitution, an N17G substitution, an L271 substitution, an A85S substitution, and a V156L substitution, in addition to combinations thereof, any of which can be modified in a substantially monomeric form of a YRS polypeptide.

As another exemplary AARS polypeptide, tryptophanyl-tRNA synthetases (WRS or TrpRS), also referred to as tryptophan-tRNA ligases, belong to the class I tRNA synthetase family. Tryptophanyl-tRNA synthetase catalyzes the aminoacylation of tRNA$^{trp}$ with tryptophan, an essential function in protein synthesis. Human WRS has a kinase domain in the N-terminal region and a serine phosphorylation site near the C-terminus.

Two main forms of human tryptophanyl-tRNA synthetase are produced in vivo through alternative mRNA splicing, to yield the full-length protein (SEQ ID NO: 5), and a fragment thereof, often designated mini-WRS. Also included are human T1-WRS and T2-WRS (SEQ ID NO:7), alternate splice variants that are produced from an IFN-gamma-sensitive promoter, the latter being an N-terminally truncated fragment of WRS, as well as monomeric variants of T2-WRS (see, e.g., SEQ ID NOS:8 and 9). Other splice variants of human WRS are known in the art (see, e.g., Liu et al., *Nucleic Acids Research*, 32(2):719-27, 2004, herein incorporated by reference). Certain embodiments exclude these naturally-occurring variants of WRS, such as T2-WRS.

Structurally, full-length bacterial WRS contains three parts, a canonical dinucleotide-binding fold, a dimer interface, and a helical domain. This enzyme has enough structural homology to tyrosyl-tRNA synthetase (YRS) that the two enzymes can be described as conformational isomers. Structural elements interacting with the activated amino acid, tryptophanyl-5' AMP, are almost exactly as seen in the tyrosyl-5' AMP complex. Also, side chains that recognize indole are also highly conserved, and require reorientation of a "specificity-determining" helix containing a conserved aspartate to assure selection of tryptophan versus tyrosine. The carboxy terminus, which is disordered and therefore not seen in YRS, forms part of the dimer interface in WRS (see Doublie et al., *Structure*. 3:17-31, 1995).

The crystal structure of human T2-WRS has been reported at 2.5 Å resolution. This variant shares a very low sequence homology of 22% with *Bacillus stearothermophilus* WRS (bWRS), however their overall structures are strikingly similar. Structural comparison of T2-WRS with bWRS reveals substantial structural differences in the substrate-binding pocket and at the entrance to the pocket that play important roles in substrate binding and tRNA binding. T2-WRS has a wide opening to the active site and adopts a compact conformation similar to the closed conformation of bWRS. Modeling studies indicate that tRNA binds with the dimeric enzyme and interacts primarily with the connective polypeptide 1 of human WRS via its acceptor arm and the α-helical domain of WRS via its anticodon loop.

The amino acid sequence of the full-length WRS polypeptide (or the main splice variant) is shown in SEQ ID NO:5. The amino acid sequence of the T2-WRS fragment is shown in SEQ ID NO:7, and the substantially monomeric F260EY201EI278E and F260EY201EH130R variants of T2-WRS are shown respectively in SEQ ID NOS:8 and 9. Accordingly, these and other substantially monomeric variants or fragments of WRS polypeptides may in certain embodiments be included within the WRS polypeptides of the present invention. As noted above, however, certain embodiments exclude the specific T2-WRS polypeptide of SEQ ID NO:7.

As another exemplary AARS polypeptide, lysyl-tRNA synthetases (KRS or LysRS) is a member of the class II aminoacyl-tRNA synthetases, and catalyzes the aminoacylation of $tRNA^{lys}$ with lysine, an essential function in protein synthesis. KRS is an $\alpha_2$ homodimer that has multiple ex-aminoacylation functions. For example, KRS interacts with microphthalmia-associated transcription factor (MITF) and upstream stimulatory factor (USF2), as part of a mechanism for transcriptional control of target genes. As another example, KRS is packaged into the HIV virion via its interaction with the Gag protein. The HIV packaging of KRS into the virion also includes a specific cognate tRNA isoacceptor—$tRNA^{Lys3}$. Because the packaged $tRNA^{Lys3}$ is the primer for reverse transcription of the HIV genome, KRS appears to have an important role in the life cycle of the virus.

The amino acid sequence of full-length human cytoplasmic KRS is described in SEQ ID NO:11. Also described is a truncated version of KRS (SEQ ID NO:11) having residues 70-584 of the full-length sequence. Certain embodiments include substantially monomeric KRS polypeptides (e.g., SEQ ID NOS:11, 12) having one or more mutations or other stabilizing modifications (e.g., chemical modifications such as pegylation, insertions) within or proximal to (e.g., on the periphery of) the primary, secondary, or tertiary structure of the dimer interface of KRS (see FIGS. 18-20). Examples of residues that lie proximal to or on the surface of the dimer interface include any one or more of residues E265, 283FIT285, G310, and 539YGLLP543, their positions being defined by full-length KRS sequence of SEQ ID NO:11.

Certain substantially monomeric KRS polypeptides may comprise one or more insertions, including, for example, insertions of homologous and/or heterologous polypeptides sequences. Included are insertions of polypeptides having about 50, 60, 70, 80, 90, 100, 110, 120, 130, 140, 150, 160, 170, 180, 190, 200, 210, 220, 230, 250, 250, or more amino acids in length, including all integers in between. In particular embodiments, an inserted polypeptide sequence has one or more of the following characteristics, such as (i) the polypeptide is not derived from a membrane protein, (ii) the polypeptide has a globular 3D structure, (iii) the polypeptide has a dimension of about 30-40 Å, and/or (iv) the N-terminus and C-terminus of the polypeptide are located in close three-dimensional proximity, including any combination of (i)-(iv). One exemplary polypeptide having all of these characteristics is the *E. coli* flavodoxin protein.

In certain embodiments, the insertion is inserted proximal to or within the dimer interface. In some embodiments, the insertion is inserted at the periphery of the dimer interface (see FIGS. 18-20). The insertion can be inserted proximal to or at residue G310, as defined by the full-length KRS sequence of SEQ ID NO:11. An example of a substantially monomeric KRS polypeptide having the flavodoxin insertion at residue G310 is SEQ ID NO:13, encoded by the nucleotide sequence of SEQ ID NO:14.

According to one aspect of the invention, there are provided substantially monomeric AARS polypeptides having "non-canonical" activities of therapeutic relevance, as well as compositions comprising the same. In certain embodiments, the monomeric AARS polypeptide is a truncated AARS polypeptide, a fragment of an AARS polypeptide, and/or a variant of an AARS polypeptide. A "truncated" AARS, as used herein, refers to an AARS protein which is shorter than its corresponding full-length AARS protein, for example, due to removal of amino acids from its N- and/or C-terminal ends. The extent of the truncation, that is, the number of N- and/or C-terminal amino acid residues removed from a full length AARS protein can vary considerably while still providing desired cellular effects when administered to a cell, tissue or subject, as described herein. In certain embodiments, at least about 5, 10, 15, 20, 25, 50, 75, 100, 150, 200, 250, 300, 350, 400, 450, amino acids, or more, including all intermediate lengths, are truncated from the N- and/or C-terminus of a full-length mammalian AARS protein (see, e.g., SEQ ID NOS:1, 5, and 11; and Table A). Specific examples of naturally-occurring truncated AARS include mini-YRS (SEQ ID NO:3) and T1-WRS and T2-WRS (SEQ ID NO:7), and a KRS fragment (SEQ ID NO:12). Intermediate lengths are intended to include all integers therebetween, for example, 6, 7, 8, etc., 51, 52, 53, etc., 201, 202, 203, etc.

Variant proteins encompassed by the present application are substantially monomeric and biologically active, that is, they continue to possess the "non-canonical" biological activity of a reference AARS polypeptide sequence (e.g., SEQ ID NOS:4 and 8-9). Such variants may result from, for example, genetic polymorphism or from human manipulation. Biologically active variants of a reference AARS polypeptide fragment will have at least 40%, 50%, 60%, 70%, generally at least 75%, 80%, 85%, usually about 90% to 95% or more, and typically about 98% or more sequence similarity or identity with the amino acid sequence of a reference protein (e.g., Table A) as determined by sequence alignment programs described elsewhere herein using default parameters. A monomeric and biologically active variant of a reference AARS polypeptide may differ from that protein generally by as much 300, 200, 100, 50 or 20 amino acid residues or suitably by as few as 1-15 amino acid residues, as few as 1-10, such as 6-10, as few as 5, as few as 4, 3, 2, or even 1 amino acid residue. In some embodiments, an AARS polypeptide differs from the reference sequences in SEQ ID NOS:1, 3-5, 8-9, or 11-13 (or in Table A) by at least one but by less than 15, 10 or 5 amino acid residues. In other embodiments, it differs from these reference sequences by at least one residue but less than 20%, 15%, 10% or 5% of the residues.

A monomeric AARS polypeptide (e.g., SEQ ID NOS:4, 8-9, or 13) may be altered in various ways including amino acid substitutions, deletions, truncations, and insertions, and still retain its substantially monomeric form (i.e., it does not substantially dimerize with itself). In certain embodiments, this end may be achieved by relying on conservative substitutions and/or insertions, as described herein.

Alternatively, an otherwise (predominantly) dimeric AARS reference polypeptide (e.g., Table A or SEQ ID NOS: 1, 3, 5, 7, 11) may be modified in various ways including amino acid substitutions, deletions, truncations, and insertions to interfere with its ability to dimerize, and thereby generate a substantially monomeric AARS polypeptide. In certain embodiments, this end may be achieved by relying on selected modifications, such as modifications to the dimer interface or residues proximal to the dimer interface in the primary, secondary or tertiary structure of the AARS polypeptide. Also included are modifications to other domains that contribute to dimerization.

Methods for such manipulations are generally known in the art. For example, amino acid sequence variants of an AARS polypeptide can be prepared by mutations in the DNA. Methods for mutagenesis and nucleotide sequence alterations are well known in the art. See, for example, Kunkel (1985, *Proc. Natl. Acad. Sci. USA.* 82: 488-492), Kunkel et al., (1987, *Methods in Enzymol,* 154: 367-382), U.S. Pat. No. 4,873,192, Watson, J. D. et al., ("Molecular Biology of the Gene", Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.). Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of AARS polypeptides. Recursive ensemble mutagenesis (REM), a technique which enhances the frequency of functional mutants in the libraries, can be used in combination with the screening assays to identify AARS polypeptide variants (Arkin and Yourvan (1992) *Proc. Natl. Acad. Sci. USA* 89: 7811-7815; Delgrave et al., (1993) *Protein Engineering,* 6: 327-331). Conservative substitutions, such as exchanging one amino acid with another having similar properties, may be desirable as discussed in more detail below.

Monomeric and biologically active AARS polypeptides or fragments thereof may contain conservative amino acid substitutions at various locations along their sequence, as compared, for example, to a reference monomeric AARS amino acid sequence (e.g., SEQ ID NOS:4, 8-9, or 13). A "conservative amino acid substitution" is one in which the amino acid residue is replaced with an amino acid residue having a similar side chain. Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

In making such changes, the hydropathic index of amino acids may also be considered. The importance of the hydropathic amino acid index in conferring interactive biologic function on a protein is generally understood in the art (Kyte and Doolittle, 1982, incorporated herein by reference). For example, it is known that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent protein. In such changes, the substitution of amino acids whose hydrophilicity values are within ±2 is preferred, those within ±1 are particularly preferred, and those within ±0.5 are even more particularly preferred.

This description also characterizes certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. Several amino acid similarity matrices are known in the art (see e.g., PAM120 matrix and PAM250 matrix as disclosed for example by Dayhoff et al., 1978, A model of evolutionary change in proteins). Matrices for determining distance relationships In M. O. Dayhoff, (ed.), Atlas of protein sequence and structure, Vol. 5, pp. 345-358, National Biomedical Research Foundation, Washington D.C.; and by Gonnet et al., (*Science*, 256: 14430-1445, 1992), however, include proline in the same group as glycine, serine, alanine and threonine. Accordingly, for the purposes of the present invention, proline is classified as a "small" amino acid.

The degree of attraction or repulsion required for classification as polar or nonpolar is arbitrary and, therefore, amino acids specifically contemplated by the invention have been classified as one or the other. Most amino acids not specifically named can be classified on the basis of known behaviour.

Amino acid residues can be further sub-classified as cyclic or non-cyclic, and aromatic or non-aromatic, self-explanatory classifications with respect to the side-chain substituent groups of the residues, and as small or large. The residue is considered small if it contains a total of four carbon atoms or less, inclusive of the carboxylcarbon, provided an additional polar substituent is present; three or less if not. Small residues are, of course, always non-aromatic. Dependent on their structural properties, amino acid residues may fall in two or more classes. For the naturally-occurring protein amino acids, sub-classification according to this scheme is presented in Table B.

TABLE B

| Amino acid sub-classification | |
|---|---|
| Sub-classes | Amino acids |
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |

TABLE B-continued

| Amino acid sub-classification | |
|---|---|
| Sub-classes | Amino acids |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

Conservative amino acid substitution also includes, groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional truncated and/or variant AARS polypeptide can readily be determined by assaying its activity, as described herein (see, e.g., Examples 2-4). Conservative substitutions are shown in Table C under the heading of exemplary substitutions Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. After the substitutions are introduced, the variants are screened for biological activity.

TABLE C

| Exemplary Amino Acid Substitutions | | |
|---|---|---|
| Original Residue | Exemplary Substitutions | Preferred Substitutions |
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |

TABLE C-continued

Exemplary Amino Acid Substitutions

| Original Residue | Exemplary Substitutions | Preferred Substitutions |
| --- | --- | --- |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, G., Biochemistry, third edition, Wm.C. Brown Publishers (1993).

Thus, a predicted non-essential amino acid residue in a monomeric AARS polypeptide may be replaced with another amino acid residue from the same side chain family. Alternatively, mutations can be introduced randomly along all or part of an AARS coding sequence, such as by saturation mutagenesis, and the resultant mutants can be screened for an activity of the parent polypeptide to identify mutants which retain that activity. Following mutagenesis of the coding sequences, the encoded peptide can be expressed recombinantly and the activity of the peptide can be determined. A "non-essential" amino acid residue is a residue that can be altered from the reference sequence of an embodiment polypeptide without abolishing or substantially altering one or more of its activities. Suitably, the alteration does not substantially abolish one of these activities, for example, the activity is at least 20%, 40%, 60%, 70% or 80% 100%, 500%, 1000% or more of the AARS reference sequence activity (e.g., CXC receptor agonist activity, angiostatic activity), or its stability as a monomer under physiological conditions or in solution. An "essential" amino acid residue is a residue that, when altered from the sequence a reference AARS polypeptide, results in abolition of an activity of the parent molecule such that less than 20% of the reference or non-canonical activity is present. For example, such essential amino acid residues include those that are conserved in AARS polypeptides across different species, including those sequences that are conserved in the active binding site(s) or motif(s) of AARS polypeptides from various sources.

As noted above, an otherwise dimeric AARS reference polypeptide (e.g., SEQ ID NO:1, 3, 5, 7, 11, or the AARS polypeptides in Table A), or dimerizing fragments or variants thereof, may be modified in various ways including amino acid substitutions, deletions, truncations, and insertions to interfere with its ability to dimerize, and thereby generate a substantially monomeric AARS polypeptide. Certain embodiments may employ one or more selective modifications (e.g., mutations, substitutions, chemical modifications) located in or proximal to the dimer interface, whether in the primary, secondary, or tertiary structure of the AARS polypeptide. Exemplary proximal residues include those that are about 1, 2, 3, 4, 5, 6, 7, 8, 9, 10, 11, 12, 13, 14, 15, 16, 17, 18, 19, or 20 residues to the C-terminal or N-terminal side of the dimer interface of an AARS polypeptide.

Certain specific embodiments may employ modifications at any one or more of residues Pro 159, Leu 160, or Leu 161, as in the full-length YRS or mini-YRS sequence, including combinations thereof. Also included are modifications to residues that are proximal to Pro 159, Leu 160, or Leu 161, whether in the primary, secondary, or tertiary structure of a selected YRS polypeptide. Certain embodiments include a deletion of Pro 159, Leu 160, and Leu 161. Certain specific embodiments may employ mutations or substitutions at any one or more of residues F260, Y201, I278, H130, or E408, as in the full-length WRS or T2-WRS sequence, including combinations thereof. Also included are modifications to residues that are proximal to F260, Y201, I278, H130, or E408, whether in the primary, secondary, or tertiary structure of a selected WRS polypeptide. Exemplary proximal residues include those that are about 1, 2, 3, 4, 5, 6, 7, 8, 9, 10, 11, 12, 13, 14, 15, 16, 17, 18, 19, or 20 residues relative to the C-terminal or N-terminal side of either Pro 159, Leu 160, or Leu 161 in a selected YRS polypeptide, or F260, Y201, I278, H130, or E408 in a selected WRS polypeptide, or residues E265, 283FIT285, G310, or 539YGLLP543 in a selected KRS polypeptide. The position of these residues is typically defined by the corresponding full-length AARS sequence.

As noted above, certain embodiments include AARS having one or more insertional stabilizing modifications. As with the other stabilizing modifications, certain insertions are made within or proximal to the dimer interface of a selected AARS polypeptide. Certain insertions can be made at the periphery of the dimer interface. Included are insertions of homologous or heterologous polypeptides of about 10, 20, 30, 40, 50, 60, 70, 80, 90, 100, 110, 120, 130, 140, 150, 160, 170, 180, 190, 200, 210, 220, 230, 250, 250, or more amino acids in length, including all integers in between. In particular embodiments, an inserted polypeptide sequence has one or more of the following characteristics, such as (i) the polypeptide is not derived from a membrane protein, (ii) the polypeptide has a globular 3D structure, (iii) the polypeptide has a dimension of about 30-40 Å, and/or (iv) the N-terminus and C-terminus of the polypeptide are located in close three-dimensional proximity, including any combination of (i)-(iv).

Accordingly, the present invention contemplates variants of the naturally-occurring AARS polypeptide sequences or their biologically-active fragments, wherein the variants are distinguished from the naturally-occurring sequence by the addition, deletion, or substitution of one or more amino acid residues, and wherein such variants or fragments are substantially monomeric in form. In general, substantially monomeric variants will display at least about 30, 40, 50, 55, 60, 65, 70, 75, 80, 85, 90, 91, 92, 93, 94, 95, 96, 97, 98, 99% similarity or sequence identity to a reference AARS polypeptide sequences, for example, as set forth in SEQ ID NOS:1, 3-5, 7-9, 11-13 or in Table A. Moreover, sequences differing from the native or parent sequences by the addition, deletion, or substitution of 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 140, 150 or more amino acids but which are substantially monomeric and possess a non-canonical activity that differs from a dimeric AARS complex are contemplated. In certain embodiments, the C-terminal or N-terminal region of any of SEQ ID NOS: 1, 3-5, 7-9, 11-13 or in Table A may be truncated by 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, 200, 250, 300, 350, 400, 450, 500, 550, 600, 650, or 700 or more amino acids, or by about 10-50, 20-50, 50-100, 100-150, 150-200, 200-250, 250-300, 300-350, 350-400, 400-450, 450-500, 550-600, 600-650, 650-700 or more amino acids, including all integers and ranges in between (e.g., 101, 102, 103, 104, 105), so long as the truncated AARS polypeptide is substantially monomeric and retains a "non-canonical" biological activity, as described herein.

In some embodiments, variant polypeptides differ from a reference AARS sequence by at least one but by less than 50, 40, 30, 20, 15, 10, 8, 6, 5, 4, 3 or 2 amino acid residue(s). In other embodiments, variant polypeptides differ from the corresponding sequences of SEQ ID NOS: 1, 3-5, 7-9, 11-13 or in Table A by at least 1% but less than 20%, 15%, 10% or 5% of the residues. (If this comparison requires alignment, the sequences should be aligned for maximum similarity. "Looped" out sequences from deletions or insertions, or mismatches, are considered differences.) In certain embodiments, the differences include changes at a non-essential residue or a conservative substitution.

In certain embodiments, a variant monomeric polypeptide includes an amino acid sequence having at least about 50%, 55%, 60%, 65%, 70%, 75%, 80%, 85%, 90%, 91%, 92%, 93%, 94% 95%, 96%, 97%, 98% or more sequence identity or similarity to a corresponding sequence of an AARS polypeptide as, for example, set forth in SEQ ID NOS:1, 3-5, 7-9, 11-13 or in Table A, which is substantially monomeric in form and has the ability to interact with or agonize CXC receptors such as CXCR-1 and CXCR-2, or has the ability to interact with VE-cadherin, or reduce angiogenesis, whether in a subject or in vitro. In relation to the wild-type sequence of human AARS, certain embodiments may employ one or more selective or stabilizing mutations to reduce ability of the AARS variant to dimerize with itself or a second AARS polypeptide.

Calculations of sequence similarity or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch, (1970, *J. Mol. Biol.* 48: 444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5. The percent identity between two amino acid or nucleotide sequences can be determined using the algorithm of E. Meyers and W. Miller (1989, *Cabios,* 4: 11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, *J. Mol. Biol,* 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997, *Nucleic Acids Res,* 25: 3389-3402). When utilizing BLAST and Gapped BLAST programs, the default parameters of the respective programs (e.g., XBLAST and NBLAST) can be used.

Variants of an AARS polypeptide can be identified by screening combinatorial libraries of mutants of an AARS polypeptide. Libraries or fragments e.g., N terminal, C terminal, or internal fragments, of AARS protein coding sequence can be used to generate a variegated population of fragments for screening and subsequent selection of variants of an AARS polypeptide.

Methods for screening gene products of combinatorial libraries made by point mutation or truncation, and for screening cDNA libraries for gene products having a selected property are known in the art. Such methods are adaptable for rapid screening of the gene libraries generated by combinatorial mutagenesis of AARS polypeptides.

In certain embodiments of the invention, there are provided fusion polypeptides, and polynucleotides encoding fusion polypeptides. Fusion polypeptides refer to polypeptides of the invention that have been covalently linked, either directly or indirectly via an amino acid linker, to one or more heterologous polypeptide sequences (fusion partners). The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order.

Fusion proteins include monomeric forms of AARS polypeptides or polypeptide fragments linked to either another AARS polypeptide (e.g., to create multiple fragments), to a non-AARS polypeptide, or to both. A "non-AARS polypeptide" refers to a "heterologous polypeptide" having an amino acid sequence corresponding to a protein which is different from an AARS protein, and which is derived from the same or a different organism. Non-AARS polypeptides may include different AARS polypeptides. The AARS polypeptide of the fusion protein can correspond to all or a portion of a biologically active AARS amino acid sequence. In certain embodiments, an AARS fusion protein includes at least one (or two) biologically active portion of an AARS protein.

The fusion partner may be designed and included for essentially any desired purpose provided they do not adversely affect the desired activity of the polypeptide. For example, in one embodiment, a fusion partner comprises a sequence that assists in expressing the protein (an expression enhancer) at higher yields than the native recombinant protein. Other fusion partners may be selected so as to increase the solubility of the protein or to enable the protein to be targeted to desired intracellular compartments. Still further fusion partners include affinity tags, which facilitate purification of the protein.

Fusion to heterologous sequences, such as an Fc fragment, may be utilized to remove unwanted characteristics or to improve the desired characteristics (e.g., pharmacokinetic properties) of an AARS polypeptide. For instance, fusion to a heterologous sequence may increase chemical stability, decrease immunogenicity, improve in vivo targeting, and/or increase half-life in circulation of an AARS polypeptide.

Fusion to heterologous sequences may also be used to create bi-functional fusion proteins, such as bi-functional proteins that are not only possess a "non-canonical" AARS biological activity, as described herein (e.g., CXC receptor agonist activity), but are also capable of modifying (i.e., stimulating or inhibiting) other pathways through the heterologous polypeptide. Examples of such pathways include, but are not limited to, various immune system-related pathways, such as innate or adaptive immune system activation pathways, or cell-growth or cell-differentiation regulatory pathways, such as hematopoiesis. In certain aspects, the heterologous polypeptide may act synergistically with the AARS polypeptide to regulate a pathway associated with a non-canonical biological activity. Examples of heterologous polypeptides that may be utilized to create a bi-functional fusion protein include, but are not limited to, thrombopoietin, cytokines (e.g., IL-11), chemokines, and various hematopoietic growth factors, in addition to biologically active fragments and/or variants thereof.

Fusion proteins may generally be prepared using standard techniques. For example, DNA sequences encoding the polypeptide components of a desired fusion may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures, if desired. Such a peptide linker sequence is incorporated into the fusion protein using standard techniques well known in the art. Certain peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39 46 (1985); Murphy et al., *Proc. Natl. Acad. Sci. USA* 83:8258 8262 (1986); U.S. Pat. No. 4,935,233 and U.S. Pat. No. 4,751, 180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

In general, polypeptides and fusion polypeptides (as well as their encoding polynucleotides) are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

In other embodiments, an AARS polypeptide of the invention may be part of a multi-unit complex. A multi-unit complex of the present invention can include, for example, at least 2, 3, 4, or 5 or more monomers. The monomers and/or multi-unit complexes of the present invention may be soluble and may be isolated or purified to homogeneity. Monomer units of a multi-unit complex may be different, homologous, substantially homologous, or identical to one another. However, a multi-unit complex of the invention includes at least one monomer comprising an AARS polypeptide as described herein or, in other embodiments, at least two or more AARS polypeptides as described herein.

Covalently linked monomers can be linked directly (by bonds) or indirectly (e.g., via a linker). For directly linking the polypeptide monomers herein, it may be beneficial to modify the polypeptides herein to enhance dimerization. For example, one or more amino acid residues of an AARS polypeptide may be modified by the addition or substation by one or more cysteines. Methods for creating amino acid substitutions, such as cysteine substitutions, or other modifications to facilitate linking, are well known to those skilled in the art.

Certain embodiments of the present invention also contemplate the use of modified AARS polypeptides, including modifications that improve desired characteristics of an AARS polypeptide, as described herein. Illustrative modifications of AARS polypeptides of the invention include, but are not limited to, chemical and/or enzymatic derivatizations at one or more constituent amino acids, including side chain modifications, backbone modifications, and N- and C-terminal modifications including acetylation, hydroxylation, methylation, glycosylation (e.g., N-linked, O-linked), amidation, and the attachment of carbohydrate or lipid moieties, cofactors, and the like. Exemplary modifications also include pegylation of an AARS polypeptide (see, e.g., Veronese and Harris, *Advanced Drug Delivery Reviews* 54: 453-456, 2002, herein incorporated by reference).

In certain aspects, chemoselective ligation technology may be utilized to modify AARS polypeptides of the invention, such as by attaching polymers in a site-specific and controlled manner. Such technology typically relies on the incorporation of chemoselective anchors into the protein backbone by either chemical or recombinant means and subsequent modification with a polymer carrying a complementary linker. As a result, the assembly process and the covalent structure of the resulting protein-polymer conjugate may be controlled, enabling the rational optimization of drug properties, such as efficacy and pharmacokinetic properties (see, e.g., Kochendoerfer, *Current Opinion in Chemical Biology* 9:555-560, 2005).

In certain embodiments, these and other forms of chemical modification may be used to generate a substantially monomeric AARS polypeptide, such as by interfering with the dimer interface or other structural feature required for dimerization (see, e.g., FIG. 1). For instance, certain embodiments may incorporate at least one stabilizing modification by chemically modifying (e.g., pegylation) one or more selected residues within or proximal to the dimer interface of the full-length AARS polypeptide, or a fragment thereof, to prevent or reduce the ability of the AARS polypeptide to dimerize with itself or with a second AARS polypeptide. Merely by way of illustration, residues located within the dimer interface or about 1, 2, 3, 4, 5, 6, 7, 8, 9, 10, 11, 12, 14, 15, 16, 17, 18, 19, 20 to the C-terminal or N-terminal side of the dimer interface, or residues proximal in the secondary or tertiary structure of the dimer interface, may be chemically modified, or may be first mutated to an appropriate residue (e.g., a residue that better accepts pegylation or glycosylation) and then chemically modified.

For YRS, any one or more of residues 159-161 (or their nearby residues, including residues within 1, 2, 3, 4, 5, 6, 7, 8, 9, 10, or more residues of 159-161, or residues proximal in the primary, secondary, or tertiary structure of YRS) may be chemically modified, or may be first mutated to an appropriate residue (e.g., a residue that better accepts pegylation or glycosylation) and then chemically modified. For WRS, any one or more of residues F260, Y201, I278, H130, or E408 (or their nearby residues, including residues within 1, 2, 3, 4, 5, 6, 7, 8, 9, 10, or more residues of F260, Y201, I278, H130, or E408, or residues proximal in the primary, secondary, or tertiary structure of WRS) may be chemically modified, or may be first mutated to an appropriate residue (e.g., a residue that better accepts pegylation) and then chemically modified.

In certain embodiments, the AARS polypeptides of the present invention may specifically include or specifically exclude any one or more of the structural and/or functional features described herein.

The substantially monomeric AARS polypeptides of the invention may be prepared by any suitable procedure known to those of skill in the art, such as by recombinant techniques. For example, AARS polypeptides may be prepared by a procedure including the steps of: (a) preparing a construct comprising a polynucleotide sequence that encodes an AARS polypeptide and that is operably linked to a regulatory element; (b) introducing the construct into a host cell; (c) culturing the host cell to express the AARS polypeptide; and (d) isolating the AARS polypeptide from the host cell. Recombinant AARS polypeptides can be conveniently prepared using standard protocols as described for example in Sambrook, et al., (1989, supra), in particular Sections 16 and 17; Ausubel et al., (1994, supra), in particular Chapters 10 and 16; and Coligan et al., Current Protocols in Protein Science (John Wiley & Sons, Inc. 1995-1997), in particular Chapters 1, 5 and 6.

In addition to recombinant production methods, polypeptides of the invention, and fragments thereof, may be produced by direct peptide synthesis using solid-phase techniques (Merrifield, *J. Am. Chem. Soc.* 85:2149-2154 (1963)). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the desired molecule.

Polynucleotide Compositions

The present invention also provides isolated polynucleotides that encode the AARS polypeptides of the invention, as well as compositions comprising such polynucleotides.

As used herein, the terms "DNA" and "polynucleotide" and "nucleic acid" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the polynucleotide sequences of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will be recognized by the skilled artisan, polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an AARS or a portion thereof) or may comprise a variant, or a biological functional equivalent of such a sequence. Polynucleotide variants may contain one or more substitutions, additions, deletions and/or insertions, as further described below, preferably such that the desired activity of the encoded polypeptide is not substantially diminished relative to the unmodified polypeptide. The effect on the activity of the encoded polypeptide may generally be assessed as described herein.

In additional embodiments, the present invention provides isolated polynucleotides comprising various lengths of contiguous stretches of sequence identical to or complementary to an AARS, wherein the isolated polynucleotides encode an AARS as described herein. Exemplary nucleotide sequences that encode the AARS polypeptides of the application encompass coding sequences, such as the polynucleotide sequence of SEQ ID NO:2 or 6 or 14 (or the coding sequences of the AARS polypeptides in Table A, including monomeric variants thereof), as well as portions of the full-length or substantially full-length nucleotide sequences of the AARS genes or their transcripts or DNA copies of these transcripts.

Portions of an AARS nucleotide sequence may encode polypeptide portions or segments that retain the non-canonical biological activity of the reference polypeptide, including for illustrative purposes the polypeptide of SEQ ID NOS:4, 8-9, or 13. A portion of an AARS nucleotide sequence that encodes a biologically active fragment of an AARS polypeptide may encode at least about 20, 21, 22, 23, 24, 25, 30, 40, 50, 60, 70, 80, 90, 100, 120, 150, 300, 400, 450 or more contiguous amino acid residues, or almost up to the total number of amino acids present in a full-length AARS polypeptide, as well as intermediate lengths, as long as it encodes a substantially monomeric form of an AARS polypeptide. It will be readily understood that "intermediate lengths," in this context and in all other contexts used herein, means any length between the quoted values, such as 101, 102, 103, etc.; 151, 152, 153, etc.; 201, 202, 203, etc.

The invention also contemplates variants of the AARS nucleotide sequences. Nucleic acid variants can be naturally-occurring, such as allelic variants (same locus), homologs (different locus), and orthologs (different organism) or can be non naturally-occurring. Naturally occurring variants such as these can be identified with the use of well-known molecular biology techniques, as, for example, with polymerase chain reaction (PCR) and hybridization techniques as known in the art. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product). For nucleotide sequences, conservative variants include those sequences that, because of the degeneracy of the genetic code, encode the amino acid sequence of a reference AARS polypeptide, such as the sequences set forth in SEQ ID NO:2 and 6 or 14. Variant nucleotide sequences also include synthetically derived nucleotide sequences, such as those generated, for example, by using site-directed mutagenesis but which still encode a monomeric AARS polypeptide, as described herein. Generally, variants of a particular monomeric AARS nucleotide sequence may have at least about 30%, 40% 50%, 55%, 60%, 65%, 70%, generally at least about 75%, 80%, 85%, desirably about 90% to 95% or more, and more suitably about 98% or more sequence identity to that particular nucleotide sequence as determined by sequence alignment programs described elsewhere herein using default parameters.

AARS nucleotide sequences can be used to isolate corresponding sequences and alleles from other organisms, particularly other organisms or microorganisms. Methods are readily available in the art for the hybridization of nucleic acid sequences. Coding sequences from other organisms may be isolated according to well known techniques based on their sequence identity with the coding sequences set forth herein. In these techniques all or part of the known coding sequence is used as a probe which selectively hybridizes to other AARS-coding sequences present in a population of cloned genomic DNA fragments or cDNA fragments (i.e., genomic or cDNA libraries) from a chosen organism.

Accordingly, the present invention also contemplates polynucleotides that hybridize to reference AARS nucleotide sequences, or to their complements, under stringency conditions described below. As used herein, the term "hybridizes under low stringency, medium stringency, high stringency, or very high stringency conditions" describes conditions for hybridization and washing. Guidance for performing hybridization reactions can be found in Ausubel et al., (1998, supra), Sections 6.3.1-6.3.6. Aqueous and non-aqueous methods are described in that reference and either can be used. Reference herein to low stringency conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M NaHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at room temperature. One embodiment of low stringency conditions includes hybridization in 6× sodium chloride/sodium citrate (SSC) at about 45°☐ C., followed by two washes in 0.2×SSC, 0.1% SDS at least at 50° C. (the temperature of the washes can be increased to 55° C. for low stringency conditions). Medium stringency conditions include and encompass from at least about 16% v/v to at least about 30% v/v formamide and from at least about 0.5 M to at least about 0.9 M salt for hybridization at 42° C., and at least about 0.1 M to at least about 0.2 M salt for washing at 55° C. Medium stringency conditions also may include 1% Bovine Serum Albumin (BSA), 1 mM EDTA, 0.5 M NaHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at 60-65° C. One embodiment of medium stringency conditions includes hybridizing in 6×SSC at about 45°☐ C., followed by one or more washes in 0.2×SSC, 0.1% SDS at 60° C. High stringency conditions include and encompass from at least about 31% v/v to at least about 50% v/v formamide and from about 0.01 M to about 0.15 M salt for hybridization at 42° C., and about 0.01 M to about 0.02 M salt for washing at 55° C. High stringency conditions also may include 1% BSA, 1 mM EDTA, 0.5 M NaHPO$_4$ (pH 7.2), 7% SDS for hybridization at 65° C., and (i) 0.2×SSC, 0.1% SDS; or (ii) 0.5% BSA, 1 mM EDTA, 40 mM NaHPO$_4$ (pH 7.2), 1% SDS for washing at a temperature in excess of 65° C. One embodiment of high stringency conditions includes hybridizing in 6×SSC at about 45° C., followed by one or more washes in 0.2×SSC, 0.1% SDS at 65° C.

In certain embodiments, an AARS polypeptide is encoded by a polynucleotide that hybridizes to a disclosed nucleotide sequence under very high stringency conditions. One embodiment of very high stringency conditions includes hybridizing in 0.5 M sodium phosphate, 7% SDS at 65° C., followed by one or more washes in 0.2×SSC, 1% SDS at 65° C.

Other stringency conditions are well known in the art and a skilled addressee will recognize that various factors can be manipulated to optimize the specificity of the hybridization. Optimization of the stringency of the final washes can serve to ensure a high degree of hybridization. For detailed examples, see Ausubel et al., supra at pages 2.10.1 to 2.10.16 and Sambrook et al. (1989, supra) at sections 1.101 to 1.104.

While stringent washes are typically carried out at temperatures from about 42° C. to 68° C., one skilled in the art will appreciate that other temperatures may be suitable for stringent conditions. Maximum hybridization rate typically occurs at about 20° C. to 25° C. below the $T_m$ for formation of a DNA-DNA hybrid. It is well known in the art that the $T_m$ is the melting temperature, or temperature at which two complementary polynucleotide sequences dissociate. Methods for estimating $T_m$ are well known in the art (see Ausubel et al., supra at page 2.10.8).

In general, the $T_m$ of a perfectly matched duplex of DNA may be predicted as an approximation by the formula: $T_m = 81.5 + 16.6 (\log_{10} M) + 0.41 (\% G+C) - 0.63 (\% \text{formamide}) - (600/\text{length})$ wherein: M is the concentration of Na$^+$, preferably in the range of 0.01 molar to 0.4 molar; % G+C is the sum of guanosine and cytosine bases as a percentage of the total number of bases, within the range between 30% and 75% G+C; % formamide is the percent formamide concentration by volume; length is the number of base pairs in the DNA duplex. The $T_m$ of a duplex DNA decreases by approximately 1° C. with every increase of 1% in the number of randomly mismatched base pairs. Washing is generally carried out at $T_m - 15°$ C. for high stringency, or $T_m - 30°$ C. for moderate stringency.

In one example of a hybridization procedure, a membrane (e.g., a nitrocellulose membrane or a nylon membrane) containing immobilized DNA is hybridized overnight at 42° C. in a hybridization buffer (50% deionized formamide, 5×SSC, 5×Denhardt's solution (0.1% ficoll, 0.1% polyvinylpyrollidone and 0.1% bovine serum albumin), 0.1% SDS and 200 mg/mL denatured salmon sperm DNA) containing a labeled probe. The membrane is then subjected to two sequential medium stringency washes (i.e., 2×SSC, 0.1% SDS for 15 min at 45° C., followed by 2×SSC, 0.1% SDS for 15 min at 50° C.), followed by two sequential higher stringency washes (i.e., 0.2×SSC, 0.1% SDS for 12 min at 55° C. followed by 0.2×SSC and 0.1% SDS solution for 12 min at 65-68° C.

Moreover, it will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention, for example polynucleotides that are optimized for human and/or primate codon selection. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a polynucleotide fragment of almost any length may be employed; with the total length preferably being limited by the ease of preparation and use in the intended recombinant DNA protocol.

Polynucleotides and fusions thereof may be prepared, manipulated and/or expressed using any of a variety of well established techniques known and available in the art. For example, polynucleotide sequences which encode polypeptides of the invention, or fusion proteins or functional equivalents thereof, may be used in recombinant DNA molecules to direct expression of an AARS polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, expression and/or activity of the gene product.

In order to express a desired polypeptide, a nucleotide sequence encoding the polypeptide, or a functional equivalent, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., Molecular Cloning, A Laboratory Manual (1989), and Ausubel et al., Current Protocols in Molecular Biology (1989).

A variety of expression vector/host systems are known and may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, vectors which direct high level expression of fusion proteins that are readily purified may be used. Such vectors include, but are not limited to, the multifunctional E. coli cloning and expression vectors such as BLUESCRIPT (Stratagene), in which the sequence encoding the polypeptide of interest may be ligated into the vector in frame with sequences for the amino-terminal Met and the subsequent 7 residues of β-galactosidase so that a hybrid protein is produced; pIN vectors (Van Heeke & Schuster, J. Biol. Chem. 264:5503 5509 (1989)); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, Saccharomyces cerevisiae, a number of vectors containing constitutive or inducible promoters such as alpha factor, alcohol oxidase, and PGH may be used. For reviews, see Ausubel et al. (supra) and Grant et al., *Methods Enzymol.* 153:516-544 (1987).

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, *EMBO J.* 6:307-311 (1987)). Alternatively, plant promoters such as the small subunit of RUBISCO or heat shock promoters may be used (Coruzzi et al., *EMBO J.* 3:1671-1680 (1984); Broglie et al., *Science* 224:838-843 (1984); and Winter et al., *Results Probl. Cell Differ.* 17:85-105 (1991)). These constructs can be introduced into plant cells by direct DNA transformation or pathogen-mediated transfection. Such techniques are described in a number of generally available reviews (see, e.g., Hobbs in McGraw Hill, *Yearbook of Science and Technology*, pp. 191-196 (1992)).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia larvae*. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia larvae* in which the polypeptide of interest may be expressed (Engelhard et al., *Proc. Natl. Acad. Sci. U.S.A.* 91:3224-3227 (1994)).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan & Shenk, *Proc. Natl. Acad. Sci. U.S.A.* 81:3655-3659 (1984)). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf. et al., *Results Probl. Cell Differ.* 20:125-162 (1994)).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler et al., *Cell* 11:223-232 (1977)) and adenine phosphoribosyltransferase (Lowy et al., *Cell* 22:817-823 (1990)) genes which can be employed in tk- or aprt-cells, respectively. Also, antimetabolite, antibiotic or herbicide resistance can be used as the basis for selection; for example, dhfr which confers resistance to methotrexate (Wigler et al., *Proc. Natl. Acad. Sci. U.S.A.* 77:3567-70 (1980)); npt, which confers resistance to the aminoglycosides, neomycin and G-418 (Colbere-Garapin et al., *J. Mol. Biol.* 150:1-14 (1981)); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman & Mulligan, *Proc. Natl. Acad. Sci. U.S.A.* 85:8047-51 (1988)). The use of visible markers has gained popularity with such markers as anthocyanins, β-glucuronidase and its substrate GUS, and luciferase and its substrate luciferin, being widely used not only to identify transformants, but also to quantify the amount of transient or stable protein expression attributable to a specific vector system (Rhodes et al., *Methods Mol. Biol.* 55:121-131 (1995)).

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). These and other assays are described, among other places, in Hampton et al., *Serological Methods, a Laboratory Manual* (1990) and Maddox et al., *J. Exp. Med.* 158:1211-1216 (1983).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins.

In addition to recombinant production methods, polypeptides of the invention, and fragments thereof, may be produced by direct peptide synthesis using solid-phase techniques (Merrifield, *J. Am. Chem. Soc.* 85:2149-2154 (1963)). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

According to another aspect of the invention, polynucleotides encoding polypeptides of the invention may be delivered to a subject in vivo, e.g., using gene therapy techniques. Gene therapy refers generally to the transfer of heterologous nucleic acids to the certain cells, target cells, of a mammal, particularly a human, with a disorder or conditions for which such therapy is sought. The nucleic acid is introduced into the selected target cells in a manner such that the heterologous DNA is expressed and a therapeutic product encoded thereby is produced.

Various viral vectors that can be utilized for gene therapy as taught herein include adenovirus, herpes virus, vaccinia, adeno-associated virus (AAV), or, preferably, an RNA virus such as a retrovirus. Preferably, the retroviral vector is a derivative of a murine or avian retrovirus, or is a lentiviral vector. The preferred retroviral vector is a lentiviral vector. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), SIV, BIV, HIV and Rous Sarcoma Virus (RSV). A number of additional retroviral vectors can incorporate multiple genes. All of these vectors can transfer or incorporate a gene for a selectable marker so that transduced cells can be identified and generated. By inserting a zinc finger derived-DNA binding polypeptide sequence of interest into the viral vector, along with another gene that encodes the ligand for a receptor on a specific target cell, for example, the vector may be made target specific. Retroviral vectors can be made target specific by inserting, for example, a polynucleotide encoding a protein (dimer). Illustrative targeting may be accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the zinc finger-nucleotide binding protein polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsulation. Helper cell lines which have deletions of the packaging signal include but are not limited to .PSI.2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced. The vector virions produced by this method can then be used to infect a tissue cell line, such as NIH 3T3 cells, to produce large quantities of chimeric retroviral virions.

"Non-viral" delivery techniques for gene therapy can also be used including, for example, DNA-ligand complexes, adenovirus-ligand-DNA complexes, direct injection of DNA, $CaPO_4$ precipitation, gene gun techniques, electroporation, liposomes, lipofection, and the like. Any of these methods are widely available to one skilled in the art and would be suitable for use in the present invention. Other suitable methods are available to one skilled in the art, and it is to be understood that the present invention can be accomplished using any of the available methods of transfection. Lipofection can be accomplished by encapsulating an isolated DNA molecule within a liposomal particle and contacting the liposomal particle with the cell membrane of the target cell. Liposomes are self-assembling, colloidal particles in which a lipid bilayer, composed of amphiphilic molecules such as phosphatidyl serine or phosphatidyl choline, encapsulates a portion of the surrounding media such that the lipid bilayer surrounds a hydrophilic interior. Unilammellar or multilammellar liposomes can be constructed such that the interior contains a desired chemical, drug, or, as in the instant invention, an isolated DNA molecule.

Antibody Compositions, Fragments Thereof, and Other Binding Agents

According to another aspect, the present invention further provides compounds (e.g., small molecules) and other binding agents, such as antibodies, antigen-binding fragments thereof, soluble receptors, etc., that exhibit binding specificity for a polypeptide or its binding partner disclosed herein, or to a portion, variant or derivative thereof, and methods of using same. Preferably, such binding agents are effective for modulating one or more of the non-canonical activities mediated by a monomeric AARS polypeptide of the invention. In certain embodiments, for example, the binding agent is one that binds to a monomeric AARS polypeptide of the invention and inhibits its ability to bind to one or more of its cellular binding partners. In certain embodiments, the binding agent does not substantially bind to an AARS dimer. A specific example is a compound or binding agent that inhibits the ability of HIV Gag to interact with monomeric KRS. Accordingly, such binding agents may be used to treat or prevent diseases, disorders or other conditions that are mediated by a monomeric AARS polypeptide of the invention by antagonizing it activity.

In specific embodiments, compounds or binding agents (e.g., antibodies and fragments thereof) specifically bind to (a) an H3 and/or H4 region of a human immunodeficiency virus (HIV) Gag-CA-CTD domain, (b) an inter-domain cavity of substantially monomeric KRS which interacts with the H3 and/or H3 region of Gag-CA-CTD domain, or both (a) and (b), and reduce the interaction between HIV Gag and monomeric KRS. In certain embodiments, the compound or binding agent binds to the bottom side of H3 or H4 or both. In certain embodiments, the compound or binding agent mimics the three-dimensional structure of the Gag-CA-CTD domain comprising the H3 and/or H4 region. Also included are methods of reducing assembly of a human immunodeficiency virus (HIV), comprising contacting an HIV-infected cell with a compound or binding described above. Such methods, compounds, and agents can be used in the treatment of HIV infection.

An antibody, or antigen-binding fragment thereof, is said to "specifically bind," "immunologically bind," and/or is "immunologically reactive" to a polypeptide of the invention if it reacts at a detectable level (within, for example, an ELISA assay) with the polypeptide, and does not react detectably with unrelated polypeptides under similar conditions.

Immunological binding, as used in this context, generally refers to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) Annual Rev. Biochem. 59:439-473.

An "antigen-binding site," or "binding portion" of an antibody, refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

A binding agent may be, for example, a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for a polypeptide of interest may be prepared, for example, using the technique of Kohler and Milstein, *Eur. J. Immunol.* 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

A number of therapeutically useful molecules are known in the art which comprise antigen-binding sites that are capable of exhibiting immunological binding properties of an antibody molecule. The proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "F(ab')$_2$" fragment which comprises both antigen-binding sites. An "Fv" fragment can be produced by preferential proteolytic cleavage of an IgM, and on rare occasions IgG or IgA immunoglobulin molecule. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule. Inbar et al. (1972) *Proc. Nat. Acad. Sci. USA* 69:2659-2662; Hochman et al. (1976) *Biochem* 15:2706-2710; and Ehrlich et al. (1980) *Biochem* 19:4091-4096.

A single chain Fv ("sFv") polypeptide is a covalently linked $V_H$::$V_L$ heterodimer which is expressed from a gene fusion including $V_H$- and $V_L$-encoding genes linked by a peptide-encoding linker. Huston et al. (1988) Proc. Nat. Acad. Sci. USA 85(16):5879-5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

Each of the above-described molecules includes a heavy chain and a light chain CDR set, respectively interposed between a heavy chain and a light chain FR set which provide support to the CDRS and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRS. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

A number of "humanized" antibody molecules comprising an antigen-binding site derived from a non-human immunoglobulin have been described, including chimeric antibodies having rodent V regions and their associated CDRs fused to human constant domains (Winter et al. (1991) Nature 349: 293-299; Lobuglio et al. (1989) Proc. Natl. Acad. Sci. USA 86:4220-4224; Shaw et al. (1987) J. Immunol. 138:4534-4538; and Brown et al. (1987) Cancer Res. 47:3577-3583), rodent CDRs grafted into a human supporting FR prior to fusion with an appropriate human antibody constant domain (Riechmann et al. (1988) Nature 332:323-327; Verhoeyen et al. (1988) Science 239:1534-1536; and Jones et al. (1986) Nature 321:522-525), and rodent CDRs supported by recombinantly veneered rodent FRs (European Patent Publication No. 519,596, published Dec. 23, 1992). These "humanized" molecules are designed to minimize unwanted immunological response toward rodent antihuman antibody molecules which limits the duration and effectiveness of therapeutic applications of those moieties in human recipients.

As used herein, the terms "veneered FRs" and "recombinantly veneered FRs" refer to the selective replacement of FR residues from, e.g., a rodent heavy or light chain V region, with human FR residues in order to provide a xenogeneic molecule comprising an antigen-binding site which retains substantially all of the native FR polypeptide folding structure. Veneering techniques are based on the understanding that the ligand binding characteristics of an antigen-binding site are determined primarily by the structure and relative disposition of the heavy and light chain CDR sets within the antigen-binding surface. Davies et al. (1990) Ann. Rev. Biochem. 59:439-473. Thus, antigen binding specificity can be preserved in a humanized antibody only wherein the CDR structures, their interaction with each other, and their interaction with the rest of the V region domains are carefully maintained. By using veneering techniques, exterior (e.g., solvent-accessible) FR residues which are readily encountered by the immune system are selectively replaced with human residues to provide a hybrid molecule that comprises either a weakly immunogenic, or substantially non-immunogenic veneered surface.

In another embodiment of the invention, monoclonal antibodies of the present invention may be coupled to one or more agents of interest. For example, a therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used.

Methods of Screening

Certain embodiments relate to the use of monomeric AARS polypeptides, antibodies, or polynucleotide references sequences in drug discovery, typically to identify agents that modulate one or more of the non-canonical activities of a monomeric AARS polypeptide. For example, certain embodiments include methods of identifying one or more "binding partners" of an AARS monomeric polypeptide, such as a cellular proteins, viral proteins, bacterial proteins, etc., that directly or physically interact with the AARS polypeptide.

Also included are methods of identifying host molecules that participate in one or more non-canonical activities of the monomeric AARS polypeptide, including molecules that directly or indirectly interact with the cellular binding partner, and either regulate its role in a non-canonical activity, or are regulated by the binding partner. Such host molecules include both upstream and downstream components of the non-canonical pathway, typically related by about 1, 2, 3, 4, 5 or more identifiable steps in the pathway, relative to the binding partner/monomeric AARS protein interaction.

Certain aspects include methods of identifying a compound (e.g., polypeptide) or other agent that agonizes or antagonizes the non-canonical activity of a monomeric AARS polypeptide or active variant thereof, such as by interacting with the monomeric AARS polypeptide and/or one or more of its binding partners. Also included are methods of identifying agents that modulate the expression (e.g., splicing) of AARS splice variants, or modulate the activity of proteases that otherwise regulate the production of endogenous AARS protein fragments (resectins) at the protein level.

Certain embodiments therefore include methods of identifying a binding partner of an monomeric AARS polypeptide, comprising a) combining the monomeric AARS polypeptide with a biological sample under suitable conditions, and b) detecting specific binding of the monomeric AARS polypeptide to a binding partner, thereby identifying a binding partner that specifically binds to the AARS polypeptide. Also included are methods of screening for a compound that specifically binds to a monomeric AARS polypeptide or a binding partner of the AARS polypeptide, comprising a) combining the polypeptide or the binding partner with at least one test compound under suitable conditions, and b) detecting binding of the polypeptide or the binding partner to the test compound, thereby identifying a compound that specifically binds to the polypeptide or its binding partner. In certain embodiments, the compound is a polypeptide or peptide. In certain embodiments, the compound is a small molecule or other (e.g., non-biological) chemical compound. In certain embodiments, the compound is a peptide mimetic.

Any method suitable for detecting protein-protein interactions may be employed for identifying cellular proteins that interact with an AARS reference polypeptide, interact with one or more of its binding partner(s), or both. Examples of traditional methods that may be employed include co-immunoprecipitation, crosslinking, and co-purification through gradients or chromatographic columns of cell lysates or proteins obtained from cell lysates, mainly to identify proteins in the lysate that interact with the monomeric AARS polypeptide.

In these and related embodiments, at least a portion of the amino acid sequence of a protein that interacts with a monomeric AARS polypeptide or its binding partner can be ascertained using techniques well known to those of skill in the art, such as via the Edman degradation technique. See, e.g., Creighton Proteins: Structures and Molecular Principles, W.H. Freeman & Co., N.Y., pp. 34 49, 1983. The amino acid sequence obtained may be used as a guide for the generation of oligonucleotide mixtures that can be used to screen for gene sequences encoding such proteins. Screening may be accomplished, for example, by standard hybridization or PCR techniques, as described herein and known in the art. Techniques for the generation of oligonucleotide mixtures and the screening are well known. See, e.g., Ausubel et al. Current Protocols in Molecular Biology Green Publishing Associates and Wiley Interscience, N.Y., 1989; and Innis et al., eds. PCR Protocols: A Guide to Methods and Applications Academic Press, Inc., New York, 1990.

Additionally, methods may be employed in the simultaneous identification of genes that encode the binding partner or other polypeptide. These methods include, for example, probing expression libraries, in a manner similar to the well known technique of antibody probing of lambda-gt11 libraries, using labeled monomeric AARS protein, or another polypeptide, peptide or fusion protein, e.g., a variant AARS polypeptide or AARS domain fused to a marker (e.g., an enzyme, fluor, luminescent protein, or dye), or an Ig-Fc domain.

One method that detects protein interactions in vivo, the two-hybrid system, is described in detail for illustration only and not by way of limitation. One example of this system has been described (Chien et al., *PNAS USA* 88:9578 9582, 1991) and is commercially available from Clontech (Palo Alto, Calif.).

Briefly, utilizing such a system, plasmids may be constructed that encode two hybrid proteins: one plasmid consists of nucleotides encoding the DNA-binding domain of a transcription activator protein fused to a monomeric AARS reference nucleotide sequence (or, in certain embodiments, its binding partner), or a variant thereof, and the other plasmid consists of nucleotides encoding the transcription activator protein's activation domain fused to a cDNA (or collection of cDNAs) encoding an unknown protein(s) that has been recombined into the plasmid as part of a cDNA library. The DNA-binding domain fusion plasmid and the activator cDNA library may be transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or other such methodology may be used to screen activation domain libraries for proteins that interact with the "bait" gene product. By way of example, and not by way of limitation, an AARS reference polypeptide or variant may be used as the bait gene product. A monomeric AARS binding partner may also be used as a "bait" gene product. Total genomic or cDNA sequences are fused to the DNA encoding an activation domain. This library and a plasmid encoding a hybrid of a bait AARS gene product fused to the DNA-binding domain are co-transformed into a yeast reporter strain, and the resulting transformants are screened for those that express the reporter gene.

A cDNA library of the cell line from which proteins that interact with bait AARS gene products are to be detected can be made using methods routinely practiced in the art. For example, the cDNA fragments can be inserted into a vector such that they are translationally fused to the transcriptional activation domain of GAL4. This library can be co-transformed along with the bait gene-GAL4 fusion plasmid into a yeast strain, which contains a lacZ gene driven by a promoter that contains GAL4 activation sequence. A cDNA encoded protein, fused to GAL4 transcriptional activation domain, that interacts with bait gene product will reconstitute an active GAL4 protein and thereby drive expression of the HIS3 gene. Colonies, which express HIS3, can be detected by their growth on Petri dishes containing semi-solid agar based media lacking histidine. The cDNA can then be purified from these strains, and used to produce and isolate the bait AARS gene-interacting protein using techniques routinely practiced in the art.

Also included are three-hybrid systems, which allow the detection of RNA-protein interactions in yeast. See, e.g., Hook et al., *RNA*. 11:227-233, 2005. Accordingly, these and related methods can be used to identify a binding partner of a monomeric AARS polypeptide, and to identify other proteins or nucleic acids that interact with the AARS polypeptide, its binding partner, or both. These and related methods can also be used to identify compounds that interfere with the interaction between a monomeric AARS polypeptide and one or more of its binding partners (e.g., cellular proteins, viral proteins, bacterial proteins).

Certain embodiments relate to the use of interactome screening approaches. Particular examples include protein domain-based screening (see, e.g., Boxem et al., *Cell*. 134: 534-545, 2008; and Yu et al., *Science*. 322:10-110, 2008).

As noted above, once isolated, binding partners can be identified and can, in turn, be used in conjunction with standard techniques to identify proteins or other compounds with which it interacts. Certain embodiments thus relate to methods of screening for a compound that specifically binds to the binding partner of a monomeric AARS polypeptide, comprising a) combining the binding partner with at least one test compound under suitable conditions, and b) detecting binding of the binding partner to the test compound, thereby identifying a compound that specifically binds to the binding partner. In certain embodiments, the test compound is a polypeptide. In certain embodiments, the test compound is a chemical compound, such as a small molecule compound or peptide mimetic. In specific embodiments, the binding partner is an HIV Gag protein and the AARS polypeptide is a monomeric form of KRS.

Certain embodiments include methods of screening for a compound that modulates the activity of a monomeric AARS polypeptide, comprising a) combining the polypeptide with at least one test compound under conditions permissive for the activity of the polypeptide, b) assessing the activity of the polypeptide in the presence of the test compound, and c) comparing the activity of the polypeptide in the presence of the test compound with the activity of the polypeptide in the absence of the test compound, wherein a change in the activity of the polypeptide in the presence of the test compound is indicative of a compound that modulates the activity of the polypeptide.

Certain embodiments include methods of screening for a compound that modulates the activity of a binding partner of a monomeric AARS polypeptide, comprising a) combining the polypeptide with at least one test compound under conditions permissive for the activity of the binding partner, b) assessing the activity of the binding partner in the presence of the test compound, and c) comparing the activity of the binding partner in the presence of the test compound with the activity of the binding partner in the absence of the test compound, wherein a change in the activity of the binding partner in the presence of the test compound is indicative of a compound that modulates the activity of the binding partner. Typically, these and related embodiments include assessing a selected non-canonical activity that is associated with the AARS polypeptide or its binding partner. Included are in vitro and in vivo conditions, such as cell culture conditions.

Certain embodiments include methods of screening a compound for effectiveness as a full or partial agonist of a monomeric AARS reference polypeptide or an active fragment or variant thereof, comprising a) exposing a sample comprising the polypeptide to a compound, and b) detecting agonist activity in the sample, typically by measuring an increase in the non-canonical activity of the monomeric AARS polypeptide. Certain methods include a) exposing a sample comprising a binding partner of the AARS polypeptide to a compound, and b) detecting agonist activity in the sample, typically by measuring an increase in the selected non-canonical activity of the AARS polypeptide. Certain embodiments include compositions that comprise an agonist compound identified by the method and a pharmaceutically acceptable carrier or excipient.

Also included are methods of screening a compound for effectiveness as a full or partial antagonist of a monomeric AARS polypeptide, comprising a) exposing a sample comprising the polypeptide to a compound, and b) detecting antagonist activity in the sample, typically by measuring a decrease in the non-canonical activity of the AARS polypeptide. Certain methods include a) exposing a sample comprising a binding partner of the AARS polypeptide to a compound, and b) detecting antagonist activity in the sample, typically by measuring a decrease in the selected non-canonical activity of the AARS polypeptide. Certain embodiments include compositions that comprise an antagonist compound identified by the method and a pharmaceutically acceptable carrier or excipient.

Specific embodiments include, for example, compositions that can be used for drug discovery or treatment (e.g., in vitro compositions), comprising a human immunodeficiency virus (HIV) Gag protein and a substantially monomeric lysyl tRNA synthetase (KRS) described herein, which typically or optionally comprises one or more stabilizing modifications that do not significantly reduce KRS binding to HIV Gag. Also included are modified cells, comprising a human immunodeficiency virus (HIV) Gag protein and an exogenous (e.g., recombinantly introduced), substantially monomeric lysyl tRNA synthetase (KRS) polypeptide described herein, which comprises one or more stabilizing modifications that do not significantly reduce KRS binding to HIV Gag. In some embodiments, the HIV Gag protein comprises the Gag-CA-CTD domain. In specific embodiments, the Gag-CA-CTD domain comprises regions H3 and H4.

Other specific embodiments include methods of identifying a compound that specifically reduces binding between a human immunodeficiency virus (HIV) Gag protein and a substantially monomeric lysyl tRNA synthetase (KRS) polypeptide, comprising (a) combining the composition or cell described above with at least one test compound under suitable conditions, and (b) detecting reduced binding between the HIV Gag protein and the substantially monomer KRS polypeptide, thereby identifying a compound that specifically reduces binding between the HIV Gag protein and the KRS polypeptide. In certain embodiments, the test compound is a polypeptide or peptide, an antibody or antigen-binding fragment thereof, a peptide mimetic, or a small molecule. In some embodiments, the test compound binds to the Gag-CA-CTD domain. In particular embodiments, the test compound binds to H3 or H4 or both of the Gag-CA-CTD domain. In specific embodiments, the test compound binds to the bottom side of H3 or H4 or both (see FIG. 18E).

In certain embodiments, in vitro systems may be designed to identify compounds capable of interacting with or modulating an AARS reference sequence or its binding partner. Certain of the compounds identified by such systems may be useful, for example, in modulating the activity of the pathway, and in elaborating components of the pathway itself. They may also be used in screens for identifying compounds that disrupt interactions between components of the pathway; or may disrupt such interactions directly. One exemplary approach involves preparing a reaction mixture of the AARS polypeptide and a test compound under conditions and for a time sufficient to allow the two to interact and bind, thus forming a complex that can be removed from and/or detected in the reaction mixture In vitro screening assays can be conducted in a variety of ways. For example, a monomeric AARS polypeptide, a binding partner, and/or test compound(s) can be anchored onto a solid phase. In these and related embodiments, the resulting complexes may be captured and detected on the solid phase at the end of the reaction. In one example of such a method, the monomeric AARS polypeptide and/or its binding partner are anchored onto a solid surface, and the test compound(s), which are not anchored, may be labeled, either directly or indirectly, so that their capture by the component on the solid surface can be detected. In other examples, the test compound(s) are anchored to the solid surface, and the AARS polypeptide and/or its binding partner, which are not anchored, are labeled or in some way detectable. In certain embodiments, microtiter plates may conveniently be utilized as the solid phase. The anchored component (or test compound) may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

To conduct an exemplary assay, the non-immobilized component is typically added to the coated surface containing the anchored component. After the reaction is complete, un-reacted components are removed (e.g., by washing) under conditions such that any specific complexes formed will remain immobilized on the solid surface. The detection of complexes anchored on the solid surface can be accomplished in a number of ways. For instance, where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the previously non-immobilized component (the antibody, in turn, may be directly labeled or indirectly labeled with a labeled anti-Ig antibody).

Alternatively, the presence or absence of binding of a test compound can be determined, for example, using surface plasmon resonance (SPR) and the change in the resonance angle as an index, wherein an AARS polypeptide or a cellular binding partner is immobilized onto the surface of a commercially available sensorchip (e.g., manufactured by Biacore™) according to a conventional method, the test compound is contacted therewith, and the sensorchip is illuminated with a light of a particular wavelength from a particular angle. The binding of a test compound can also be measured by detecting the appearance of a peak corresponding to the test compound by a method wherein an AARS polypeptide or a cellular binding partner is immobilized onto the surface of a protein chip adaptable to a mass spectrometer, a test compound is contacted therewith, and an ionization method such as MALDI-MS, ESI-MS, FAB-MS and the like is combined with a mass spectrometer (e.g., double-focusing mass spectrometer, quadrupole mass spectrometer, time-of-flight mass spectrometer, Fourier transformation mass spectrometer, ion cyclotron mass spectrometer and the like).

In certain embodiments, cell-based assays, membrane vesicle-based assays, or membrane fraction-based assays can be used to identify compounds that modulate interactions in the non-canonical pathway of the selected AARS polypeptide. To this end, cell lines that express an AARS polypeptide and/or a binding partner, or a fusion protein containing a domain or fragment of such proteins (or a combination thereof), or cell lines (e.g., COS cells, CHO cells, HEK293 cells, Hela cells etc.) that have been genetically engineered to express such protein(s) or fusion protein(s) can be used. Test compound(s) that influence the non-canonical activity can be identified by monitoring a change (e.g., a statistically significant change) in that activity as compared to a control or a predetermined amount.

Antibodies to AARS monomers can also be used in screening assays, such as to identify an agent that specifically binds to an AARS, confirm the specificity or affinity of an agent that binds to an AARS monomer, or identify the site of interaction between the agent and the AARS monomer. Included are assays in which the antibody is used as a competitive inhibitor of the agent. For instance, an antibody that specifically binds to an AARS monomer with a known affinity can act as a competitive inhibitor of a selected agent, and be used to calculate the affinity of the agent for the AARS monomer. Also, one or more antibodies that specifically bind to known epitopes or sites of an AARS monomer can be used as a competitive inhibitor to confirm whether or not the agent binds at that same site. Other variations will be apparent to persons skilled in the art.

Also included are any of the above methods, or other screening methods known in the art, which are adapted for high-throughput screening (HTS). HTS typically uses automation to run a screen of an assay against a library of candidate compounds, for instance, an assay that measures an increase or a decrease in a non-canonical activity, as described herein.

Any of the screening methods provided herein may utilize small molecule libraries or libraries generated by combinatorial chemistry. Libraries of chemical and/or biological mixtures, such as fungal, bacterial, or algal extracts, are known in the art and can be screened with any of the assays of the invention. Examples of methods for the synthesis of molecular libraries can be found in: (Carell et al., 1994a; Carell et al., 1994b; Cho et al., 1993; DeWitt et al., 1993; Gallop et al., 1994; Zuckermann et al., 1994).

Libraries of compounds may be presented in solution (Houghten et al., 1992) or on beads (Lam et al., 1991), on chips (Fodor et al., 1993), bacteria, spores (Ladner et al., U.S. Pat. No. 5,223,409, 1993), plasmids (Cull et al., 1992) or on phage (Cwirla et al., 1990; Devlin et al., 1990; Felici et al., 1991; Ladner et al., U.S. Pat. No. 5,223,409, 1993; Scott and Smith, 1990). Embodiments of the present invention encompass the use of different libraries for the identification of small molecule modulators of one or more AARS monomers, their binding partners, and/or their related non-canonical activities. Libraries useful for the purposes of the invention include, but are not limited to, (1) chemical libraries, (2) natural product libraries, and (3) combinatorial libraries comprised of random peptides, oligonucleotides and/or organic molecules.

Chemical libraries consist of structural analogs of known compounds or compounds that are identified as "hits" or "leads" via natural product screening. Natural product libraries are derived from collections of microorganisms, animals, plants, or marine organisms which are used to create mixtures for screening by: (1) fermentation and extraction of broths from soil, plant or marine microorganisms or (2) extraction of plants or marine organisms. Natural product libraries include polyketides, non-ribosomal peptides, and variants (non-naturally occurring) thereof. See, e.g., Cane et al., *Science* 282: 63-68, 1998. Combinatorial libraries may be composed of large numbers of peptides, oligonucleotides or organic compounds as a mixture. They are relatively easy to prepare by traditional automated synthesis methods, PCR, cloning or proprietary synthetic methods.

More specifically, a combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

For a review of combinatorial chemistry and libraries created therefrom, see, e.g., Huc, I. and Nguyen, R. (2001) Comb. Chem. High Throughput Screen 4:53-74; Lepre, C A. (2001) Drug Discov. Today 6:133-140; Peng, S. X. (2000) Biomed. Chromatogr. 14:430-441; Bohm, H. J. and Stahl, M. (2000) Curr. Opin. Chem. Biol. 4:283-286; Barnes, C. and Balasubramanian, S. (2000) Curr. Opin. Chem. Biol. 4:346-350; Lepre, Enjalbal, C, et al., (2000) Mass Septrom Rev. 19:139-161; Hall, D. G., (2000) Nat. Biotechnol. 18:262-262; Lazo, J. S., and Wipf, P. (2000) J. Pharmacol. Exp. Ther. 293:705-709; Houghten, R. A., (2000) Ann. Rev. Pharmacol. Toxicol. 40:273-282; Kobayashi, S. (2000) Curr. Opin. Chem. Biol. (2000) 4:338-345; Kopylov, A. M. and Spiridonova, V. A. (2000) Mol. Biol. (Mosk) 34:1097-1113; Weber, L. (2000) Curr. Opin. Chem. Biol. 4:295-302; Dolle, R. E. (2000) J. Comb. Chem. 2:383-433; Floyd, C D., et al., (1999) Prog. Med. Chem. 36:91-168; Kundu, B., et al., (1999) Prog. Drug Res. 53:89-156; Cabilly, S. (1999) Mol. Biotechnol. 12:143-148; Lowe, G. (1999) Nat. Prod. Rep. 16:641-651; Dolle, R. E. and Nelson, K. H. (1999) J. Comb. Chem. 1:235-282; Czarnick, A. W. and Keene, J. D. (1998) Curr. Biol. 8:R705-R707; Dolle, R. E. (1998) Mol. Divers. 4:233-256; Myers, P. L., (1997) Curr. Opin. Biotechnol. 8:701-707; and Pluckthun, A. and Cortese, R. (1997) Biol. Chem. 378: 443.

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd., Moscow, RU, 3D Pharmaceuticals, Exton, Pa., Martek Biosciences, Columbia, Md., etc.).

Formulation and Administration

The compositions of the invention (e.g., polypeptides, polynucleotides, antibodies, etc.) are generally formulated in pharmaceutically-acceptable or physiologically-acceptable solutions for administration to a cell, tissue or animal, either alone, or in combination with one or more other modalities of therapy. It will also be understood that, if desired, the compositions of the invention may be administered in combination with other agents as well, such as, e.g., other proteins or polypeptides or various pharmaceutically-active agents. There is virtually no limit to other components that may also be included in the compositions, provided that the additional agents do not adversely affect the desired effects desired to be achieved with an AARS polypeptide of the invention.

In the pharmaceutical compositions of the invention, formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, intracranial and intramuscular administration and formulation.

In certain applications, the pharmaceutical compositions disclosed herein may be delivered via oral administration to a subject. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain circumstances it will be desirable to deliver the pharmaceutical compositions disclosed herein parenterally, intravenously, intramuscularly, or even intraperitoneally as described, for example, in U.S. Pat. No. 5,543,158; U.S. Pat. No. 5,641,515 and U.S. Pat. No. 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., *Remington's Pharmaceutical Sciences*, 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions can be prepared by incorporating the active compounds in the required amount in the appropriate solvent with the various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

In certain embodiments, the pharmaceutical compositions may be delivered by intranasal sprays, inhalation, and/or other aerosol delivery vehicles. Methods for delivering genes, polynucleotides, and peptide compositions directly to the lungs via nasal aerosol sprays has been described e.g., in U.S. Pat. No. 5,756,353 and U.S. Pat. No. 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

In certain embodiments, the delivery may occur by use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

Kits Comprising Compositions of the Invention

The invention, in other aspects, provides kits comprising one or more containers filled with one or more of the polypeptides, polynucleotides, antibodies, multiunit complexes, compositions thereof, etc., of the invention, as described herein. The kits can include written instructions on how to use such compositions (e.g., to modulate cellular signaling, angiogenesis, cancer, inflammatory conditions, etc.).

The kits herein may also include a one or more additional therapeutic agents or other components suitable or desired for the indication being treated. An additional therapeutic agent may be contained in a second container, if desired. Examples of additional therapeutic agents include, but are not limited to anti-neoplastic agents, anti-inflammatory agents, antibacterial agents, antiviral agents, angiogenic agents, etc.

The kits herein can also include one or more syringes or other components necessary or desired to facilitate an intended mode of delivery (e.g., stents, implantable depots, etc.).

Methods of Use

Embodiments of the present invention relates to methods of using substantially monomeric AARS polypeptides and compositions comprising the same for treating a cell, tissue, or subject in need thereof. The cells or tissue that may be modulated by the present invention are preferably mammalian cells, or more preferably human cells. Such cells can be of a healthy state or of a diseased state.

In certain embodiments, for example, methods are provided for modulating therapeutically relevant cellular activities including, but not limited to, cellular metabolism, cell differentiation (e.g., hematopoiesis), cell proliferation, cell death, cell mobilization, cell migration, gene transcription, mRNA translation, cell impedance, cytokine production, cytokine receptor activity, and the like, comprising contacting a cell with an AARS composition as described herein. The monomeric AARS compositions may therefore be used in any of a number of therapeutic contexts including, for example, those relating to the treatment or prevention of neoplastic diseases, inflammatory conditions, immune system diseases (e.g., autoimmune diseases and inflammation), infectious diseases, metabolic diseases, neuronal/neurological diseases, muscular/cardiovascular diseases, diseases associated with aberrant hematopoiesis, diseases associated with aberrant angiogenesis or reduced angiogenesis, diseases associated with aberrant cell survival, and others.

In certain embodiments, monomeric AARS polypeptides agonize CXCR receptors. Certain embodiments therefore relate to methods of modulating the levels or activity of CXCR-1 or CXCR-2 in a cell, comprising contacting the cell with monomeric AARS polypeptide described herein. Certain embodiments include increasing the levels or activity of CXCR-1 or CXCR-2 in the cell, which may be in a subject or in vitro. Certain in vivo embodiments include increasing polymorphonuclear cell (PMNC) migration in the subject.

Given the role of CXC receptors such as CXCR-1 and CXCR-2 and related chemokines such as IL-8 in modulating inflammatory responses, in certain illustrative embodiments, the monomeric AARS compositions of the invention may be used to modulate inflammation in a subject, e.g., via modulation of cytokine signaling. Therefore, in related embodiments, the compositions of the invention may be employed in the treatment of essentially any cell or tissue or subject that would benefit from modulation of inflammation. For example, in some embodiments, a cell or tissue or subject experiencing or susceptible to inflammation, or requiring a pro-inflammatory response (e.g., an immunosuppressed condition), may be contacted with a suitable composition of the invention to stimulate an inflammatory response.

"Inflammation" refers generally to the biological response of tissues to harmful stimuli, such as pathogens, damaged cells (e.g., wounds), and irritants. The term "inflammatory response" refers to the specific mechanisms by which inflammation is achieved and regulated, including, merely by way of illustration, immune cell activation or migration, cytokine production, vasodilation, including kinin release, fibrinolysis, and coagulation, among others described herein and known in the art. Ideally, inflammation is a protective attempt by the body to both remove the injurious stimuli and initiate the healing process for the affected tissue or tissues. In the absence of inflammation, wounds and infections would never heal, creating a situation in which progressive destruction of the tissue would threaten survival. On the other hand, excessive or chronic inflammation may associate with a variety of diseases, such as hay fever, atherosclerosis, and rheumatoid arthritis, among others described herein and known in the art.

Monomeric AARS polypeptides of the invention may modulate acute inflammation, chronic inflammation, or both. Certain embodiments relate to increasing acute inflammation or acute inflammatory responses, and certain embodiments relate to increasing chronic inflammation or chronic inflammatory responses. Depending on the needs of the subject, certain embodiments relate to reducing acute inflammation or inflammatory responses, and certain embodiments relate to reducing chronic inflammation or chronic inflammatory responses.

Acute inflammation relates to the initial response of the body to presumably harmful stimuli and involves increased movement of plasma and leukocytes from the blood into the injured tissues. It is a short-term process, typically beginning within minutes or hours and ending upon the removal of the injurious stimulus. Acute inflammation may be characterized by any one or more of redness, increased heat, swelling, pain, and loss of function. Redness and heat are due mainly to increased blood flow at body core temperature to the inflamed site, swelling is caused by accumulation of fluid, pain is typically due to release of chemicals that stimulate nerve endings, and loss of function has multiple causes.

Acute inflammatory responses are initiated mainly by local immune cells, such as resident macrophages, dendritic cells, histiocytes, Kuppfer cells and mastocytes. At the onset of an infection, burn, or other injuries, these cells undergo activation and release inflammatory mediators responsible for the clinical signs of inflammation, such as vasoactive amines and eicosanoids. Vasodilation and its resulting increased blood flow cause the redness and increased heat. Increased permeability of the blood vessels results in an exudation or leakage of plasma proteins and fluid into the tissue, which creates swelling. Certain released mediators such as bradykinin increase sensitivity to pain, and alter the blood vessels to permit the migration or extravasation of leukocytes, such as neutrophils, which typically migrate along a chemotactic gradient created by the local immune cells.

Acute inflammatory responses also includes one or more acellular biochemical cascade systems, consisting of pre-formed plasma proteins modulate, which act in parallel to initiate and propagate the inflammatory response. These systems include the complement system, which is mainly activated by bacteria, and the coagulation and fibrinolysis systems, which are mainly activated by necrosis, such as the type of tissue damage that is caused by certain infections, burns, or other trauma. Hence, monomeric AARS polypeptides may be used to modulate acute inflammation, or any of one or more of the individual acute inflammatory responses.

Chronic inflammation, a prolonged and delayed inflammatory response, is characterized by a progressive shift in the type of cells that are present at the site of inflammation, and often leads to simultaneous or near simultaneous destruction and healing of the tissue from the inflammatory process. At the cellular level, chronic inflammatory responses involve a variety of immune cells such as monocytes, macrophages, lymphocytes, plasma cells, and fibroblasts, though in contrast to acute inflammation, which is mediated mainly by granulocytes, chronic inflammation is mainly mediated by mononuclear cells such as monocytes and lymphocytes. Chronic inflammation also involves a variety of inflammatory mediators, such as IFN-γ and other cytokines, growth factors, reactive oxygen species, and hydrolytic enzymes. Chronic inflammation may last for many months or years, and may result in undesired tissue destruction and fibrosis.

Clinical signs of chronic inflammation are dependent upon duration of the illness, inflammatory lesions, cause and anatomical area affected. (see, e.g., Kumar et al., Robbins Basic Pathology-$8^{th}$ Ed., 2009 Elsevier, London; Miller, L M, Pathology Lecture Notes, Atlantic Veterinary College, Charlottetown, PEI, Canada). Chronic inflammation is associated with a variety of pathological conditions or diseases, including, for example, allergies, Alzheimer's disease, anemia, aortic valve stenosis, arthritis such as rheumatoid arthritis and osteoarthritis, cancer, congestive heart failure, fibromyalgia, fibrosis, heart attack, kidney failure, lupus, pancreatitis, stroke, surgical complications, inflammatory lung disease, inflammatory bowel disease, atherosclerosis, and psoriasis, among others described herein and known in the art. Hence, monomeric AARS polypeptides may be used to treat or manage chronic inflammation, modulate any of one or more of the individual chronic inflammatory responses, or treat any one or more diseases or conditions associated with chronic inflammation.

Monomeric AARS polypeptides may also modulate proliferative inflammation, an inflammatory process characterized by an increase in the number of tissue cells. These can encompass skin conditions such as psoriasis, seborrhea or eczema, or can also be thought of in terms of cancers and abnormal growths especially in light of accumulating evidence based on more efficient molecular methods to document even low grade chronic inflammation.

In certain embodiments, monomeric AARS polypeptides may modulate inflammatory responses at the cellular level, such as by modulating the activation, inflammatory molecule secretion (e.g., cytokine or kinin secretion), proliferation, activity, migration, or adhesion of various cells involved in inflammation. Examples of such cells include immune cells and vascular cells. Immune cells include, for example, granulocytes such as neutrophils, eosinophils and basophils, macrophages/monocytes, lymphocytes such as B-cells, killer T-cells (i.e., CD8+ T-cells), helper T-cells (i.e., CD4+ T-cells, including $T_h1$ and $T_h2$ cells), natural killer cells, γδ T-cells, dendritic cells, and mast cells. Examples of vascular cells include smooth muscle cells, endothelial cells, and fibroblasts. Also included are methods of modulating an inflammatory condition associated with one or more immune cells or vascular cells, including neutrophil-mediated, macrophage-mediated, and lymphocyte-mediated inflammatory conditions. In certain embodiments, monomeric AARS polypeptides increase the levels, migration, or recruitment of PMNCs such as neutrophils, basophils, and eosinophils.

In certain embodiments, monomeric AARS polypeptides may modulate the levels or activity of inflammatory molecules, including plasma-derived inflammatory molecules and cell-derived inflammatory molecules. Included are pro-inflammatory molecules and anti-inflammatory molecules. Examples of plasma-derived inflammatory molecules include, without limitation, proteins or molecules of any one or more of the complement system, kinin system, coagulation system, and the fibrinolysis system. Examples of members of the complement system include C1, which exists in blood serum as a molecular complex containing about 6 molecules of C1q, 2 molecules of C1r, and 2 molecules of C1s, C2 (a and b), C3 (a and B), C4 (a and b), C5, and the membrane attack complex of C5a, C5b, C6, C7, C8, and C9. Examples of the kinin system include bradykinin, kallidin, kallidreins, carboxypeptidases, angiotensin-converting enzyme, and neutral endopeptidase.

Examples of cell-derived inflammatory molecules include, without limitation, enzymes contained within lysosome granules, vasoactive amines, eicosanoids, cytokines, acute-phase proteins, and soluble gases such as nitric oxide. Vasoactive amines contain at least one amino group, and target blood vessels to alter their permeability or cause vasodilation. Examples of vasoactive amines include histamine and serotonin. Eicosanoids refer to signaling molecules made by oxidation of twenty-carbon essential fatty acids, and include prostaglandins, prostacyclins, thromboxanes, and leukotrienes.

Cytokines refer to a variety of substances that are secreted by immune cells, and include polypeptides and glycoproteins. Typically, cytokines are categorized as either autocrine cytokines, which act on the same type of cell from which the cytokine is secreted, or paracrine cytokines, which are restricted to acting on a different cell type from which the cytokine is secreted.

Each cytokine typically has a corresponding cytokine receptor. Examples of classes of cytokine receptors include, without limitation, receptors from the immunoglobulin (Ig) superfamily, such as the IL-1 receptor types, which share structural homology with immunoglobulins (antibodies), cell adhesion molecules, and even some cytokines, and receptors from the hematopoietic growth factor family, such as the IL-2 receptor family and the receptors for GM-CSF, IL-3, and IL-5, receptors from the interferon (type 2) family, including receptors for IFN β and γ. Additional examples include receptors from the tumor necrosis factors (TNF) (type 3) family, which share a cysteine-rich common extracellular binding domain and interact with several other non-cytokine ligands such as CD40, CD27 and CD30, receptors from the seven transmembrane helix family, including G-protein coupled receptors, and chemokine receptors such as CXCR-1, CXCR-2, CXCR4 and CCR5, as well as receptors for IL-8, MIP-1 and RANTES. Hence, in certain embodiments, monomeric AARS polypeptides may modulate the levels or activity of one or more selected cytokines, the levels or activity of one or more selected cytokine receptors, the interaction between cytokines and their receptors, or any combination thereof.

Monomeric AARS polypeptides may also modulate levels or activity of acute-phase proteins. Examples of acute-phase proteins include C-reactive protein, serum amyloid A, serum amyloid P, and vasopressin. In certain instances, expression of acute-phase proteins can cause a range of undesired systemic effects including amyloidosis, fever, increased blood pressure, decreased sweating, malaise, loss of appetite, and somnolence. Accordingly, monomeric AARS polypeptides may modulate the levels or activity of acute-phase proteins, their systemic effects, or both.

In certain embodiments, monomeric AARS polypeptides modulate local inflammation, systemic inflammation, or both. In certain embodiments, monomeric AARS polypeptides may increase or maintain (i.e., prevent further reductions) local inflammation or local inflammatory responses. In certain embodiments, depending on the needs of the subject, monomeric AARS polypeptides may increase systemic inflammation or systemic inflammatory responses.

In certain embodiments, the modulation of inflammation or inflammatory responses can be associated with one or more tissues or organs. Non-limiting examples of such tissues or organs include skin (e.g., dermis, epidermis, subcutaneous layer), hair follicles, nervous system (e.g., brain, spinal cord, peripheral nerves), auditory system or balance organs (e.g., inner ear, middle ear, outer ear), respiratory system (e.g., nose, trachea, lungs), gastroesophogeal tissues, the gastrointestinal system (e.g., mouth, esophagus, stomach, small intestines, large intestines, rectum), vascular system (e.g., heart, blood vessels and arteries), liver, gallbladder, lymphatic/immune system (e.g., lymph nodes, lymphoid follicles, spleen, thymus, bone marrow), uro-genital system (e.g., kidneys, ureter, bladder, urethra, cervix, Fallopian tubes, ovaries, uterus, vulva, prostate, bulbourethral glands, epidiymis, prostate, seminal vesicles, testicles), musculoskeletal system (e.g., skeletal muscles, smooth muscles, bone, cartilage, tendons, ligaments), adipose tissue, mammaries, and the endocrine system (e.g., hypothalamus, pituitary, thyroid, pancreas, adrenal glands). Accordingly, monomeric AARS polypeptides may be used to modulate inflammation associated with any of these tissues or organs, such as to treat conditions or diseases that are associated with the inflammation of these tissues or organs.

Certain embodiments may employ monomeric AARS polypeptides to increase inflammation. For instance, depending on the needs of the subject, certain embodiments may increase acute inflammation or increase acute inflammatory responses or both. Certain embodiments may increase chronic inflammation or chronic inflammatory responses or both. Certain embodiments may increase both acute and chronic inflammation. Certain embodiments may increase local or systemic inflammation or both. These and related embodiments may be useful for treating or managing conditions associated with reduced inflammation or insufficient inflammatory responses.

In certain embodiments, monomeric AARS polypeptides may be used to treat or manage immunodeficiencies, including primary immunodeficiencies and secondary immunodeficiencies, in which the body may not mount an adequate inflammatory response. Examples of primary immunodeficiencies include various autosomal recessive and X-linked genetic conditions such as T-cell and B-cell immunodeficiencies, including combined T-cell and B-cell immunodeficiencies, antibody deficiencies, well-defined syndromes, immune dysregulation diseases, phagocyte disorders, innate immunity disorders, and complement deficiencies.

Examples of T-cell and B-cell immunodeficiencies include T−/B+ deficiencies such as γc deficiency, JAK3 deficiency, interleukin 7 receptor chain α deficiency, CD45 deficiency, CD3δ/CD3ε deficiency; and T−/B− deficiencies such as RAG 1/2 deficiency, DCLRE1C deficiency, adenosine deaminase (ADA) deficiency, reticular dysgenesis. Additional examples include Omenn syndrome, DNA ligase type IV deficiency, CD40 ligand deficiency, CD40 deficiency, purine nucleoside phosphorylase (PNP) deficiency, MHC class II deficiency, CD3γ deficiency, CD8 deficiency, ZAP-70 deficiency, TAP-1/2 deficiency, and winged helix deficiency.

Examples of antibody deficiencies include X-linked agammaglobulinemia (btk deficiency, or Bruton's agammaglobulinemia), μ-Heavy chain deficiency, 1-5 deficiency, Igα deficiency, BLNK deficiency, thymoma with immunodeficiency, common variable immunodeficiency (CVID), ICOS deficiency, CD19 deficiency, TACI (TNFRSF13B) deficiency, and BAFF receptor deficiency. Additional examples include AID deficiency, UNG deficiency, heavy chain deletions, kappa chain deficiency, isolated IgG subclass deficiency, IgA with IgG subclass deficiency, selective immunoglobulin A deficiency, and transient hypogammaglobulinemia of infancy (THI).

Examples of "well-defined syndromes" include Wiskott-Aldrich syndrome, ataxia telangiectasia, ataxia-like syndrome, Nijmegen breakage syndrome, Bloom syndrome, DiGeorge syndrome, immuno-osseous dysplasias such as cartilage-hair hypoplasia, Schimke syndrome, Hermansky-Pudlak syndrome type 2, Hyper-IgE syndrome, chronic mucocutaneous candidiasis.

Examples of immune dysregulation diseases include immunodeficiency with hypopigmentation or albinism such as Chediak-Higashi syndrome and Griscelli syndrome type 2, familial hemophagocytic lymphohistiocytosis such as perforin deficiency, MUNC13D deficiency, and syntaxin 11 deficiency, X-linked lymphoproliferative syndrome, autoimmune lymphoproliferative syndrome such as type 1a (CD95 defects), type 1b (Fas ligand defects), type 2a (CASP10 defects), and type 2b (CASP8 defects), autoimmune polyendocrinopathy with candidiasis and ectodermal dystrophy, and immunodysregulation polyendocrinopathy enteropathy X-linked syndrome. Additionally, diseases affecting the bone marrow may result in abnormal or few leukocytes, such as leukopenia. Leukopenia can be induced by certain infections and diseases, including viral infection, *Rickettsia* infection, some protozoa, tuberculosis, and certain cancers.

Examples of phagocyte disorders include severe congenital neutropenia such as ELA2 deficiency (e.g., with myelodysplasia), GFI1 deficiency (with T/B lymphopenia) or G-CSFR deficiency (G-CSF-unresponsive), Kostmann syndrome, cyclic neutropenia, X-linked neutropenia/myelodysplasia, leukocyte adhesion deficiency types 1, 2 and 3, RAC2 deficiency, β-actin deficiency, localized juvenile periodontitis, Papillon-Lefèvre syndrome, specific granule deficiency, Shwachman-Diamond syndrome, chronic granulomatous disease, including X-linked and autosomal forms, neutrophil glucose-6-phosphate dehydrogenase deficiency, IL-12 and IL-23 β1 chain deficiency, IL-12p40 deficiency, interferon γ receptor 1 deficiency, interferon γ receptor 2 deficiency, and STAT1 deficiency.

Examples of innate immunity deficiencies include hypohidrotic ectodermal dysplasia such as NEMO deficiency and IKBA deficiency, IRAK-4 deficiency, WHIM syndrome (warts, hypogammaglobulinaemia, infections, myleokathexis), and epidermodysplasia verruciformis. Examples of complement deficiencies and exemplary associated conditions include C1q deficiency (e.g., lupus-like syndrome, rheumatoid disease, infections), C1r deficiency, C4 deficiency, C2 deficiency (e.g., lupus-like syndrome, vasculitis, polymyositis, pyogenic infections), C3 deficiency (e.g., recurrent pyogenic infections), C5 deficiency (e.g., neisserial infections), C6 deficiency, C7 deficiency (e.g., vasculitis), C8a and C8b deficiency, C9 deficiency (e.g., neisserial infections), C1-inhibitor deficiency (e.g., hereditary angioedema), Factor I deficiency (pyogenic infections), Factor H deficiency (e.g., haemolytic-uraemic syndrome, membranoproliferative glomerulonephritis), Factor D deficiency (e.g., neisserial infections), Properdin deficiency (e.g., neisserial infections), MBP deficiency (e.g., pyogenic infections), and MASP2 deficiency.

Primary immune deficiencies can be diagnosed according to routine techniques in the art. Exemplary diagnostic tests include, without limitation, performing counts of the different types of mononuclear cells in the blood (e.g., lymphocytes and monocytes, including lymphocytes, different groups of B lymphocytes such as CD19+, CD20+, and CD21+ lymphocytes, natural killer cells, and monocytes positive for CD15+), measuring the presence of activation markers (e.g., HLA-DR, CD25, CD80), performing tests for T cell function such as skin tests for delayed-type hypersensitivity, cell responses to mitogens and allogeneic cells, cytokine production by cells, performing tests for B cell function such as by identifying antibodies to routine immunizations and commonly acquired infections and by quantifying IgG subclasses, and performing tests or phagocyte function, such as by measuring the reduction of nitro blue tetrazolium chloride, and performing assays of chemotaxis and bactericidal activity. Monomeric AARS polypeptides may therefore be used to stimulate or maintain acute inflammation or acute inflammatory responses in subjects with a primary immunodeficiency, as described herein and known in the art.

Examples of causes of secondary immunodeficiencies include malnutrition, aging, and medications (e.g., chemotherapy, disease-modifying anti-rheumatic drugs, immunosuppressive drugs after organ transplants, glucocorticoids). Additional causes include various cancers, including cancers of the bone marrow and blood cells (e.g., leukemia, lymphoma, multiple myeloma), and certain chronic infections, such as acquired immunodeficiency syndrome (AIDS), caused by the human immunodeficiency virus (HIV). Monomeric AARS polypeptides may be used to stimulate or maintain acute inflammation or acute inflammatory responses in subjects with an immunodeficiency, as described herein and known in the art. Monomeric AARS polypeptides may also be used to stimulate or maintain chronic inflammation or chronic inflammatory responses in subjects with a secondary immunodeficiency, as described herein and known in the art.

Monomeric AARS polypeptides may also be employed to treat or manage idiopathic inflammation or inflammation of unknown etiology. Also included are combination therapies, in which one or more monomeric AARS polypeptides are administered or utilized in combination with one or more other therapies for any of the inflammatory diseases or conditions described herein, including those therapies that are commonly available and known in the art. Examples of combination therapies include the use of standard anti-inflammatory agents such as non-steroidal anti-inflammatory drugs (NSAIDs), immune selective anti-inflammatory derivatives (ImSAIDs), and steroids (e.g., corticosteroids), anti-infectives such as antibiotics and anti-viral agents, anti-oxidants, cytokines, chemotherapeutic agents and other anti-cancer therapies, and immunosuppressive therapies.

Criteria for assessing the signs and symptoms of inflammatory and other conditions, including for purposes of making differential diagnosis and also for monitoring treatments such as determining whether a therapeutically effective dose has been administered in the course of treatment, e.g., by determining improvement according to accepted clinical criteria, will be apparent to those skilled in the art and are exemplified by the teachings of e.g., Berkow et al., eds., The Merck Manual, $16^{th}$ edition, Merck and Co., Rahway, N.J., 1992; Goodman et al., eds., Goodman and Gilman's The Pharmacological Basis of Therapeutics, $10^{th}$ edition, Pergamon Press, Inc., Elmsford, N.Y., (2001); Avery's Drug Treatment: Principles and Practice of Clinical Pharmacology and Therapeutics, 3rd edition, ADIS Press, Ltd., Williams and Wilkins, Baltimore, Md. (1987); Ebadi, Pharmacology, Little, Brown and Co., Boston, (1985); Osolci al., eds., Remington's Pharmaceutical Sciences, $18^{th}$ edition, Mack Publishing Co., Easton, Pa. (1990); Katzung, Basic and Clinical Pharmacology, Appleton and Lange, Norwalk, Conn. (1992).

As noted above, in certain illustrative embodiments, the monomeric AARS compositions of the invention may be used to modulate angiogenesis, e.g., via modulation of endothelial cell proliferation and/or signaling. Endothelial cell proliferation and/or cell signaling may be monitored using an appropriate cell line (e.g., Human microvascular endothelial lung cells (HMVEC-L) and Human umbilical vein endothelial cells (HUVEC)), and using an appropriate assay (e.g., endothelial cell migration assays, endothelial cell proliferation assays, tube-forming assays, matrigel plug assays, etc.), many of which are known and available in the art.

Therefore, in related embodiments, the compositions of the invention may be employed in the treatment of essentially any cell or tissue or subject that would benefit from modulation of angiogenesis. For example, in some embodiments, a cell or tissue or subject experiencing or susceptible to angiogenesis (e.g., an angiogenic condition) may be contacted with a suitable composition of the invention to inhibit an angiogenic condition.

Certain embodiments include methods of reducing cadherin-mediated cell-cell adhesion, comprising contacting one or more cells with substantially monomeric AARS polypeptide described herein. Also included are methods of modulating the levels, phosphorylation state, or a biological activity of VE-cadherin in a cell, comprising contacting the cell with substantially monomeric AARS polypeptide. Certain embodiments include reducing the levels of VE-cadherin in the cell, which may be in a subject. Certain embodiments include reducing the levels of circulating VE-cadherin in the host, which has been associated with various cancers (see, e.g., Rabascio et al., Cancer Research 64:4373-4377, 2004).

Certain embodiments include reducing the phosphorylation of VE-cadherin at one or more tyrosine residues, and certain embodiments include reducing the biological activity of VE-cadherin. Examples of VE-cadherin-related biological activities include the ability to associate with, or promote the signaling of, vascular endothelial cell growth factor receptor (VEGFR2), and the ability of one or more VE-cadherin polypeptides to self-assemble, or to associate with other VE-cadherin polypeptides. In certain embodiments, the substantially monomeric AARS polypeptides directly bind to VE-cadherin and thereby reduce its biological activity.

Given the role of cadherins such as VE-cadherin in regulating various biological processes, the AARS polypeptides of the present invention may be used for modulating cadherin-mediated activities in a subject. One example of a cadherin-mediated activity is angiogenesis, which is mediated by VE-cadherin. Other examples include regulating the growth or development of neural tissues, placental tissues, vascular tissues, epithelial tissues, retinal tissues, renal tissues, muscle tissues, liver tissues, intestinal tissues, and bone tissues.

In certain embodiments, as noted above, the monomeric AARS polypeptides provided herein may reduce angiogenesis, such as by disrupting the formation or activity of VE-cadherin homophilic complexes, and thereby reducing their angiogenesis stimulating activity. Other mechanisms include disrupting the angiogenic signaling of other proteins or ligands, such as angiogenic aminoacyl-tRNA synthetases, including dimeric AARS polypeptides. Given also the role of CXC receptors such as CXCR-2 and CXCR-2 and related chemokines such as IL-8 in modulating angiogenesis, in certain embodiments, the monomeric AARS polypeptides provided herein that agonize their activity may modulate or increase angiogenesis, e.g., via modulation of cytokine signaling.

"Angiogenesis" refers generally to the growth of new capillary blood vessels, whether in vivo or in vitro, and may include any one or more of the growth of new blood vessels from pre-existing vessels (i.e., sprouting angiogenesis), spontaneous blood-vessel formation (i.e., vasculogenesis), new blood vessel formation by the splitting of an existing vessel (i.e., splitting angiogenesis), or the formation of medium-sized blood vessels possessing tunica media plus adventitia (i.e., arteriogenesis).

Sprouting angiogenesis occurs in well-defined stages. First, angiogenic growth factors activate endothelial cells in pre-existing blood vessels via certain cell-surface receptors. The activated endothelial cells then release proteases to degrade the basement membrane, allowing them to migrate from the parent vessel wall. The endothelial cells then proliferate into the surrounding matrix and form solid sprouts to connect with neighboring vessels. As these sprouts extend toward the source of the angiogenic stimulus, endothelial cells migrate in tandem, using adhesion molecules such as integrins. As cells migrate to the site of angiogenesis, these sprouts then form loops to generate a full-fledged vessel lumen.

Splitting angiogenesis also occurs in well-defined stages. First, two opposing vessel walls establish a zone of contact, after which the endothelial cell junctions are reorganized and the vessel bilayer is perforated to allow growth factors and cells to penetrate into the lumen. Then, a core of pericytes and myofibroblasts is formed between the two new vessels at the zone of contact. The cells in this core then begin laying collagen fibers into the core to provide an extracellular matrix for growth of the vessel lumen. Finally, the core is fleshed out with little or no alterations to the basic structure.

In certain embodiments, the modulation (i.e., stimulation or reduction) of angiogenesis can be associated with one or more tissues or organs. Non-limiting examples of such tissues or organs include skin (e.g., dermis, epidermis, subcutaneous layer), hair follicles, nervous system (e.g., brain, spinal cord, peripheral nerves), auditory system or balance organs (e.g., inner ear, middle ear, outer ear), respiratory system (e.g., nose, trachea, lungs), gastroesophogeal tissues, the gastrointestinal system (e.g., mouth, esophagus, stomach, small intestines, large intestines, rectum), vascular system (e.g., heart, blood vessels and arteries), liver, gallbladder, lymphatic/immune system (e.g., lymph nodes, lymphoid follicles, spleen, thymus, bone marrow), uro-genital system (e.g., kidneys, ureter, bladder, urethra, cervix, Fallopian tubes, ovaries, uterus, vulva, prostate, bulbourethral glands, epidiymis, prostate, seminal vesicles, testicles), musculoskeletal system (e.g., skeletal muscles, smooth muscles, bone, cartilage, tendons, ligaments), adipose tissue, mammaries, and the endocrine system (e.g., hypothalamus, pituitary, thyroid, pancreas, adrenal glands). Accordingly, the monomeric AARS polypeptides provided herein may be used to modulate angiogenesis, including aberrant angiogenesis, associated with any of these tissues or organs. Examples include the treatment of conditions associated with inflammation or cancer of these tissues or organs, or conditions associated with an insufficient angiogenic response.

As noted above, cadherins such as VE-cadherin play a central role in stimulating angiogenesis. Certain monomeric AARS polypeptides may therefore be employed to treat or manage conditions associated with aberrant or increased angiogenesis. Examples of conditions associated with aberrant angiogenesis include, without limitation, cancer, coronary heart disease, tumor metastasis, inflammatory vascular disease, inflammation, ischemia-reperfusion injury, hypertension, rheumatoid arthritis, diabetic retinopathy, macular degeneration, and diabetes, in addition to others described herein.

Certain monomeric AARS polypeptides provided herein may be used in treating cancer. Cancer refers to the uncontrolled growth of abnormal cells in the body. In certain embodiments cancerous cells include malignant cells. Most if not all cancerous tumors, for example, release angiogenic growth factor proteins that stimulate blood vessels to grow into the tumor, providing it with oxygen and nutrients. Anti-angiogenic therapies starve the tumor of its blood supply by interfering with this process.

Cancer as used herein refers to the uncontrolled growth of abnormal cells in the body. In certain embodiments cancerous cells include malignant cells. Examples of cancers include, without limitation, prostate cancer, breast cancer, colon cancer, rectal cancer, lung cancer, ovarian cancer, testicular cancer, stomach cancer, bladder cancer, pancreatic cancer, liver cancer, kidney cancer, brain cancer, melanoma, non-melanoma skin cancer, bone cancer, lymphoma, leukemia, thyroid cancer, endometrial cancer, multiple myeloma, acute myeloid leukemia, neuroblastoma, and glioblastoma. Also included is Kaposi's sarcoma, in which lesions result in part from abnormal growth of blood vessels. Certain embodiments include treating metastatic forms of these cancers, or cancers that have spread (metastasizes) from their original site to another area of the body. Also included are conditions such as hemangiomas, colon polyps, and precancerous skin lesions.

The methods provided herein can also be applied to cancers of the blood and lymphatic systems, including lymphomas, leukemia, and myelomas. Examples of specific cancers that may be treated according to the invention include, but are not limited to, Hodgkin's and non-Hodgkin's Lymphoma (NHL), including any type of NHL as defined according to any of the various classification systems such as the Working formulation, the Rappaport classification and, preferably, the REAL classification. Such lymphomas include, but are not limited to, low-grade, intermediate-grade, and high-grade lymphomas, as well as both B-cell and T-cell lymphomas. Included in these categories are the various types of small cell, large cell, cleaved cell, lymphocytic, follicular, diffuse, Burkitt's, Mantle cell, NK cell, CNS, AIDS-related, lymphoblastic, adult lymphoblastic, indolent, aggressive, transformed and other types of lymphomas. Examples of specific myeloproliferative disorders that may be treated according to methods of the present invention include, e.g., polycythemia vera, essential thrombocythemia, agnogenic myeloid metaplasia, myelofibrosis, myelodysplastic syndrome, and chronic myelocytic leukemia. The methods of the present invention can be used for adult or childhood forms of lymphoma, as well as lymphomas at any stage, e.g., stage I, II, III, or IV.

Certain embodiments may reduce the proliferation of one or more cancer cells. Certain embodiments may reduce the metastases or spread of one or more cancer cells. Certain embodiments may increase the migration of PMNCs or leukocytes to the tumor site. Certain embodiments may reduce tumor size. Certain embodiments may reduce or manage the clinical symptoms associated with one or more cancers, such as pain, chills, fatigue, fever, loss of appetite, malaise, night sweats, and weight loss.

In certain embodiments, the monomeric AARS polypeptides provided herein may be administered as first line treatments or as secondary treatments, as an adjunct to various cancer treatments. Examples of cancer treatments include surgery, radiation therapy, chemotherapy, targeted therapies, immunotherapy, hormonal therapy, stem-cell therapies, bone marrow replacement therapies, symptom control, complementary or alternative therapies, or others. In addition, they may be administered as a primary chemotherapeutic treatment or as adjuvant or neoadjuvant chemotherapy.

The monomeric AARS polypeptides provided herein may be used in combination therapies with chemotherapeutic agents. Examples of chemotherapeutic agents that may be administered as combination therapies include chlorambucil, cyclophosphamide, lomustine (CCNU), melphalan, procarbazine, thiotepa, carmustine (BCNU), busulfan, daunorubicin, doxorubicin, idarubicin, epirubicin, mitoxantrone, bleomycin, cisplatin, carboplatin, oxaliplatin, camptothecins, irinotecan, topotecan, amsacrine, etoposide, etoposide phosphate, teniposide, vincristine, vinblastine, vinorelbine, vindesine, paclitaxel, mechlorethamine, ifosfamide, nitrosurea, dactinomycin, plicomycin, mitomycin, tamoxifen, raloxifene, estrogen receptor binding agents, gemcitabien, navelbine, farnesyl-protein transferase inhibitors, transplatinum, 5-fluorouracil, methotrexate, and temazolomide. Examples of cancer-related transplant therapies that may be used in conjunction with the monomeric AARS polypeptides provided herein include bone marrow transplants, cord blood transplants, hematopoietic stem cell transplants, and autologous peripheral blood cell progenitor transplants, among others.

Also included are methods of modulating angiogenesis associated with infections, including bacterial, viral, and parasitic infections. As one example, Verruga peruana is a clinical syndrome caused by the bacterium *Bartonella bacilliformis*, and is characterized by the development of hemangioma-like lesions, in which bacteria colonize endothelial cells. High-level expression of angiopoietin-2 and VEGF receptors has been observed in the endothelium of verruga peruana, and infection of cultured endothelium with *B. bacilliformis* results in induction of angiopoetin-2 in vitro, demonstrating a collaboration between infected endothelium and overlying epidermis to induce angiogenesis. Hence, the monomeric AARS polypeptides provided herein may reduce the angiogenesis associated with this and similar bacteria.

As a further example, human cytomegalovirus (HCMV) infection is associated with atherosclerosis, transplant vascular sclerosis, and coronary restenosis. A common theme in these vascular diseases is an increased rate of angiogenesis. HCMV infection results in increased EC proliferation, motility, and capillary tube formation. HCMV-induced angiogenic response depends on viral binding to and signaling through the $\beta_1$ and $\beta_3$ integrins and the epidermal growth factor receptor, via their ability to activate the phosphatidylinositol 3-kinase and the mitogen-activated protein kinase signaling pathways. Since a proangiogenic response drives the neovascularization observed in atherosclerotic disease, HCMV infection may contribute to vascular disease by inducing angiogenesis. Hence, the monomeric AARS polypeptides provided herein may reduce the angiogenesis associated with this and similar viruses. The monomeric AARS polypeptides provided herein may be used to reduce the angiogenesis associated with one or more infectious agents, either alone or in combination with anti-infective agents.

Exemplary parasites that induce angiogenesis include parasitic nematodes such as *Trichinella spiralis* and *Onchocerca volvulus*, and helminth parasites such as *Schistosoma mansoni*. Hence, the monomeric AARS polypeptides provided herein may reduce the angiogenesis associated with this and similar parasites.

Further illustrative examples of angiogenic conditions include, but are not limited to, age-related macular degeneration (AMD), cancer (both solid and hematologic), developmental abnormalities (organogenesis), diabetic blindness, endometriosis, ocular neovascularization, psoriasis, rheumatoid arthritis (RA), and skin discolorations (e.g., hemangioma, nevus flammeus or nevus simplex).

As noted above, chemokines such as IL-8 and CXC receptors such CXCR-1 and CXCR-2 play a role in stimulating angiogenesis. Certain monomeric AARS polypeptides, which agonize CXCR-1 and CXCR-2, may therefore be employed as pro-angiogenic agents to treat or manage conditions associated with reduced angiogenesis. Examples of conditions associated with reduced angiogenesis or that could benefit from pro-angiogenic treatment include, without limitation, cardiovascular disease, restenosis, tissue damage after reperfusion of ischemic tissue or cardiac failure, chronic inflammation and wound healing.

The monomeric AARS polypeptides provided herein may therefore be useful in the treatment of vascular or cardiovascular diseases or conditions. Examples include coronary artery disease, coronary heart disease, peripheral arterial disease, wound healing, ischemic-reperfusion injury such as stroke, and others. Also included are atherosclerosis, stenosis, restenosis such as coronary restenosis, and transplant vascular sclerosis. In certain embodiments, stenosis may occur after a coronary artery bypass graft (CABG) operation. In certain embodiments, restenosis may occur after angioplasty, vascular surgery, cardiac surgery, or other treatment to clear arterial blockage, including blockage in the coronary or peripheral arteries.

Monomeric AARS polypeptides may be employed in the treatment of physical injuries or wounds. Examples include abrasions, bruises, cuts, puncture wounds, lacerations, impact wounds, concussions, contusions, thermal burns, frostbite, chemical burns, sunburns, gangrene, necrosis, desiccations, radiation burns, radioactivity burns, smoke inhalation, torn muscles, pulled muscles, torn tendons, pulled tendons, pulled ligaments, torn ligaments, hyperextensions, torn cartilage, bone fractures, pinched nerves, ulcers, and gunshot or other traumatic wounds.

As a further illustrative example, and without wishing to be bound by any one theory, certain AARS polypeptides (e.g., monomeric YRS) agonize CXC receptors, similar to IL-8, and IL-8 has been shown to induce the regression of macroscopic tumors in a model of peritoneal carcinomatosis in the rat. In this model, IL-8 was shown to recruit PMNCs to the challenge site but did not enhance PMNC infiltration of the tumor or the cytotoxic activity of PMNCs. Regardless, IL-8 did have significant therapeutic activity which may be secondary to PMNC cytotoxicity and associated with other intermediate cells. It was suggested, for example, that lymphocytes were involved since IL-8 has also demonstrated the ability to stimulate T-cell chemotaxisis. (Lejeune et al, *Cancer Immunol Immunotherapy.* 38:167-170, 1994). Because certain monomeric AARS polypeptides agonize CXCR-1 and CXCR-2 and stimulate PMNC migration, similar to the activity of IL-8, they may likewise possess anti-cancer therapeutic activity. Accordingly, certain AARS polypeptides that stimulate angiogenesis may be useful in treating cancers, as described herein.

Also included are methods of increasing angiogenesis as a method of treating various infections, including bacterial, viral, and parasitic infections. Without wishing to be bound by any on theory, it is believed that similarly acting chemokines such as interleukin-8 have shown anti-infective therapeutic activity. For example, interleukin-8 has shown therapeutic activity in non-neutropenic mice that received IL-8 shortly before challenge and at the site of infectious challenge with either *P. aeruginosa, Klebsiella pneumoniae,* or *Plasmodium berghei* (see, e.g., Vogels et al., *Antimicrob-Agents-Chemother.* 37:276-280, 1993). Monomer AARS polypeptides, which agonize CXCR-1 and CXCR-2, may thus be employed in certain instances as an anti-infective, alone or in combination with standard anti-infectives, such as antibiotics, anti-virals, and other anti-microbial agents.

In still further embodiments, the compositions of the invention may be used in the treatment of neuronal/neurological diseases or disorders, illustrative examples of which include Parkinson's disease, Alzheimer's disease, Pick's disease, Creutzfeldt-Jacob disease, Huntington's chorea, alternating hemiplegia, amyotrophic lateral sclerosis, ataxia, cerebral palsy, chronic fatigue syndrome, chronic pain syndromes, congenital neurological anomalies, cranial nerve diseases, delirium, dementia, demyelinating diseases, dysautonomia, epilepsy, headaches, Huntington's disease, hydrocephalus, meningitis, movement disorders, muscle diseases, nervous system neoplasms, neurocutaneous syndromes, neurodegenerative diseases, neurotoxicity syndromes, ocular motility disorders, peripheral nervous system disorders, pituitary disorders, porencephaly, Rett syndrome, sleep disorders, spinal cord disorders, stroke, sydenham's chorea, tourette syndrome, nervous system trauma and injuries, etc.

Furthermore, additional embodiments relate to the use of the compositions of the invention in the treatment of metabolic disorders such as adrenoleukodystrophy, Krabbe's disease (globoid cell leukodystrophy), metachromatic leukodystrophy, Alexander's disease, Canavan's disease (spongiform leukodystrophy), Pelizaeus-Merzbacher disease, Cockayne's syndrome, Hurler's disease, Lowe's syndrome, Leigh's disease, Wilson's disease, Hallervorden-Spatz disease, Tay-Sachs disease, etc. The utility of the compositions of the invention in modulating angiogenic or metabolic processes may be monitored using any of a variety of techniques known and available in the art including, for example, assays which measure adipocyte lipogenesis or adipocyte lipolysis.

In more, specific embodiments of the invention, the monomeric AARS compositions of the invention may be used to modulate cellular signaling, for example, via cell signaling proteins such as chemokines or chemokine receptors, including CXCR-1 and CXCR-2, or cadherins such as VE-cadherin. Cell signaling may be monitored using any of a number of well known assays. Detection of cell signaling activities in response to treatment of cells with monomeric AARS polypeptides therefore serves as an indicator of distinct biological effects. Target proteins used for this assay may be selected so as to encompass key components of major cellular signaling cascades, thereby providing a broad picture of the cell signaling landscape and its therapeutic relevance. In certain embodiments, such assays involve cell treatment with monomeric AARS polypeptides followed by immunodetection with antibodies that specifically detect the levels of phosphorylated or un-phosphorylated forms of the target proteins.

Of course, it will be recognized that other classes of proteins, such as cell adhesion molecules (e.g., cadherins, integrins, claudins, catenins, selectins, etc.) and/or ion channel proteins may also be assayed for monitoring cellular events or activities modulated by the compositions of the invention.

Generally, a therapeutically effective amount of polypeptide is administered to a subject or patient. In particular embodiments, the amount of polypeptide administered will typically be in the range of about 0.1 µg/kg to about 0.1 mg/kg to about 50 mg/kg of patient body weight. Depending on the type and severity of the disease, about 0.1 µg/kg to about 0.1 mg/kg to about 50 mg/kg body weight (e.g., about 0.1-15 mg/kg/dose) of polypeptide can be an initial candidate dosage for administration to the patient, whether, for example, by one or more separate administrations, or by continuous infusion. For example, a dosing regimen may comprise administering an initial loading dose of about 4 mg/kg, followed by a weekly maintenance dose of about 2 mg/kg of the polypeptide, or about half of the loading dose. However, other dosage regimens may be useful. A typical daily dosage might range from about 0.1 µg/kg to about 1 µg/kg to 100 mg/kg or more, depending on the factors mentioned above. For repeated administrations over several days or longer, depending on the condition, the treatment is sustained until a desired suppression of disease symptoms occurs. The progress of these and other therapies (e.g., ex vivo therapies) can be readily monitored by conventional methods and assays and based on criteria known to the physician or other persons of skill in the art.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLE 1

Generation and Characterization of Stable Monomeric and Dimeric Forms of YRS

The N-terminal fragment of human tyrosyl-tRNA synthetase, mini-YRS, is a leukocyte chemo-attractant and an angiogenic factor. However, the details of how mini-YRS mediates cytokine signaling are unclear. Mini-YRS exists as both a monomer and a dimer at physiological conditions. Because mini-YRS mediates cytokine signaling at a concentration of 10 nM and dimerizes at ≥100 nM, and because its stimulating effect exhibits a bell-shaped concentration dependence, it was hypothesized that the monomer form is the active cytokine and the dimer is a nonfunctional receptor binding form. To test this hypothesis, a non-associating monomeric and a non-dissociating dimeric forms of YRS were rationally designed and characterized, as detailed below.

The three-dimensional structure of mini-YRS shows that three residues (Pro 159, Leu 160 and Leu 161) in the CP1 dimerization domain form backbone H-bonding interactions with the other subunit (See FIG. 2B), and these three residues were deleted to generate a stable and substantially monomeric form of YRS.

Figure 2A:
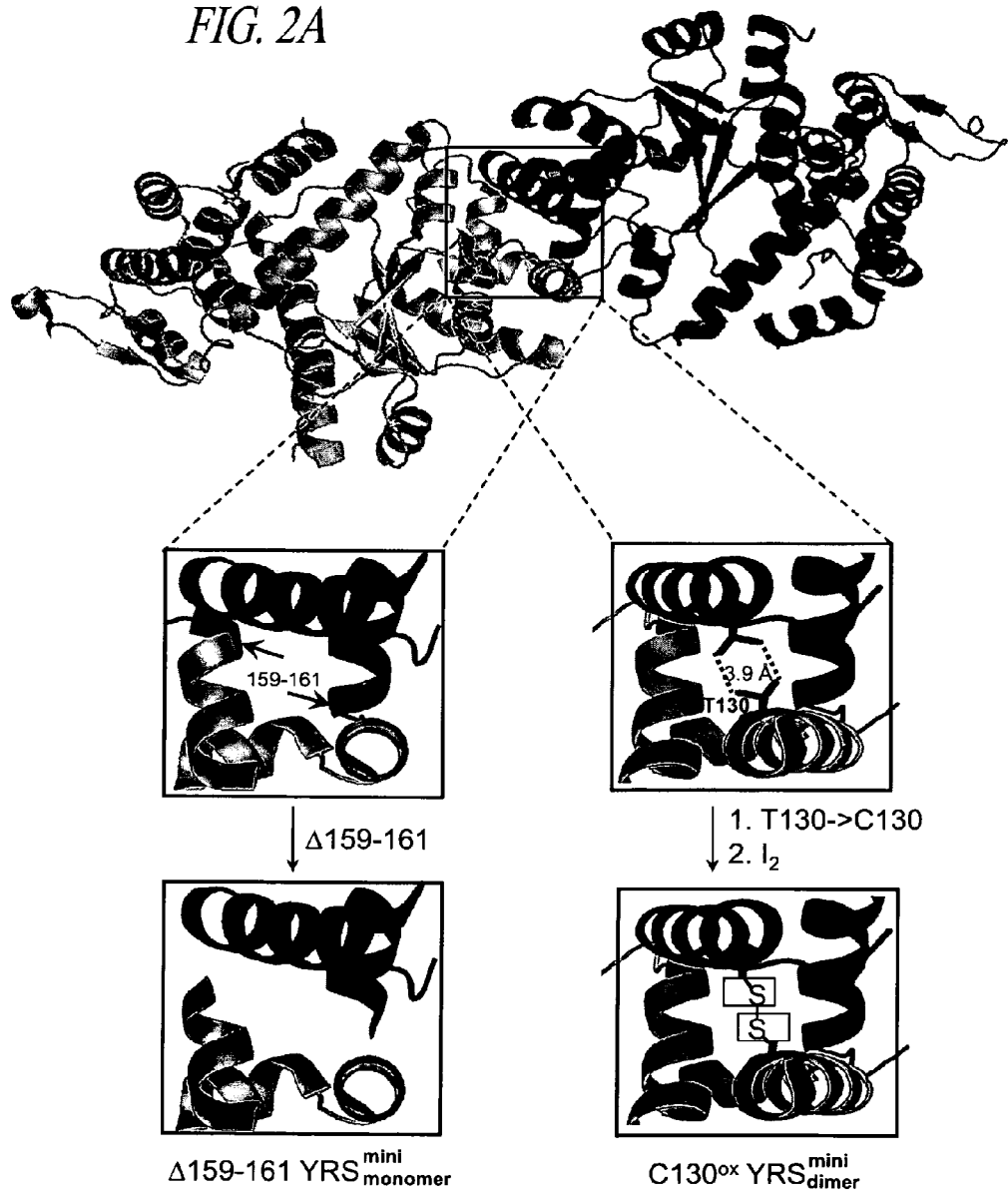
FIG. 2A shows the structure of a mini-YRS dimer with individual monomers shown in light grey and dark grey (PDB 1q11).

To generate a non-dissociating dimer, a disulfide trap strategy was employed, in which an exposed cysteine residue was introduced at the dimer interface of each individual monomer so that the —SH groups are spatially proximal to each other, and upon oxidation resulted in a single disulfide link across the dimer interface. As shown in FIG. 2C, Thr 130 was replaced with Cys, followed by $I_2$ oxidation to form disulfide bond between two subunits (named $C130^{OX}$).

Plasmid Construction, Expression, and Purification of Mini-YRS Variants.

Plasmid encoding wild-type (WT) human mini-YRS has been cloned previously, and this plasmid template was used to generate mini-YRS variants by site-directed mutagenesis using QuikChange™ mutagenesis kit from Stratagene (La Jolla, Calif.). Primers were purchased from Integrated DNA Technology, Inc. (Coralville, Iowa). Recombinant proteins were expressed and purified according to routine techniques in the art. To perform b oxidation, T130C mini-YRS (1 mg/ml) was incubated with $I_2$ (0.5 mM) in phosphate saline buffer (PBS) for 15 min at 37° C., followed by extensive dialysis overnight against PBS at 37° C. to remove $I_2$. Endotoxin was removed by running through EndoTrap Red column (Lonza Walkersville, Inc., Walkerville, Md.) twice.

To confirm that the stable monomeric Δ159-161 and dimeric $C130^{OX}$ were folded correctly, a circular dichroism (CD) analysis was performed. Circular dichroism (CD) spectra were obtained with CD Spectrometer 400 (Biomedical, Inc. Lakewood, N.J.). Prior to CD measurements, protein samples were extensively dialyzed overnight against PBS. The measurements were performed using 100 µL of each protein sample at 10 µM for far-UV spectra and 500 µL at 50 µM for near-UV spectra. For thermal melting scans, protein samples were monitored at a fixed wavelength of 220 nm as a function of temperature.

Figure 3A:
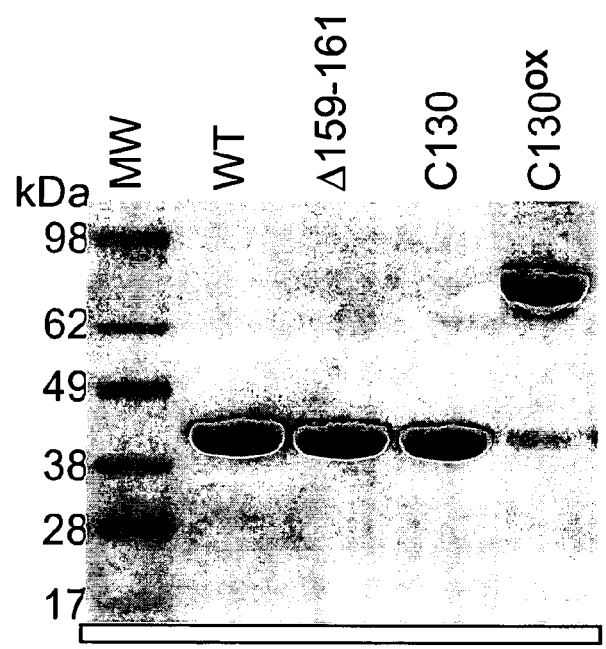
FIG. 3A is a non-reducing SDS-PAGE analysis showing Δ159-161 and $C130^{OX}$ variants electrophoresis as monomer and dimer, respectively.
Figure 3B:
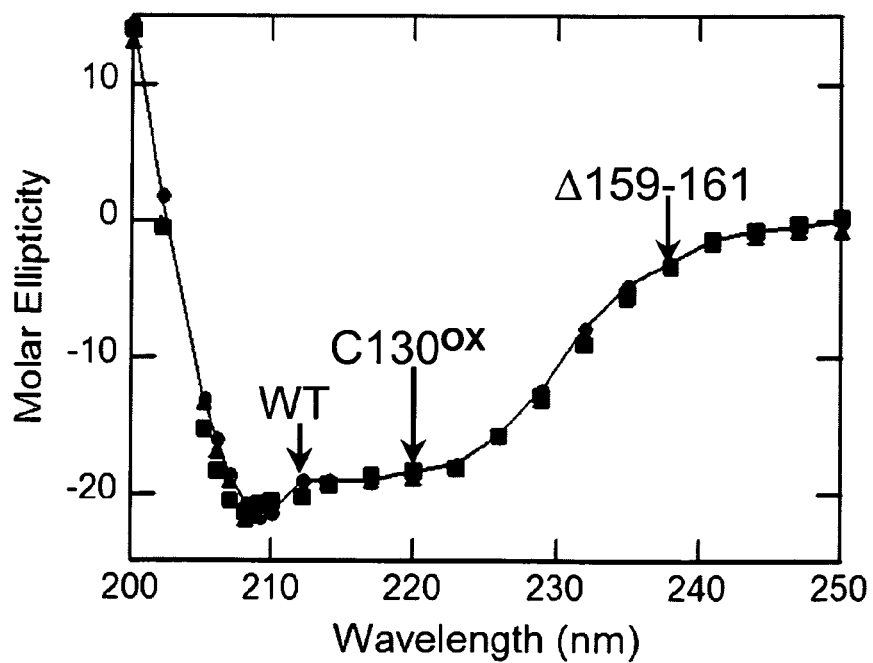
FIG. 3B is a far-UV CD spectra of WT (●), Δ159-161 (▲) and $C130^{OX}$ (■).
Figure 3C:
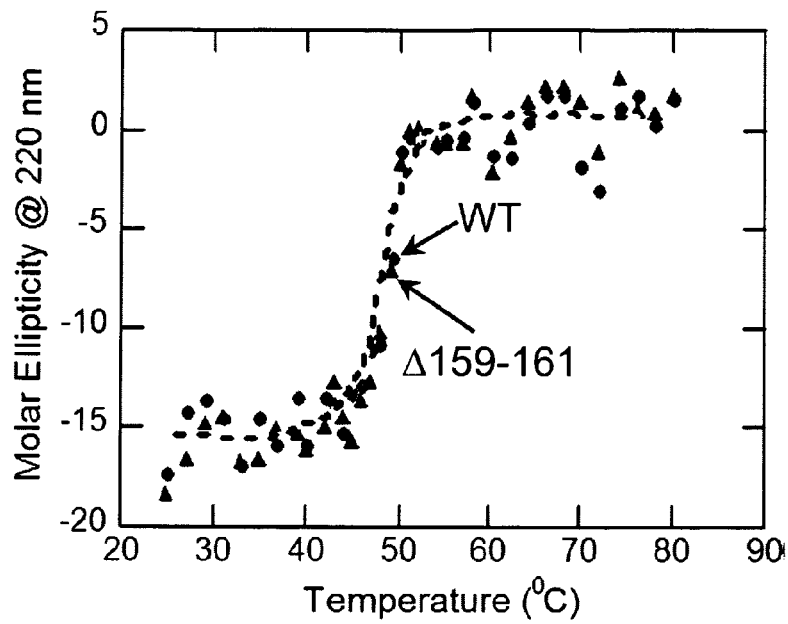
FIG. 3C is a thermal melting CD spectra of WT (●) versus Δ159-161 (▲).
Figure 3D:
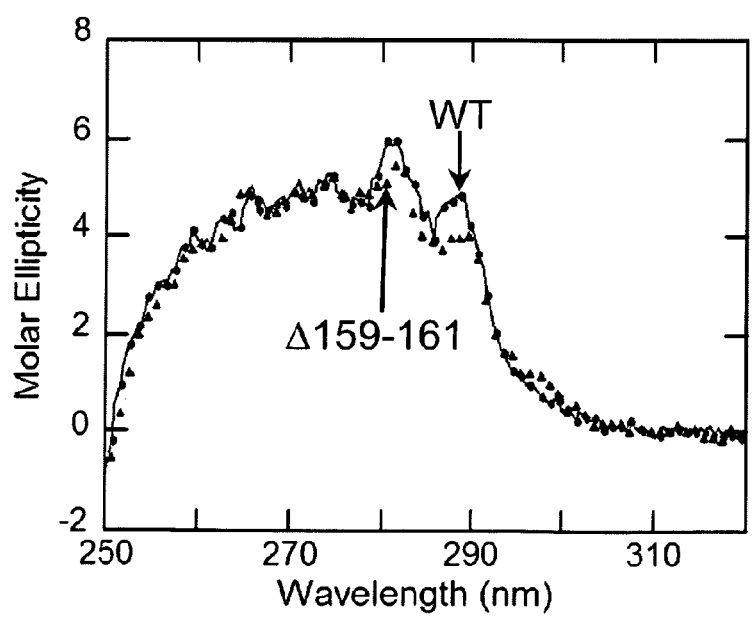
FIG. 3D is a near-UV CD spectra of WT (●) versus Δ159-161 (▲).

These analyses show that the secondary structures of Δ159-161 and $C130^{OX}$ are similar to that of the WT (FIG. 3B). Thermal melting also indicates that there is no change in stability of the Δ159-161 compared to the WT (FIG. 3C). Near-UV CD spectral region of 260-320 nm arises from aromatic amino acids, which can be used as a tertiary structure fingerprint. Here, there is no significant difference in the CD spectra of the WT and the Δ159-161 except at the region of 275-285 nm (FIG. 3D). This region corresponds to the signal of tyrosine residues. Based on the three-dimensional structure, tyrosine residues are the only aromatic amino acid proximal to the dimer interface, which is consistent with disruption of dimer interface.

An amino acid activation assay was then performed to determine whether the monomeric Δ159-161 and dimeric C130$^{OX}$ YRS polypeptides have the ability to amino-acylate their cognate tRNAs. Homodimerization and half-of-the sites activity of YRS are required for aminoacylation function. Thus, if any mutations interfere with the dimerization dynamics they would likewise affect aminoacylation activity.

Figure 3E:
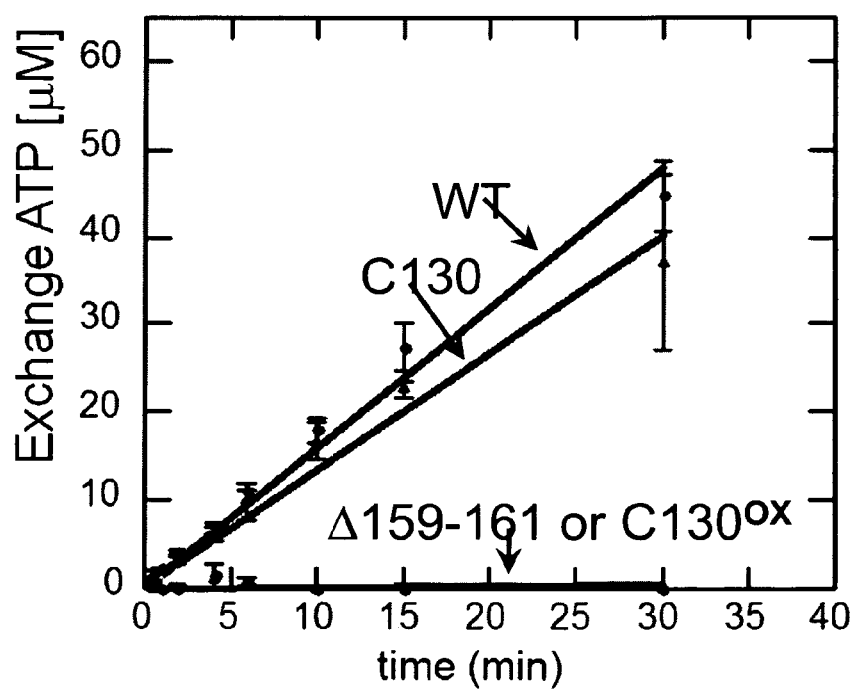
FIG. 3E is an amino acid activation assay comparing activity of WT, Δ159-161 and $C130^{OX}$ variants.

The amino acid activation was performed at 25° C. according to standard protocols, with some modifications to adapt to a 96-well format. Briefly, each reaction mixture contained 100 mM Tris-HCl, pH 7.4, 10 mM MgCl$_2$, 1 mM ATP, 0.1 mg/ml bovine serum albumin, 0.5 mM sodium pyrophosphate including [$^{32}$P]-pyrophosphate (Perkin Elmer; with specific activity of 37 TBq/mml), 5 mM β-mercaptoethanol, 2 mM tyrosine, and 100 nM of WT or its variants. Aliquots were quenched at different time points in 96-well Multiscreen filter plate (Millipore, Billerica, Mass.) containing 200 mM sodium pyrophosphate, 1 M HCl and 4% (w/v) activated charcoal. After washing four times with a solution of 200 mM sodium pyrophosphate and 1 M HCl, charcoal-absorbed [$^{32}$P]-ATP samples were punched from the plate and quantified by scintillation counting. FIG. 3E shows that the Δ159-161 and C130$^{OX}$ constructs lack aminoacylation activity (FIG. 3E).

Figure 4A:
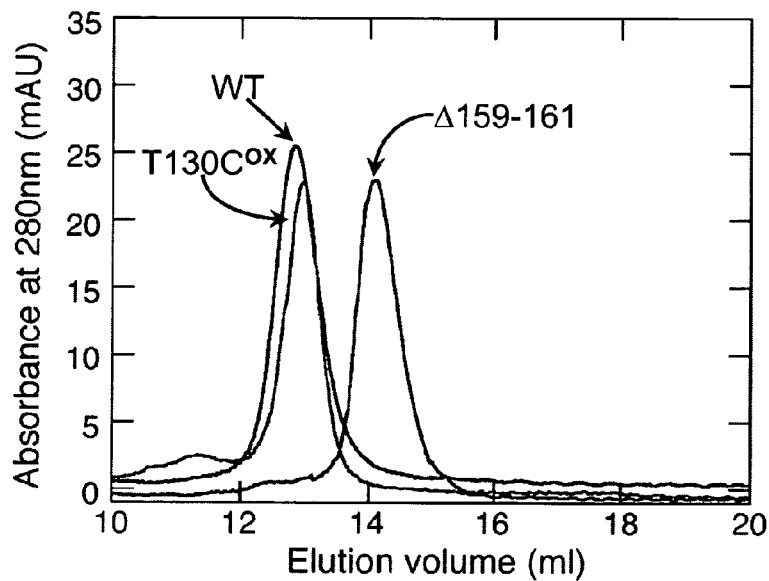
FIG. 4A shows an analytical gel chromatography of WT, Δ159-161 and $C130^{OX}$, in which the WT and $C130^{OX}$ peaks correspond to dimeric mini-YRS and Δ159-161 peak corresponds to monomeric mini-YRS. Also shown is the estimation of dimer-monomer equilibrium dissociation constant for Δ159-161 (4B) by gel filtration chromatography and WT (4C) by gel chromatography in combination with immunoblotting.
Figure 4B:
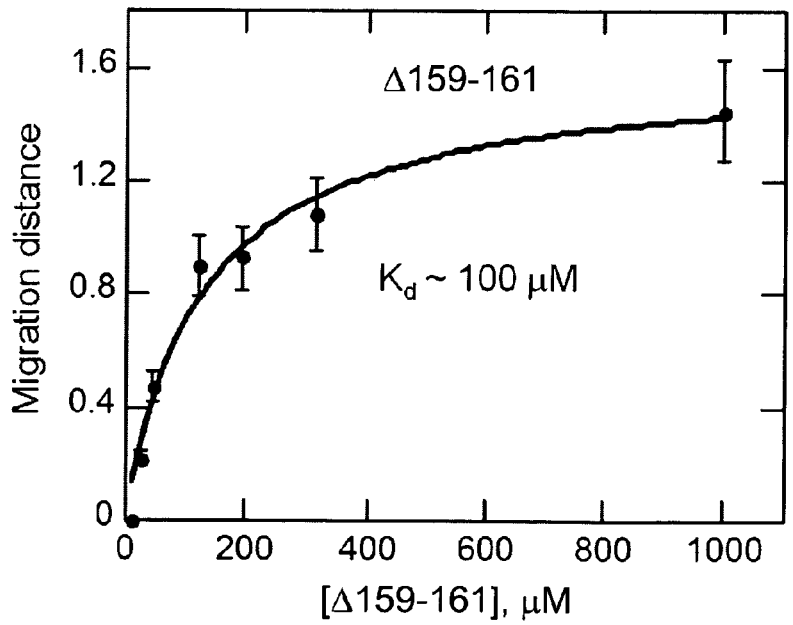
FIG. 4 shows the determination of dimer-monomer equilibrium dissociation constants for WT min-YRS and Δ159-161 mini-YRS.
Figure 4C:
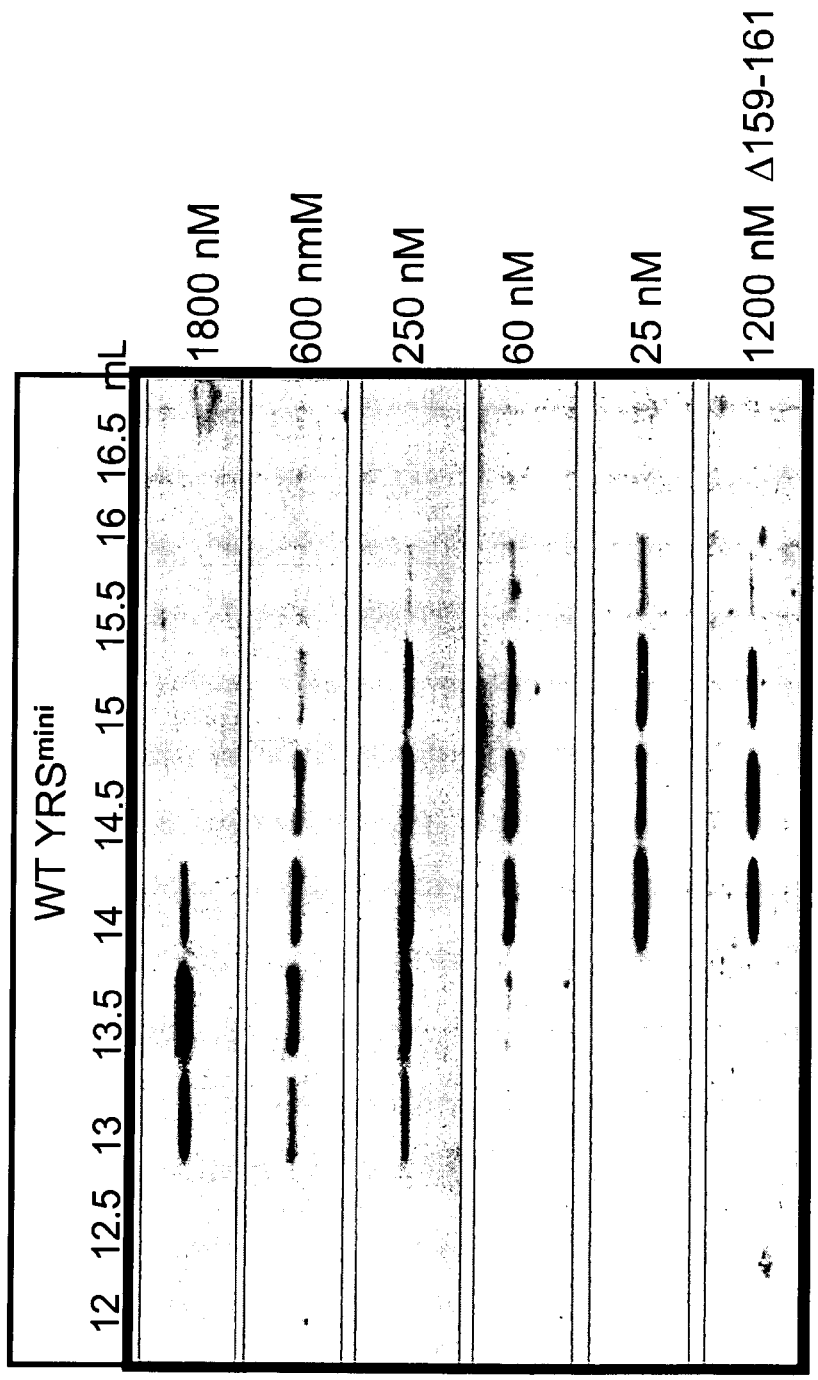

Analytical gel filtration chromatography was then performed on the stable monomeric Δ159-161 and dimeric C130$^{OX}$ YRS polypeptides, in comparison to WT mini-YRS. Each protein sample (200 μl of 20 μM) was injected to Superdex 200 chromatography column (GE Healthcare, 10/300GL) in PBS containing 5 mM β-mercaptoethanol. The column was then calibrated by standard proteins. These results show that the WT and the C130$^{OX}$ elute as dimeric species, whereas the Δ159-161 shifts the equilibrium distribution toward monomeric species at 10 μM concentration (FIG. 4A). To determine the dissociation constant for dimer-monomer equilibrium, gel chromatography was carried out as a function of protein concentration. As shown in FIG. 4B, the dissociation constant for Δ159-161 was estimated to be ~100 μM. Due to undetectable UV-absorbance at low concentration of the WT, fractions were collected and immuno-blotted with a YRS polyclonal antibody. FIG. 4C shows that at concentrations of 60 nM and 250 nM, WT exists predominantly as monomers and dimers, respectively. Based on these data, it was estimated that the dissociation constant for dimer-monomer equilibrium of WT mini-YRS is ~100 nM, which is about 1000-fold lower than for the monomeric Δ159-161 YRS polypeptide.

EXAMPLE 2

Effects of Stable Monomeric and Dimeric Forms of YRS on Polymorphonuclear Cell Migration To test the hypothesis that the monomer form is the active cytokine for mini-YRS signaling and that the dimer binds to the receptor but does not signal, the effect of the monomeric Δ159-161 and dimeric C130$^{OX}$ variants on human polymorphonuclear (PMN) leukocytes was examined. Also, to understand why the WT min-YRS exhibits a bell-shaped concentration dependence response but the Δ159-161 does not, competitive cell migration assays were performed, in which PMN cells were pre-treated with a progressive increase in either monomer or dimer concentrations prior to the cell migration assay.

Transwell Cell Migration Assay.

Human PMN cells were prepared from heparin-treated whole blood from healthy volunteers using RosetteSep Human Granulocyte Enrichment Kit (StemCell Technologies, Vancouver, BC, Canada). Isolated PMN cells were resuspended in cell migration medium containing RPMI 1640 (American Type Culture Collection, Manassas, Va.) and 0.5% heat-inactivated fetal bovine serum (FBS) (Invitrogen Corporation, Carlsbad, Calif.) and incubated with Calcein AM (Invitrogen Corporation, Carlsbad, Calif.) at 37° C. in a 5% CO$_2$ incubator for 30 minutes. After the incubation, cells were then collected and washed with RPMI 1640 containing 0.5% FBS two times and resuspended in cell migration medium at a concentration of 10×10$^6$ cells/ml.

Cell migration was performed using 24-well transwell permeable support with 5 μM pores (Corning Inc., Lowell, Mass.). Briefly, 100 μL of cells were plated in upper transwell insert and 600 μL of proteins at various concentrations as labeled in Figure legends were added to the lower chamber. Cells were allowed to migrate at 37° C. in a 5% CO$_2$ incubator for 45 minutes. The migrated cells were then collected and fluorescence intensity of migrated cells were counted using Synergy HT Microplate reader with filters set to 485 nm for excitation and 520 nm for emission (BioTek Instruments, Inc, Vinooski, Vt.). Fold migration over control was calculated as fluorescence intensity of cells migrating to proteins divided by fluorescence intensity of cells migrating to medium.

Figure 5A:
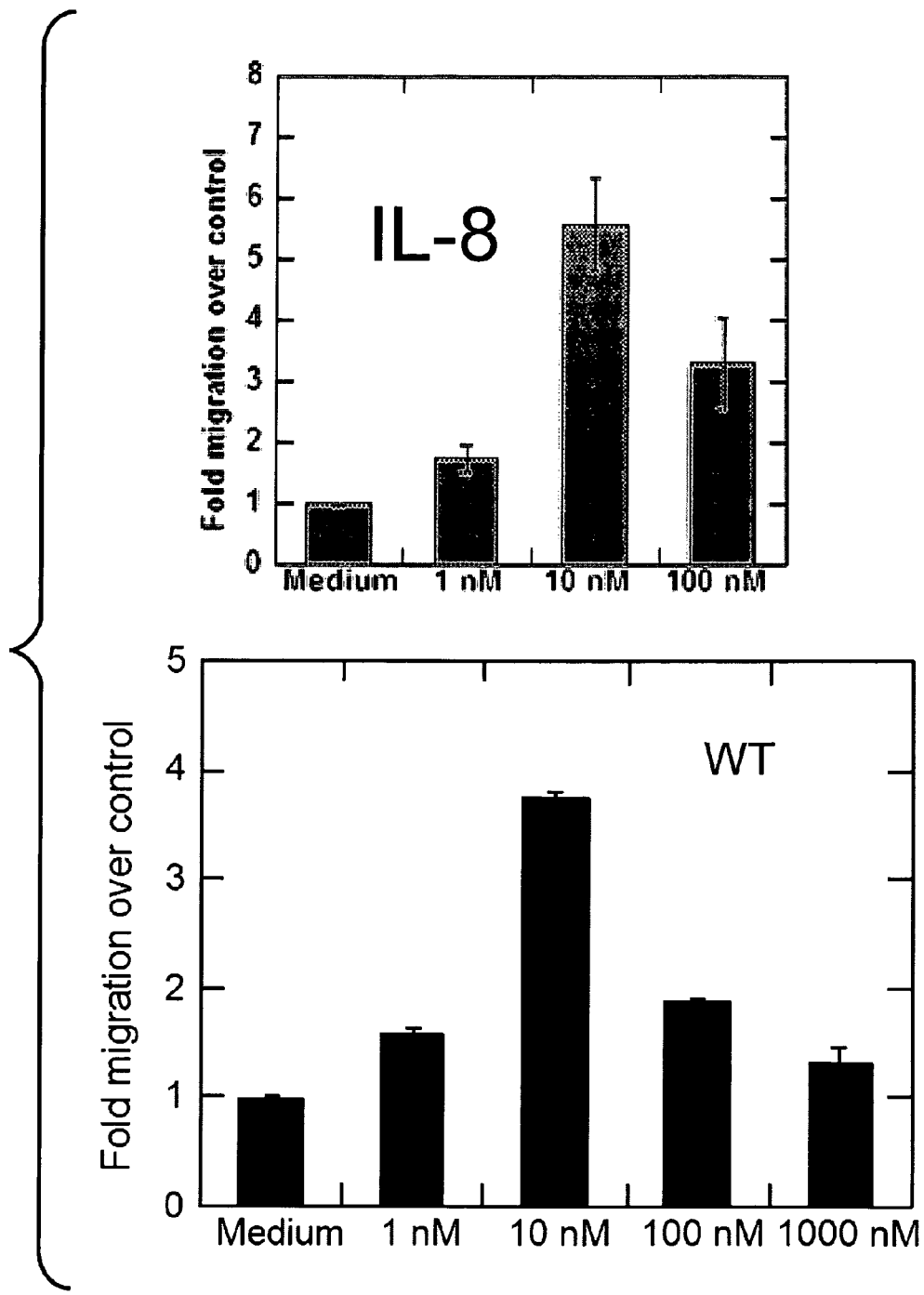
In FIG. 5A, WT exhibits bell-shaped concentration response consistent with previous studies.
Figure 5B:
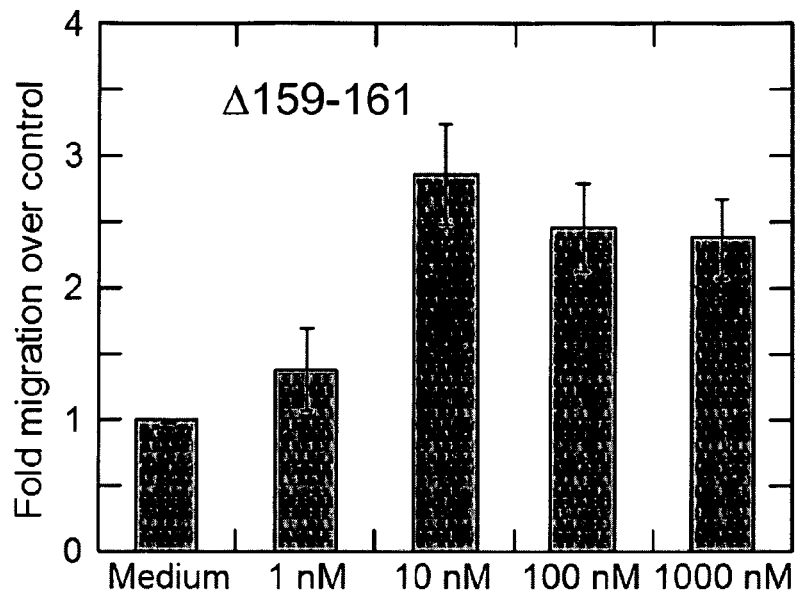
In FIG. 5B, the monomeric Δ159-161 YRS is functionally active and shows no decrease in migration activity at high concentrations.
Figure 5C:
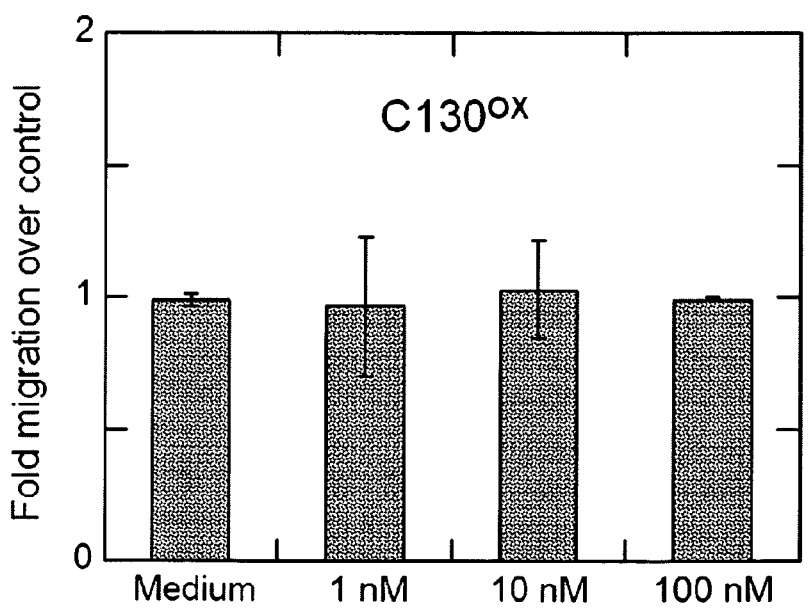
In FIG. 5C, the dimeric $C130^{OX}$ is unable to stimulate cell migration.
Figure 6:
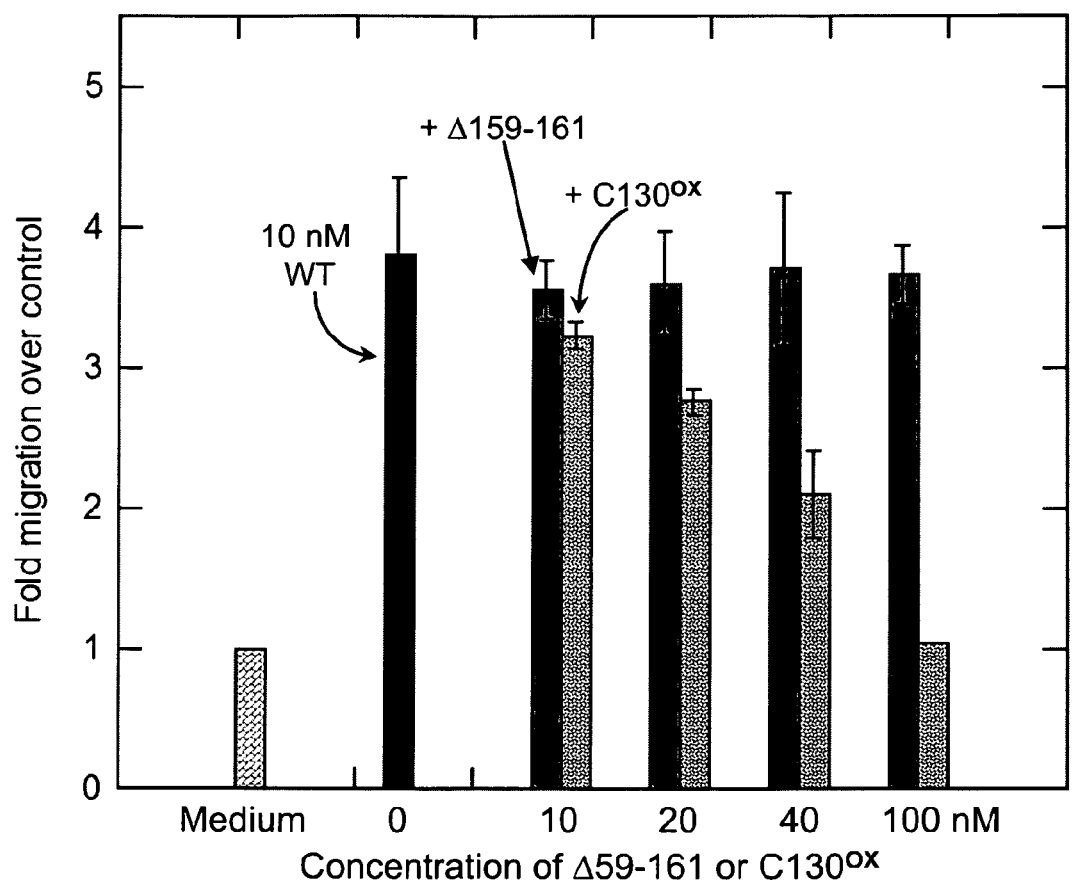
FIG. 6 shows that $C130^{OX}$ inhibits WT mini-YRS-induced PMN cell migration.

The results are shown in FIGS. 5 and 6. At low concentration regime, the monomeric Δ159-161 stimulates PMN cell migration as effective as the WT (compare FIGS. 5A and B, at 1 nM and 10 nM). Since the K$_d$ for dimer-monomer equilibrium of WT is ~100 nM, at this low concentration regime WT exists predominantly as monomers. In addition, no migration activity was observed in the treatment with the C130$^{OX}$ (FIG. 5C). Taken together these results suggest that the monomer is the active ligand and the dimer is inactive with respect to inducing PMN migration.

For the competitive cell migration assays, the dimer inhibited cell migration in a dose-dependence manner, but the monomer did not show any inhibition (FIG. 6). These data show that the dimer is not only the inactive form but also inhibits the cytokine activity of the monomer.

EXAMPLE 3

Cytokine Receptor-Binding Characteristics of Stable Monomeric and Dimeric Forms of YRS The monomeric Δ159-161 and dimeric C130$^{OX}$ YRS variants were tested for their ability to bind CXCR-1 and CXCR-2 on the cell surface. Also, competitive binding assays were performed in the presence of fixed concentration of WT min-YRS and increasing concentration of dimer to determine whether the dimer competes with WT mini-YRS for binding to the receptor. In these assays, HEK 293 cells that stably express either CXCR1 or CXCR2 receptors were incubated with purified His$_6$-tagged WT mini-YRS, monomeric Δ159-161 mini-YRS, or the C130$^{OX}$ dimeric variant.

Receptor Binding Assay.

HEK 193 cells that express CXCR-1 or CXCR-2 (a gift from Dr. Adit Ben-Baruch at Tel Aviv University) were incubated with purified His$_6$-tagged WT or Δ159-161 mini-YRS for 1 hr at 4° C. Cells were then washed twice with PBS, lysed with M-PER buffer (Thermo Scientific, Rockford, Ill.) and analyzed by immunoblotting using anti-His$_6$ (Immunology Consultants Laboratory, Inc. Newberg, Oreg.) and anti-actin (Sigma-Aldrich, St. Louis, Mo.) antibodies to detect mini-YRS binding and relative number of cells, respectively. The expression of CXCR-1 or CXCR-2 in these cells was confirmed by flow cytometric analysis (data not shown).

Figure 7:
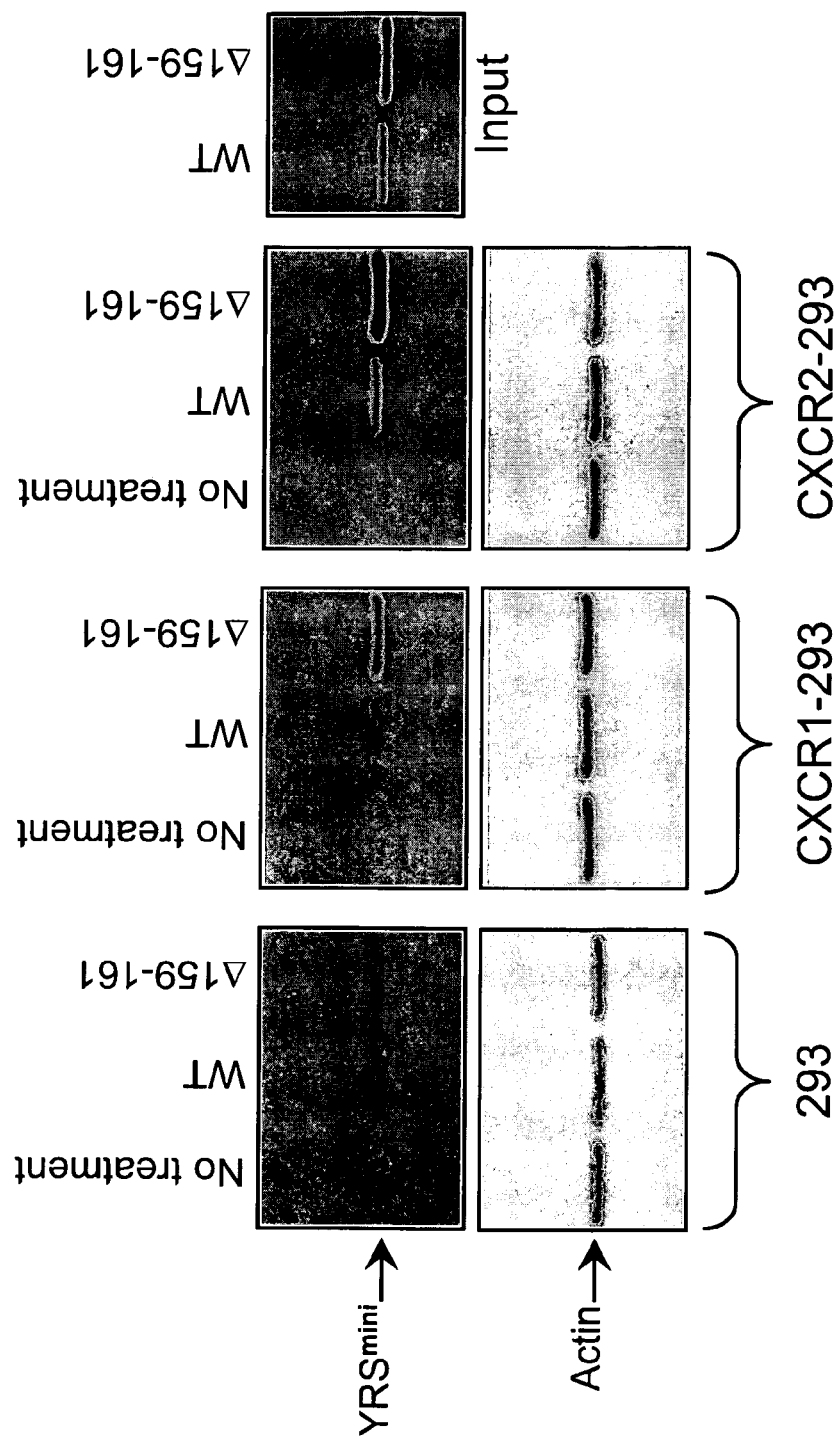
FIG. 7 shows that the monomeric Δ159-161 YRS binds to CXCR-1 and CXCR-2.
Figure 8:
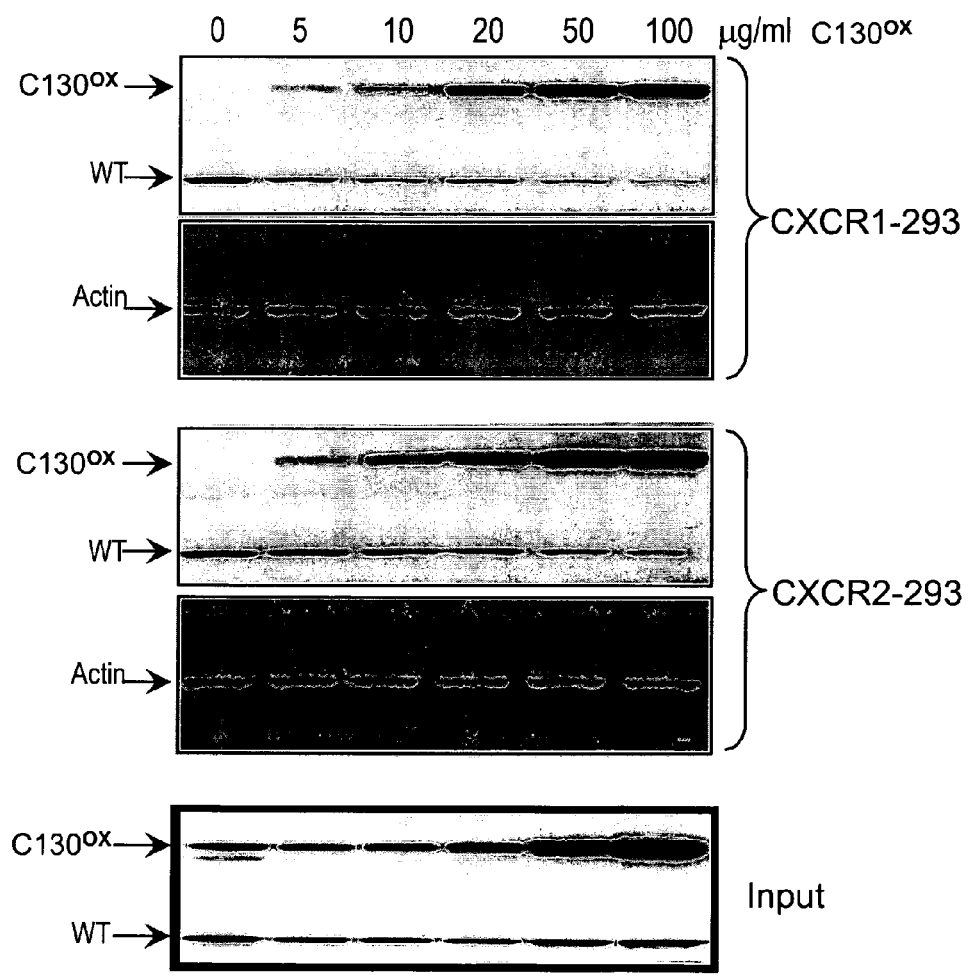
FIG. 8 shows that the dimeric $C130^{OX}$ YRS competes with WT mini-YRS for binding to CXCR-1 and CXCR-2.
Figure 9:
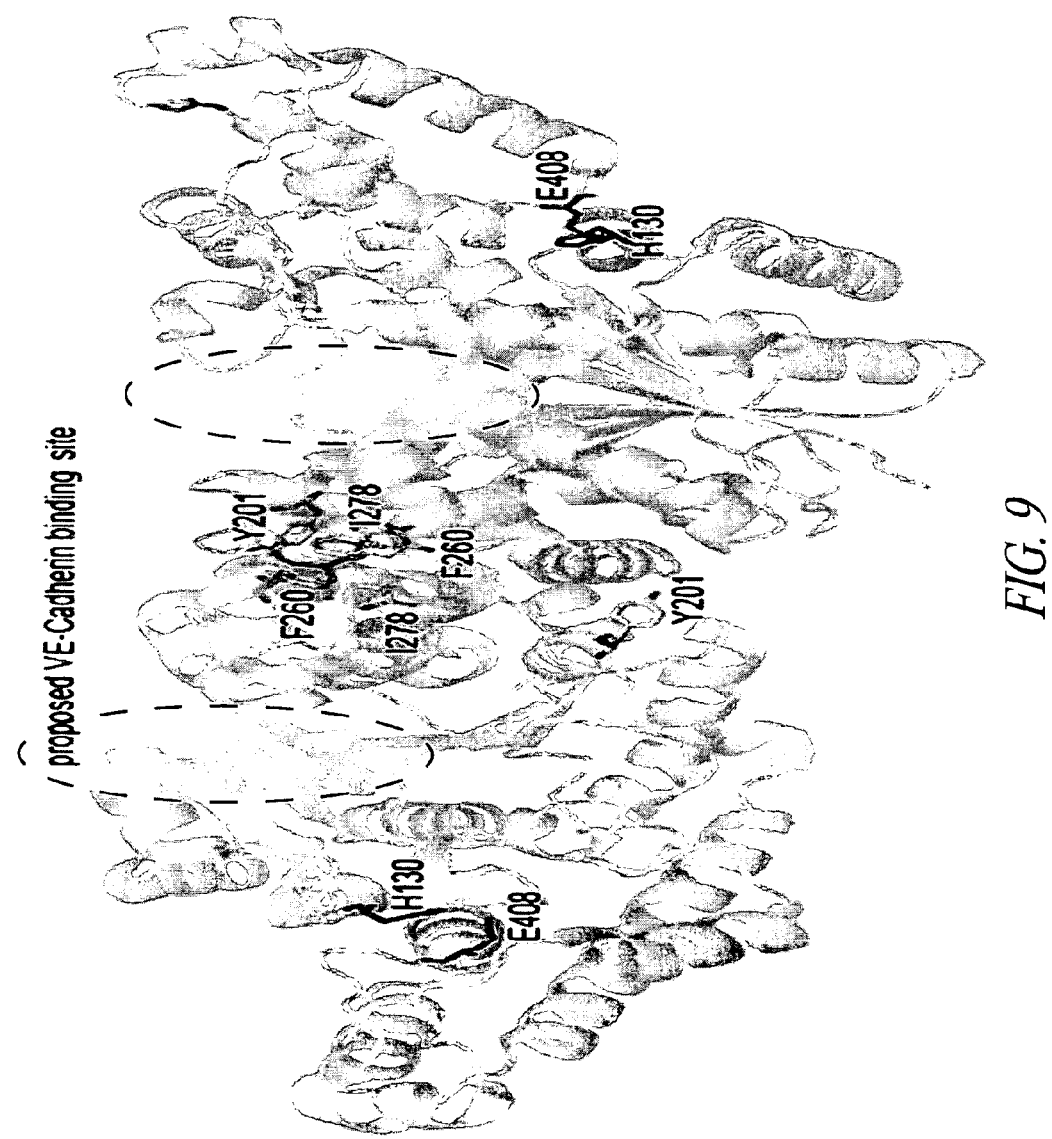
FIG. 9 illustrates the bases of the design of exemplary T2-WRS variants that form stable monomers. The T2-WRS dimer is shown in ribbon (grey), and certain relevant amino acids F260, Y201 and I278 located in the dimer interface are shown in stick figures of these amino acids (center). The active site on each subunit, which is also the proposed VE-cadherin binding site, is highlighted by dashed ellipses on either side of the dimer interface. H130 is located outside the active site, and when mutated to Arg, interacts with E408 to induce a conformational change that is otherwise induced by Zn2+ binding. The H130R mutation may therefore remove the $Zn^{2+}$ dependence of the T2-WRS and VE-cadherin interaction, as shown by the data in FIG. 10C.

These results are shown in FIGS. 7 and 8. As shown in FIG. 7, the monomer binds to cells expressing the CXCR-1 and CXCR-2 receptors as effective as the WT. In addition, no binding was observed to the non-receptor-expressing parental HEK 293 cell line. As shown in FIG. 8, increasing concentration of the C130$^{OX}$ dimer results in decrease in binding of the WT mini-YRS.

The results herein show that the dissociated monomer is functionally active and the dimer is not active. Moreover, the dimer functions as an antagonist by competing with the monomer for receptor binding, resulting in shutting down the monomer-induced cytokine activity. This work provides a new mechanism for understanding how new surfaces can be exploited to expand new functions of tRNA synthetase.

EXAMPLE 4

VE-Cadherin Interacts with Monomeric Form of T2-WRS

To test the nature of the interaction between human tryptophanyl tRNA synthetase and the extracellular domain EC1 of VE-cadherin, the T2-WRS fragment of WRS and the EC1 domain of VE-cadherin were recombinantly expressed and purified. These purified polypeptides were then mixed together, and separated by size exclusion chromatography, as detailed below.

Expression and Purification of Recombinant T2-WRS.

Human T2-WRS cDNA (residues 94-471 of full-length WRS) with a C-terminal His6 tag was cloned into plasmid pET20b. T2-WRS was expressed in E. coli strain BL21 (DE3) (Novagen) by induction for 4 hr with 1 mM isopropyl β-D-thiogalactopyranoside. Protein was purified from the supernatants of lysed cells using Ni-NTA agarose column chromatography (Qiagen) according to the manufacturer's instruction.

Expression and Purification of VE-Cadherin Extracellular Domain EC1.

VE-Cadherin extracellular domain EC1 (residues 48-155 of full-length VE-Cadherin) was cloned into pGEX-6p-1 (GE Healthcare) vector with a glutathione transferase (GST) tag at its N-terminal, and the resulting plasmid was transformed into Escherichia coli BL21(DE3) cells. The recombinant GST fusion protein, GST-VE-EC1, was purified by GST-glutathione affinity chromatography. A Factor Xa recognition sequence Ile-Glu-Gly-Arg was cloned between the first residue of VE-EC1 and the GST tag to allow the cleavage of GST tag from VE-EC1. The Factor Xa cleavage reaction was performed at 4° C. for 20 hours in a buffer containing 25 mM Tris pH8.0, 100 mM NaCl and 2 mM CaCl$_2$. The tag-free VE-EC1 was then purified by gel filtration chromatography (Superdex200 HR 10/30, GE Healthcare) in a buffer containing 25 mM Tris-HCl (pH 8.0), 150 mM NaCl.

Figure 10A:
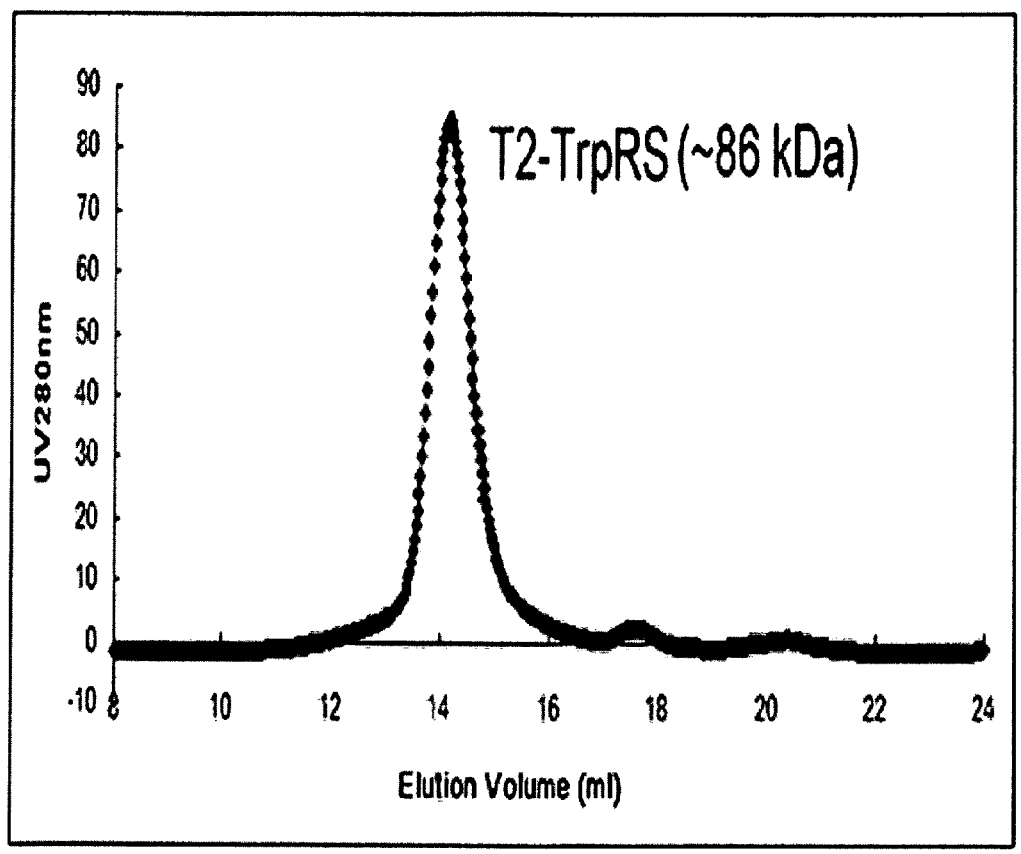
FIGS. 10A-10D show size exclusions chromatography that illustrates the interaction of a monomer form of T2-WRS with the VE-Cadherin EC1 domain. See Example 4.
Figure 10B:
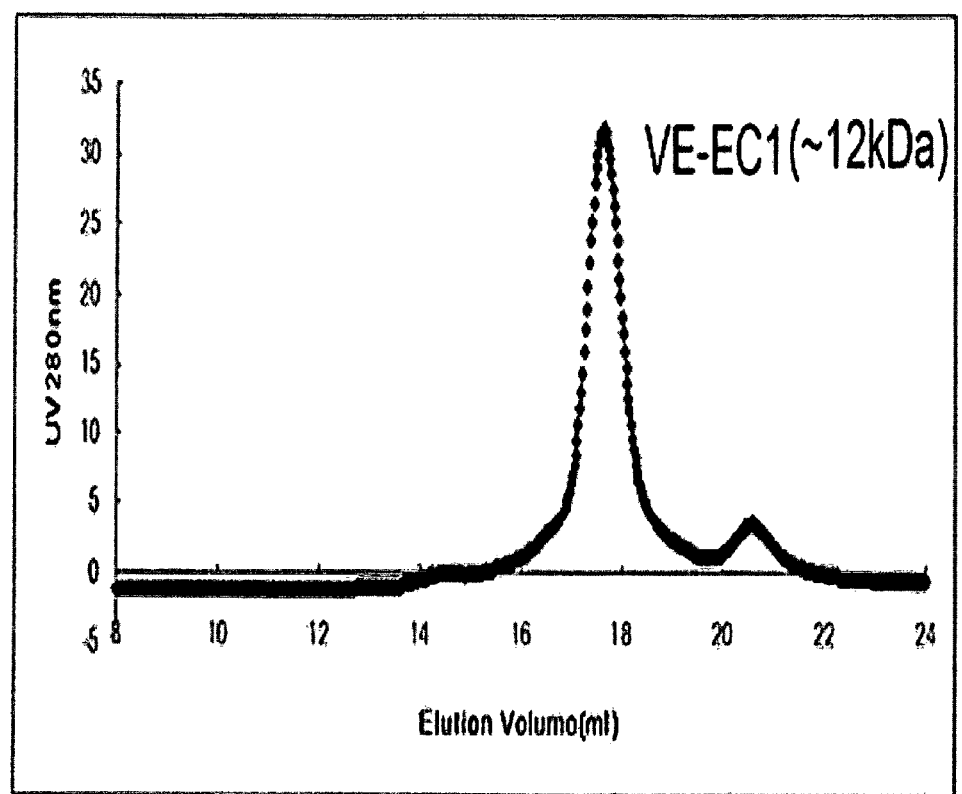
Figure 10C:
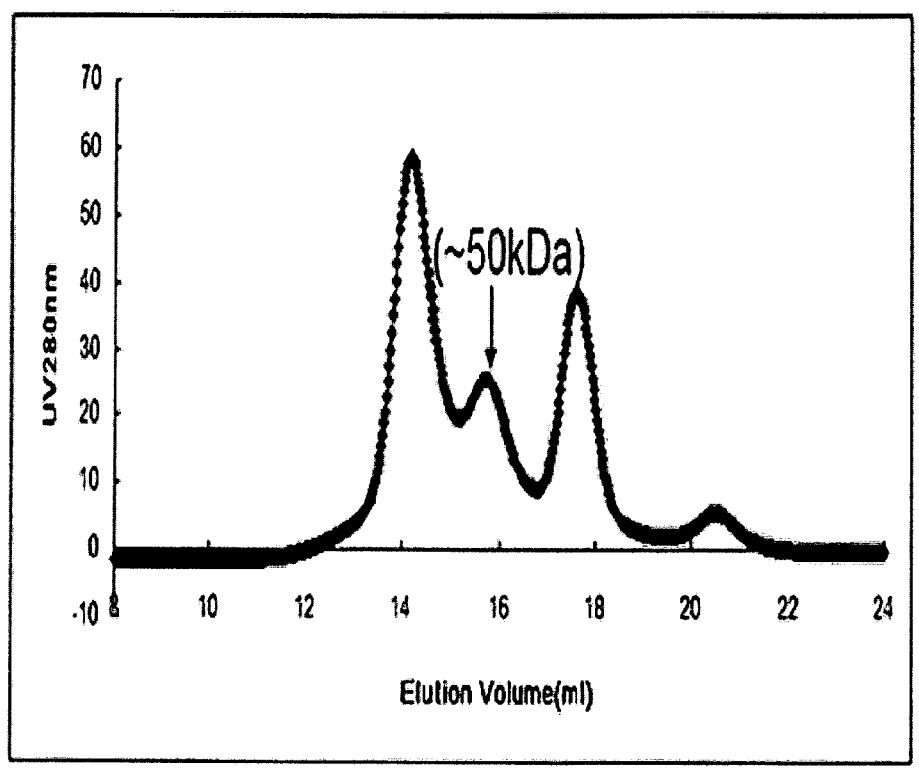
Figure 10D:
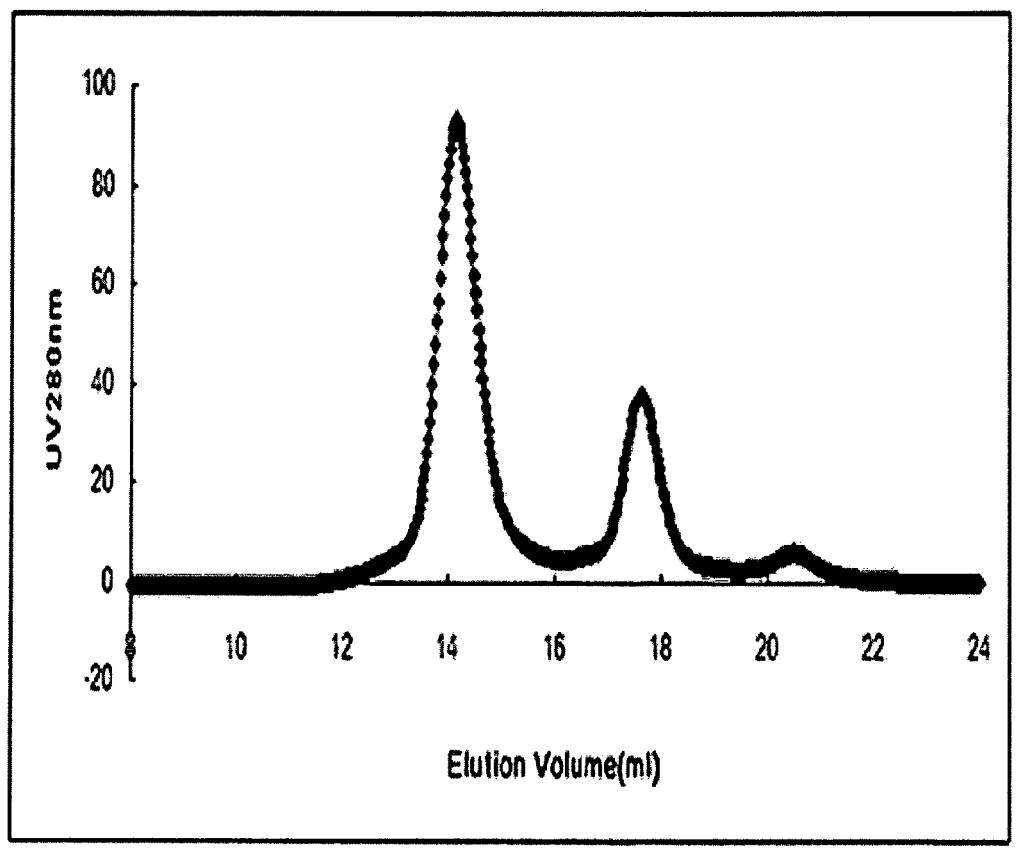

To perform the size exclusion chromatography experiment, T2-WRS and VE-EC1 were loaded separately or together at a molar ratio of 1:1 on Superdex 200 HR 10/30 column, and then eluted at 0.5 mL min$^{-1}$ with a buffer containing 25 mM Tris-HCl (pH 8.0), 150 mM NaCl. The results are shown in FIG. 10; FIG. 10A shows the results for T2-WRS, FIG. 10B shows the results for VE-Cadherin EC1 domain, FIG. 10C shows the results for T2-WRS and VE-EC1 at 1:1 ratio with 0.1 mM Zn$^{2+}$, and FIG. 10D shows the results for T2-WRS and VE-EC1 at 1:1 ratio with 0.1 mM Zn$^{2+}$ and 30 uM Trp-SA. These results illustrate the selective association of the EC1 domain of VE-cadherin with monomeric forms of WRS.

EXAMPLE 5

Generation and Characterization of WRS Variants that Form Stable Monomers

To construct monomeric forms of WRS, the 3D structure of T2-WRS was first analyzed to identify potentially relevant residues (e.g., F260, Y201 and I278) in the dimer interface, and also to identify alternate residues of potential relevance (e.g., H130 and E408). See FIG. 11. Certain residues were then selected for point mutation, to generate the exemplary F260EY201EI278E (SEQ ID NO:8) and F260EY201EH130R (SEQ ID NO:9) variants of T2-WRS.

T2-WRS variants were constructed by QuikChange Site-Directed Mutagenesis Kit (Stratagene). The point mutations were confirmed by DNA sequencing. Plasmid contains specific mutational amino acids was transformed to E. coli BL21 (DE3) for protein expression. The variants F260EY201EI278E and F260EY201EH130R were induced at room temperature for 4 hours with 0.2 mM isopropyl β-D-thiogalactopyranoside, and were purified by Ni-NTA affinity chromatography. The elutes were further purified by ion-exchange chromatography (MonoQ HR5/5, GE Healthcare), and eluted at 0.5 mL min$^{-1}$ with a buffer containing 25 mM Tris-HCl (pH 8.0) and gradient concentration of NaCl.

Figure 11A:
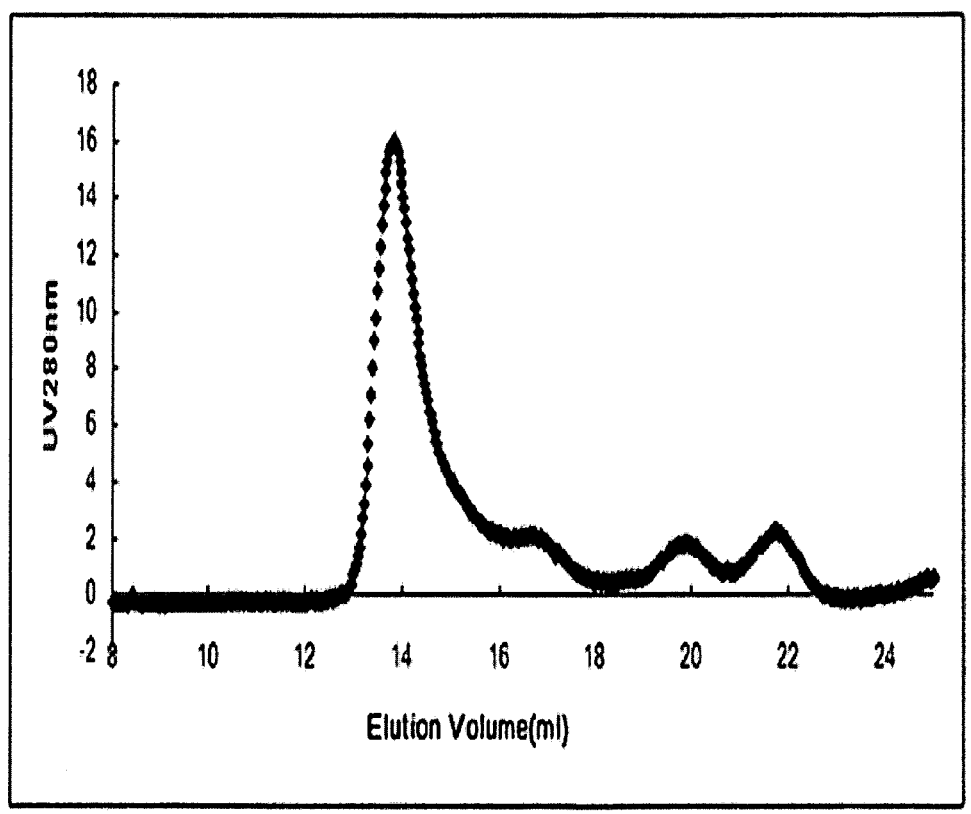
FIGS. 11A-11C show size exclusion chromatography analysis confirming that T2-WRS variants F260EY201EI278E and F260EY201EH130R exist as monomers in solution. WT T2-WRS (FIG. 11A), F260EY201EI278E T2-WRS (FIG. 11B) and F260EY201EH130R T2-WRS (FIG. 11C) were loaded on Superdex200 HR 10/30 column and eluted at 0.5 mL min$^{-1}$ with a buffer containing 25 mM Tris-HCl (pH 8.0), 150 mM NaCl. See Example 5.
Figure 11B:
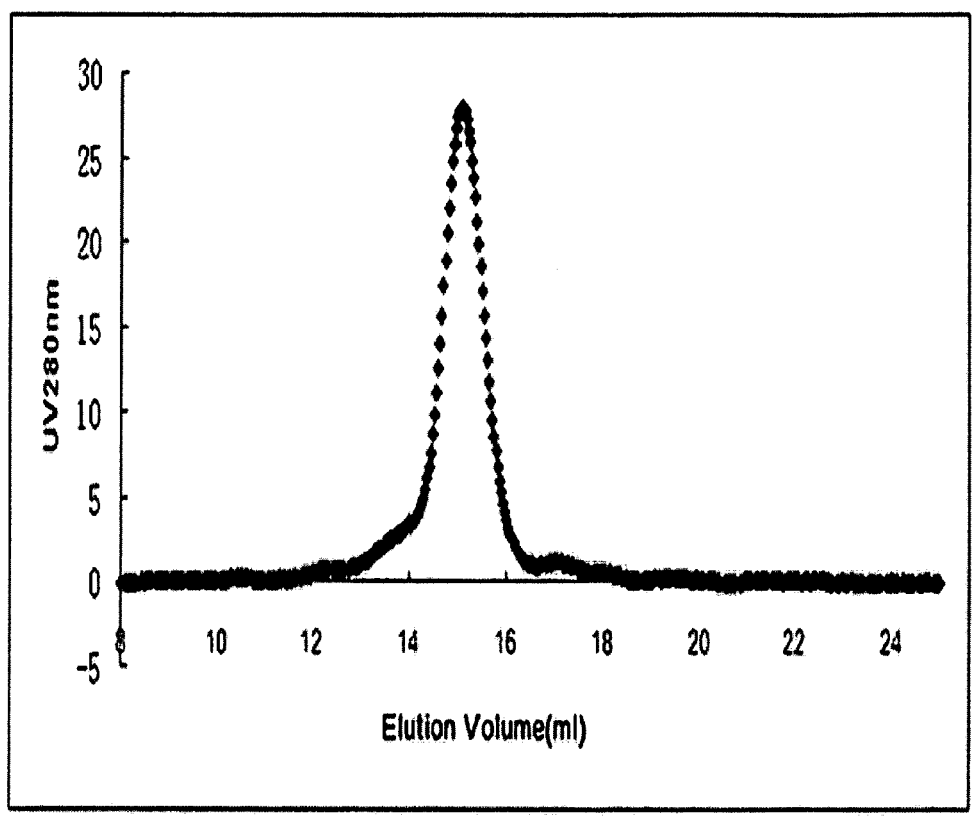
Figure 11C:
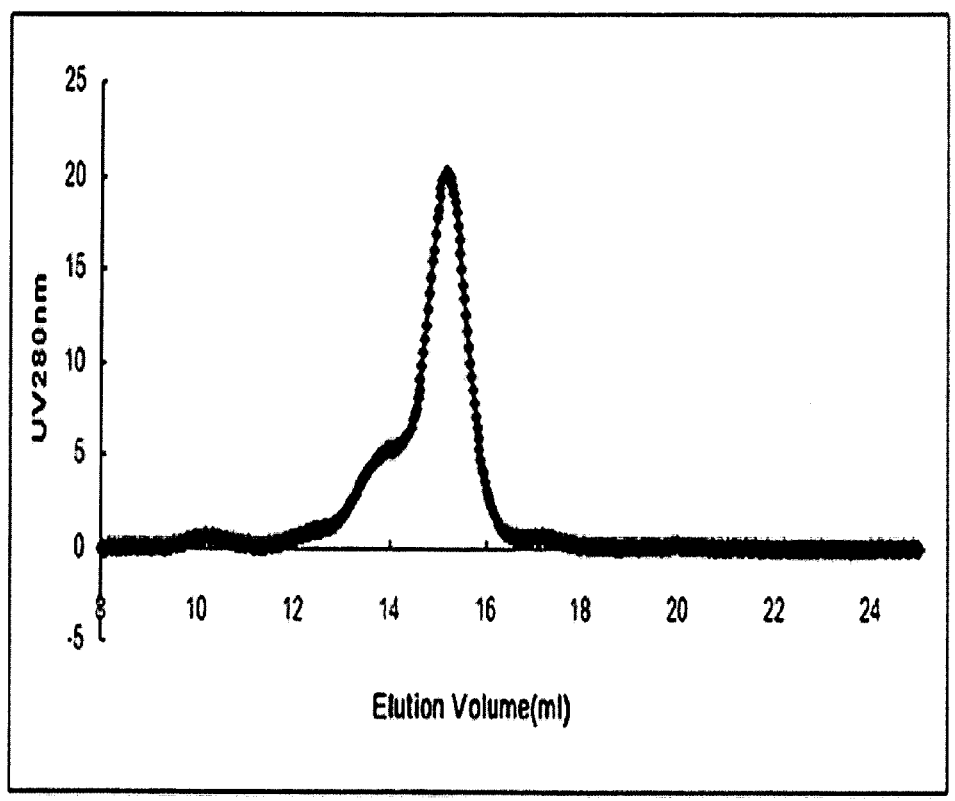

The oligomeric or monomeric state of the variant proteins was then verified by gel filtration chromatography (Superdex200 HR 10/30, GE Healthcare) in a buffer containing 25 mM Tris-HCl (pH 8.0), 150 mM NaCl. Specifically, as shown in FIG. 11, WT T2-WRS (FIG. 11A), F260EY201EI278E T2-WRS (FIG. 11B) and F260EY201EH130R T2-WRS (FIG. 11C) were loaded on Superdex200 HR 10/30 column and eluted at 0.5 mL min$^{-1}$ with a buffer containing 25 mM Tris-HCl (pH 8.0), 150 mM NaCl. This size exclusion chromatography analysis confirms that T2-WRS variants F260EY201EI278E and F260EY201EH130R exist as monomers in solution.

Figure 14A:
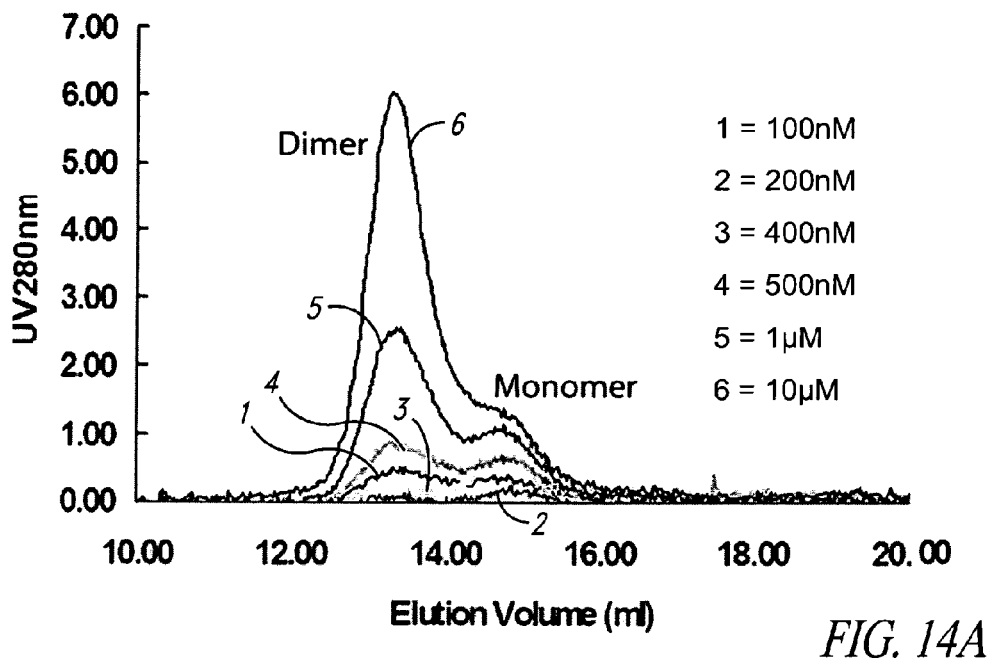
FIG. 14 shows the results of experiments to determine the dimer-monomer dissociation constant of T2-WRS using concentrations ranging from 100 nM to 10 µM, as shown in FIG. 14A.
In FIG. 14B, the percentage of dimers was calculated and plotted as a function of the protein concentration to determine the dimer-monomer dissociation constant ($K_d$=0.437±0.03 µM).
Figure 14B:
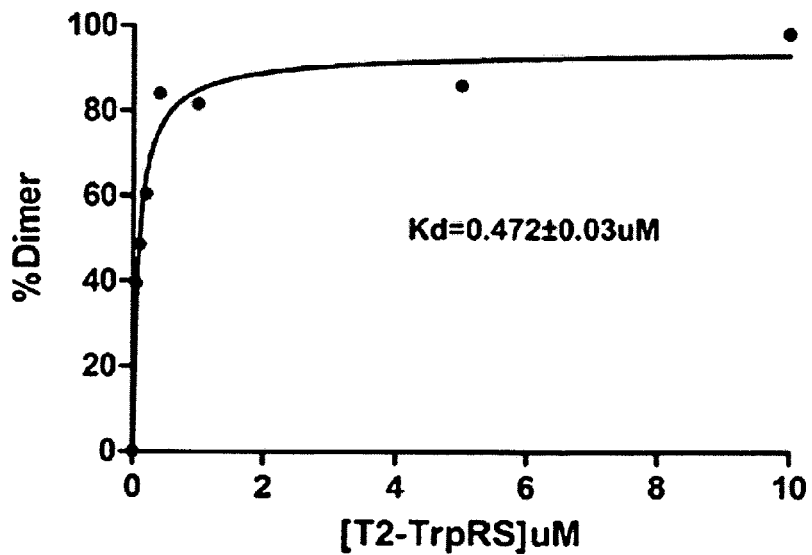

Size exclusion chromatography was then used to determine the dimer-monomer dissociation constant of T2-WRS. T2-WRS was loaded on Superdex 200 HR 10/30 column and eluted at 0.5 mL min$^{-1}$ with a buffer containing 25 mM Tris-HCl (pH 8.0), 150 mM NaCl. The concentration of T2-WRS was from 100 nM to 10 uM (see FIG. 14A). As shown in FIG. 14B, the percentage of dimers was calculated and plotted as a function of the protein concentration to determine the dimer-monomer dissociation constant ($K_d$=0.437±0.03 μM). Similar experiments were performed for the T2-WRS\ (F260EY201EI278E) monomer; however, the $K_d$ for the monomeric form was not able to be accurately determined by this method. Even at the highest concentration prepared (~270 μM), the protein was still predominately in monomeric conformation. The $K_d$ for T2-WRS\ (F260EY201EI278E) was thus estimated to be greater than 1 mM.

EXAMPLE 6

WRS Monomers Interact with VE-EC1 and Induce Degradation of B-Catenin

Immunoprecipitation experiments were performed to characterize the interaction of WRS monomers with the extracellular domain EC1 of VE-cadherin. Briefly, VE-EC1 was biotinylated and incubated with Strep-Tactin beads as bait. After incubation with T2-WRS and its variants (100 nM), the beads were washed three times and the bound T2-WRS and its variants were detected by anti-6×His antibody by Western blotting. To investigate the Zn2+ dependence of the interaction, $ZnCl_2$ (10 uM) or Zinc chelator 1,10-phenanthroline (1 uM) were added in the assay.

Preparation of Biotinylated VE-EC1.

VE-EC 1 was constructed with a Cysteine at its C-terminal, and then the engineered protein was purified and biotinylated using Maleimide-PEG2-Biotin (Thermo Scientific), which contains a spacer arm of 29.1 Å.

Immunoprecipitation Assay.

VE-EC1-biotin was immobilized to Strep-Tactin beads as bait to pull down T2-WRS and its variants F260EY201EI278E and F260EY201EH130. VE-EC 1-biotin and T2-WRS and its variants were incubated in a buffer containing 25 mM Tris-Cl pH8.0, 150 mM NaCl and 0.1% Triton X-100 for 1 hours at 4° C., then it was centrifuged and washed by binding buffer three times, and the bound protein was then washed with 30 µl of reduced slab gel sample buffer (final 5% SDS, 5 mM β-ME) and the sample was heated at 95° C. for 5 min and centrifuged at 10,000 rpm for 10 min, the supernatant was resolved by 4-20% gradient Tris-glycine SDS-PAGE and transferred to a nitrocellulose membrane.

Western Blotting.

After blocking with 5% milk-TBS-TW20, immunoblotting was performed using HRP conjugated rabbit anti-6×His antibody (Immuno Consultants Laboratory) human WRS or goat anti-human IgG-Fc antibody (Jackson Immuno Research), and with SuperSignal chemiluminescence substrate (Thermo Scientific). The bands were visualized by x-ray autoradiography.

Figure 12:
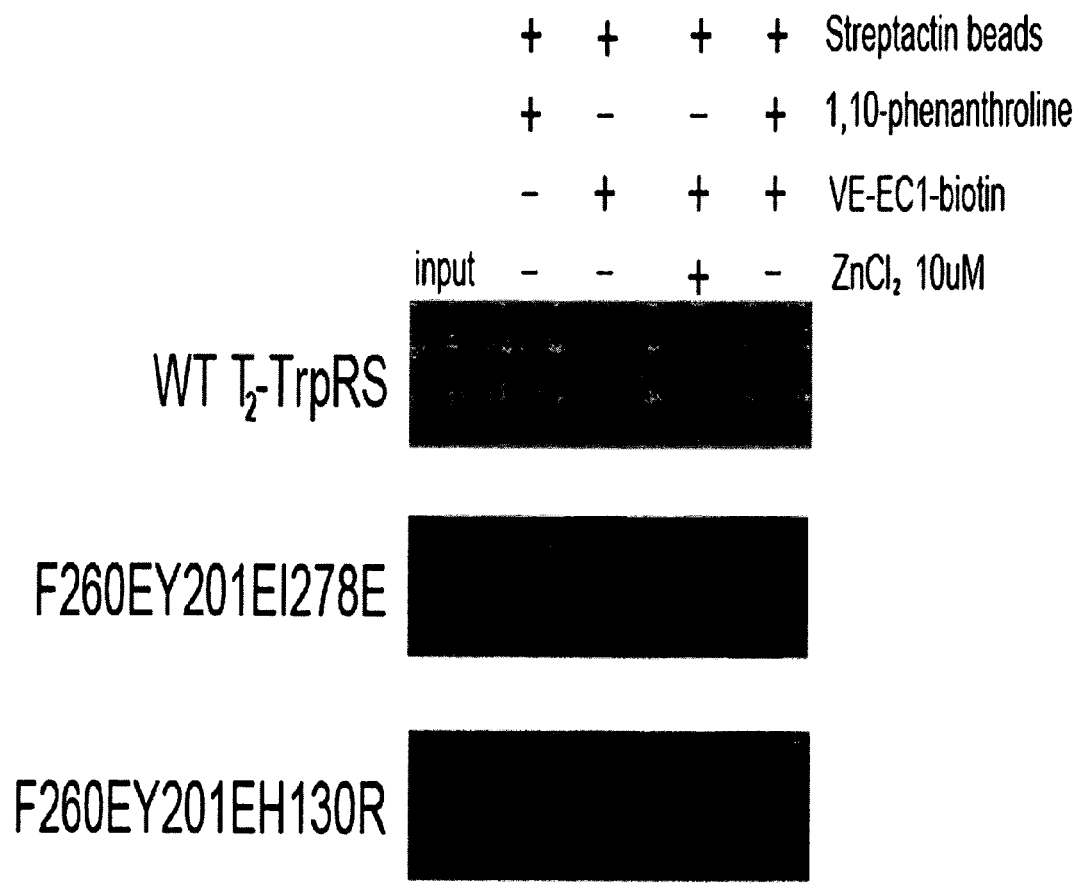
FIG. 12 shows the results of an immunoprecipitation assay in which monomers F260EY201EI278E T2-WRS and F260EY201EH130R T2-WRS bind stronger to VE-EC1 than does the WT T2-WRS, in the absence of Zinc. See Example 6.

The results are shown in FIG. 12. As indicated in this Figure, the T2-WRS variants F260EY201EI278E T2-WRS and F260EY201EH130R T2-WRS bind strongly to VE-EC1 under a variety of conditions, and in the absence of zinc bind stronger to VE-EC1 than T2-WRS.

Biacore Analysis.

Figure 15A:
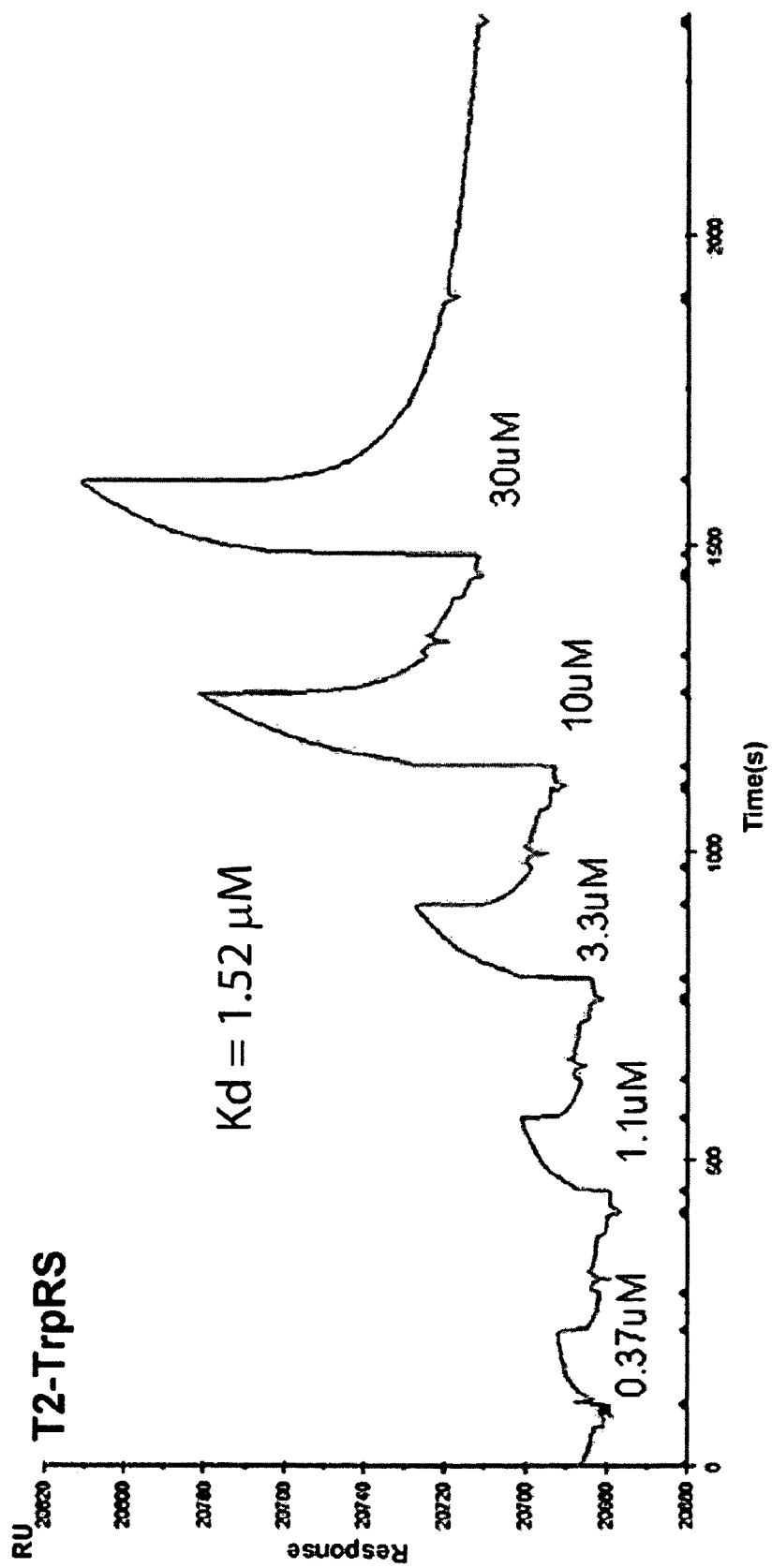
FIG. 15 shows the dissociation constant for WT T2-WRS (15A) and the monomer T2-WRS (15B), as measured by surface plasmon resonance analysis (Biacore).
Figure 15B:
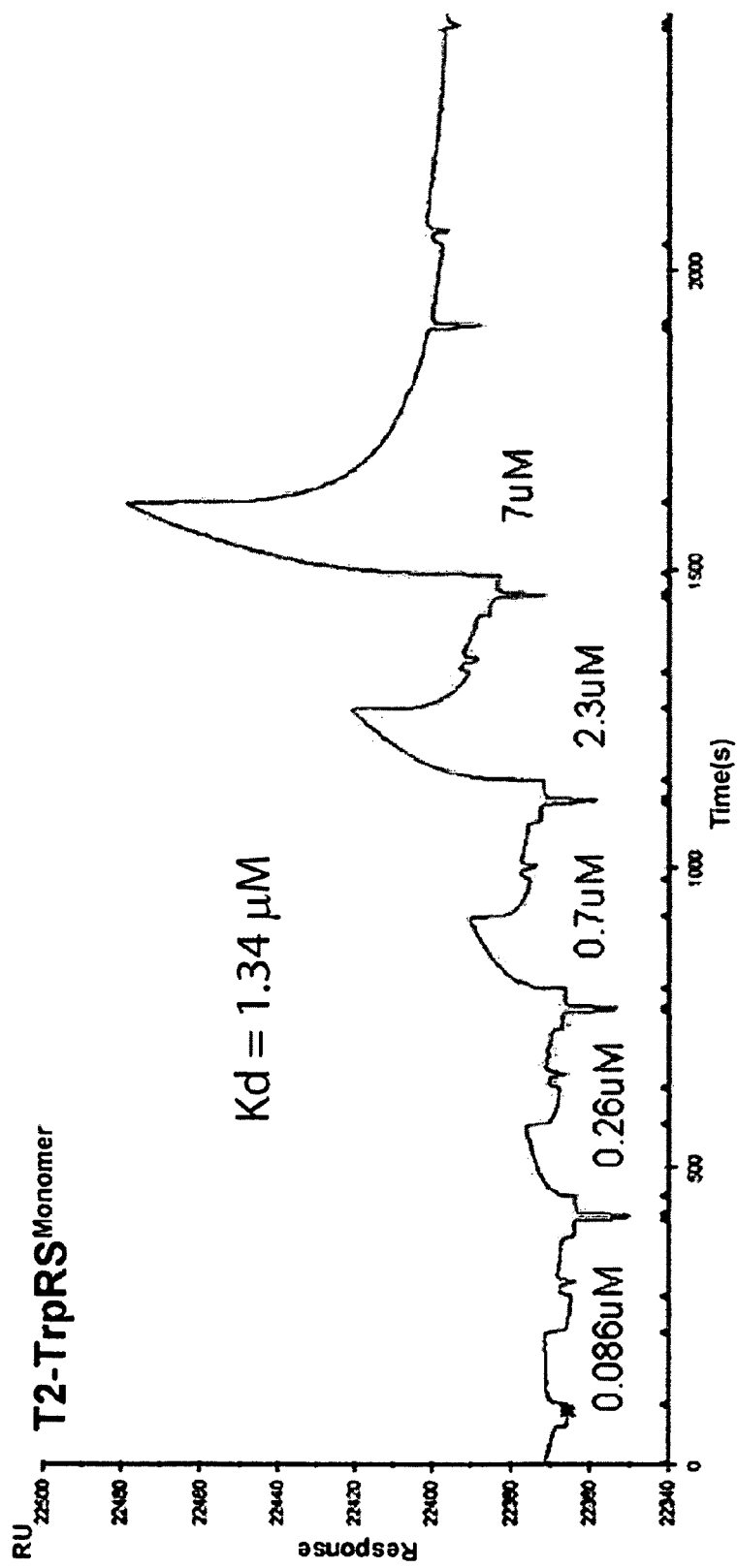

Surface plasmon resonance analysis (Biacore) was then used to measure and compare the interaction between the VE-Cadherin EC1 domain and two different T2-WRS\ polypeptides (wild-type T2-TprRS; and the monomer F260EY201EI278E T2-WRS). Each T2-WRS polypeptide was separately immobilized to a CM5 sensor chip by direct amine coupling through the side chain of Lys residues. Recombinantly engineered VE-Cadherin EC1 domain was then allowed to flow through the surface of the chip at different concentration series in buffer containing 10 mM Hepes pH7.5, 150 mM NaCl, 0.1 mM $ZnCl_2$, and 0.005% surfactant P-20. As shown in FIGS. 15A and 15B, the dissociation constant was measured by kinetic titration fitting as 1.52 µM for WT T2-WRS (15A) and 1.34 µM for the monomer T2-WRS (15B). The relatively low binding between T2-WRS and EC1 suggests that domains outside EC1 may also contribute to binding of T2-WRS. Nevertheless, the monomer T2-WRS binds to EC1 domain as tight as the WT protein, if not tighter.

Figure 16B:
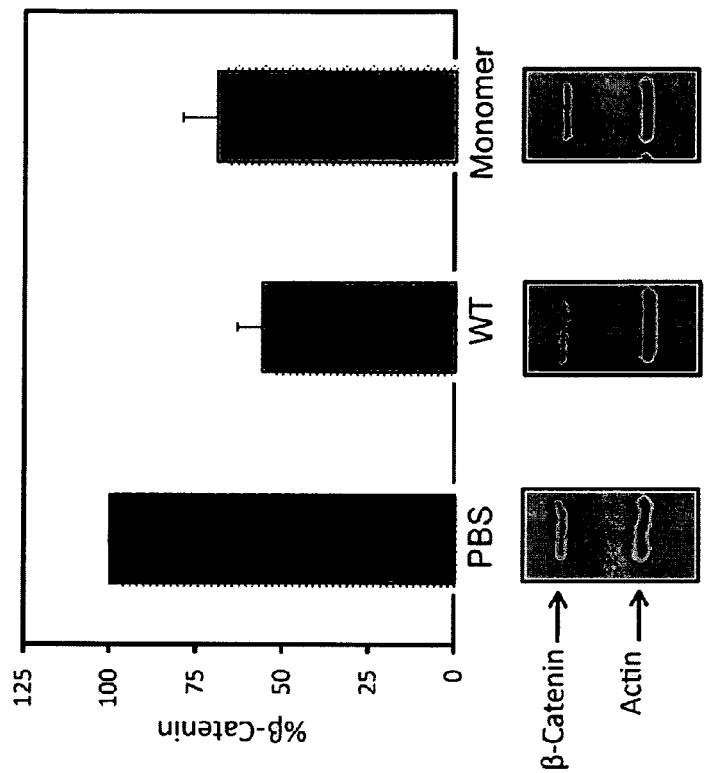
FIG. 16B shows that treatment of VE-Cadherin expressing C8161 melanoma cells with 1 µM of either WT T2-WRS or monomer T2-WRS (F260EY201EI278E) caused a sharp decrease in β-catenin protein levels.
Figure 16A:
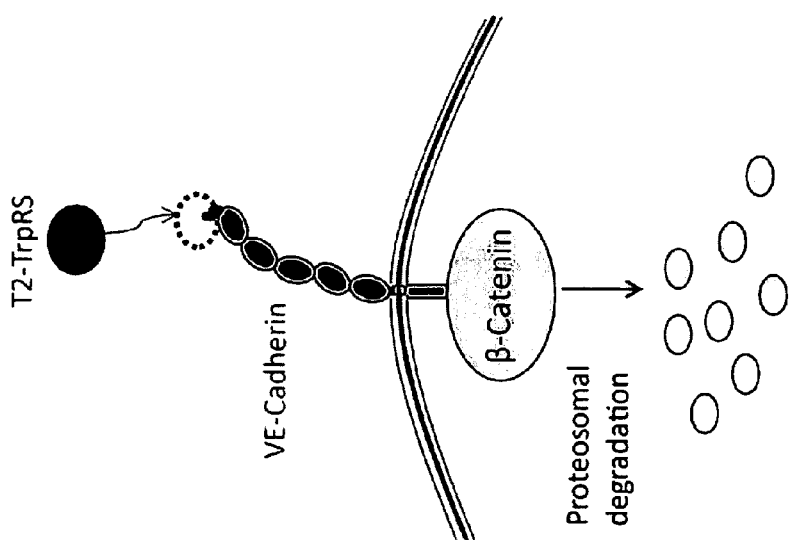
FIG. 16A illustrates how dissociated β-catenin is degraded by the proteosome.

WT T2-WRS and monomer T2-WRS also induce degradation of β-catenin. Because β-catenin is one of the intracellular association factors of VE-Cadherin, and dissociated β-catenin is degraded by the proteosome (see FIG. 16A), tests were then performed to determine whether binding of T2-WRS polypeptides would disassociate β-catenin from VE-Cadherin and lead to its degradation. As shown in FIG. 16B, treatment of VE-Cadherin expressing C8161 melanoma cells with 1 of either WT T2-WRS or monomer T2-WRS (F260EY201EI278E) caused a sharp decrease in β-catenin protein levels.

Figure 16C:
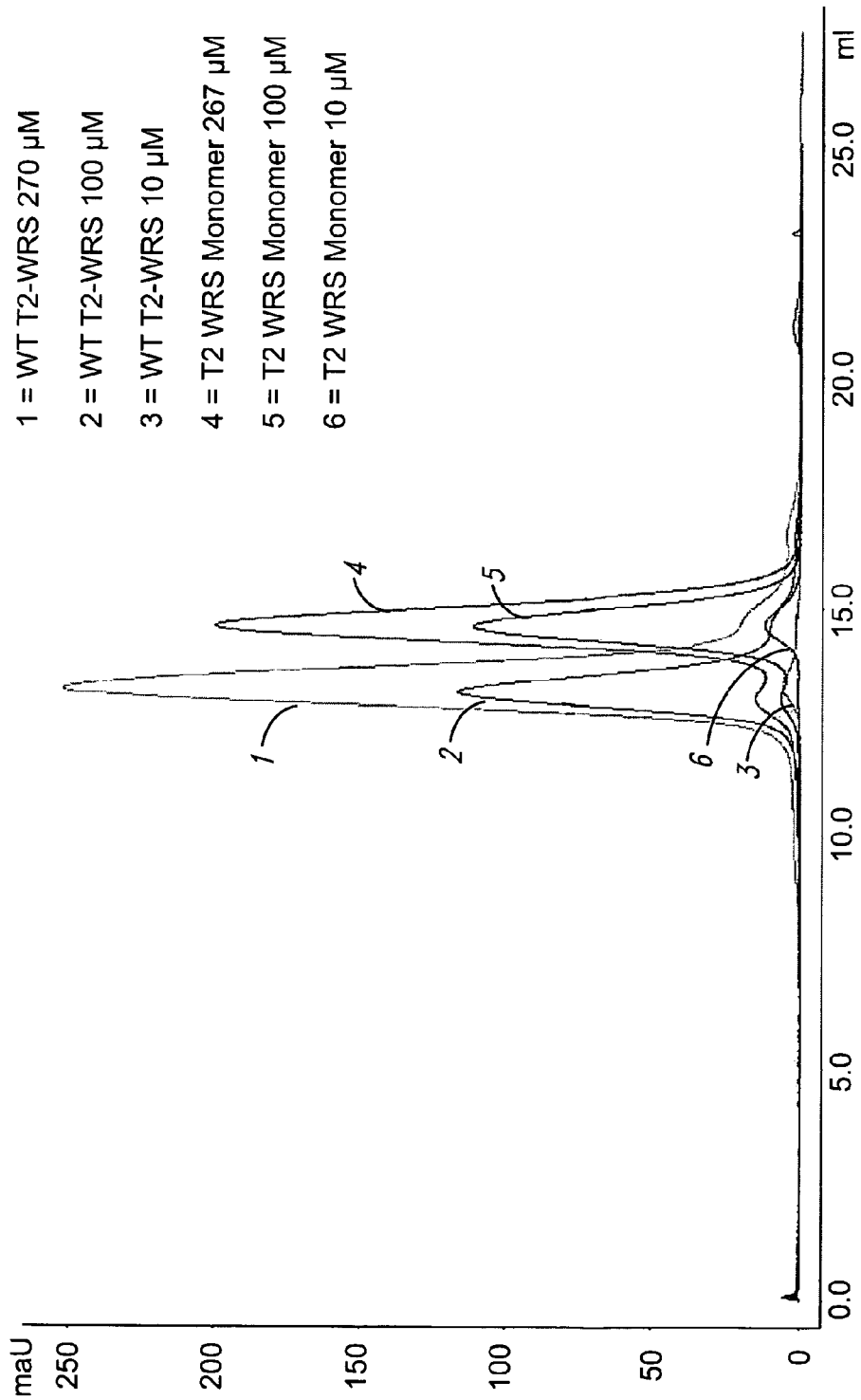
FIG. 16C shows that even at 270 µM (well above the 1 µM concentration used in this experiment), F260EY201EI278E T2-TrpRS is still predominately in monomeric conformation. The estimated dimer-monomer dissociation constant (Kd) for F260EY201EI278E T2-TrpRS is greater than 1 mM.

To confirm that F260EY201EI278E T2-WRS retains its monomeric form at higher concentrations (e.g., above 1 µM), such as those used in the β-catenin experiment described above, WT and F260EY201EI278E T2-TrpRS were loaded on a Superdex 200 HR 10/30 column and eluted at 0.5 mL $min^{-1}$ with a buffer containing 25 mM Tris-HCl (pH 8.0), 150 mM NaCl. Concentrations of WT and monomeric T2-TrpRS were 100 µM and 270 µM. FIG. 16C shows that even at 270 F260EY201EI278E T2-TrpRS is still predominately in monomeric conformation. The estimated dimer-monomer dissociation constant (Kd) for F260EY201EI278E T2-TrpRS is greater than 1 mM.

EXAMPLE 7

WRS Monomers Reduce Angiogenesis

To test the angiogenic-modulating activity of WRS monomers, an endothelial cell tuber formation assay was performed. Endothelial cell line (3B11, ATCC) was maintained in RPMI 1640 medium (Invitrogen) supplemented with 10% FBS (Invitrogen) and 1× solution of penicillin and streptomycin in an atmosphere of 5% $CO_2$ in air at 37° C. Two days before performing the tube formation assay, $6×10^5$ 3B11 cells were cultured in a T75 flask. The cells reached 80 to 95% confluence on the day of the tube formation assay.

The assay was performed as previously described (see, e.g., Zhou et al., 2008). Briefly, 150 µl of matrigel was transferred to 48-well plates and incubated for 30 min at 37° C. in an atmosphere of 5% $CO_2$. 100 µl of purified T2-WRS or other testing agents were mixed with 100 µl endothelial cells ($4×10^5$/ml in RPMI 1640 complete medium), and the mixture (200 µl) was transferred to each well containing the matrigel matrix. The plates were incubated at 37° C., 5% $CO_2$ for 3-8 h. The cells were imaged with a Leica DC350F CCD camera attached to an inverted Leica DMIL microscope, and then captured using ProMax software (Bio-TEC Instruments). Images were then converted to high resolution tif files that were used for analysis.

Figure 13:
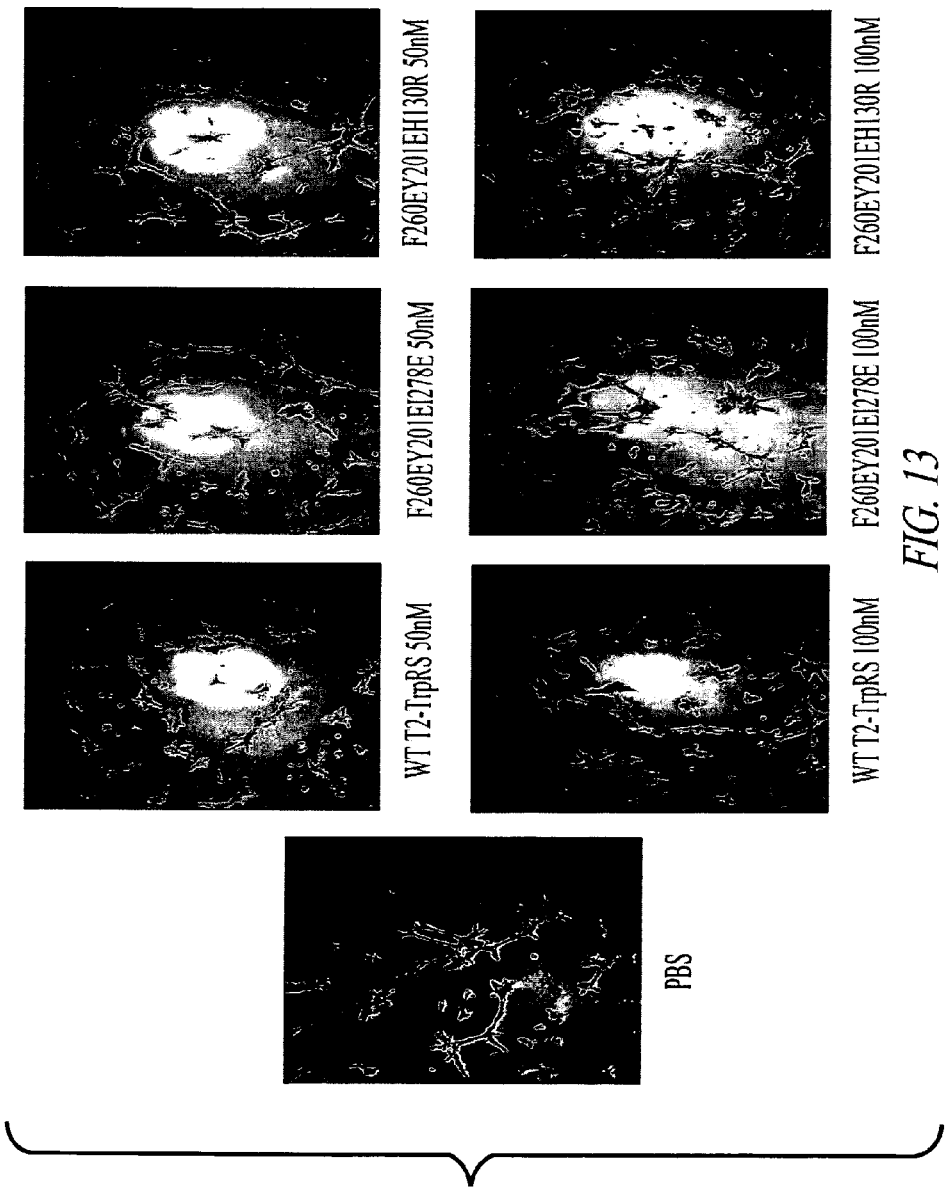
FIG. 13 shows a tuber formation assay in which the engineered T2-WRS monomers are active in reducing angiogenesis. WT T2-WRS and its variants F260EY201EI278E and F260EY201EH130R were tested at different concentration in 3B11 cells which were cultured for 6.5 hours. See Example 7.

The results for T2-WRS, F260EY201EI278E T2-WRS, and F260EY201EH130R T2-WRS are shown in FIG. 13. These images illustrate that the engineered T2-WRS monomers are active in inhibiting angiogenesis.

Figure 17:
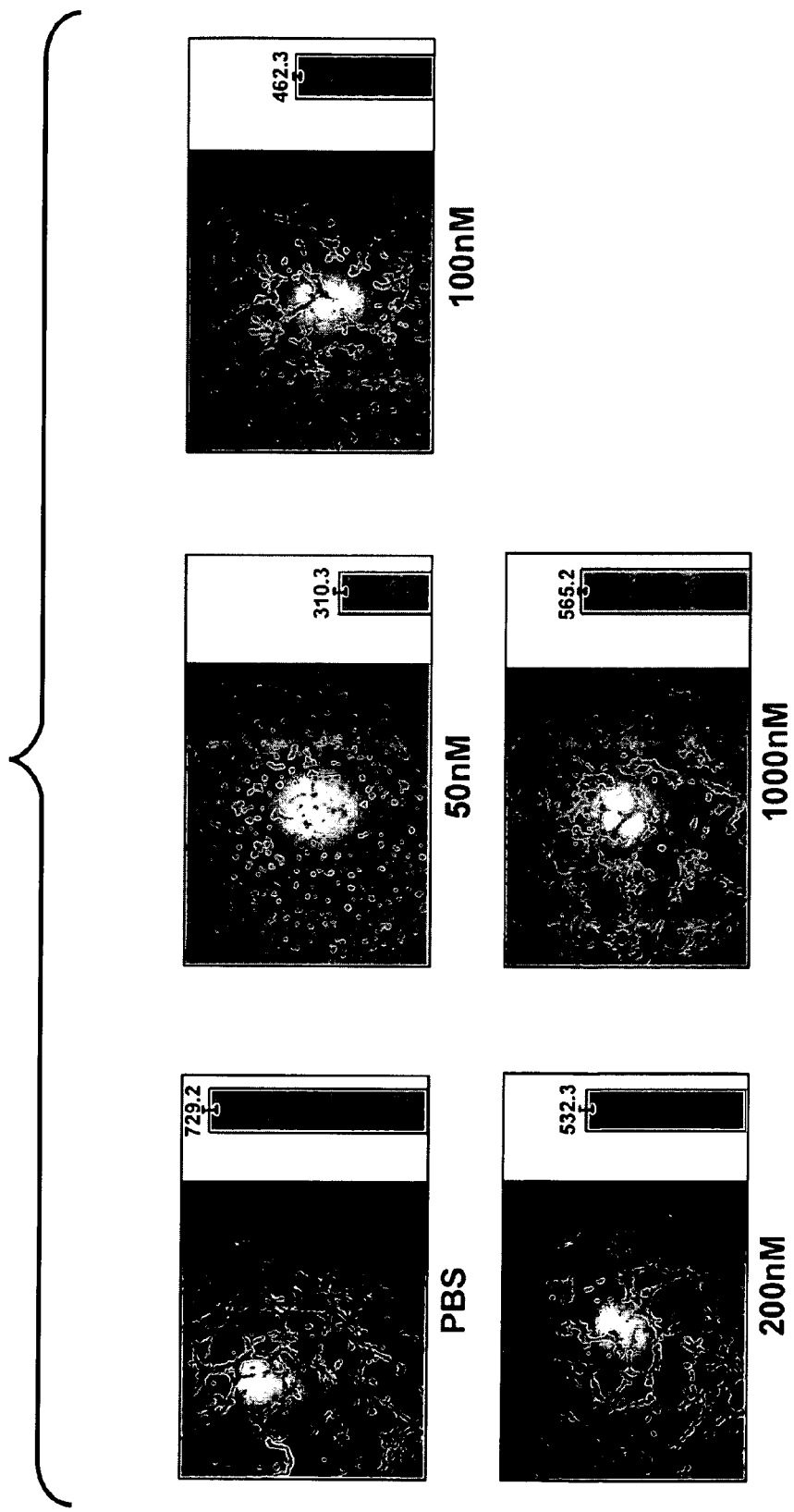
FIG. 17 shows the results of a tuber formation assay using various concentrations of WT-T2WRS. This assay demonstrates that the most potent angiostatic activity of WT T2-TrpRS is at 50 nM, a concentration at which WT T2-TrpRS has a predominately monomer conformation according to its dimer-monomer dissociation constant of 472 nM.

As shown in FIG. 17, an additional tuber formation assay was performed to demonstrate that the most potent angiostatic activity of WT T2-TrpRS is at 50 nM, a concentration at which WT T2-TrpRS has a predominately monomer conformation according to its dimer-monomer dissociation constant of 472 nM. For each experiment, multiple repetitions were performed. The length (mm) of the connected vessels in each experiment was calculated and the average length+/−SEM (standard error of the mean) for each group is shown side-by-side with a representative image.

EXAMPLE 8

Generation and Characterization of Lysyl-tRNA Synthetase (KRS) Variants that Form Stable Monomers The interactions between KRS (also LysRS), HIV Gag, and $tRNA^{Lys}$ were explored by modeling to help design and determine the characteristics of monomeric versions of KRS. First, ab initio computational methods together with high resolution 3-D structure of human KRS produced an energy-minimized docking model where Gag, $tRNA^{Lys}$, and KRS form a ternary complex. Interestingly, the model required otherwise homodimeric KRS to dissociate into a monomer that bridges between Gag and $tRNA^{Lys3}$—in part because the KRS-Gag interface was seen to overlap the covered surface of the $\alpha_2$ KRS dimer interface. This result raised the possibility that the dynamic equilibrium of KRS between monomer and dimer states could direct the protein from aminoacylation (which requires the dimer) to HIV packaging (monomer, which is inactive for aminoacylation).

Docking Model.

Briefly, coordinates of Gag-CA-CTD were taken from the crystal structure of CTD (pdb ID: 1A8O). Initial docking of CTD on both monomer and dimer structures of human KRS (pdb3BJU) was estimated using ZDOCK. The solutions were clustered by ClusPro with binding energies calculated by both FastContact and Dcomplex. Then a blind-docking of CTD on the monomer structure of human KRS was performed with the default parameter on 3 docking programs, HEX, ZDOCK and Dot.[12-14] The binding site was screened by docking the CA-CTD domain on all surfaces of the human KRS structure (pdb3BJU, chain A). Next, the docking of the CA-CTD domain was refined in a 50-Å size cubic space centering on the dimer interface. A thorough rigid-body docking was carried out using AutoDock. After searching with the maximum grids and clustering, the large cluster with the lowest energy showed apparent separation from all the others. Then, this lowest energy solution was subjected to molecular dynamic refinement in four steps by CNS: rigid-body torsion angle dynamics of two groups (KRS and CA-CTD, 500 MD cooling steps from 2000 K with a 8 fs time step), rigid-body torsion angle dynamics of three groups (KRS_N, KRS_C and CA-CTD, 500 MD steps from 2000K), semi-flexible simulated annealing (1000 MD steps from 1000 K with 4 fs time steps) with side chains of the interface residues, and a final semi-flexible simulated annealing (1000 MD steps from 1000K to 50K with 2fs time steps), where both side chains and backbones of the interface residues were allowed to move to allow for conformational arrangement. After the MD refinement, the interaction energy (sum of $E_{elec}$, $E_{vdw}$, $E_{ACS}$) decreased from −10691.001 to −11788.829 kcal/mol.

Results.

Using Zdock, as noted above, a systematic rigid-body docking of Gag-CA-CTD was performed with both the monomer and, separately, the dimeric structure of human KRS. In the top 10 clusters of CTD dockings to dimeric KRS, nine showed CTD binding to only one subunit of dimeric KRS. For one cluster, CTD bound to both subunits of dimeric KRS, but with only about half the binding energy compared to the other top hits. Thus, binding of CTD of the two subunits of dimeric KRS is unfavorable. When CTD was docked on the monomeric structure of human KRS, the docking sites were localized predominantly to the exposed residues used to form the dimer interface. This interface is covered and, therefore, inaccessible in dimeric KRS. Thus, the congruence of the primary docking trial suggested CTD has a tendency to bind to monomeric human KRS.

Figure 18A:
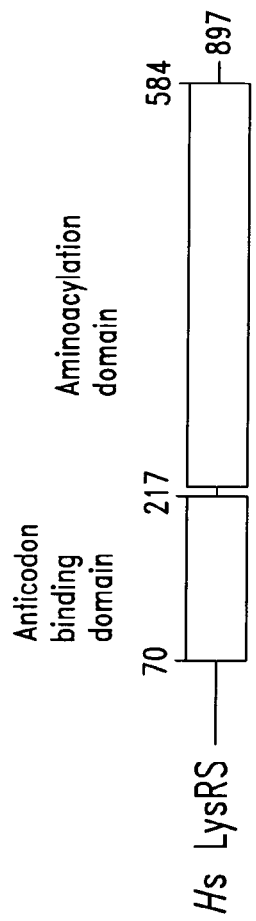
FIG. 18A shows a schematic of human KRS and the rigid-body docking results of CTD on the human KRS structure by HEX, ZDOCK and Dot. Each dot represents the core of docked CTD structures.
Figure 18A:
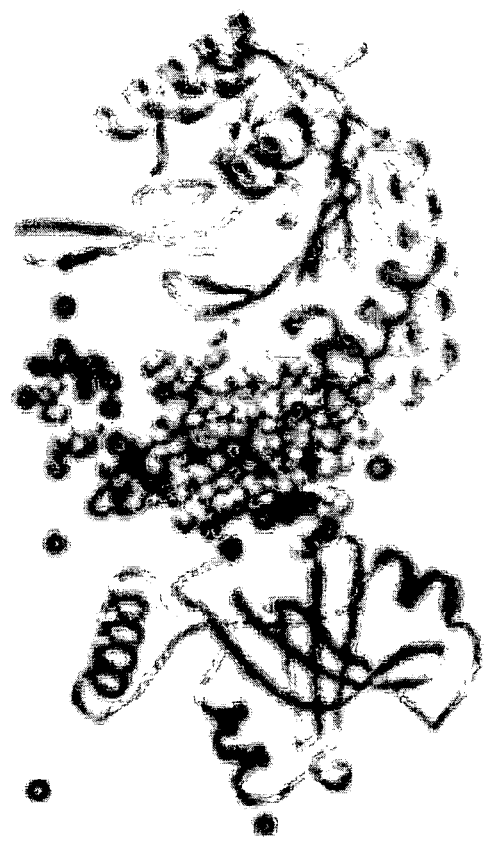
Figure 18B:
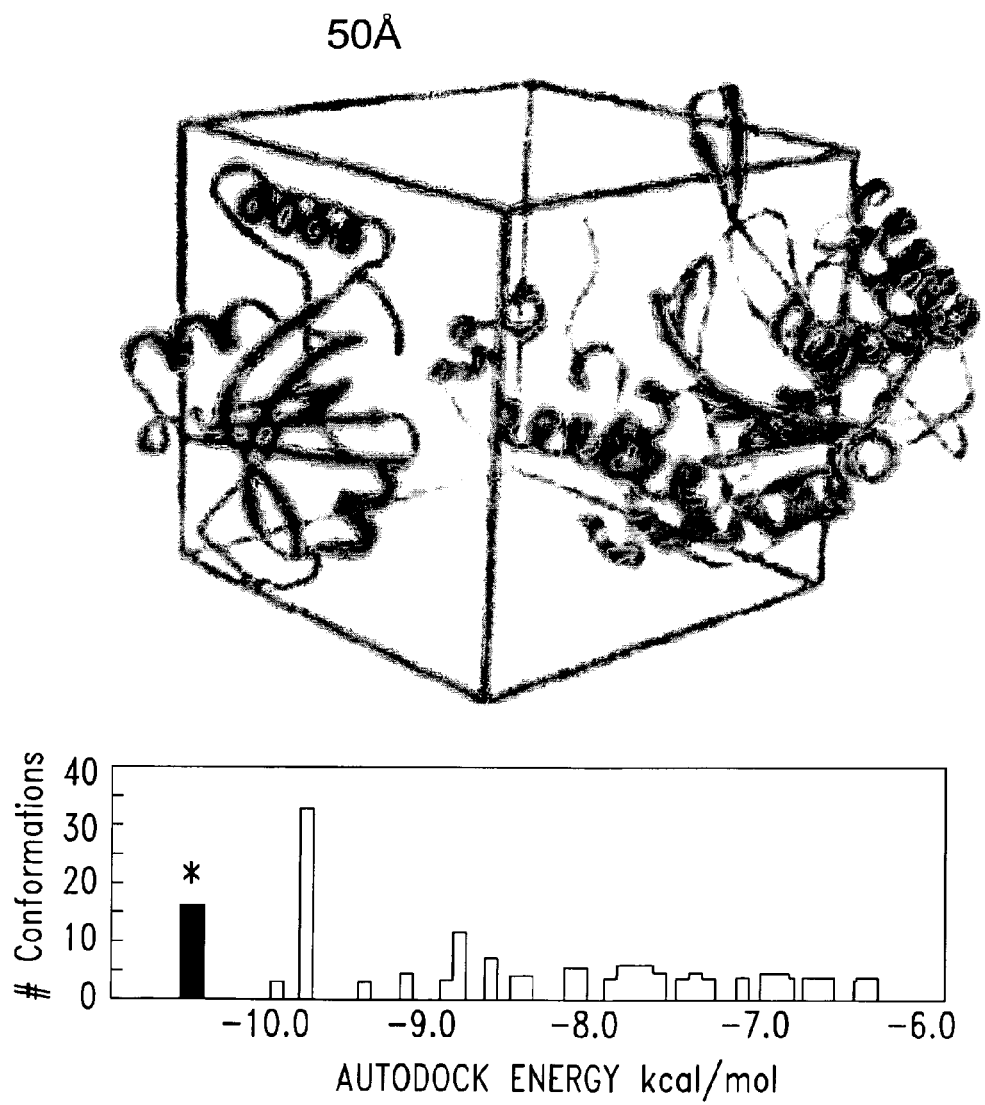
FIG. 18B shows the docking of CTD on human KRS in the refined space by AutoDock. The energy distribution of each cluster of solutions is shown below the image.
Figure 19:
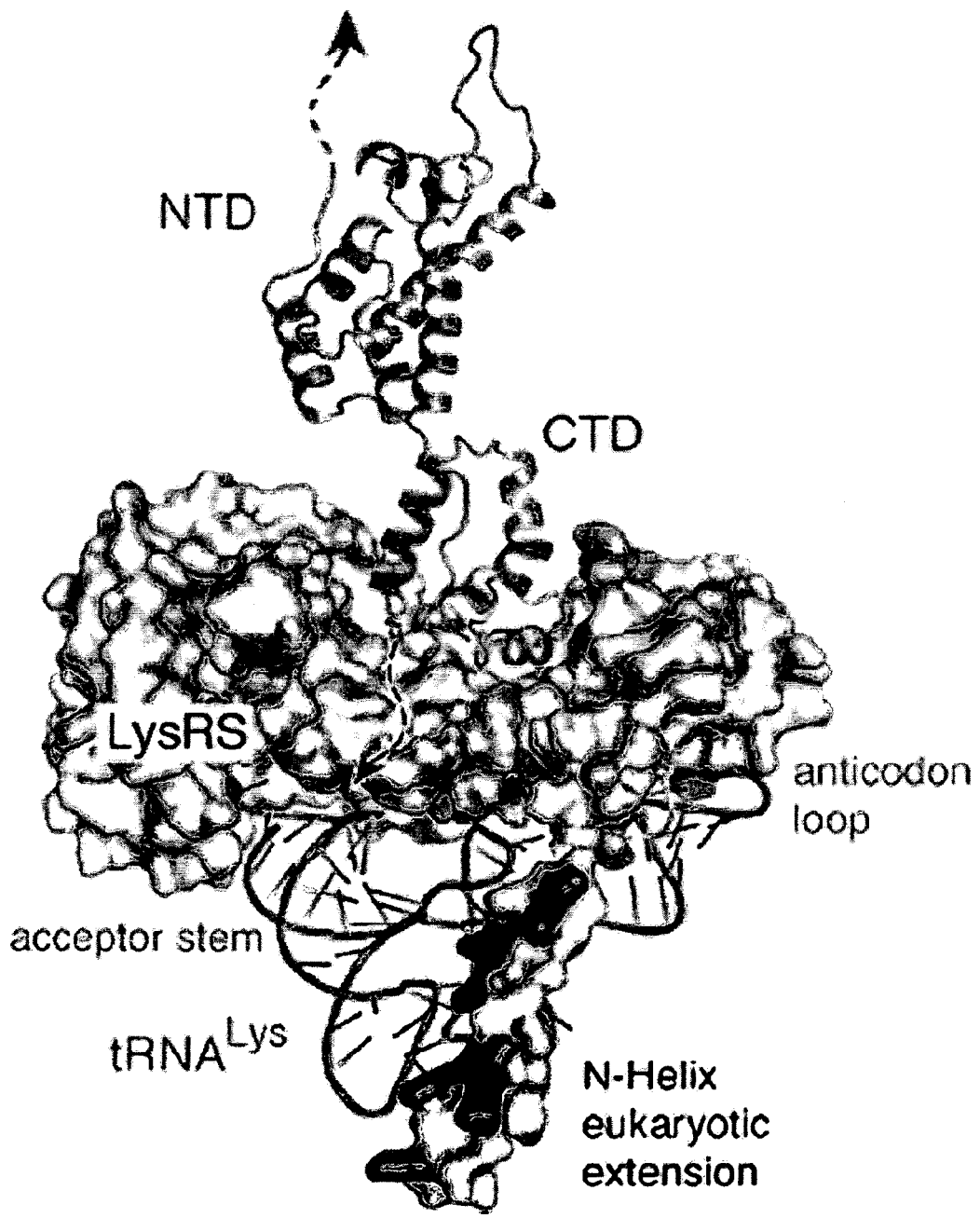
FIG. 19 shows a model of the human KRS/tRNA$^{Lys3}$/Gag-CA ternary complex. The NTD of Gag capsid (Gag-CA) is shown at top. The N-terminal helix of human KRS is shown as a surface representation. All Lys/Arg residues on the N-terminal helix extension are shown in dark grey shading, with most of them facing the bound tRNA. The arrows indicate the potential location of N-terminal and C-terminal regions of Gag outside of the CA structure.

To confirm this result, a few well-developed computational docking programs were tested to achieve an unbiased fit of monomeric KRS with Gag-CA-CTD. Complete searches of all orientations between the two proteins were done by systematically rotating and translating a moving Gag-CA-CTD with a stationary KRS. Interaction energies were computed as the sum of van der Waals and electrostatic terms (see Methods). Significantly, docking Gag-CA-CTD to monomeric human KRS by each of 3 programs (HEX, Zdock, Dot) identified one common Gag-CA-CTD binding site. As shown in FIG. 18A, this common site fell within 90-95% of the solutions represented in the 200 top-ranked solutions for all 3 programs. For this common docking site, Gag-CA-CTD docking solutions were located in a 35-A wide cavity of KRS formed by the N-terminal anticodon-binding domain and the C-terminal aminoacylation domain. This cavity is a major part of the surface needed to form the KRS homodimer, and constitutes ~60% of the entire dimeric interface between individual KRS monomers. The bottom of this cavity forms the largest hydrophobic patch of the KRS surface. The extensive overlap of these docking solutions from independent docking algorithms strongly suggests that this cavity is the preferred site for binding of KRS to Gag-CA-CTD.

To enumerate all possible binding orientations, Autodock was then utilized as above to enumerate all possible binding orientations, a technique that can be used for accurate placement of small molecules on proteins. This second step 'Autodock analysis' was performed in a defined cubic space (50 Å×50 Å×50 Å) centered on the inter-domain cavity (formed between aminoacylation and anticodon-binding domains) that was seen in the profile of the initial general searches (see FIG. 18B). Significantly, Autodock gave a cluster of docking orientations having the lowest energy, and well separated from other clusters. The largest grouping is the $2^{nd}$ lowest energy cluster, located within a broad but shallow energy state. In contrast, the lowest energy cluster sits in a deep but narrow energy funnel. Thus, a specific orientation of the two molecules defines the lowest energy interaction.

Model of Human KRS/tRNA$^{Lys3}$/Gag-CA Ternary Complex.

With the KRS/CA-CTD docking model as a reference, a model of the tRNA$^{Lys3}$/KRS/Gag-CA-CTD complex was constructed. This process utilized structural information on *E. coli* AspRS in complex with tRNA$^{Asp}$ (KRS is more closely related to AspRS than to any other tRNA synthetase). The tRNA from the *E. coli* AspRS-tRNA$^{Asp}$ complex structure (pdb1ASY) was built onto human KRS by simple superposition of the respective catalytic domains (see FIG. 19). To complete the full structure of human KRS, the N-terminal eukaryotic extension was added—this structure is thought to bind nonspecifically to the acceptor-TΨC stem-loop domain of tRNA. The N-terminal portion of the extension is predicted as a long helix that is positioned on the elbow region of the modeled tRNA This positioning utilized the functionally similar A1 domain of *Thermus thermophilus* PheRS bound to tRNAPhe (pdb1EIY). This strongly dipolar lysine-rich helix has a positive electrostatic potential extending out from one side of the protein to form part of the RNA-binding site. The N-terminal domain (NTD) of the capsid protein was then manually docked onto the complex by superimposing Gag-CA-CTD from the known structure of the Fab-capsid complex (pdb1E6J). Although the linker between N- and C-domains of the capsid protein is flexible, and the capsid protein can adopt multiple conformations that are important for virion assembly, Gag-CA-CTD was positioned far from tRNA$^{Lys}$ in the KRS-tRNA$^{Lys3}$ complex—a position with least impact on the binding interface (see FIG. 19). Here, the C-terminal end of CTD (shown as lower arrow in FIG. 19) points to tRNA$^{Lys}$ in the modeled complex, thus allowing the C-terminal nucleocapsid part of Gag to easily access the packaged tRNA. This model suggests that Gag-CA-CTD alone is sufficient to bind to KRS, and that the rest of Gag is dispensable for binding to KRS.

Because the KRS/Gag-CA-CTD interface overlaps with the core of the KRS homodimer interface, a monomer form of KRS is required to access that interface. Given that dimeric KRS and the modeled KRS/Gag-CA-CTD complex share the interface, a stabilized monomer form of KRS was designed and tested to see if its potential Gag binding interface remaining intact, and to measure its capacity for binding tRNA$^{Lys3}$.

One goal was to disrupt the KRS dimer interface without affecting the interface of KRS with Gag-CA-CTD.

One approach utilized a large globular insertion (at least about 30 Å in diameter) on the periphery of the dimer interface, to provide enough steric hindrance to block dimer formation. The following criteria were preferred: (i) the insertional sequence is not a membrane protein (so as to not introduce an extra hydrophobic surface for protein-protein interactions), (ii) it has a globular 3D structure, (iii) having about 30-40 Å dimension, and (iv) its N-terminus and C-terminus are located in close proximity, for instance, to minimize a structural change when inserted it into a single site. The structure of E. coli Flavodoxin (pdblahn) is one example of an insertion that satisfies all of these critereria. As briefly described below, the gene encoding this ~180 amino acid protein was then amplified, cloned and inserted at the G310 position of human KRS (see FIG. 20C). The resulting recombinant Flavo-KRS fusion protein was expressed and purified.

Constructs and Protein Expression.

All constructs were generated using a standard polymerase chain reaction-based cloning strategy. Full length KRS (1-597) and its truncated form (70-584) were expressed in the bacterial strain BL21 (DE3) CodonPlus using the pET20b vector (Novagen). Both proteins contained a C-terminal 6×His tag, and were purified to homogeneity by a Ni-NTA affinity column (Qiagen, Valencia, Calif.) and a Q high performance column (GE Healthcare, Little Chalfont, Buckinghamsire, U.K.). All proteins were concentrated in 5 mM Tris-HCl buffer, pH 8.0, 50 mM NaCl and 5 mM beta-mercaptoethanol.

Engineering of KRS.

Mutations on the truncated form of human KRS (70-584) were introduced by the QuikChange Mutagenesis PCR method (Stratagene) and verified by DNA sequencing. The E. coli fldB gene encoding Flavodoxin-2 (UniprotKB: P0ABY4) was amplified from E. coli K-12 genome DNA. It was then inserted into either empty pET20b vector, or into the human KRS expression plasmid using the QuikChange method modified for large insertions. All proteins were expressed and purified identically to native human KRS.

Gel Filtration Chromatography.

For each assay, 500 µl of purified truncated human KRS (70-584) and its mutants were applied to a Superdex 200 (10/300 GL) chromatography column (GE Healthcare, 10/300 GL) in a buffer containing 25 mM HEPES, pH7.5, 150 mM NaCl and 5 mM beta-mercaptoethanol. The peak fractions were analyzed by SDS-PAGE and visualized by Coomassie blue staining.

Crosslinking Assay.

A T285C mutation was introduced into native human KRS (70-584) and Flavo-KRS (70-584). All proteins were expressed and purified as mentioned above, except that no beta-mercaptoethanol was added. The purified proteins were diluted to 1 mg/ml in 25 mM HEPES (pH7.5, 150 mM NaCl) and incubated for 15 minutes at 4° C. with or without 10 mM DTT (dithiothreitol). Proteins samples (10 µl) were mixed with an equal amount of 2× loading buffer (without reducing reagent) and boiled for 1 min before loading onto a SDS-PAGE gel.

Figure 20A:
In FIG. 20A, the human KRS dimer is shown with one subunit as a schematic cartoon and the other as a surface representation.
Figure 20B:
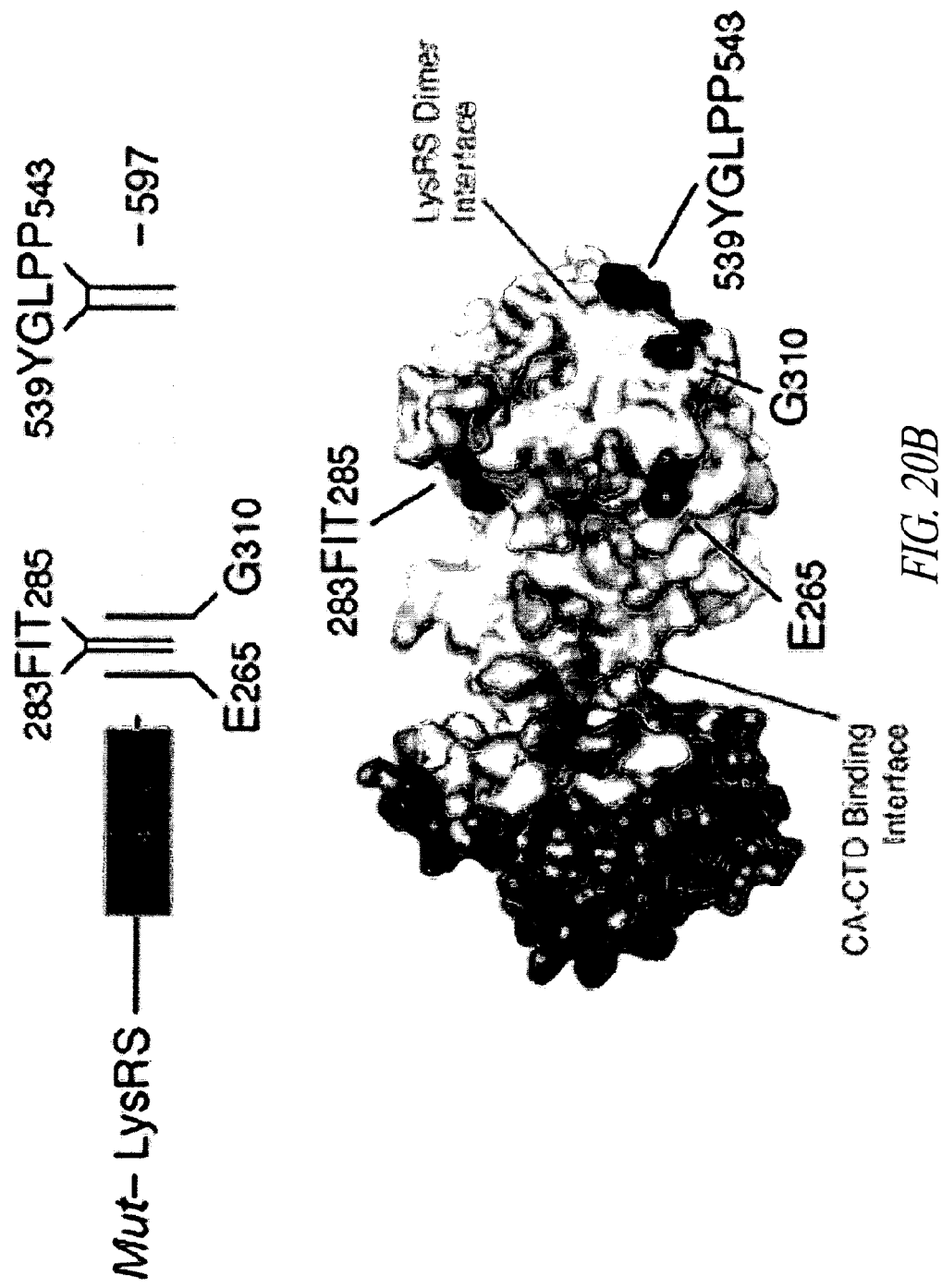
FIG. 20B shows the design of the mutagenesis on the peripheral region of the dimer interface. The predicted CTD binding site is located at the core of the KRS dimer interface (colored in grey). The peripheral region of the dimer interface is shown in white, with the selected sites of mutations in black. The corresponding positions of these sites are also shown in the sequence scheme of KRS.
Figure 20C:
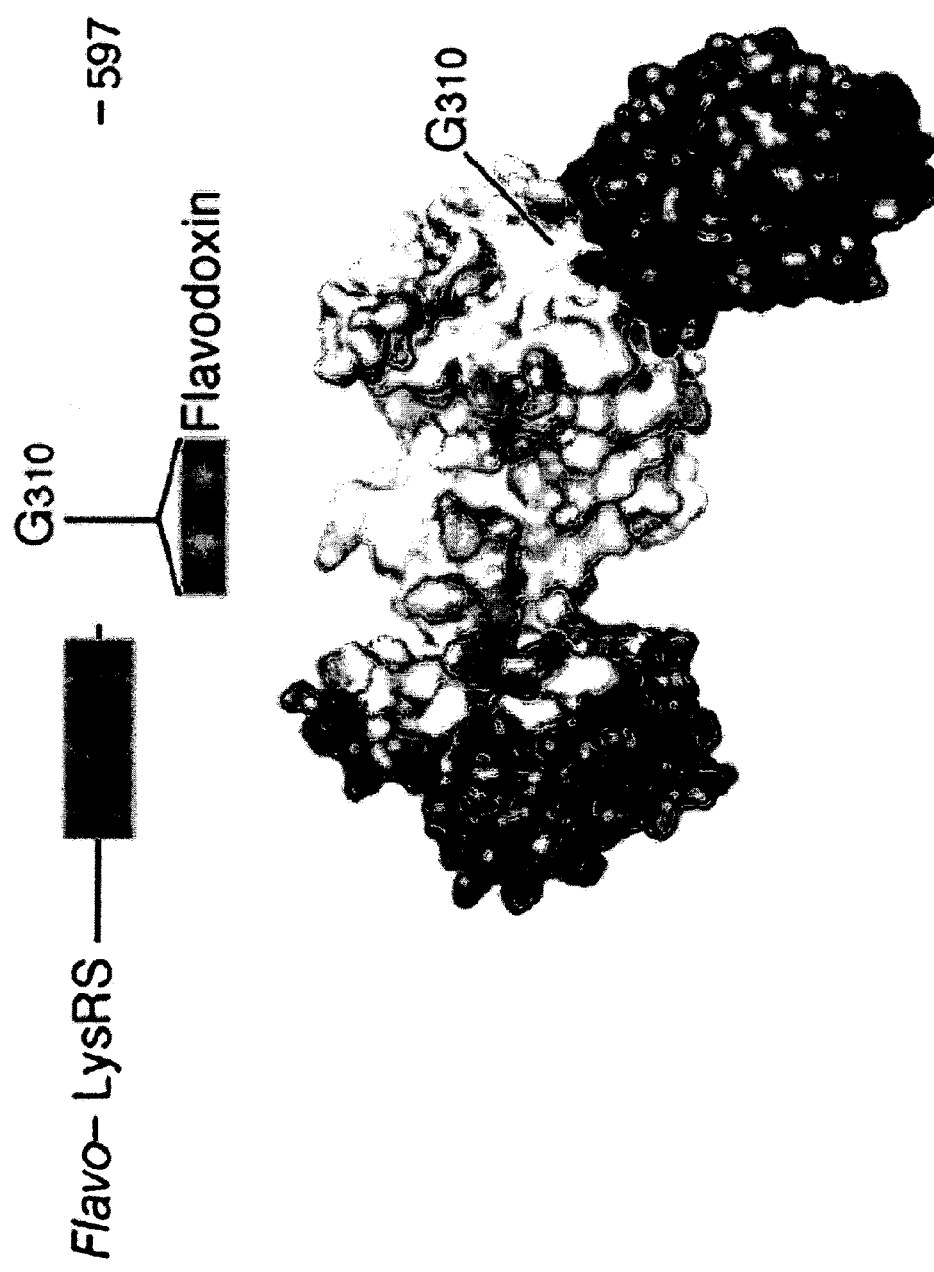
FIG. 20C shows flavodoxin insertion into human KRS. E. coli Flavodoxin was inserted at the position of G310 on the peripheral region of the KRS dimer interface. The linker was kept short to reduce the potential structural flexibility. A model of the fused Flavo-KRS is shown with the flavodoxin structure in dark grey (right side, below the G310 residue).
Figure 20D:
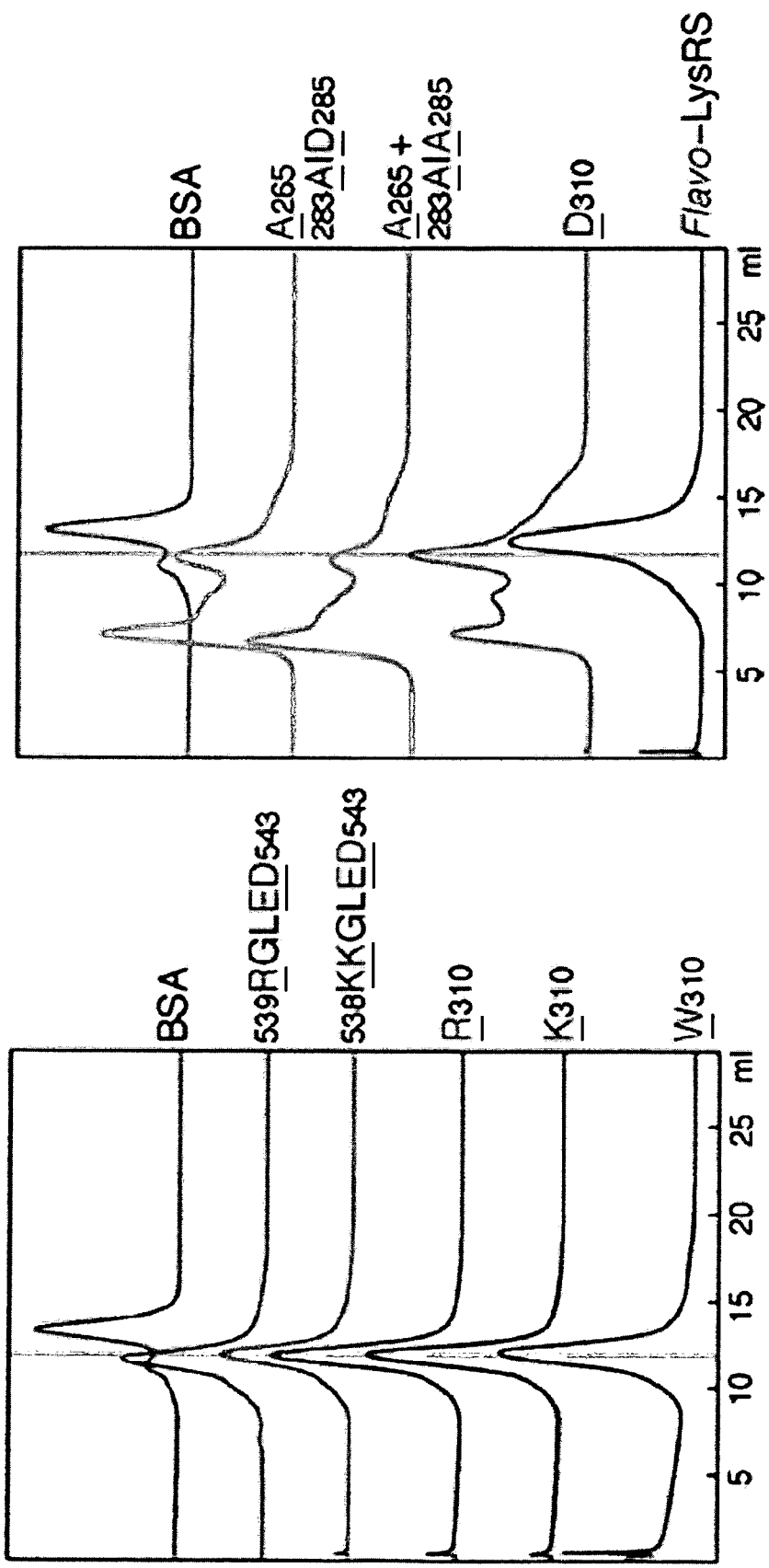
FIG. 20D shows an overlay of Superdex 200 gel filtration profiles of human KRS mutants. Mutated residues are underlined. All proteins were loaded at a concentration range of 0.5-2 µM. The vertical line gives the position of the KRS dimer; only Flavo-KRS ran as a monomer. BSA is bovine serum albumin.
Figure 21A:
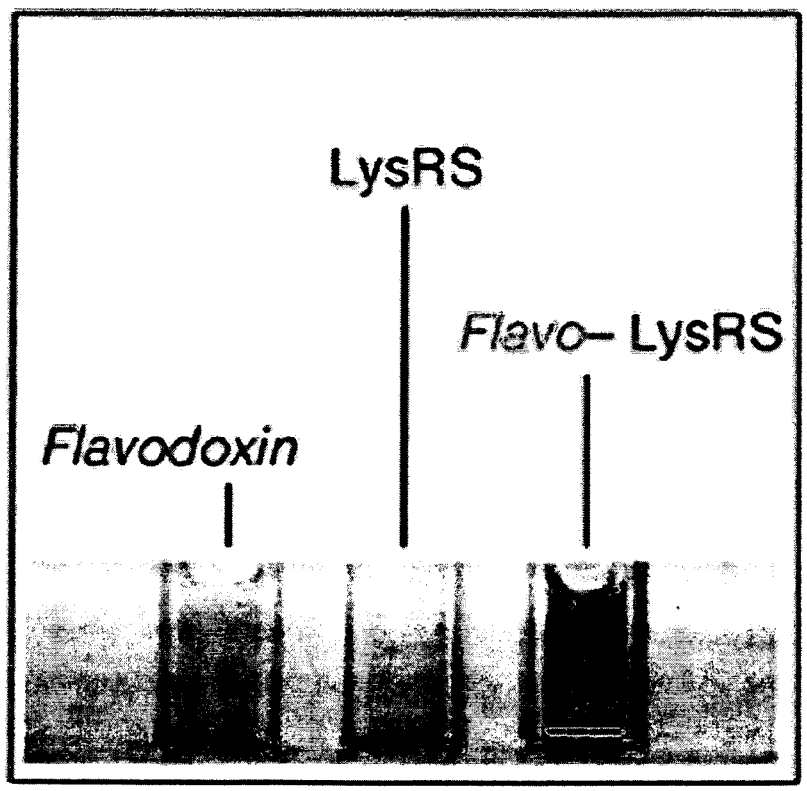
In FIG. 21A, E. coli flavodoxin and the purified Flavo-KRS show a similar result (bright yellow color), indicating a properly folded flavodoxin domain in the fusion protein.

Gel filtration, at a loading concentration of 2 µM, showed that Flavo-KRS ran mostly as a monomer (see FIG. 20D). FMN (flavin mononucleotide) bound to native E. coli flavodoxin has a characteristic absorbance centered at 466 nm, thus giving a bright yellow color. Purified Flavo-KRS had a similar absorbance spectrum, consistent with the flavodoxin domain of the fusion protein being in the native conformation (see FIG. 21A).

Figure 21B:
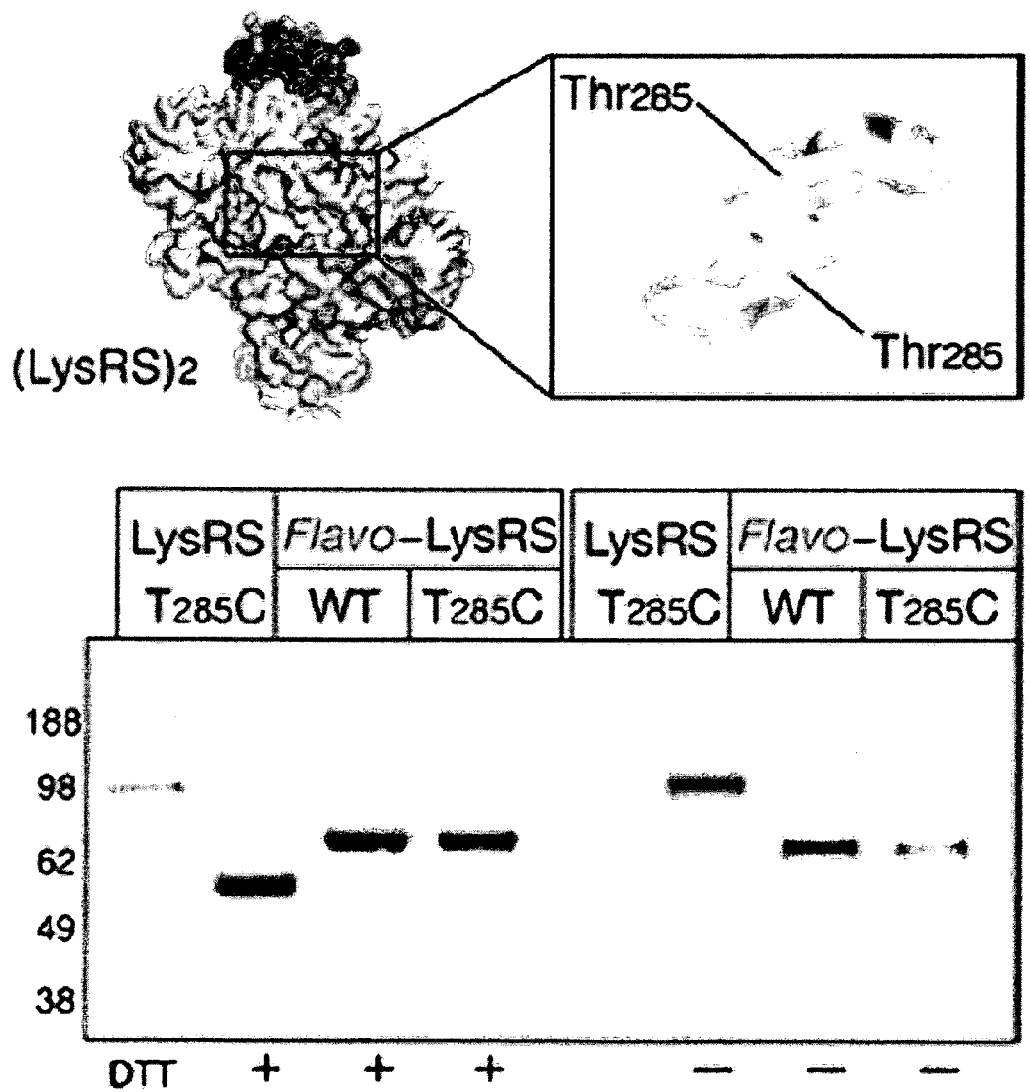
FIG. 21B shows a crosslinking assay of Thr385Cys mutants of both native KRS and Flavo-KRS; this assay was performed in the presence and absence of the DTT reducing agent, and shows that Flavo-KRS does not form a dimer in solution.

To verify the monomeric state of Flavo-KRS seen by gel filtration, the above-noted crosslinking assay was then carried out in solution. For this purpose, it was noted that two β-hairpins in the aminoacylation domain of each monomer form an anti-parallel hydrogen bonded β-sheet interaction, as part of the dimer interface. The Thr285 side chains of these hairpins on the two subunits are 4.5 Å apart (see FIG. 21B). Because this spacing could accommodate a disulfide crosslink, a T285C mutation was introduced into both native- and Flavo-KRS. With this T285C substitution, native KRST285C spontaneously formed a covalent dimer during purification; in contrast, native KRS did not. Addition of 5 mM dithiothreitol (DTT) converted the covalent dimer into a monomer on the SDS-PAGE gel (see FIG. 21B). In contrast, for WT and T285C Flavo-KRS, both forms showed the same pattern, with little crosslinked dimer found on the SDS-PAGE gel (see FIG. 21B). Thus, the flavodoxin insertion efficiently disrupted the tight dimerization of KRS.

EXAMPLE 9

Monomeric Lysyl-tRNA Synthetase (KRS) Retains HIV GAG and tRNA$^{Lys3}$ Binding

Figure 22A:
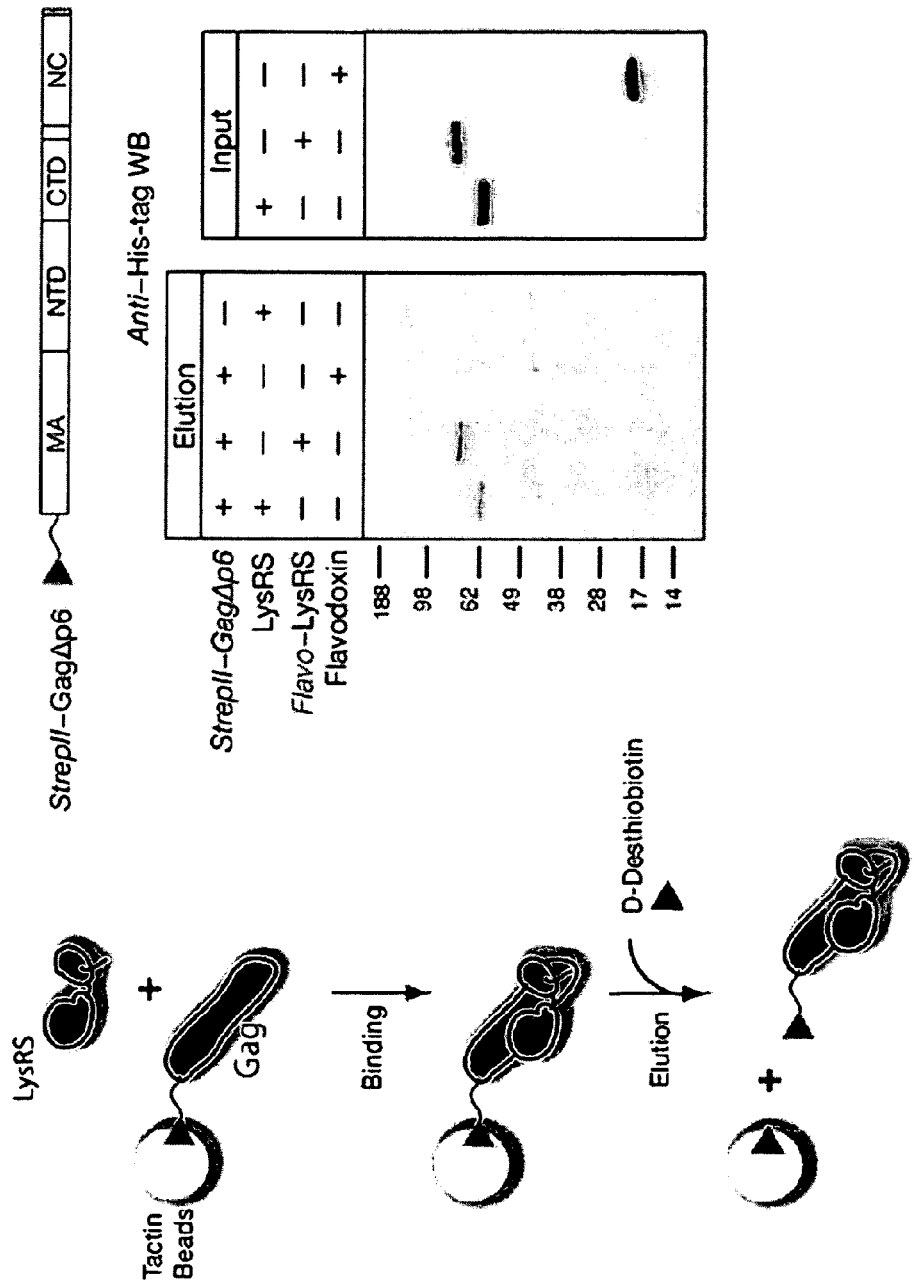
FIG. 22A illustrates a StrepII-tag pull-down assay of binding to GagΔP6 that has been immobilized on Tactin beads through a D-desthiobiotin-eluatable tag.

Based on the KRS/tRNA$^{Lys}$/Gag-CA model, the flavodoxin was designed to insert at a site with KRS that would minimize steric interference and thus allow complex formation. To confirm this model, the binding of Flavo-KRS to Gag was experimentally examined. As described below, and illustrated in FIG. 22A, a GagΔp6 construct fused with the StrepII-tag and bound to Strep-Tactin beads was used bait in a pull-down assay to measure monomeric KRS binding to Gag.

Pull-Down Assay.

The region 1-448 of GagΔp6 (encodes matrix, capsid and nucleocapsid) was subcloned into a home-made GST fusion vector, pHisGSTtev. An octapeptide StrepII-tag (sequence WSHPQFEK) was inserted at the N-terminus of GagΔp6. The HisGSTtev-StrepII-GagΔp6 fusion protein was expressed and purified identically to the procedure used for human KRS. The N-terminal HisGST was cleaved by TEV protease (1:100) at 4° C. overnight and removed by passing through a Ni-NTA affinity column. The purified StrepII-GagΔp6 protein was bound onto 50 µl Strep-Tactin beads (IBA, Germany) and washed. Then 200 µl of 20 µM WT KRS, Flavo-KRS or E. coli Flavodoxin was added to the beads and incubated at 4° C. for 2 hours. Unbound proteins were washed with standard washing buffer (100 mM Tris-HCl (pH8.0), 150 mM NaCl, 1 mM EDTA). Bound proteins were then eluted with elution buffer (2.5 mM desthiobiotin in washing buffer). The samples were checked by Western blot using anti-His antibody.

Figure 22D:
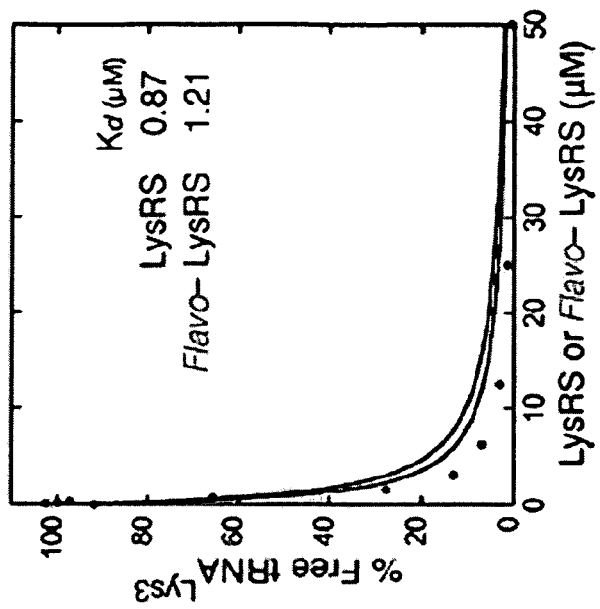
FIGS. 22B-D show EMSA assays of full-length KRS (22B) and Flavo-KRS (22C) binding to in vitro transcribed human tRNA$^{Lys3}$. The binding affinity shown in FIG. 22D was calculated from the percentage of free/unbound tRNA on the gel.
Figure 22C:
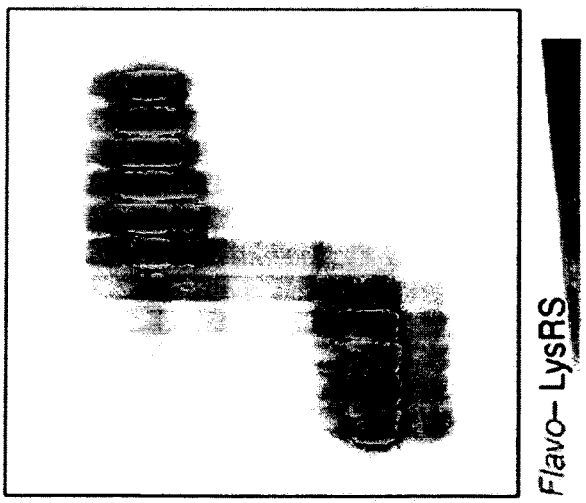
Figure 22B:
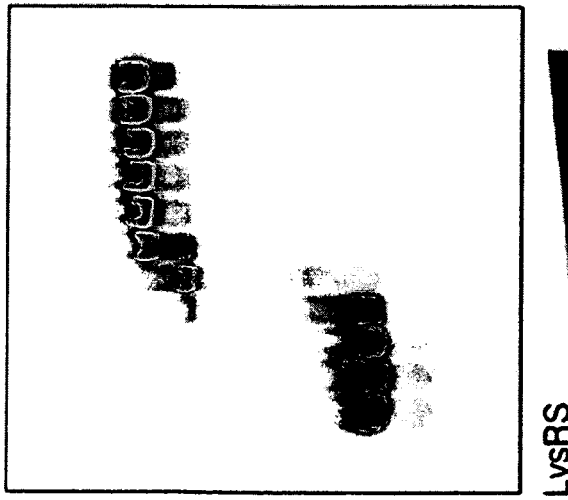

As shown in FIG. 22B, monomeric Flavo-KRS bound to Gag, while flavodoxin alone showed no binding to Gag. In this study, Flavo-KRS also appeared to bind to Gag better than KRS.

Because packaging in vivo of tRNA$^{Lys3}$ into the HIV virion requires KRS, electrophoretic mobility shift assay (EMSA) was then performed to investigate binding of tRNA$^{Lys3}$ to KRS. Human tRNA$^{Lys3}$ was prepared by in vitro transcription based on previously described methods. The annealed human tRNA$^{Lys3}$ was then radiolabeled with $^{32}$P at the 3'-end. For each complex formation reaction, about 10,000 cpm of tRNA (diluted with cold tRNA$^{Lys3}$ to a final concentration of 0.1 µM) was incubated for 10 min on ice with variable concentrations of human KRS or Flavo-KRS (full-length, 1-597) in a total volume of 20 µl containing 20 mM HEPES (pH 7.5), 20 mM KCl, 5 mM MgCl2, and 2 mM DTT. Glycerol was added to a final concentration of 5% in each sample prior to loading on a native 6% 29:1 polyacrylamide gel. The gel ran at 100 V for 1.5 hr at 4° C. in 0.5×TBE, was fixed by 7% HOAC for 5 min at 4° C., and then dried onto analytical filter paper.

Using the EMSA method, as shown in FIGS. 22B-D, both native (22B)- and Flavo-KRS (22C) bound tRNA$^{Lys3}$ with similar affinities. FIG. 22D shows that Flavo-KRS had a slightly weaker affinity of 1.21 μM relative to native KRS (0.87 μM). Monomeric Flavo-KRS thus retains the ability to bind tRNA$^{Lys3}$.

Discussion.

Here, with only structural information, a three-stage approach was used to predict the binding of human KRS with Gag-CA-CTD (see FIG. 18). Based on the predominance of both energy and cluster populations, each program (HEX, Zdock, Dot) yielded binding sites around the dimer interface of KRS. Thus, the inter-domain cavity, which is exposed in monomeric KRS, forms a natural binding site for Gag-CA-CTD.

The refined docking model also predicted that H3, H4 and the C-loop of CA-CTD form the binding interface. Consistent with this prediction, in vitro immunoprecipitation experiments have shown that removal of H4 (205-231) abolished the ability of CA-CTD to bind to KRS. In addition, immunoprecipitation assays with whole cell lysates showed that, without the C-terminal half of CA-CTD (191-231) that spans the C-loop, the partially deleted Gag loses its interaction with endogenous KRS. Further dissection showed a peptide constituting H4 and the C-terminal loop (211-227) in CA can bind to KRS with an affinity similar to that of CA-CTD. In the present model, the C-terminal half of the CA-CTD domain, consisting of helices H3 (196-205) and H4 (211-218), was positioned into the deeper part of the KRS inter-domain cavity (see FIG. 18E); upon addition of the C-terminal loop (220-231) of CA-CTD into the docking model, potential contacts were observed between this loop and KRS (see FIG. 19). These predicted contacts might explain why the loop residues were previously shown to give the strongest shifts in an NMR titration of KRSs with CA-CTD.

Figure 18C:
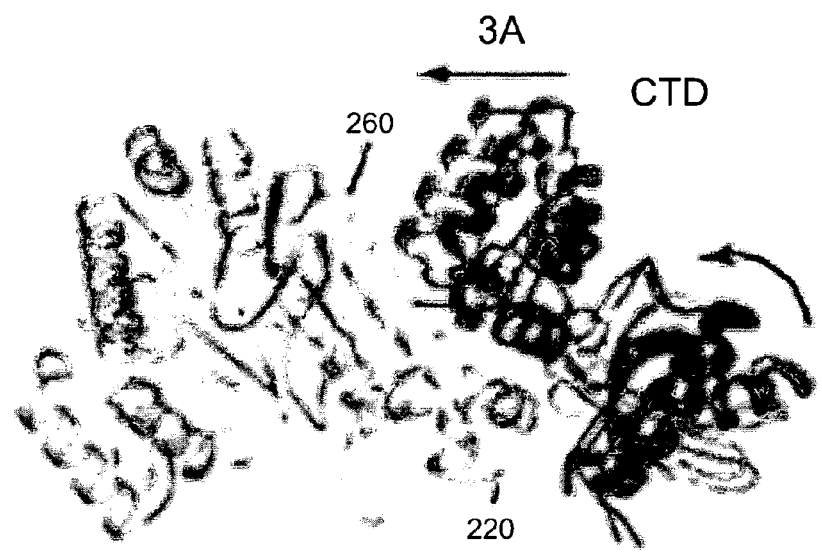
FIG. 18C shows the molecular dynamics refinement of the lowest energy model from AutoDock. After the MD refinement, CTD moved 3 Å towards the aminoacylation domain of KRS and formed a tighter contact. The AutoDock solution of CTD and of the anticodon-binding domain of human KRS are shown. The MD final solution of CTD, and of anticodon-binding domain are also shown; the region 220-260 in the catalytic domain of human KRS includes a hydrophobic patch (231-245) that overlaps with the characteristic motif-1 (238-260) in Class II AARSs.
Figure 18D:
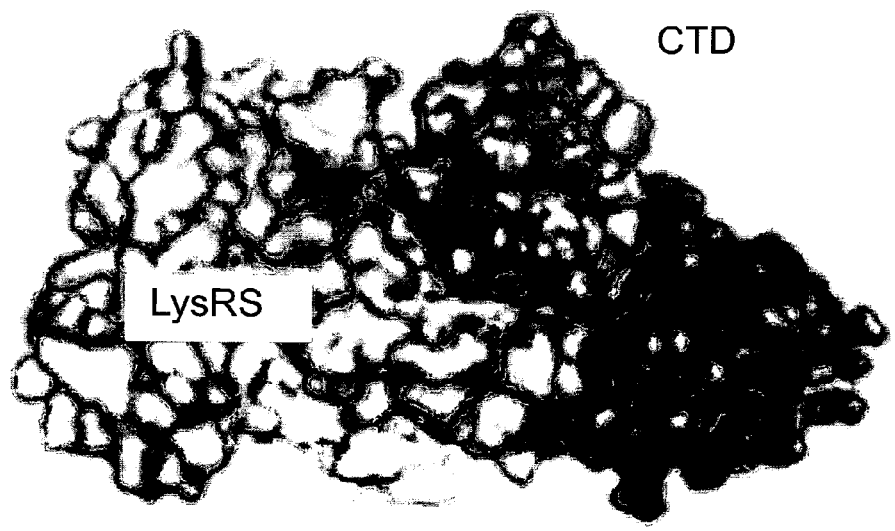
FIG. 18D shows a surface representation of the final docking model.
Figure 18E:
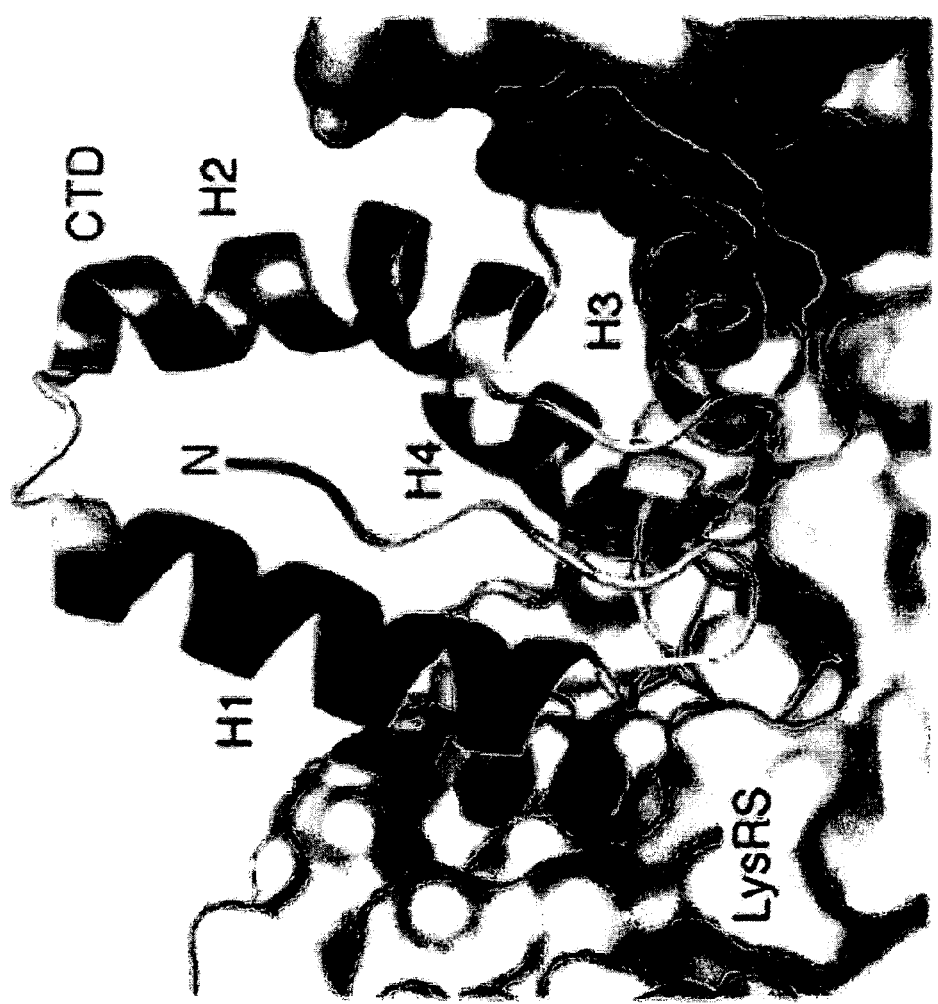
FIG. 18E shows a closeup view of KRS/CTD complex model. Helices 1-4 of CTD were colored from N-terminus (H1) to C-terminus (H4).

The present docking model also showed that the minimal CA-CTD binding site is located within a segment at the N-terminal side of motif 1 (228-255) of KRS (see FIGS. 18C-E). In vitro assays of others showed that residues 1-308 and 220-597 of KRS each bind to Gag-CA-CTD with an affinity similar to that of full-length KRS. Further, in vivo packaging assays also showed that residues 1-259 and 208-597 can be efficiently incorporated into Gag-containing viral-like-particles. Collectively, these experimental assays mapped out the minimal binding region of KRS to residues 220-259. This minimal binding region fits well with the predicted binding site of 228-255 (see FIG. 18E).

Based on the present docking model, the full-length KRS/tRNA/Gag-CA complex has the C-terminal end of the Gag protein located on the same side as bound tRNA on KRS. In contrast, the N-terminal end of Gag is on the opposite side. This orientation would make the packaged tRNA easy to be accessed by the C-terminal nucleocapsid part of Gag, and GagPol, for productive packaging of tRNA$^{Lys3}$ and annealing to the HIV genome.

These docking results also showed that H3 and H4 of CA-CTD bind to the inter-domain cavity of the KRS monomer (see FIG. 18E). It has been suggested that the available interaction sites on CA-CTD are limited, with only one site being suitable as a target for effective inhibitor binding. A 12 mer peptide was reported to bind to a groove spanning H1, H2 and the top of H3 and H4. However, the present model indicates that the bottom side of H3 and H4 could form an interaction interface with human KRS and thus represent a drug target. Because H3, H4 and the C-terminal loop of CA-CTD are critical for HIV virion assembly, an inhibitor covering the 'bottom side' of H3 and H4 may not only inhibit KRS binding and tRNA$^{Lys}$ incorporation, but also effectively block virion assembly. This model of the complex suggests that binding of KRS could potentially block efficient dimerization of the CA-CTD domain; a consideration that suggests KRS-bound Gag may be present in a different polymeric state compared to other Gag molecules in the virion.

Although monomeric KRS is inactive for aminoacylation, these results showed that disruption of KRS dimerization seems not to have a major affect on tRNA binding. The N-terminal helix motif specific to eukaryotic KRS plays a critical role for capturing tRNA$^{Lys}$ and contributes significantly to the binding. On the other hand, based on the crystal structure of the bacterial KRS-tRNA$^{Lys}$ complex, tRNA$^{Lys}$ is mainly anchored through the interaction of the anticodon stem-loop with the anticodon-binding domain, with minimal interaction being seen with the catalytic domain of the synthetase. Because tRNA binding affinity of monomeric Flavo-KRS is close to that of the native dimeric KRS, monomeric KRS can efficiently capture tRNA. Other interactions between tRNA$^{Lys3}$ with Gag-Pol may further stabilize the ternary complex. Thus, among other uses, the monomeric Flavo-KRS described herein could be a valuable tool for studying the mechanism of tRNA$^{Lys3}$ incorporation into the HIV virion.

As noted, the disclosure above is descriptive, illustrative and exemplary and is not to be taken as limiting the scope defined by the appended claims which follow.

What is claimed is:

1. A method of increasing an inflammatory response in a subject, comprising administering to the subject the modified tyrosyl-tRNA (TyrRS) synthetase polypeptide having a non-canonical biological activity, wherein the polypeptide is substantially in a monomeric form under physiological conditions or in solution, and comprises one or more stabilizing modifications relative to a wild-type TyrRS sequence that reduce its ability to dimerize with itself or with another TyrRS polypeptide wherein said TyrRS polypeptide comprises a deletion of amino acid Pro 159, Leu160 and Leu161 (Δ159-161) relative to SEQ ID NO: 3.

2. The method of claim 1, wherein the polypeptide is a substantially monomeric form of tyrosyl-tRNA synthetase (YRS).

3. The method of claim 2, where the TyrRS that increases the inflammatory response in the subject is TyrRS of SEQ ID NO: 4.

4. The method of claim 3, further comprising one or more stabilizing modifications proximal to residues 159-161 in the primary, secondary or tertiary structure of the polypeptide.

5. The method of claim 4, comprising an amino acid sequence at least 95%, 98%, or 100% identical to SEQ ID NO: 4, and comprising the stabilizing modification Δ159-161.

* * * * *